US006183121B1

(12) United States Patent
Kim et al.

(10) Patent No.: US 6,183,121 B1
(45) Date of Patent: Feb. 6, 2001

(54) HEPATITIS C VIRUS HELICASE CRYSTALS AND COORDINATES THAT DEFINE HELICASE BINDING POCKETS

(75) Inventors: Joseph L. Kim, Natick, MA (US); Kurt A. Morgenstern, Derry, NH (US); Paul R. Caron, Malden; Chao Lin, Brookline, both of MA (US)

(73) Assignee: Vertex Pharmaceuticals Inc., Cambridge, MA (US)

( * ) Notice: Under 35 U.S.C. 154(b), the term of this patent shall be extended for 0 days.

(21) Appl. No.: 09/128,314

(22) Filed: Aug. 3, 1998

Related U.S. Application Data

(60) Provisional application No. 60/055,772, filed on Aug. 14, 1997.

(51) Int. Cl.[7] ........................... G01N 23/20; C07H 21/04; C07K 16/00
(52) U.S. Cl. ........................ 364/496; 364/499; 364/578; 378/71; 378/73; 378/79; 536/23.1; 530/364; 530/388.21
(58) Field of Search ..................................... 364/499, 496, 364/578; 376/79, 71, 73; 536/23.1; 530/364, 388.21

(56) References Cited

U.S. PATENT DOCUMENTS

| 4,833,233 | 5/1989 | Carter ................................... 530/363 |
| 5,353,236 | 10/1994 | Subbiah ................................ 364/499 |
| 5,847,135 | * 12/1998 | Bemis et al. .......................... 544/264 |

FOREIGN PATENT DOCUMENTS

| WO 92/14211 | 8/1992 | (WO) .............................. G06F/15/00 |
| WO 94/25860 | 11/1994 | (WO) .............................. G01N/24/00 |
| WO 97/15588 | 1/1997 | (WO) .............................. C07K/1/14 |
| WO 97/12043 | 4/1997 | (WO) .............................. C12N/15/62 |

OTHER PUBLICATIONS

Kim et al. Structure vol. 6 pp. 89–100, 1998.*
D.G. Brown et al., "Crystallography in the Study of Protein–DNA Interactions", *Methods in Molecular Biology*, 56, pp. 293–318 (1996).
P.N. Bryan, "Protein Engineering", *Biotech Adv.*, 5, pp. 221–234 (1987).
I.D. Campbell et al., "Diffraction, in Biological Spectroscopy", The Benjamin/Cummings Publishing Company, Inc., Menlo Park, CA, pp. 299–326 (1984).
J. Jancarik et al., "Sparce Matrix Sampling: A Screening Method for Crystallization of Proteins", *J. Appl. Cryst.*, 24, pp. 409–411 (1991).
A. Kajihara et al., "Protein Modelling Using a Chimera Reference Protein From Exons", *Protein Eng'g*, 6, pp. 615–620 (1993).
K.A. Morgenstern et al., "Polynucleotide Modulation of the Protease, Nucleoside Triphosphatase, and Helicase Activities of a Hepatitis C Virus NS3–NS4A Complex Isolated from Transfected COS Cells", J. of Virology, 71, pp. 3767–3775 (1997).
A.J. Russell et al., "Rational Modification of Enzyme Catalysis by Engineering Surface Charge", *Nature*, 328, pp. 496–500 (1987).
U. Uhlin et al., "Crystallization and Crystallographic Investigations of Ribonucleotide Reductase Protein R1 From *Escherichia coli*", *FEBS*, 336(1), pp. 148–152 (1993).
N. Yao et al., "Structure of the Hepatitis C Virus RNA Helicase Domain", *Nature Structural Biology*, 4, pp. 463–467 (1997).

* cited by examiner

*Primary Examiner*—Kenneth R. Horlick
*Assistant Examiner*—Jeffrey Siew
(74) *Attorney, Agent, or Firm*—Andrew S. Marks

(57) ABSTRACT

The invention relates to the X-ray crystal structure of the hepatitis C virus helicase domain. More specifically, the invention relates to crystallized complexes of HCV helicase and an oligonucleotide, to crystallizable compositions of HCV helicase and an oligonucleotide and to methods of crystallizing an HCV helicase-oligonucleotide complex. The invention further relates to a computer programmed with the structure coordinates of the HCV helicase oligonucleotide binding pocket or the HCV helicase nucleotide triphosphate pocket wherein said computer is capable of displaying a three-dimensional representation of that binding pocket.

17 Claims, 84 Drawing Sheets

FIGURE 1A

HCV NS3 HELICASE COORDINATES

|  |  | Atom Type | Resid | # | X | Y | Z | OCC | B |
|---|---|---|---|---|---|---|---|---|---|
| ATOM | 1 | N | PRO | 190 | -0.567 | 24.363 | 16.753 | 1.00 | 49.28 |
| ATOM | 2 | CD | PRO | 190 | -0.755 | 25.375 | 17.807 | 1.00 | 48.44 |
| ATOM | 3 | CA | PRO | 190 | -0.399 | 23.026 | 17.339 | 1.00 | 49.21 |
| ATOM | 4 | CB | PRO | 190 | -0.793 | 23.252 | 18.793 | 1.00 | 48.67 |
| ATOM | 5 | CG | PRO | 190 | -0.283 | 24.643 | 19.036 | 1.00 | 48.14 |
| ATOM | 6 | C | PRO | 190 | -1.288 | 21.990 | 16.644 | 1.00 | 49.61 |
| ATOM | 7 | O | PRO | 190 | -2.520 | 22.007 | 16.772 | 1.00 | 49.44 |
| ATOM | 8 | N | PRO | 191 | -0.669 | 21.098 | 15.857 | 1.00 | 49.77 |
| ATOM | 9 | CD | PRO | 191 | 0.761 | 21.088 | 15.505 | 1.00 | 50.59 |
| ATOM | 10 | CA | PRO | 191 | -1.389 | 20.053 | 15.125 | 1.00 | 49.68 |
| ATOM | 11 | CB | PRO | 191 | -0.296 | 19.432 | 14.245 | 1.00 | 49.43 |
| ATOM | 12 | CG | PRO | 191 | 0.723 | 20.544 | 14.109 | 1.00 | 50.11 |
| ATOM | 13 | C | PRO | 191 | -2.024 | 19.007 | 16.033 | 1.00 | 49.16 |
| ATOM | 14 | O | PRO | 191 | -1.368 | 18.447 | 16.911 | 1.00 | 49.03 |
| ATOM | 15 | N | ALA | 192 | -3.309 | 18.751 | 15.823 | 1.00 | 48.24 |
| ATOM | 16 | CA | ALA | 192 | -4.000 | 17.745 | 16.616 | 1.00 | 47.12 |
| ATOM | 17 | CB | ALA | 192 | -5.477 | 17.713 | 16.265 | 1.00 | 47.93 |
| ATOM | 18 | C | ALA | 192 | -3.356 | 16.408 | 16.283 | 1.00 | 45.46 |
| ATOM | 19 | O | ALA | 192 | -2.803 | 16.234 | 15.193 | 1.00 | 44.90 |
| ATOM | 20 | N | VAL | 193 | -3.398 | 15.481 | 17.230 | 1.00 | 43.63 |
| ATOM | 21 | CA | VAL | 193 | -2.823 | 14.164 | 17.009 | 1.00 | 42.13 |
| ATOM | 22 | CB | VAL | 193 | -2.825 | 13.322 | 18.299 | 1.00 | 40.58 |
| ATOM | 23 | CG1 | VAL | 193 | -2.060 | 12.023 | 18.080 | 1.00 | 39.57 |
| ATOM | 24 | CG2 | VAL | 193 | -2.217 | 14.124 | 19.442 | 1.00 | 38.30 |
| ATOM | 25 | C | VAL | 193 | -3.641 | 13.482 | 15.909 | 1.00 | 42.80 |
| ATOM | 26 | O | VAL | 193 | -4.810 | 13.132 | 16.109 | 1.00 | 42.17 |
| ATOM | 27 | N | PRO | 194 | -3.033 | 13.309 | 14.124 | 1.00 | 42.99 |
| ATOM | 28 | CD | PRO | 194 | -1.601 | 13.536 | 14.488 | 1.00 | 43.90 |
| ATOM | 29 | CA | PRO | 194 | -3.638 | 12.690 | 13.546 | 1.00 | 43.17 |
| ATOM | 30 | CB | PRO | 194 | -2.493 | 12.691 | 12.536 | 1.00 | 43.02 |
| ATOM | 31 | CG | PRO | 194 | -1.571 | 13.753 | 13.016 | 1.00 | 43.69 |
| ATOM | 32 | C | PRO | 194 | -4.068 | 11.265 | 13.819 | 1.00 | 43.70 |
| ATOM | 33 | O | PRO | 194 | -3.519 | 10.595 | 14.691 | 1.00 | 44.16 |
| ATOM | 34 | N | ALA | 195 | -5.031 | 10.794 | 13.038 | 1.00 | 43.76 |
| ATOM | 35 | CA | ALA | 195 | -5.522 | 9.433 | 13.176 | 1.00 | 43.44 |
| ATOM | 36 | CB | ALA | 195 | -6.782 | 9.247 | 12.327 | 1.60 | 44.50 |
| ATOM | 37 | C | ALA | 195 | -4.422 | 8.466 | 12.732 | 1.00 | 42.59 |
| ATOM | 38 | O | ALA | 195 | -4.320 | 7.345 | 13.235 | 1.00 | 43.20 |
| ATOM | 39 | N | SER | 196 | -3.607 | 8.914 | 11.783 | 1.00 | 41.07 |
| ATOM | 40 | CA | SER | 196 | -2.507 | 8.117 | 11.255 | 1.00 | 40.13 |
| ATOM | 41 | CB | SER | 196 | -2.859 | 7.604 | 9.851 | 1.00 | 41.51 |
| ATOM | 42 | OG | SER | 196 | -3.572 | 8.583 | 9.106 | 1.00 | 43.93 |
| ATOM | 43 | C | SER | 196 | -1.225 | 8.957 | 11.233 | 1.00 | 37.38 |
| ATOM | 44 | O | SER | 196 | -1.274 | 10.181 | 11.393 | 1.00 | 36.47 |
| ATOM | 45 | N | PHE | 197 | -0.082 | 8.303 | 11.037 | 1.00 | 35.00 |
| ATOM | 46 | CA | PHE | 197 | 1.193 | 9.017 | 11.014 | 1.00 | 31.57 |
| ATOM | 47 | CB | PHE | 197 | 2.373 | 8.079 | 10.744 | 1.00 | 28.81 |
| ATOM | 48 | CG | PHE | 197 | 3.697 | 8.794 | 10.693 | 1.00 | 25.08 |
| ATOM | 49 | CD1 | PHE | 197 | 4.343 | 9.162 | 11.863 | 1.00 | 23.41 |
| ATOM | 50 | CD2 | PHE | 197 | 4.254 | 9.167 | 9.482 | 1.00 | 23.23 |
| ATOM | 51 | CE1 | PHE | 197 | 5.505 | 9.887 | 11.824 | 1.00 | 21.81 |
| ATOM | 52 | CE2 | PHE | 197 | 5.420 | 9.894 | 9.437 | 1.00 | 21.64 |
| ATOM | 53 | CZ | PHE | 197 | 6.045 | 10.256 | 10.606 | 1.00 | 22.04 |

FIGURE 1B

| ATOM | 54 | C | PHE | 197 | 1.262 | 10.163 | 10.020 | 1.00 | 30.70 |
|---|---|---|---|---|---|---|---|---|---|
| ATOM | 55 | O | PHE | 197 | 1.089 | 9.965 | 8.816 | 1.00 | 31.02 |
| ATOM | 56 | N | GLN | 198 | 1.582 | 11.345 | 10.536 | 1.00 | 30.64 |
| ATOM | 57 | CA | GLN | 198 | 1.731 | 12.550 | 9.732 | 1.00 | 30.20 |
| ATOM | 58 | CB | GLN | 198 | 0.478 | 13.438 | 9.818 | 1.00 | 33.70 |
| ATOM | 59 | CG | GLN | 198 | -0.893 | 12.720 | 9.747 | 1.00 | 38.79 |
| ATOM | 60 | CD | GLN | 198 | -1.331 | 12.268 | 8.350 | 1.00 | 41.73 |
| ATOM | 61 | OE1 | GLN | 198 | -2.254 | 11.462 | 8.218 | 1.00 | 44.20 |
| ATOM | 62 | NE2 | GLN | 198 | -0.696 | 12.802 | 7.310 | 1.00 | 44.35 |
| ATOM | 63 | C | GLN | 198 | 2.921 | 13.340 | 10.279 | 1.00 | 28.49 |
| ATOM | 64 | O | GLN | 198 | 3.341 | 13.148 | 11.423 | 1.00 | 27.20 |
| ATOM | 65 | N | VAL | 199 | 3.485 | 14.191 | 9.431 | 1.00 | 28.09 |
| ATOM | 66 | CA | VAL | 199 | 4.595 | 15.074 | 9.786 | 1.00 | 27.30 |
| ATOM | 67 | CB | VAL | 199 | 5.798 | 14.949 | 8.803 | 1.00 | 27.93 |
| ATOM | 68 | CG1 | VAL | 199 | 6.783 | 16.106 | 9.018 | 1.00 | 26.84 |
| ATOM | 69 | CG2 | VAL | 199 | 6.510 | 13.607 | 8.984 | 1.00 | 27.42 |
| ATOM | 70 | C | VAL | 199 | 3.989 | 16.464 | 9.624 | 1.00 | 26.70 |
| ATOM | 71 | O | VAL | 199 | 3.425 | 16.784 | 8.579 | 1.00 | 26.24 |
| ATOM | 72 | N | ALA | 200 | 4.115 | 17.298 | 10.640 | 1.00 | 26.58 |
| ATOM | 73 | CA | ALA | 200 | 3.538 | 18.624 | 10.574 | 1.00 | 25.57 |
| ATOM | 74 | CB | ALA | 200 | 2.364 | 18.725 | 11.544 | 1.00 | 24.63 |
| ATOM | 75 | C | ALA | 200 | 4.567 | 19.677 | 10.906 | 1.00 | 25.17 |
| ATOM | 76 | O | ALA | 200 | 5.569 | 19.400 | 11.558 | 1.00 | 24.12 |
| ATOM | 77 | N | HIS | 201 | 4.306 | 20.891 | 10.442 | 1.00 | 25.38 |
| ATOM | 78 | CA | HIS | 201 | 5.178 | 22.022 | 10.698 | 1.00 | 25.85 |
| ATOM | 79 | CB | HIS | 201 | 5.417 | 22.812 | 9.413 | 1.00 | 24.66 |
| ATOM | 80 | CG | HIS | 201 | 6.130 | 22.041 | 8.353 | 1.00 | 24.83 |
| ATOM | 81 | CD2 | HIS | 201 | 5.683 | 21.125 | 7.461 | 1.00 | 26.76 |
| ATOM | 82 | ND1 | HIS | 201 | 7.480 | 22.171 | 8.124 | 1.00 | 24.29 |
| ATOM | 83 | CE1 | HIS | 201 | 7.838 | 21.367 | 7.139 | 1.00 | 27.15 |
| ATOM | 84 | NE2 | HIS | 201 | 6.767 | 20.722 | 6.719 | 1.00 | 28.31 |
| ATOM | 85 | C | HIS | 201 | 4.469 | 22.927 | 11.689 | 1.00 | 26.56 |
| ATOM | 86 | O | HIS | 201 | 3.264 | 23.163 | 11.556 | 1.00 | 27.65 |
| ATOM | 87 | N | LEU | 202 | 5.191 | 23.399 | 12.698 | 1.00 | 26.07 |
| ATOM | 88 | CA | LEU | 202 | 4.601 | 24.317 | 13.659 | 1.00 | 25.58 |
| ATOM | 89 | CB | LEU | 202 | 4.621 | 23.756 | 15.085 | 1.00 | 25.67 |
| ATOM | 90 | CG | LEU | 202 | 4.182 | 24.740 | 16.183 | 1.00 | 25.11 |
| ATOM | 91 | CD1 | LEU | 202 | 2.710 | 25.088 | 16.033 | 1.00 | 22.05 |
| ATOM | 92 | CD2 | LEU | 202 | 4.459 | 24.159 | 17.554 | 1.00 | 23.90 |
| ATOM | 93 | C | LEU | 202 | 5.398 | 25.609 | 13.585 | 1.00 | 25.03 |
| ATOM | 94 | O | LEU | 202 | 6.563 | 25.645 | 13.962 | 1.00 | 26.19 |
| ATOM | 95 | N | HIS | 203 | 4.796 | 26.637 | 13.000 | 1.00 | 24.59 |
| ATOM | 96 | CA | HIS | 203 | 5.449 | 27.923 | 12.874 | 1.00 | 26.20 |
| ATOM | 97 | CB | HIS | 203 | 5.295 | 28.476 | 11.451 | 1.00 | 25.91 |
| ATOM | 98 | CG | HIS | 203 | 5.862 | 27.588 | 10.384 | 1.00 | 24.03 |
| ATOM | 99 | CD2 | HIS | 203 | 5.581 | 27.497 | 9.062 | 1.00 | 24.35 |
| ATOM | 100 | ND1 | HIS | 203 | 6.827 | 26.637 | 10.633 | 1.00 | 25.58 |
| ATOM | 101 | CE1 | HIS | 203 | 7.115 | 25.994 | 9.517 | 1.00 | 23.23 |
| ATOM | 102 | NE2 | HIS | 203 | 6.372 | 26.498 | 8.548 | 1.00 | 24.13 |
| ATOM | 103 | C | HIS | 203 | 4.763 | 28.836 | 13.877 | 1.00 | 28.92 |
| ATOM | 104 | O | HIS | 203 | 3.590 | 29.174 | 13.711 | 1.00 | 29.53 |
| ATOM | 105 | N | ALA | 204 | 5.479 | 29.191 | 14.939 | 1.00 | 30.12 |
| ATOM | 106 | CA | ALA | 204 | 4.936 | 30.043 | 15.982 | 1.00 | 30.61 |
| ATOM | 107 | CB | ALA | 204 | 4.275 | 29.193 | 17.066 | 1.00 | 30.68 |
| ATOM | 108 | C | ALA | 204 | 6.093 | 30.831 | 16.556 | 1.00 | 31.44 |
| ATOM | 109 | O | ALA | 204 | 7.201 | 30.310 | 16.662 | 1.00 | 32.28 |
| ATOM | 110 | N | PRO | 205 | 5.847 | 32.092 | 16.957 | 1.00 | 32.18 |
| ATOM | 111 | CD | PRO | 205 | 4.523 | 32.742 | 16.982 | 1.00 | 32.11 |

FIGURE 1C

| ATOM | 112 | CA  | PRO | 205 | 6.872  | 32.978 | 17.524 | 1.00 | 31.56 |
|------|-----|-----|-----|-----|--------|--------|--------|------|-------|
| ATOM | 113 | CB  | PRO | 205 | 6.102  | 34.282 | 17.748 | 1.00 | 31.92 |
| ATOM | 114 | CG  | PRO | 205 | 4.708  | 33.804 | 18.033 | 1.00 | 31.71 |
| ATOM | 115 | C   | PRO | 205 | 7.525  | 32.474 | 18.805 | 1.00 | 30.91 |
| ATOM | 116 | O   | PRO | 205 | 6.924  | 31.728 | 19.566 | 1.00 | 30.86 |
| ATOM | 117 | N   | THR | 206 | 8.764  | 32.888 | 19.037 | 1.00 | 31.28 |
| ATOM | 118 | CA  | THR | 206 | 9.492  | 32.486 | 20.228 | 1.00 | 32.05 |
| ATOM | 119 | CB  | THR | 206 | 10.872 | 33.160 | 20.276 | 1.00 | 32.26 |
| ATOM | 120 | OG1 | THR | 206 | 11.616 | 32.779 | 19.115 | 1.00 | 35.41 |
| ATOM | 121 | CG2 | THR | 206 | 11.641 | 32.740 | 21.506 | 1.00 | 32.09 |
| ATOM | 122 | C   | THR | 206 | 8.674  | 32.894 | 21.444 | 1.00 | 32.25 |
| ATOM | 123 | O   | THR | 206 | 8.038  | 33.942 | 21.439 | 1.00 | 34.50 |
| ATOM | 124 | N   | GLY | 207 | 8.664  | 32.052 | 22.470 | 1.00 | 31.86 |
| ATOM | 125 | CA  | GLY | 207 | 7.894  | 32.358 | 23.661 | 1.00 | 31.13 |
| ATOM | 126 | C   | GLY | 207 | 6.455  | 31.860 | 23.626 | 1.00 | 30.15 |
| ATOM | 127 | O   | GLY | 207 | 5.765  | 31.891 | 24.642 | 1.00 | 31.27 |
| ATOM | 128 | N   | SER | 208 | 6.005  | 31.362 | 22.480 | 1.00 | 29.48 |
| ATOM | 129 | CA  | SER | 208 | 4.642  | 30.868 | 22.374 | 1.00 | 28.52 |
| ATOM | 130 | CB  | SER | 208 | 4.182  | 30.872 | 20.908 | 1.00 | 27.20 |
| ATOM | 131 | OG  | SER | 208 | 5.029  | 30.097 | 20.086 | 1.00 | 25.55 |
| ATOM | 132 | C   | SER | 208 | 4.415  | 29.497 | 23.033 | 1.00 | 28.55 |
| ATOM | 133 | O   | SER | 208 | 3.271  | 29.044 | 23.149 | 1.00 | 29.28 |
| ATOM | 134 | N   | GLY | 209 | 5.494  | 28.840 | 23.463 | 1.00 | 28.23 |
| ATOM | 135 | CA  | GLY | 209 | 5.367  | 27.540 | 24.120 | 1.00 | 28.17 |
| ATOM | 136 | C   | GLY | 209 | 5.508  | 26.273 | 23.279 | 1.00 | 29.13 |
| ATOM | 137 | O   | GLY | 209 | 5.108  | 25.181 | 23.721 | 1.00 | 27.88 |
| ATOM | 138 | N   | LYS | 210 | 6.110  | 26.398 | 22.096 | 1.00 | 29.07 |
| ATOM | 139 | CA  | LYS | 210 | 6.318  | 25.267 | 21.180 | 1.00 | 28.86 |
| ATOM | 140 | CB  | LYS | 210 | 7.066  | 25.726 | 19.920 | 1.00 | 29.78 |
| ATOM | 141 | CG  | LYS | 210 | 6.367  | 26.802 | 19.103 | 1.00 | 30.86 |
| ATOM | 142 | CD  | LYS | 210 | 7.072  | 27.040 | 17.770 | 1.00 | 30.40 |
| ATOM | 143 | CE  | LYS | 210 | 8.506  | 27.502 | 17.959 | 1.00 | 31.43 |
| ATOM | 144 | NZ  | LYS | 210 | 8.607  | 28.803 | 18.689 | 1.00 | 33.79 |
| ATOM | 145 | C   | LYS | 210 | 7.092  | 24.098 | 21.797 | 1.00 | 28.32 |
| ATOM | 146 | O   | LYS | 210 | 6.829  | 22.935 | 21.498 | 1.00 | 28.11 |
| ATOM | 147 | N   | SER | 211 | 8.072  | 24.411 | 22.630 | 1.00 | 28.62 |
| ATOM | 148 | CA  | SER | 211 | 8.876  | 23.377 | 23.256 | 1.00 | 28.88 |
| ATOM | 149 | CB  | SER | 211 | 10.348 | 23.763 | 23.172 | 1.00 | 30.34 |
| ATOM | 150 | OG  | SER | 211 | 10.516 | 25.162 | 23.338 | 1.00 | 32.24 |
| ATOM | 151 | C   | SER | 211 | 8.509  | 23.084 | 24.700 | 1.00 | 28.90 |
| ATOM | 152 | O   | SER | 211 | 9.241  | 22.376 | 25.384 | 1.00 | 29.14 |
| ATOM | 153 | N   | THR | 212 | 7.367  | 23.599 | 25.152 | 1.00 | 29.90 |
| ATOM | 154 | CA  | THR | 212 | 6.925  | 23.399 | 26.532 | 1.00 | 29.80 |
| ATOM | 155 | CB  | THR | 212 | 7.371  | 24.579 | 27.415 | 1.00 | 28.95 |
| ATOM | 156 | OG1 | THR | 212 | 7.033  | 25.814 | 26.768 | 1.00 | 29.28 |
| ATOM | 157 | CG2 | THR | 212 | 8.870  | 24.531 | 27.651 | 1.00 | 26.88 |
| ATOM | 158 | C   | THR | 212 | 5.412  | 23.193 | 26.686 | 1.00 | 29.89 |
| ATOM | 159 | O   | THR | 212 | 4.949  | 22.153 | 27.166 | 1.00 | 29.41 |
| ATOM | 160 | N   | LYS | 213 | 4.641  | 24.191 | 26.277 | 1.00 | 31.79 |
| ATOM | 161 | CA  | LYS | 213 | 3.185  | 24.128 | 26.374 | 1.00 | 31.17 |
| ATOM | 162 | CB  | LYS | 213 | 2.576  | 25.486 | 26.013 | 1.00 | 31.92 |
| ATOM | 163 | CG  | LYS | 213 | 1.066  | 25.565 | 26.123 | 1.00 | 33.79 |
| ATOM | 164 | CD  | LYS | 213 | 0.627  | 27.019 | 26.126 | 1.00 | 36.61 |
| ATOM | 165 | CE  | LYS | 213 | -0.887 | 27.169 | 26.155 | 1.00 | 38.22 |
| ATOM | 166 | NZ  | LYS | 213 | -1.254 | 28.563 | 26.558 | 1.00 | 38.71 |
| ATOM | 167 | C   | LYS | 213 | 2.636  | 23.043 | 25.464 | 1.00 | 30.15 |
| ATOM | 168 | O   | LYS | 213 | 1.836  | 22.212 | 25.894 | 1.00 | 29.46 |
| ATOM | 169 | N   | VAL | 214 | 3.110  | 23.026 | 24.222 | 1.00 | 29.37 |

FIGURE 1D

```
ATOM   170  CA   VAL  214   2.657  22.042  23.247  1.00  29.35
ATOM   171  CB   VAL  214   3.274  22.317  21.845  1.00  30.43
ATOM   172  CG1  VAL  214   2.805  21.296  20.826  1.00  29.20
ATOM   173  CG2  VAL  214   2.881  23.719  21.381  1.00  31.27
ATOM   174  C    VAL  214   2.903  20.604  23.725  1.00  27.79
ATOM   175  O    VAL  214   1.980  19.781  23.722  1.00  29.24
ATOM   176  N    PRO  215   4.146  20.268  24.125  1.00  25.78
ATOM   177  CD   PRO  215   5.439  20.966  24.012  1.00  24.07
ATOM   178  CA   PRO  215   4.338  18.887  24.586  1.00  24.86
ATOM   179  CB   PRO  215   5.862  18.782  24.767  1.00  22.92
ATOM   180  CG   PRO  215   6.298  20.185  24.983  1.00  23.18
ATOM   181  C    PRO  215   3.556  18.590  25.878  1.00  23.85
ATOM   182  O    PRO  215   3.157  17.448  26.109  1.00  24.03
ATOM   183  N    ALA  216   3.322  19.615  26.700  1.00  24.13
ATOM   184  CA   ALA  216   2.555  19.466  27.946  1.00  24.64
ATOM   185  CB   ALA  216   2.592  20.754  28.741  1.00  23.09
ATOM   186  C    ALA  216   1.100  19.089  27.616  1.00  25.20
ATOM   187  O    ALA  216   0.517  18.192  28.232  1.00  25.36
ATOM   188  N    ALA  217   0.524  19.773  26.631  1.00  25.49
ATOM   189  CA   ALA  217  -0.836  19.501  26.187  1.00  25.40
ATOM   190  CB   ALA  217  -1.277  20.565  25.194  1.00  23.76
ATOM   191  C    ALA  217  -0.905  18.104  25.547  1.00  25.48
ATOM   192  O    ALA  217  -1.878  17.373  25.725  1.00  25.77
ATOM   193  N    TYR  218   0.136  17.735  24.807  1.00  25.42
ATOM   194  CA   TYR  218   0.191  16.422  24.165  1.00  24.86
ATOM   195  CB   TYR  218   1.410  16.306  23.243  1.00  24.75
ATOM   196  CG   TYR  218   1.253  16.946  21.882  1.00  24.58
ATOM   197  CD1  TYR  218   0.072  16.795  21.146  1.00  23.47
ATOM   198  CE1  TYR  218  -0.048  17.332  19.858  1.00  24.75
ATOM   199  CD2  TYR  218   2.310  17.656  21.303  1.00  23.47
ATOM   200  CE2  TYR  218   2.205  18.192  20.021  1.00  23.76
ATOM   201  CZ   TYR  218   1.025  18.028  19.299  1.00  25.01
ATOM   202  OH   TYR  218   0.924  18.553  18.023  1.00  24.22
ATOM   203  C    TYR  218   0.245  15.294  25.183  1.00  23.95
ATOM   204  O    TYR  218  -0.499  14.324  25.065  1.00  25.49
ATOM   205  N    ALA  219   1.140  15.410  26.160  1.00  23.90
ATOM   206  CA   ALA  219   1.305  14.388  27.204  1.00  25.10
ATOM   207  CB   ALA  219   2.553  14.673  28.033  1.00  23.15
ATOM   208  C    ALA  219   0.079  14.281  28.115  1.00  26.52
ATOM   209  O    ALA  219  -0.257  13.193  28.595  1.00  26.05
ATOM   210  N    ALA  220  -0.591  15.416  28.328  1.00  28.32
ATOM   211  CA   ALA  220  -1.789  15.484  29.161  1.00  27.69
ATOM   212  CB   ALA  220  -2.224  16.933  29.346  1.00  28.77
ATOM   213  C    ALA  220  -2.904  14.666  28.528  1.00  27.42
ATOM   214  O    ALA  220  -3.873  14.315  29.190  1.00  27.84
ATOM   215  N    GLN  221  -2.762  14.380  27.236  1.00  28.01
ATOM   216  CA   GLN  221  -3.733  13.576  26.492  1.00  27.15
ATOM   217  CB   GLN  221  -3.782  13.991  25.027  1.00  28.76
ATOM   218  CG   GLN  221  -4.413  15.331  24.739  1.00  30.06
ATOM   219  CD   GLN  221  -4.084  15.798  23.335  1.00  32.54
ATOM   220  OE1  GLN  221  -4.457  15.159  22.346  1.00  34.37
ATOM   221  NE2  GLN  221  -3.350  16.895  23.238  1.00  34.38
ATOM   222  C    GLN  221  -3.321  12.119  26.554  1.00  26.58
ATOM   223  O    GLN  221  -3.881  11.284  25.851  1.00  27.44
ATOM   224  N    GLY  222  -2.285  11.833  27.334  1.00  25.93
ATOM   225  CA   GLY  222  -1.828  10.472  27.487  1.00  24.98
ATOM   226  C    GLY  222  -0.767   9.987  26.530  1.00  26.33
ATOM   227  O    GLY  222  -0.561   8.783  26.414  1.00  27.70
```

FIGURE 1E

```
ATOM   228  N    TYR  223   -0.057  10.896  25.875  1.00  26.89
ATOM   229  CA   TYR  223    0.995  10.498  24.940  1.00  25.87
ATOM   230  CB   TYR  223    0.901  11.316  23.665  1.00  25.29
ATOM   231  CG   TYR  223   -0.373  11.111  22.906  1.00  25.96
ATOM   232  CD1  TYR  223   -1.399  12.045  22.974  1.00  25.65
ATOM   233  CE1  TYR  223   -2.559  11.873  22.250  1.00  27.75
ATOM   234  CD2  TYR  223   -0.542   9.993  22.096  1.00  26.27
ATOM   235  CE2  TYR  223   -1.692   9.808  21.372  1.00  27.03
ATOM   236  CZ   TYR  223   -2.698  10.749  21.446  1.00  28.75
ATOM   237  OH   TYR  223   -3.839  10.573  20.695  1.00  32.89
ATOM   238  C    TYR  223    2.415  10.629  25.483  1.00  26.22
ATOM   239  O    TYR  223    2.697  11.441  26.373  1.00  25.06
ATOM   240  N    LYS  224    3.308   9.826  24.919  1.00  27.21
ATOM   241  CA   LYS  224    4.721   9.850  25.270  1.00  27.71
ATOM   242  CB   LYS  224    5.325   8.460  25.107  1.00  29.76
ATOM   243  CG   LYS  224    4.827   7.470  26.139  1.00  35.42
ATOM   244  CD   LYS  224    5.314   7.887  27.525  1.60  39.88
ATOM   245  CE   LYS  224    4.771   7.005  28.652  1.00  41.50
ATOM   246  NZ   LYS  224    5.385   7.396  29.969  1.00  42.40
ATOM   247  C    LYS  224    5.309  10.821  24.258  1.00  26.68
ATOM   248  O    LYS  224    5.265  10.571  23.047  1.00  27.78
ATOM   249  N    VAL  225    5.785  11.959  24.746  1.00  25.81
ATOM   250  CA   VAL  225    6.333  12.998  23.883  1.00  24.37
ATOM   251  CB   VAL  225    5.649  14.354  24.161  1.00  24.83
ATOM   252  CG1  VAL  225    5.997  15.359  23.075  1.00  23.06
ATOM   253  CG2  VAL  225    4.137  14.166  24.274  1.00  25.36
ATOM   254  C    VAL  225    7.834  13.190  24.046  1.00  23.03
ATOM   255  O    VAL  225    8.355  13.220  25.166  1.00  20.40
ATOM   256  N    LEU  226    8.513  13.330  22.914  1.00  22.55
ATOM   257  CA   LEU  226    9.954  13.551  22.878  1.00  21.32
ATOM   258  CB   LEU  226   10.627  12.471  22.037  1.00  18.45
ATOM   259  CG   LEU  226   12.082  12.710  21.656  1.00  18.51
ATOM   260  CD1  LEU  226   12.985  12.577  22.884  1.00  16.54
ATOM   261  CD2  LEU  226   12.473  11.717  20.570  1.00  19.37
ATOM   262  C    LEU  226   10.192  14.926  22.253  1.00  20.71
ATOM   263  O    LEU  226    9.629  15.245  21.202  1.00  20.63
ATOM   264  N    VAL  227   10.993  15.752  22.912  1.00  22.06
ATOM   265  CA   VAL  227   11.290  17.087  22.404  1.00  22.02
ATOM   266  CB   VAL  227   10.915  18.173  23.425  1.00  20.33
ATOM   267  CG1  VAL  227   10.933  19.532  22.757  1.00  19.96
ATOM   268  CG2  VAL  227    9.561  17.881  24.043  1.00  19.10
ATOM   269  C    VAL  227   12.787  17.165  22.111  1.00  22.26
ATOM   270  O    VAL  227   13.612  17.040  23.023  1.00  23.12
ATOM   271  N    LEU  228   13.135  17.322  20.839  1.00  21.87
ATOM   272  CA   LEU  228   14.534  17.397  20.435  1.00  21.87
ATOM   273  CB   LEU  228   14.770  16.590  19.162  1.00  20.02
ATOM   274  CG   LEU  228   14.576  15.079  19.254  1.00  18.46
ATOM   275  CD1  LEU  228   14.817  14.488  17.874  1.00  17.50
ATOM   276  CD2  LEU  228   15.522  14.477  20.304  1.00  15.84
ATOM   277  C    LEU  228   14.961  18.833  20.216  1.00  22.19
ATOM   278  O    LEU  228   14.338  19.566  19.450  1.00  23.01
ATOM   279  N    ASN  229   16.063  19.211  20.849  1.00  22.54
ATOM   280  CA   ASN  229   16.587  20.567  20.756  1.00  22.64
ATOM   281  CB   ASN  229   16.276  21.301  22.067  1.00  23.81
ATOM   282  CG   ASN  229   16.582  22.770  22.008  1.00  24.90
ATOM   283  OD1  ASN  229   17.732  23.196  22.184  1.00  26.02
ATOM   284  ND2  ASN  229   15.548  23.568  21.794  1.00  24.10
ATOM   285  C    ASN  229   18.101  20.482  20.517  1.00  22.10
```

FIGURE 1F

```
ATOM   286  O    ASN  229   18.756  19.525  20.938  1.00  19.92
ATOM   287  N    PRO  230   18.659  21.429  19.753  1.00  23.12
ATOM   288  CD   PRO  230   17.987  22.400  18.872  1.00  21.71
ATOM   289  CA   PRO  230   20.107  21.397  19.495  1.00  23.95
ATOM   290  CB   PRO  230   20.269  22.383  18.336  1.00  23.83
ATOM   291  CG   PRO  230   19.114  23.319  18.510  1.00  23.76
ATOM   292  C    PRO  230   21.011  21.755  20.688  1.00  24.47
ATOM   293  O    PRO  230   22.114  21.211  20.834  1.00  25.45
ATOM   294  N    SER  231   20.512  22.595  21.584  1.00  24.28
ATOM   295  CA   SER  231   21.290  23.036  22.727  1.00  24.31
ATOM   296  CB   SER  231   20.886  24.461  23.088  1.00  23.88
ATOM   297  OG   SER  231   21.566  24.896  24.251  1.00  27.81
ATOM   298  C    SER  231   21.236  22.165  23.975  1.00  25.03
ATOM   299  O    SER  231   20.157  21.870  24.496  1.00  25.25
ATOM   300  N    VAL  232   22.413  21.805  24.480  1.00  24.64
ATOM   301  CA   VAL  232   22.525  21.011  25.694  1.00  24.77
ATOM   302  CB   VAL  232   24.006  20.628  25.975  1.00  24.98
ATOM   303  CG1  VAL  232   24.184  20.163  27.417  1.00  24.08
ATOM   304  CG2  VAL  232   24.458  19.534  25.019  1.00  20.75
ATOM   305  C    VAL  232   21.976  21.862  26.852  1.00  26.64
ATOM   306  O    VAL  232   21.174  21.394  27.668  1.00  28.40
ATOM   307  N    ALA  233   22.365  23.133  26.879  1.00  26.57
ATOM   308  CA   ALA  233   21.916  24.051  27.922  1.00  26.13
ATOM   309  CB   ALA  233   22.592  25.417  27.759  1.00  25.46
ATOM   310  C    ALA  233   20.401  24.203  27.907  1.00  25.51
ATOM   311  O    ALA  233   19.764  24.124  28.952  1.00  26.22
ATOM   312  N    ALA  234   19.831  24.397  26.718  1.00  25.47
ATOM   313  CA   ALA  234   18.385  24.553  26.567  1.00  24.61
ATOM   314  CB   ALA  234   18.031  24.857  25.138  1.00  23.89
ATOM   315  C    ALA  234   17.653  23.304  27.015  1.00  25.81
ATOM   316  O    ALA  234   16.652  23.393  27.728  1.00  25.42
ATOM   317  N    THR  235   18.157  22.144  26.591  1.00  26.43
ATOM   318  CA   THR  235   17.556  20.868  26.951  1.00  26.97
ATOM   319  CB   THR  235   18.339  19.673  26.345  1.00  27.79
ATOM   320  OG1  THR  235   18.322  19.768  24.916  1.00  27.58
ATOM   321  CG2  THR  235   17.704  18.343  26.748  1.00  26.60
ATOM   322  C    THR  235   17.499  20.746  28.472  1.00  27.43
ATOM   323  O    THR  235   16.440  20.488  29.035  1.00  28.23
ATOM   324  N    LEU  236   18.624  20.984  29.138  1.00  27.19
ATOM   325  CA   LEU  236   18.670  20.898  30.595  1.00  27.35
ATOM   326  CB   LEU  236   20.086  21.185  31.096  1.00  28.04
ATOM   327  CG   LEU  236   21.174  20.151  30.842  1.00  27.41
ATOM   328  CD1  LEU  236   22.519  20.838  30.894  1.00  28.18
ATOM   329  CD2  LEU  236   21.086  19.028  31.858  1.00  26.49
ATOM   330  C    LEU  236   17.715  21.898  31.235  1.00  26.83
ATOM   331  O    LEU  236   17.054  21.601  32.232  1.00  27.18
ATOM   332  N    GLY  237   17.651  23.086  30.648  1.00  26.16
ATOM   333  CA   GLY  237   16.804  24.131  31.178  1.00  26.03
ATOM   334  C    GLY  237   15.333  23.812  31.228  1.00  25.39
ATOM   335  O    GLY  237   14.651  24.230  32.151  1.00  25.99
ATOM   336  N    PHE  238   14.841  23.065  30.252  1.00  25.78
ATOM   337  CA   PHE  238   13.428  22.721  30.205  1.00  27.27
ATOM   338  CB   PHE  238   13.138  21.811  29.013  1.00  27.38
ATOM   339  CG   PHE  238   13.274  22.495  27.691  1.00  29.37
ATOM   340  CD1  PHE  238   12.493  23.610  27.388  1.00  29.67
ATOM   341  CD2  PHE  238   14.202  22.052  26.756  1.00  29.17
ATOM   342  CE1  PHE  238   12.641  24.273  26.169  1.00  29.22
ATOM   343  CE2  PHE  238   14.354  22.707  25.541  1.00  28.63
```

FIGURE 1G

```
ATOM    344  CZ   PHE   238     13.571   23.822   25.248  1.00  27.73
ATOM    345  C    PHE   238     12.908   22.087   31.488  1.00  28.44
ATOM    346  O    PHE   238     11.740   22.267   31.838  1.00  28.75
ATOM    347  N    GLY   239     13.782   21.377   32.199  1.00  29.43
ATOM    348  CA   GLY   239     13.387   20.728   33.439  1.00  30.17
ATOM    349  C    GLY   239     12.724   21.653   34.447  1.00  30.46
ATOM    350  O    GLY   239     11.590   21.420   34.874  1.00  30.46
ATOM    351  N    ALA   240     13.429   22.711   34.825  1.00  30.54
ATOM    352  CA   ALA   240     12.904   23.667   35.785  1.00  31.68
ATOM    353  CB   ALA   240     14.007   24.611   36.258  1.00  30.45
ATOM    354  C    ALA   240     11.732   24.460   35.216  1.00  31.56
ATOM    355  O    ALA   240     16.736   24.673   35.904  1.00  32.32
ATOM    356  N    TYR   241     11.836   24.873   33.957  1.00  31.75
ATOM    357  CA   TYR   241     10.770   25.653   33.340  1.00  30.92
ATOM    358  CB   TYR   241     11.139   26.095   31.920  1.00  31.44
ATOM    359  CG   TYR   241     10.037   26.903   31.250  1.00  33.57
ATOM    360  CD1  TYR   241     10.086   28.294   31.220  1.00  35.11
ATOM    361  CE1  TYR   241      9.052   29.038   30.657  1.00  36.03
ATOM    362  CD2  TYR   241      8.919   26.276   30.690  1.00  33.41
ATOM    363  CE2  TYR   241      7.889   27.006   30.133  1.00  34.12
ATOM    364  CZ   TYR   241      7.958   28.384   30.122  1.00  36.46
ATOM    365  OH   TYR   241      6.915   29.107   29.601  1.00  39.06
ATOM    366  C    TYR   241      9.464   24.885   33.288  1.00  29.43
ATOM    367  O    TYR   241      8.402   25.452   33.500  1.00  28.88
ATOM    368  N    MET   242      9.547   23.613   32.932  1.00  28.93
ATOM    369  CA   MET   242      8.368   22.767   32.824  1.00  29.09
ATOM    370  CB   MET   242      8.735   21.464   32.106  1.00  28.71
ATOM    371  CG   MET   242      8.956   21.646   30.602  1.00  27.19
ATOM    372  SD   MET   242      7.445   22.198   29.767  1.00  24.74
ATOM    373  CE   MET   242      6.543   20.617   29.574  1.00  25.21
ATOM    374  C    MET   242      7.732   22.501   34.191  1.00  28.87
ATOM    375  O    MET   242      6.507   22.451   34.339  1.00  25.61
ATOM    376  N    SER   243      8.581   22.366   35.195  1.00  31.13
ATOM    377  CA   SER   243      8.125   22.137   36.543  1.00  31.64
ATOM    378  CB   SER   243      9.325   21.864   37.445  1.00  32.82
ATOM    379  OG   SER   243      8.916   21.422   38.725  1.00  37.37
ATOM    380  C    SER   243      7.378   23.390   36.994  1.00  31.87
ATOM    381  O    SER   243      6.226   23.320   37.420  1.00  32.45
ATOM    382  N    ALA   244      8.000   24.547   36.806  1.00  31.20
ATOM    383  CA   ALA   244      7.387   25.806   37.218  1.00  30.80
ATOM    384  CB   ALA   244      8.414   26.947   37.163  1.00  30.58
ATOM    385  C    ALA   244      6.148   26.182   36.420  1.00  29.56
ATOM    386  O    ALA   244      5.144   26.608   36.985  1.00  30.91
ATOM    387  N    ALA   245      6.205   25.994   35.113  1.00  27.79
ATOM    388  CA   ALA   245      5.093   26.369   34.261  1.00  27.16
ATOM    389  CB   ALA   245      5.601   26.694   32.871  1.00  26.05
ATOM    390  C    ALA   245      3.966   25.363   34.171  1.00  27.41
ATOM    391  O    ALA   245      2.804   25.742   34.001  1.00  27.65
ATOM    392  N    HIS   246      4.295   24.083   34.278  1.00  27.72
ATOM    393  CA   HIS   246      3.280   23.050   34.134  1.00  26.52
ATOM    394  CB   HIS   246      3.437   22.414   32.751  1.00  26.99
ATOM    395  CG   HIS   246      3.348   23.395   31.626  1.00  24.43
ATOM    396  CD2  HIS   246      4.309   23.992   30.882  1.00  26.07
ATOM    397  ND1  HIS   246      2.147   23.885   31.161  1.00  26.33
ATOM    398  CE1  HIS   246      2.369   24.741   30.179  1.00  25.34
ATOM    399  NE2  HIS   246      3.673   24.825   29.991  1.00  26.40
ATOM    400  C    HIS   246      3.245   21.961   35.208  1.00  26.80
ATOM    401  O    HIS   246      2.446   21.035   35.119  1.00  25.51
```

FIGURE 1H

| ATOM | 402 | N   | GLY | 247 | 4.097  | 22.073 | 36.223 | 1.00 | 26.76 |
|------|-----|-----|-----|-----|--------|--------|--------|------|-------|
| ATOM | 403 | CA  | GLY | 247 | 4.123  | 21.069 | 37.267 | 1.00 | 26.09 |
| ATOM | 404 | C   | GLY | 247 | 4.509  | 19.740 | 36.657 | 1.00 | 27.58 |
| ATOM | 405 | O   | GLY | 247 | 3.899  | 18.701 | 36.945 | 1.00 | 28.05 |
| ATOM | 406 | N   | VAL | 248 | 5.497  | 19.782 | 35.768 | 1.00 | 27.72 |
| ATOM | 407 | CA  | VAL | 248 | 5.985  | 18.589 | 35.088 | 1.00 | 27.72 |
| ATOM | 408 | CB  | VAL | 248 | 5.712  | 18.668 | 33.558 | 1.00 | 28.05 |
| ATOM | 409 | CG1 | VAL | 248 | 6.274  | 17.450 | 32.854 | 1.00 | 28.78 |
| ATOM | 410 | CG2 | VAL | 248 | 4.220  | 18.792 | 33.278 | 1.00 | 27.03 |
| ATOM | 411 | C   | VAL | 248 | 7.488  | 18.441 | 35.307 | 1.00 | 27.70 |
| ATOM | 412 | O   | VAL | 248 | 8.229  | 19.414 | 35.224 | 1.00 | 27.56 |
| ATOM | 413 | N   | ASP | 249 | 7.923  | 17.228 | 35.622 | 1.00 | 29.51 |
| ATOM | 414 | CA  | ASP | 249 | 9.342  | 16.928 | 35.813 | 1.00 | 31.97 |
| ATOM | 415 | CB  | ASP | 249 | 9.563  | 16.290 | 37.187 | 1.00 | 36.65 |
| ATOM | 416 | CG  | ASP | 249 | 8.834  | 17.029 | 38.296 | 1.00 | 42.98 |
| ATOM | 417 | OD1 | ASP | 249 | 9.183  | 18.198 | 38.578 | 1.00 | 48.26 |
| ATOM | 418 | OD2 | ASP | 249 | 7.897  | 16.448 | 38.884 | 1.00 | 47.15 |
| ATOM | 419 | C   | ASP | 249 | 9.655  | 15.927 | 34.697 | 1.00 | 30.40 |
| ATOM | 420 | O   | ASP | 249 | 9.444  | 14.721 | 34.854 | 1.00 | 32.54 |
| ATOM | 421 | N   | PRO | 250 | 10.112 | 16.412 | 33.531 | 1.00 | 28.60 |
| ATOM | 422 | CD  | PRO | 250 | 10.397 | 17.809 | 33.145 | 1.00 | 28.10 |
| ATOM | 423 | CA  | PRO | 250 | 10.411 | 15.500 | 32.424 | 1.00 | 27.32 |
| ATOM | 424 | CB  | PRO | 250 | 10.356 | 16.432 | 31.218 | 1.00 | 25.82 |
| ATOM | 425 | CG  | PRO | 250 | 10.998 | 17.658 | 31.748 | 1.00 | 25.77 |
| ATOM | 426 | C   | PRO | 250 | 11.756 | 14.787 | 32.504 | 1.00 | 27.35 |
| ATOM | 427 | O   | PRO | 250 | 12.581 | 15.083 | 33.368 | 1.00 | 27.56 |
| ATOM | 428 | N   | ASN | 251 | 11.944 | 13.805 | 31.629 | 1.00 | 27.78 |
| ATOM | 429 | CA  | ASN | 251 | 13.213 | 13.090 | 31.553 | 1.00 | 27.99 |
| ATOM | 430 | CB  | ASN | 251 | 13.046 | 11.776 | 30.802 | 1.00 | 27.88 |
| ATOM | 431 | CG  | ASN | 251 | 11.944 | 10.914 | 31.380 | 1.00 | 29.52 |
| ATOM | 432 | OD1 | ASN | 251 | 12.136 | 10.211 | 32.377 | 1.00 | 29.08 |
| ATOM | 433 | ND2 | ASN | 251 | 10.770 | 10.978 | 30.768 | 1.00 | 30.24 |
| ATOM | 434 | C   | ASN | 251 | 14.131 | 14.026 | 30.763 | 1.00 | 28.29 |
| ATOM | 435 | O   | ASN | 251 | 13.687 | 14.685 | 29.808 | 1.00 | 27.76 |
| ATOM | 436 | N   | ILE | 252 | 15.387 | 14.131 | 31.185 | 1.00 | 28.26 |
| ATOM | 437 | CA  | ILE | 252 | 16.349 | 15.004 | 30.517 | 1.00 | 27.72 |
| ATOM | 438 | CB  | ILE | 252 | 16.891 | 16.081 | 31.491 | 1.00 | 25.56 |
| ATOM | 439 | CG2 | ILE | 252 | 17.909 | 16.978 | 30.780 | 1.00 | 24.45 |
| ATOM | 440 | CG1 | ILE | 252 | 15.731 | 16.880 | 32.116 | 1.00 | 23.07 |
| ATOM | 441 | CD1 | ILE | 252 | 14.946 | 17.753 | 31.147 | 1.00 | 20.19 |
| ATOM | 442 | C   | ILE | 252 | 17.511 | 14.157 | 29.995 | 1.00 | 29.20 |
| ATOM | 443 | O   | ILE | 252 | 18.148 | 13.435 | 30.759 | 1.00 | 29.28 |
| ATOM | 444 | N   | ARG | 253 | 17.776 | 14.230 | 28.695 | 1.00 | 29.57 |
| ATOM | 445 | CA  | ARG | 253 | 18.862 | 13.455 | 28.109 | 1.00 | 29.87 |
| ATOM | 446 | CB  | ARG | 253 | 18.306 | 12.366 | 27.207 | 1.00 | 30.75 |
| ATOM | 447 | CG  | ARG | 253 | 17.023 | 11.733 | 27.695 | 1.00 | 32.49 |
| ATOM | 448 | CD  | ARG | 253 | 16.943 | 10.331 | 27.175 | 1.00 | 35.54 |
| ATOM | 449 | NE  | ARG | 253 | 18.046 | 9.553  | 27.726 | 1.00 | 40.71 |
| ATOM | 450 | CZ  | ARG | 253 | 18.431 | 8.369  | 27.272 | 1.00 | 41.75 |
| ATOM | 451 | NH1 | ARG | 253 | 19.449 | 7.743  | 27.846 | 1.00 | 42.45 |
| ATOM | 452 | NH2 | ARG | 253 | 17.814 | 7.822  | 26.233 | 1.00 | 44.21 |
| ATOM | 453 | C   | ARG | 253 | 19.858 | 14.296 | 27.309 | 1.00 | 31.31 |
| ATOM | 454 | O   | ARG | 253 | 19.547 | 14.791 | 26.218 | 1.00 | 30.51 |
| ATOM | 455 | N   | THR | 254 | 21.046 | 14.484 | 27.876 | 1.00 | 32.71 |
| ATOM | 456 | CA  | THR | 254 | 22.114 | 15.225 | 27.214 | 1.00 | 33.25 |
| ATOM | 457 | CB  | THR | 254 | 22.386 | 16.599 | 27.876 | 1.00 | 31.25 |
| ATOM | 458 | OG1 | THR | 254 | 22.880 | 16.414 | 29.206 | 1.00 | 29.55 |
| ATOM | 459 | CG2 | THR | 254 | 21.118 | 17.427 | 27.921 | 1.00 | 30.34 |

FIGURE 1I

```
ATOM  460  C    THR  254  23.374  14.370  27.289  1.00  35.29
ATOM  461  O    THR  254  23.378  13.313  27.926  1.00  34.39
ATOM  462  N    GLY  255  24.435  14.818  26.625  1.00  37.19
ATOM  463  CA   GLY  255  25.680  14.075  26.656  1.00  38.93
ATOM  464  C    GLY  255  26.217  14.023  28.072  1.00  40.31
ATOM  465  O    GLY  255  26.605  12.963  28.566  1.00  40.42
ATOM  466  N    VAL  256  26.192  15.169  28.744  1.00  41.59
ATOM  467  CA   VAL  256  26.684  15.252  30.111  1.00  43.59
ATOM  468  CB   VAL  256  26.869  16.712  30.597  1.00  43.46
ATOM  469  CG1  VAL  256  28.182  17.268  30.084  1.00  46.24
ATOM  470  CG2  VAL  256  25.705  17.591  30.153  1.00  43.43
ATOM  471  C    VAL  256  25.839  14.516  31.137  1.00  44.62
ATOM  472  O    VAL  256  26.356  13.667  31.860  1.00  45.65
ATOM  473  N    ARG  257  24.540  14.810  31.172  1.00  45.28
ATOM  474  CA   ARG  257  23.651  14.203  32.156  1.00  44.14
ATOM  475  CB   ARG  257  23.445  15.197  33.311  1.00  45.53
ATOM  476  CG   ARG  257  22.434  14.762  34.357  1.00  49.87
ATOM  477  CD   ARG  257  22.485  15.627  35.618  1.00  52.65
ATOM  478  NE   ARG  257  21.615  15.118  36.686  1.00  56.84
ATOM  479  CZ   ARG  257  21.608  13.858  37.140  1.00  58.71
ATOM  480  NH1  ARG  257  22.424  12.935  36.632  1.00  58.53
ATOM  481  NH2  ARG  257  20.778  13.513  38.119  1.00  59.13
ATOM  482  C    ARG  257  22.291  13.718  31.654  1.00  42.81
ATOM  483  O    ARG  257  21.629  14.385  30.856  1.00  42.13
ATOM  484  N    THR  258  21.896  12.544  32.136  1.00  42.22
ATOM  485  CA   THR  258  20.601  11.949  31.834  1.00  41.75
ATOM  486  CB   THR  258  20.730  10.521  31.268  1.00  41.55
ATOM  487  OG1  THR  258  21.112  10.588  29.890  1.00  43.65
ATOM  488  CG2  THR  258  19.411   9.770  31.376  1.00  41.26
ATOM  489  C    THR  258  19.864  11.902  33.173  1.00  41.88
ATOM  490  O    THR  258  20.431  11.489  34.191  1.00  43.37
ATOM  491  N    ILE  259  18.635  12.398  33.184  1.00  40.14
ATOM  492  CA   ILE  259  17.815  12.424  34.382  1.00  38.42
ATOM  493  CB   ILE  259  17.506  13.870  34.799  1.00  37.89
ATOM  494  CG2  ILE  259  16.631  13.891  36.043  1.00  38.14
ATOM  495  CG1  ILE  259  18.805  14.649  35.011  1.00  37.37
ATOM  496  CD1  ILE  259  18.593  16.115  35.332  1.00  37.01
ATOM  497  C    ILE  259  16.516  11.736  33.998  1.00  38.66
ATOM  498  O    ILE  259  15.754  12.258  33.185  1.00  38.35
ATOM  499  N    THR  260  16.307  10.532  34.510  1.00  39.27
ATOM  500  CA   THR  260  15.090   9.790  34.208  1.00  40.28
ATOM  501  CB   THR  260  15.384   8.297  33.979  1.00  41.32
ATOM  502  OG1  THR  260  16.401   8.165  32.977  1.00  42.58
ATOM  503  CG2  THR  260  14.125   7.573  33.504  1.00  42.71
ATOM  504  C    THR  260  14.075   9.989  35.333  1.00  39.99
ATOM  505  O    THR  260  14.356   9.733  36.504  1.00  39.99
ATOM  506  N    THR  261  12.894  10.452  34.958  1.00  39.53
ATOM  507  CA   THR  261  11.842  10.740  35.910  1.00  39.43
ATOM  508  CB   THR  261  11.392  12.185  35.717  1.00  40.25
ATOM  509  OG1  THR  261  12.527  13.049  35.864  1.00  42.32
ATOM  510  CG2  THR  261  10.337  12.562  36.723  1.00  42.64
ATOM  511  C    THR  261  10.628   9.829  35.793  1.00  38.62
ATOM  512  O    THR  261   9.843   9.700  36.736  1.00  39.27
ATOM  513  N    GLY  262  10.476   9.177  34.648  1.00  36.63
ATOM  514  CA   GLY  262   9.316   8.323  34.462  1.00  34.27
ATOM  515  C    GLY  262   8.185   9.149  33.875  1.00  32.70
ATOM  516  O    GLY  262   7.037   8.708  33.802  1.00  32.40
ATOM  517  N    SER  263   8.525  10.368  33.464  1.00  30.97
```

FIGURE 1J

```
ATOM  518  CA   SER  263   7.571  11.282  32.861  1.00  28.52
ATOM  519  CB   SER  263   8.148  12.705  32.871  1.00  27.84
ATOM  520  OG   SER  263   7.276  13.641  32.251  1.00  26.21
ATOM  521  C    SER  263   7.286  10.852  31.420  1.00  27.13
ATOM  522  O    SER  263   8.092  10.151  30.796  1.00  25.11
ATOM  523  N    PRO  264   6.091  11.189  30.907  1.00  25.91
ATOM  524  CD   PRO  264   4.919  11.756  31.593  1.00  24.44
ATOM  525  CA   PRO  264   5.757  10.825  29.528  1.00  25.37
ATOM  526  CB   PRO  264   4.252  11.072  29.466  1.00  24.70
ATOM  527  CG   PRO  264   4.059  12.176  30.433  1.00  25.43
ATOM  528  C    PRO  264   6.516  11.761  28.575  1.00  25.19
ATOM  529  O    PRO  264   6.637  11.488  27.378  1.00  24.68
ATOM  530  N    ILE  265   7.009  12.874  29.113  1.00  25.11
ATOM  531  CA   ILE  265   7.760  13.839  28.323  1.00  24.64
ATOM  532  CB   ILE  265   7.395  15.284  28.689  1.00  24.85
ATOM  533  CG2  ILE  265   8.045  16.250  27.706  1.00  24.63
ATOM  534  CG1  ILE  265   5.880  15.463  28.623  1.00  25.72
ATOM  535  CD1  ILE  265   5.398  16.810  29.116  1.00  27.30
ATOM  536  C    ILE  265   9.257  13.646  28.498  1.00  23.56
ATOM  537  O    ILE  265   9.756  13.474  29.612  1.00  23.63
ATOM  538  N    THR  266   9.974  13.683  27.386  1.00  23.74
ATOM  539  CA   THR  266  11.419  13.510  27.391  1.00  22.48
ATOM  540  CB   THR  266  11.799  12.115  26.833  1.00  21.23
ATOM  541  OG1  THR  266  11.288  11.107  27.707  1.00  20.89
ATOM  542  CG2  THR  266  13.295  11.952  26.716  1.00  21.86
ATOM  543  C    THR  266  12.060  14.585  26.530  1.00  21.76
ATOM  544  O    THR  266  11.674  14.770  25.376  1.00  20.29
ATOM  545  N    TYR  267  12.981  15.341  27.119  1.00  21.86
ATOM  546  CA   TYR  267  13.702  16.372  26.388  1.00  22.28
ATOM  547  CB   TYR  267  13.833  17.654  27.211  1.00  22.75
ATOM  548  CG   TYR  267  12.563  18.464  27.278  1.00  24.36
ATOM  549  CD1  TYR  267  11.666  18.297  28.327  1.00  22.30
ATOM  550  CE1  TYR  267  10.493  19.034  28.386  1.00  22.80
ATOM  551  CD2  TYR  267  12.253  19.396  26.281  1.00  23.66
ATOM  552  CE2  TYR  267  11.080  20.139  26.332  1.00  24.13
ATOM  553  CZ   TYR  267  10.206  19.949  27.391  1.00  23.99
ATOM  554  OH   TYR  267   9.045  20.674  27.465  1.00  23.95
ATOM  555  C    TYR  267  15.078  15.805  26.108  1.00  22.43
ATOM  556  O    TYR  267  15.679  15.165  26.978  1.00  23.25
ATOM  557  N    SER  268  15.573  16.031  24.900  1.00  22.28
ATOM  558  CA   SER  268  16.884  15.532  24.512  1.00  22.21
ATOM  559  CB   SER  268  16.750  14.082  24.010  1.00  22.96
ATOM  560  OG   SER  268  17.948  13.556  23.441  1.00  19.87
ATOM  561  C    SER  268  17.484  16.401  23.419  1.00  22.55
ATOM  562  O    SER  268  16.774  17.111  22.706  1.00  23.40
ATOM  563  N    THR  269  18.809  16.391  23.348  1.00  23.70
ATOM  564  CA   THR  269  19.547  17.102  22.310  1.00  22.50
ATOM  565  CB   THR  269  21.031  17.245  22.694  1.00  22.70
ATOM  566  OG1  THR  269  21.510  15.986  23.193  1.00  19.49
ATOM  567  CG2  THR  269  21.218  18.313  23.744  1.00  20.70
ATOM  568  C    THR  269  19.495  16.149  21.110  1.00  22.45
ATOM  569  O    THR  269  19.222  14.950  21.269  1.00  22.71
ATOM  570  N    TYR  270  19.746  16.656  19.910  1.00  22.86
ATOM  571  CA   TYR  270  19.746  15.777  18.747  1.00  22.07
ATOM  572  CB   TYR  270  19.812  16.581  17.446  1.00  20.62
ATOM  573  CG   TYR  270  18.535  17.330  17.123  1.00  19.62
ATOM  574  CD1  TYR  270  18.392  18.677  17.452  1.00  20.22
ATOM  575  CE1  TYR  270  17.242  19.389  17.118  1.00  18.98
```

FIGURE 1K

| ATOM | 576 | CD2 | TYR | 270 | 17.488 | 16.704 | 16.454 | 1.00 | 18.83 |
|------|-----|-----|-----|-----|--------|--------|--------|------|-------|
| ATOM | 577 | CE2 | TYR | 270 | 16.331 | 17.406 | 16.115 | 1.00 | 20.81 |
| ATOM | 578 | CZ | TYR | 270 | 16.218 | 18.752 | 16.451 | 1.00 | 20.32 |
| ATOM | 579 | OH | TYR | 270 | 15.086 | 19.457 | 16.112 | 1.00 | 18.84 |
| ATOM | 580 | C | TYR | 270 | 20.943 | 14.828 | 18.852 | 1.00 | 21.56 |
| ATOM | 581 | O | TYR | 270 | 20.850 | 13.654 | 18.486 | 1.00 | 23.69 |
| ATOM | 582 | N | GLY | 271 | 22.043 | 15.333 | 19.406 | 1.00 | 19.54 |
| ATOM | 583 | CA | GLY | 271 | 23.242 | 14.534 | 19.555 | 1.00 | 19.07 |
| ATOM | 584 | C | GLY | 271 | 23.012 | 13.299 | 20.394 | 1.00 | 19.18 |
| ATOM | 585 | O | GLY | 271 | 23.330 | 12.192 | 19.980 | 1.00 | 19.27 |
| ATOM | 586 | N | LYS | 272 | 22.494 | 13.499 | 21.600 | 1.00 | 21.00 |
| ATOM | 587 | CA | LYS | 272 | 22.209 | 12.399 | 22.516 | 1.00 | 22.97 |
| ATOM | 588 | CB | LYS | 272 | 21.709 | 12.968 | 23.850 | 1.00 | 24.05 |
| ATOM | 589 | CG | LYS | 272 | 21.538 | 11.960 | 24.963 | 1.00 | 26.57 |
| ATOM | 590 | CD | LYS | 272 | 22.761 | 11.085 | 25.118 | 1.00 | 28.96 |
| ATOM | 591 | CE | LYS | 272 | 22.573 | 10.081 | 26.243 | 1.00 | 30.16 |
| ATOM | 592 | NZ | LYS | 272 | 23.623 | 9.033 | 26.198 | 1.00 | 31.88 |
| ATOM | 593 | C | LYS | 272 | 21.187 | 11.424 | 21.885 | 1.00 | 23.97 |
| ATOM | 594 | O | LYS | 272 | 21.351 | 10.198 | 21.964 | 1.00 | 24.73 |
| ATOM | 595 | N | PHE | 273 | 20.173 | 11.967 | 21.204 | 1.00 | 23.94 |
| ATOM | 596 | CA | PHE | 273 | 19.151 | 11.153 | 20.538 | 1.00 | 22.60 |
| ATOM | 597 | CB | PHE | 273 | 18.170 | 12.068 | 19.790 | 1.00 | 20.76 |
| ATOM | 598 | CG | PHE | 273 | 17.188 | 11.333 | 18.917 | 1.00 | 19.28 |
| ATOM | 599 | CD1 | PHE | 273 | 16.138 | 10.611 | 19.476 | 1.00 | 19.37 |
| ATOM | 600 | CD2 | PHE | 273 | 17.299 | 11.382 | 17.536 | 1.00 | 17.87 |
| ATOM | 601 | CE1 | PHE | 273 | 15.211 | 9.951 | 18.670 | 1.00 | 18.22 |
| ATOM | 602 | CE2 | PHE | 273 | 16.382 | 10.727 | 16.724 | 1.00 | 19.02 |
| ATOM | 603 | CZ | PHE | 273 | 15.334 | 10.010 | 17.293 | 1.00 | 17.46 |
| ATOM | 604 | C | PHE | 273 | 19.840 | 10.191 | 19.561 | 1.00 | 21.90 |
| ATOM | 605 | O | PHE | 273 | 19.619 | 8.970 | 19.580 | 1.00 | 20.97 |
| ATOM | 606 | N | LEU | 274 | 20.685 | 10.766 | 18.712 | 1.00 | 22.63 |
| ATOM | 607 | CA | LEU | 274 | 21.455 | 10.020 | 17.726 | 1.00 | 21.66 |
| ATOM | 608 | CB | LEU | 274 | 22.324 | 10.989 | 16.921 | 1.00 | 21.04 |
| ATOM | 609 | CG | LEU | 274 | 21.624 | 11.852 | 15.874 | 1.00 | 18.37 |
| ATOM | 610 | CD1 | LEU | 274 | 22.546 | 12.969 | 15.437 | 1.00 | 16.98 |
| ATOM | 611 | CD2 | LEU | 274 | 21.233 | 10.972 | 14.697 | 1.00 | 16.49 |
| ATOM | 612 | C | LEU | 274 | 22.346 | 8.971 | 18.403 | 1.00 | 21.93 |
| ATOM | 613 | O | LEU | 274 | 22.503 | 7.853 | 17.903 | 1.00 | 19.56 |
| ATOM | 614 | N | ALA | 275 | 22.944 | 9.362 | 19.525 | 1.00 | 23.03 |
| ATOM | 615 | CA | ALA | 275 | 23.818 | 8.493 | 20.300 | 1.00 | 24.57 |
| ATOM | 616 | CB | ALA | 275 | 24.585 | 9.301 | 21.322 | 1.00 | 21.93 |
| ATOM | 617 | C | ALA | 275 | 23.033 | 7.381 | 20.992 | 1.00 | 26.77 |
| ATOM | 618 | O | ALA | 275 | 23.580 | 6.302 | 21.237 | 1.00 | 28.37 |
| ATOM | 619 | N | ASP | 276 | 21.764 | 7.631 | 21.314 | 1.00 | 27.59 |
| ATOM | 620 | CA | ASP | 276 | 20.952 | 6.604 | 21.968 | 1.00 | 28.62 |
| ATOM | 621 | CB | ASP | 276 | 19.859 | 7.225 | 22.847 | 1.00 | 28.88 |
| ATOM | 622 | CG | ASP | 276 | 20.412 | 7.872 | 24.107 | 1.00 | 28.41 |
| ATOM | 623 | OD1 | ASP | 276 | 21.515 | 7.500 | 24.553 | 1.00 | 28.79 |
| ATOM | 624 | OD2 | ASP | 276 | 19.741 | 8.767 | 24.649 | 1.00 | 29.37 |
| ATOM | 625 | C | ASP | 276 | 20.350 | 5.614 | 20.971 | 1.00 | 29.04 |
| ATOM | 626 | O | ASP | 276 | 19.589 | 4.719 | 21.346 | 1.00 | 30.14 |
| ATOM | 627 | N | GLY | 277 | 20.700 | 5.775 | 19.701 | 1.00 | 29.48 |
| ATOM | 628 | CA | GLY | 277 | 20.201 | 4.876 | 18.677 | 1.00 | 29.82 |
| ATOM | 629 | C | GLY | 277 | 18.987 | 5.363 | 17.904 | 1.00 | 30.86 |
| ATOM | 630 | O | GLY | 277 | 18.343 | 4.574 | 17.211 | 1.00 | 31.50 |
| ATOM | 631 | N | GLY | 278 | 18.667 | 6.650 | 17.997 | 1.00 | 30.29 |
| ATOM | 632 | CA | GLY | 278 | 17.517 | 7.152 | 17.269 | 1.00 | 29.28 |
| ATOM | 633 | C | GLY | 278 | 16.193 | 6.655 | 17.827 | 1.00 | 28.58 |

FIGURE 1L

| ATOM | 634 | O | GLY | 278 | 16.005 | 6.611 | 19.037 | 1.00 | 28.84 |
|---|---|---|---|---|---|---|---|---|---|
| ATOM | 635 | N | CME | 279 | 15.279 | 6.255 | 16.956 | 1.00 | 27.25 |
| ATOM | 636 | CA | CME | 279 | 13.973 | 5.792 | 17.394 | 1.00 | 28.61 |
| ATOM | 637 | C | CME | 279 | 13.976 | 4.530 | 18.265 | 1.00 | 30.15 |
| ATOM | 638 | O | CME | 279 | 13.004 | 4.243 | 18.959 | 1.00 | 31.77 |
| ATOM | 639 | CB | CME | 279 | 13.043 | 5.619 | 16.190 | 1.00 | 27.21 |
| ATOM | 640 | SG | CME | 279 | 12.348 | 7.190 | 15.561 | 1.00 | 27.85 |
| ATOM | 641 | 2SG | CME | 279 | 11.574 | 8.053 | 17.229 | 1.00 | 28.77 |
| ATOM | 642 | 2CB | CME | 279 | 9.954 | 7.230 | 17.445 | 1.00 | 24.45 |
| ATOM | 643 | 2CA | CME | 279 | 9.943 | 5.999 | 18.329 | 1.00 | 22.60 |
| ATOM | 644 | OG | CME | 279 | 10.230 | 6.331 | 19.673 | 1.00 | 21.99 |
| ATOM | 645 | N | SER | 280 | 15.075 | 3.788 | 18.256 | 1.00 | 32.02 |
| ATOM | 646 | CA | SER | 280 | 15.171 | 2.566 | 19.054 | 1.00 | 31.88 |
| ATOM | 647 | CB | SER | 280 | 16.161 | 1.604 | 18.408 | 1.00 | 32.23 |
| ATOM | 648 | OG | SER | 280 | 17.471 | 2.145 | 18.447 | 1.00 | 33.11 |
| ATOM | 649 | C | SER | 280 | 15.637 | 2.873 | 20.467 | 1.00 | 32.76 |
| ATOM | 650 | O | SER | 280 | 15.710 | 1.978 | 21.299 | 1.00 | 34.40 |
| ATOM | 651 | N | GLY | 281 | 16.014 | 4.127 | 20.710 | 1.00 | 33.60 |
| ATOM | 652 | CA | GLY | 281 | 16.479 | 4.540 | 22.022 | 1.00 | 33.70 |
| ATOM | 653 | C | GLY | 281 | 15.357 | 4.781 | 23.017 | 1.00 | 34.64 |
| ATOM | 654 | O | GLY | 281 | 15.609 | 4.974 | 24.210 | 1.00 | 35.32 |
| ATOM | 655 | N | GLY | 282 | 14.119 | 4.767 | 22.531 | 1.00 | 34.83 |
| ATOM | 656 | CA | GLY | 282 | 12.963 | 4.979 | 23.388 | 1.00 | 34.77 |
| ATOM | 657 | C | GLY | 282 | 11.697 | 4.820 | 22.571 | 1.00 | 34.68 |
| ATOM | 658 | O | GLY | 282 | 11.780 | 4.727 | 21.346 | 1.00 | 36.05 |
| ATOM | 659 | N | ALA | 283 | 10.536 | 4.761 | 23.222 | 1.00 | 33.24 |
| ATOM | 660 | CA | ALA | 283 | 9.276 | 4.615 | 22.495 | 1.00 | 32.26 |
| ATOM | 661 | CB | ALA | 283 | 8.515 | 3.397 | 22.983 | 1.00 | 34.72 |
| ATOM | 662 | C | ALA | 283 | 8.479 | 5.879 | 22.732 | 1.00 | 31.42 |
| ATOM | 663 | O | ALA | 283 | 8.072 | 6.157 | 23.857 | 1.00 | 33.31 |
| ATOM | 664 | N | TYR | 284 | 8.286 | 6.655 | 21.673 | 1.00 | 29.86 |
| ATOM | 665 | CA | TYR | 284 | 7.590 | 7.930 | 21.756 | 1.00 | 26.87 |
| ATOM | 666 | CB | TYR | 284 | 8.586 | 9.068 | 21.499 | 1.00 | 25.67 |
| ATOM | 667 | CG | TYR | 284 | 9.898 | 8.953 | 22.270 | 1.00 | 25.12 |
| ATOM | 668 | CD1 | TYR | 284 | 11.066 | 8.484 | 21.650 | 1.00 | 24.08 |
| ATOM | 669 | CE1 | TYR | 284 | 12.280 | 8.406 | 22.342 | 1.00 | 23.42 |
| ATOM | 670 | CD2 | TYR | 284 | 9.977 | 9.338 | 23.611 | 1.00 | 25.92 |
| ATOM | 671 | CE2 | TYR | 284 | 11.186 | 9.263 | 24.316 | 1.00 | 26.34 |
| ATOM | 672 | CZ | TYR | 284 | 12.334 | 8.800 | 23.675 | 1.00 | 27.01 |
| ATOM | 673 | OH | TYR | 284 | 13.526 | 8.765 | 24.383 | 1.00 | 26.66 |
| ATOM | 674 | C | TYR | 284 | 6.501 | 7.977 | 20.706 | 1.00 | 27.07 |
| ATOM | 675 | O | TYR | 284 | 6.697 | 7.507 | 19.583 | 1.00 | 27.54 |
| ATOM | 676 | N | ASP | 285 | 5.360 | 8.562 | 21.060 | 1.00 | 26.33 |
| ATOM | 677 | CA | ASP | 285 | 4.237 | 8.665 | 20.128 | 1.00 | 25.48 |
| ATOM | 678 | CB | ASP | 285 | 2.906 | 8.695 | 20.888 | 1.00 | 27.66 |
| ATOM | 679 | CG | ASP | 285 | 2.754 | 7.540 | 21.867 | 1.00 | 29.66 |
| ATOM | 680 | OD1 | ASP | 285 | 2.833 | 6.357 | 21.451 | 1.00 | 30.75 |
| ATOM | 681 | OD2 | ASP | 285 | 2.537 | 7.822 | 23.060 | 1.00 | 30.49 |
| ATOM | 682 | C | ASP | 285 | 4.365 | 9.942 | 19.308 | 1.00 | 24.75 |
| ATOM | 683 | O | ASP | 285 | 4.021 | 9.982 | 18.122 | 1.00 | 24.16 |
| ATOM | 684 | N | ILE | 286 | 4.864 | 10.991 | 19.957 | 1.00 | 24.04 |
| ATOM | 685 | CA | ILE | 286 | 5.025 | 12.289 | 19.321 | 1.00 | 22.60 |
| ATOM | 686 | CB | ILE | 286 | 4.036 | 13.310 | 19.936 | 1.00 | 21.83 |
| ATOM | 687 | CG2 | ILE | 286 | 4.185 | 14.677 | 19.265 | 1.00 | 19.78 |
| ATOM | 688 | CG1 | ILE | 286 | 2.601 | 12.776 | 19.805 | 1.00 | 20.82 |
| ATOM | 689 | CD1 | ILE | 286 | 1.539 | 13.664 | 20.395 | 1.00 | 19.00 |
| ATOM | 690 | C | ILE | 286 | 6.458 | 12.804 | 19.470 | 1.00 | 22.69 |
| ATOM | 691 | O | ILE | 286 | 7.052 | 12.730 | 20.556 | 1.00 | 22.52 |

FIGURE 1M

```
ATOM    692  N    ILE   287      7.028  13.274  18.361  1.00  22.96
ATOM    693  CA   ILE   287      8.381  13.822  18.373  1.00  22.01
ATOM    694  CB   ILE   287      9.375  13.029  17.459  1.00  21.82
ATOM    695  CG2  ILE   287     10.741  13.732  17.432  1.00  20.37
ATOM    696  CG1  ILE   287      9.543  11.586  17.945  1.00  20.76
ATOM    697  CD1  ILE   287      8.661  10.601  17.227  1.00  19.72
ATOM    698  C    ILE   287      8.348  15.267  17.890  1.00  20.35
ATOM    699  O    ILE   287      7.944  15.540  16.756  1.00  18.88
ATOM    700  N    ILE   288      8.746  16.184  18.763  1.00  20.27
ATOM    701  CA   ILE   288      8.792  17.595  18.420  1.00  22.23
ATOM    702  CB   ILE   288      8.399  18.525  19.624  1.00  24.13
ATOM    703  CG2  ILE   288      8.370  19.992  19.183  1.00  23.03
ATOM    704  CG1  ILE   288      7.041  18.132  20.224  1.00  25.74
ATOM    705  CD1  ILE   288      5.866  18.329  19.292  1.00  27.52
ATOM    706  C    ILE   288     10.247  17.883  18.076  1.00  20.12
ATOM    707  O    ILE   288     11.118  17.740  18.925  1.00  20.16
ATOM    708  N    CYS   289     10.514  18.173  16.810  1.00  20.26
ATOM    709  CA   CYS   289     11.855  18.520  16.349  1.00  19.98
ATOM    710  CB   CYS   289     12.057  18.095  14.899  1.00  18.98
ATOM    711  SG   CYS   289     12.188  16.314  14.684  1.00  18.93
ATOM    712  C    CYS   289     11.916  20.030  16.466  1.00  20.28
ATOM    713  O    CYS   289     11.550  20.757  15.542  1.00  21.53
ATOM    714  N    ASP   290     12.322  20.482  17.642  1.00  20.55
ATOM    715  CA   ASP   290     12.407  21.892  17.969  1.00  22.05
ATOM    716  CB   ASP   290     12.530  22.030  19.490  1.00  22.57
ATOM    717  CG   ASP   290     12.197  23.413  19.979  1.00  24.81
ATOM    718  OD1  ASP   290     12.731  23.789  21.040  1.00  25.61
ATOM    719  OD2  ASP   290     11.410  24.127  19.312  1.00  27.06
ATOM    720  C    ASP   290     13.564  22.591  17.247  1.00  22.93
ATOM    721  O    ASP   290     14.611  21.983  17.004  1.00  24.56
ATOM    722  N    GLU   291     13.364  23.866  16.905  1.00  22.47
ATOM    723  CA   GLU   291     14.361  24.674  16.190  1.00  21.59
ATOM    724  CB   GLU   291     15.600  24.947  17.055  1.00  22.46
ATOM    725  CG   GLU   291     15.341  25.261  18.533  1.00  23.21
ATOM    726  CD   GLU   291     14.639  26.573  18.786  1.00  24.42
ATOM    727  OE1  GLU   291     14.159  27.222  17.840  1.00  27.28
ATOM    728  OE2  GLU   291     14.552  26.961  19.964  1.00  28.33
ATOM    729  C    GLU   291     14.783  23.938  14.922  1.00  20.30
ATOM    730  O    GLU   291     15.945  23.954  14.535  1.00  20.16
ATOM    731  N    CYS   292     13.804  23.375  14.228  1.00  20.51
ATOM    732  CA   CYS   292     14.057  22.608  13.021  1.00  20.48
ATOM    733  CB   CYS   292     12.762  21.929  12.573  1.00  21.07
ATOM    734  SG   CYS   292     11.485  23.089  12.067  1.00  22.23
ATOM    735  C    CYS   292     14.682  23.411  11.880  1.00  19.98
ATOM    736  O    CYS   292     14.876  42.906  10.777  1.00  18.04
ATOM    737  N    HIS   293     14.962  24.683  12.144  1.00  22.14
ATOM    738  CA   HIS   293     15.592  25.557  11.157  1.00  22.17
ATOM    739  CB   HIS   293     15.198  27.009  11.419  1.00  20.03
ATOM    740  CG   HIS   293     15.718  27.534  12.718  1.00  20.67
ATOM    741  CD2  HIS   293     16.944  27.991  13.068  1.00  20.00
ATOM    742  ND1  HIS   293     14.962  27.549  13.868  1.00  21.26
ATOM    743  CE1  HIS   293     15.701  27.986  14.872  1.00  21.87
ATOM    744  NE2  HIS   293     16.907  28.261  14.413  1.00  20.16
ATOM    745  C    HIS   293     17.121  25.434  11.259  1.00  22.50
ATOM    746  O    HIS   293     17.834  25.959  10.414  1.00  23.46
ATOM    747  N    SER   294     17.611  24.787  12.319  1.00  23.32
ATOM    748  CA   SER   294     19.049  24.621  12.553  1.00  23.42
ATOM    749  CB   SER   294     19.294  23.913  13.878  1.00  21.98
```

FIGURE 1N

```
ATOM   750  OG   SER   294      18.708   24.650   14.930  1.00  25.79
ATOM   751  C    SER   294      19.767   23.878   11.441  1.00  24.00
ATOM   752  O    SER   294      19.379   22.774   11.061  1.00  24.59
ATOM   753  N    THR   295      20.845   24.473   10.946  1.00  24.29
ATOM   754  CA   THR   295      21.590   23.866    9.868  1.00  24.56
ATOM   755  CB   THR   295      21.764   24.855    8.697  1.00  25.03
ATOM   756  OG1  THR   295      22.307   26.091    9.175  1.00  24.69
ATOM   757  CG2  THR   295      20.411   25.132    8.038  1.00  24.54
ATOM   758  C    THR   295      22.916   23.247   10.297  1.00  25.11
ATOM   759  O    THR   295      23.773   22.952    9.467  1.00  25.90
ATOM   760  N    ASP   296      23.083   23.035   11.596  1.00  24.58
ATOM   761  CA   ASP   296      24.297   22.405   12.097  1.00  25.65
ATOM   762  CB   ASP   296      24.430   22.642   13.593  1.00  28.87
ATOM   763  CG   ASP   296      23.307   22.010   14.372  1.00  32.27
ATOM   764  OD1  ASP   296      22.182   22.547   14.308  1.00  34.23
ATOM   765  OD2  ASP   296      23.541   20.956   15.009  1.00  35.53
ATOM   766  C    ASP   296      24.142   20.904   11.806  1.00  24.87
ATOM   767  O    ASP   296      23.027   20.374   11.883  1.00  24.43
ATOM   768  N    ALA   297      25.251   20.220   11.524  1.00  23.24
ATOM   769  CA   ALA   297      25.228   18.796   11.185  1.00  22.47
ATOM   770  CB   ALA   297      26.633   18.247   11.066  1.00  20.82
ATOM   771  C    ALA   297      24.414   17.923   12.122  1.00  21.78
ATOM   772  O    ALA   297      23.643   17.079   11.672  1.00  22.68
ATOM   773  N    THR   298      24.571   18.134   13.420  1.00  22.79
ATOM   774  CA   THR   298      23.846   17.338   14.404  1.00  24.28
ATOM   775  CB   THR   298      24.334   17.649   15.813  1.00  24.90
ATOM   776  OG1  THR   298      25.767   17.588   15.822  1.00  26.90
ATOM   777  CG2  THR   298      23.780   16.639   16.800  1.00  24.31
ATOM   778  C    THR   298      22.320   17.460   14.321  1.00  21.89
ATOM   779  O    THR   298      21.614   16.458   14.441  1.00  21.95
ATOM   780  N    SER   299      21.817   18.665   14.074  1.00  20.47
ATOM   781  CA   SER   299      20.373   18.865   13.969  1.00  19.52
ATOM   782  CB   SER   299      20.025   20.352   14.038  1.00  16.97
ATOM   783  OG   SER   299      20.393   20.874   15.300  1.00  15.99
ATOM   784  C    SER   299      19.835   18.243   12.688  1.00  18.61
ATOM   785  O    SER   299      18.810   17.570   12.698  1.00  18.83
ATOM   786  N    ILE   300      20.567   18.418   11.597  1.00  18.65
ATOM   787  CA   ILE   300      20.155   17.863   10.322  1.00  19.88
ATOM   788  CB   ILE   300      21.085   18.343    9.190  1.00  20.48
ATOM   789  CG2  ILE   300      20.691   17.693    7.846  1.00  19.34
ATOM   790  CG1  ILE   300      21.022   19.867    9.098  1.00  19.44
ATOM   791  CD1  ILE   300      22.063   20.436    8.226  1.00  20.43
ATOM   792  C    ILE   300      20.135   16.337   10.358  1.00  20.31
ATOM   793  O    ILE   300      19.194   15.717    9.867  1.00  21.85
ATOM   794  N    LEU   301      21.161   15.733   10.950  1.00  20.00
ATOM   795  CA   LEU   301      21.243   14.280   11.022  1.00  19.61
ATOM   796  CB   LEU   301      22.626   13.852   11.516  1.00  20.91
ATOM   797  CG   LEU   301      22.986   12.379   11.326  1.00  23.01
ATOM   798  CD1  LEU   301      23.023   12.031    9.851  1.00  21.44
ATOM   799  CD2  LEU   301      24.336   12.111   11.964  1.00  24.76
ATOM   800  C    LEU   301      20.156   13.742   11.942  1.00  19.65
ATOM   801  O    LEU   301      19.517   12.729   11.642  1.00  19.47
ATOM   802  N    GLY   302      19.929   14.450   13.044  1.00  19.18
ATOM   803  CA   GLY   302      18.919   14.048   14.002  1.00  18.63
ATOM   804  C    GLY   302      17.522   14.119   13.425  1.00  19.58
ATOM   805  O    GLY   302      16.731   13.194   13.606  1.00  20.16
ATOM   806  N    ILE   303      17.220   15.206   12.719  1.00  19.27
ATOM   807  CA   ILE   303      15.906   15.383   12.113  1.00  19.24
```

FIGURE 1O

```
ATOM    808  CB   ILE   303     15.732   16.799   11.518  1.00   18.46
ATOM    809  CG2  ILE   303     14.466   16.879   10.680  1.00   19.48
ATOM    810  CG1  ILE   303     15.646   17.818   12.653  1.00   18.58
ATOM    811  CD1  ILE   303     15.483   19.232   12.199  1.00   19.42
ATOM    812  C    ILE   303     15.675   14.324   11.057  1.00   19.21
ATOM    813  O    ILE   303     14.631   13.685   11.044  1.00   21.27
ATOM    814  N    GLY   304     16.662   14.120   10.191  1.00   20.04
ATOM    815  CA   GLY   304     16.547   13.110    9.160  1.00   20.49
ATOM    816  C    GLY   304     16.323   11.730    9.765  1.00   21.95
ATOM    817  O    GLY   304     15.555   10.930    9.226  1.00   22.92
ATOM    818  N    THR   305     17.009   11.435   10.869  1.00   22.89
ATOM    819  CA   THR   305     16.854   10.150   11.552  1.00   23.21
ATOM    820  CB   THR   305     17.722   10.087   12.830  1.00   22.58
ATOM    821  OG1  THR   305     19.101   10.155   12.458  1.00   26.30
ATOM    822  CG2  THR   305     17.494    8.794   13.603  1.00   20.55
ATOM    823  C    THR   305     15.377    9.988   11.919  1.00   23.59
ATOM    824  O    THR   305     14.734    9.028   11.504  1.00   22.98
ATOM    825  N    VAL   306     14.830   10.974   12.632  1.00   24.39
ATOM    826  CA   VAL   306     13.423   10.954   13.039  1.00   22.55
ATOM    827  CB   VAL   306     13.022   12.258   13.751  1.00   19.96
ATOM    828  CG1  VAL   306     11.516   12.293   13.977  1.00   19.45
ATOM    829  CG2  VAL   306     13.748   12.380   15.061  1.00   18.75
ATOM    830  C    VAL   306     12.499   10.773   11.837  1.00   21.61
ATOM    831  O    VAL   306     11.629    9.908   11.840  1.00   22.37
ATOM    832  N    LEU   307     12.701   11.581   10.805  1.00   21.43
ATOM    833  CA   LEU   307     11.855   11.513    9.622  1.00   21.34
ATOM    834  CB   LEU   307     12.238   12.605    8.626  1.00   19.20
ATOM    835  CG   LEU   307     11.804   14.002    9.057  1.00   17.60
ATOM    836  CD1  LEU   307     12.361   15.033    8.111  1.00   17.57
ATOM    837  CD2  LEU   307     10.293   14.074    9.095  1.00   16.93
ATOM    838  C    LEU   307     11.891   10.155    8.960  1.00   22.33
ATOM    839  O    LEU   307     10.875    9.661    8.490  1.00   24.71
ATOM    840  N    ASP   308     13.051    9.522    8.971  1.00   23.84
ATOM    841  CA   ASP   308     13.184    8.221    8.356  1.00   23.32
ATOM    842  CB   ASP   308     14.655    7.938    8.062  1.00   23.50
ATOM    843  CG   ASP   308     14.859    6.634    7.316  1.00   23.73
ATOM    844  OD1  ASP   308     14.468    6.559    6.136  1.00   25.35
ATOM    845  OD2  ASP   308     15.403    5.682    7.907  1.00   22.72
ATOM    846  C    ASP   308     12.617    7.111    9.230  1.00   23.73
ATOM    847  O    ASP   308     11.878    6.259    8.752  1.00   24.61
ATOM    848  N    GLN   309     12.927    7.159   10.518  1.00   23.54
ATOM    849  CA   GLN   309     12.529    6.130   11.465  1.00   24.40
ATOM    850  CB   GLN   309     13.609    6.003   12.538  1.00   24.46
ATOM    851  CG   GLN   309     14.985    5.638   12.022  1.00   24.18
ATOM    852  CD   GLN   309     16.023    5.622   13.128  1.00   23.84
ATOM    853  OE1  GLN   309     15.702    5.805   14.301  1.00   24.42
ATOM    854  NE2  GIN   309     17.276    5.415   12.760  1.00   25.37
ATOM    855  C    GLN   309     11.169    6.173   12.168  1.00   26.09
ATOM    856  O    GIN   309     10.580    5.116   12.401  1.00   25.68
ATOM    857  N    ALA   310     10.698    7.367   12.537  1.00   27.06
ATOM    858  CA   ALA   310      9.432    7.554   13.273  1.00   28.07
ATOM    859  CB   ALA   310      8.983    9.012   13.224  1.00   27.02
ATOM    860  C    ALA   310      8.251    6.646   12.956  1.00   28.11
ATOM    861  O    ALA   310      7.831    5.866   13.814  1.00   28.35
ATOM    862  N    GLU   311      7.714    6.735   11.742  1.00   29.49
ATOM    863  CA   GLU   311      6.560    5.916   11.376  1.00   31.72
ATOM    864  CB   GLU   311      6.125    6.161    9.932  1.00   31.31
ATOM    865  CG   GLU   311      4.847    5.405    9.558  1.00   33.59
```

FIGURE 1P

| | | | | | | | | |
|---|---|---|---|---|---|---|---|---|
| ATOM | 866 | CD | GLU | 311 | 4.180 | 5.925 | 8.291 | 1.00 34.98 |
| ATOM | 867 | OE1 | GLU | 311 | 2.993 | 5.602 | 8.065 | 1.00 36.53 |
| ATOM | 868 | OE2 | GLU | 311 | 4.834 | 6.657 | 7.519 | 1.00 37.12 |
| ATOM | 869 | C | GLU | 311 | 6.784 | 4.429 | 11.614 | 1.00 33.13 |
| ATOM | 870 | O | GLU | 311 | 5.993 | 3.784 | 12.303 | 1.00 35.45 |
| ATOM | 871 | N | THR | 312 | 7.880 | 3.898 | 11.085 | 1.00 32.86 |
| ATOM | 872 | CA | THR | 312 | 8.200 | 2.487 | 11.249 | 1.00 32.32 |
| ATOM | 873 | CB | THR | 312 | 9.488 | 2.140 | 10.477 | 1.00 32.72 |
| ATOM | 874 | OG1 | THR | 312 | 9.289 | 2.449 | 9.092 | 1.00 33.20 |
| ATOM | 875 | CG2 | THR | 312 | 9.829 | 0.661 | 10.611 | 1.00 31.35 |
| ATOM | 876 | C | THR | 312 | 8.329 | 2.104 | 12.727 | 1.00 31.60 |
| ATOM | 877 | O | THR | 312 | 8.016 | 0.980 | 13.114 | 1.00 32.69 |
| ATOM | 878 | N | ALA | 313 | 8.741 | 3.057 | 13.554 | 1.00 30.31 |
| ATOM | 879 | CA | ALA | 313 | 8.899 | 2.806 | 14.977 | 1.00 29.28 |
| ATOM | 880 | CB | ALA | 313 | 9.949 | 3.731 | 15.563 | 1.00 28.71 |
| ATOM | 881 | C | ALA | 313 | 7.575 | 2.950 | 15.722 | 1.00 28.65 |
| ATOM | 882 | O | ALA | 313 | 7.520 | 2.786 | 16.939 | 1.00 29.03 |
| ATOM | 883 | N | GLY | 314 | 6.514 | 3.278 | 14.996 | 1.00 28.36 |
| ATOM | 884 | CA | GLY | 314 | 5.207 | 3.409 | 15.618 | 1.00 29.07 |
| ATOM | 885 | C | GLY | 314 | 4.836 | 4.749 | 16.231 | 1.00 28.95 |
| ATOM | 886 | O | GLY | 314 | 4.048 | 4.822 | 17.173 | 1.00 28.57 |
| ATOM | 887 | N | ALA | 315 | 5.418 | 5.821 | 15.724 | 1.00 29.15 |
| ATOM | 888 | CA | ALA | 315 | 5.080 | 7.131 | 16.239 | 1.00 27.89 |
| ATOM | 889 | CB | ALA | 315 | 6.218 | 8.106 | 15.987 | 1.00 27.99 |
| ATOM | 890 | C | ALA | 315 | 3.820 | 7.561 | 15.499 | 1.00 27.19 |
| ATOM | 891 | O | ALA | 315 | 3.509 | 7.042 | 14.421 | 1.00 25.84 |
| ATOM | 892 | N | ARG | 316 | 3.090 | 8.493 | 16.092 | 1.00 27.55 |
| ATOM | 893 | CA | ARG | 316 | 1.863 | 9.010 | 15.502 | 1.00 27.08 |
| ATOM | 894 | CB | ARG | 316 | 0.777 | 9.155 | 16.582 | 1.00 31.00 |
| ATOM | 895 | CG | ARG | 316 | -0.529 | 9.805 | 16.099 | 1.00 35.35 |
| ATOM | 896 | CD | ARG | 316 | -1.404 | 8.835 | 15.306 | 1.00 38.97 |
| ATOM | 897 | NE | ARG | 316 | -1.989 | 7.798 | 16.158 | 1.00 42.10 |
| ATOM | 898 | CZ | ARG | 316 | -2.953 | 8.008 | 17.055 | 1.00 43.29 |
| ATOM | 899 | NH1 | ARG | 316 | -3.462 | 9.220 | 17.232 | 1.00 43.63 |
| ATOM | 900 | NH2 | ARG | 316 | -3.393 | 7.004 | 17.799 | 1.00 43.76 |
| ATOM | 901 | C | ARG | 316 | 2.095 | 10.366 | 14.854 | 1.00 25.15 |
| ATOM | 902 | O | ARG | 316 | 1.521 | 10.679 | 13.805 | 1.00 25.12 |
| ATOM | 903 | N | LEU | 317 | 2.962 | 11.164 | 15.457 | 1.00 22.37 |
| ATOM | 904 | CA | LEU | 317 | 3.185 | 12.493 | 14.931 | 1.00 20.99 |
| ATOM | 905 | CB | LEU | 317 | 2.234 | 13.482 | 15.648 | 1.00 18.70 |
| ATOM | 906 | CG | LEU | 317 | 2.297 | 14.999 | 15.402 | 1.00 16.65 |
| ATOM | 907 | CD1 | LEU | 317 | 1.898 | 15.327 | 13.972 | 1.00 15.36 |
| ATOM | 908 | CD2 | LEU | 317 | 1.384 | 15.723 | 16.375 | 1.00 16.28 |
| ATOM | 909 | C | LEU | 317 | 4.612 | 12.987 | 15.060 | 1.00 21.09 |
| ATOM | 910 | O | LEU | 317 | 5.293 | 12.705 | 16.053 | 1.00 21.51 |
| ATOM | 911 | N | VAL | 318 | 5.061 | 13.686 | 14.020 | 1.00 20.92 |
| ATOM | 912 | CA | VAL | 318 | 6.368 | 14.319 | 14.009 | 1.00 21.69 |
| ATOM | 913 | CB | VAL | 318 | 7.324 | 13.760 | 12.924 | 1.00 21.79 |
| ATOM | 914 | CG1 | VAL | 318 | 8.541 | 14.686 | 12.772 | 1.00 20.61 |
| ATOM | 915 | CG2 | VAL | 318 | 7.801 | 12.375 | 13.320 | 1.00 21.19 |
| ATOM | 916 | C | VAL | 318 | 6.061 | 15.787 | 13.736 | 1.00 21.64 |
| ATOM | 917 | O | VAL | 318 | 5.367 | 16.112 | 12.767 | 1.00 20.75 |
| ATOM | 918 | N | VAL | 319 | 6.523 | 16.660 | 14.626 | 1.00 21.64 |
| ATOM | 919 | CA | VAL | 319 | 6.291 | 18.088 | 14.489 | 1.00 21.71 |
| ATOM | 920 | CB | VAL | 319 | 5.581 | 18.679 | 15.751 | 1.00 21.72 |
| ATOM | 921 | CG1 | VAL | 319 | 5.321 | 20.171 | 15.579 | 1.00 19.36 |
| ATOM | 922 | CG2 | VAL | 319 | 4.280 | 17.947 | 16.020 | 1.00 21.02 |
| ATOM | 923 | C | VAL | 319 | 7.619 | 18.793 | 14.308 | 1.00 20.25 |

FIGURE 1Q

```
ATOM   924  O    VAL  319   8.520  18.635  15.127  1.00  19.92
ATOM   925  N    LEU  320   7.739  19.555  13.226  1.00  20.09
ATOM   926  CA   LEU  320   8.946  20.323  12.934  1.00  18.99
ATOM   927  CB   LEU  320   9.276  20.236  11.442  1.00  18.78
ATOM   928  CG   LEU  320   9.265  18.835  10.803  1.00  20.01
ATOM   929  CD1  LEU  320   9.449  18.951   9.309  1.00  20.04
ATOM   930  CD2  LEU  320  10.342  17.940  11.400  1.00  20.17
ATOM   931  C    LEU  320   8.609  21.754  13.352  1.00  17.86
ATOM   932  O    LEU  320   7.887  22.459  12.655  1.00  17.59
ATOM   933  N    ALA  321   9.102  22.160  14.515  1.00  18.47
ATOM   934  CA   ALA  321   8.807  23.476  15.055  1.00  20.27
ATOM   935  CB   ALA  321   8.365  23.354  16.522  1.00  19.53
ATOM   936  C    ALA  321   9.926  24.499  14.935  1.00  22.46
ATOM   937  O    ALA  321  11.105  24.199  15.192  1.00  22.78
ATOM   938  N    THR  322   9.531  25.732  14.615  1.00  23.57
ATOM   939  CA   THR  322  10.463  26.839  14.463  1.00  24.42
ATOM   940  CB   THR  322  11.384  26.632  13.224  1.00  23.87
ATOM   941  OG1  THR  322  12.368  27.677  13.159  1.00  22.26
ATOM   942  CG2  THR  322  10.561  26.606  11.935  1.00  20.90
ATOM   943  C    THR  322   9.721  28.166  14.301  1.00  25.40
ATOM   944  O    THR  322   8.632  28.227  13.719  1.00  25.14
ATOM   945  N    ALA  323  10.317  29.220  14.841  1.00  25.81
ATOM   946  CA   ALA  323   9.768  30.559  14.729  1.00  25.79
ATOM   947  CB   ALA  323  10.219  31.412  15.902  1.00  25.93
ATOM   948  C    ALA  323  10.288  31.153  13.423  1.00  26.98
ATOM   949  O    ALA  323   9.758  32.153  12.932  1.00  28.83
ATOM   950  N    THR  324  11.325  30.531  12.862  1.00  25.90
ATOM   951  CA   THR  324  11.925  31.003  11.617  1.00  24.88
ATOM   952  CB   THR  324  13.319  31.611  11.876  1.00  24.01
ATOM   953  OG1  THR  324  14.106  30.689  12.641  1.00  25.50
ATOM   954  CG2  THR  324  13.201  32.908  12.648  1.00  23.67
ATOM   955  C    THR  324  12.048  29.943  10.508  1.00  24.40
ATOM   956  O    THR  324  13.123  29.369  10.293  1.00  24.97
ATOM   957  N    PRO  325  10.935  29.624   9.829  1.00  22.47
ATOM   958  CD   PRO  325   9.557  30.088  10.041  1.00  21.14
ATOM   959  CA   PRO  325  10.978  28.634   8.755  1.00  22.40
ATOM   960  CB   PRO  325   9.500  28.446   8.422  1.00  20.85
ATOM   961  CG   PRO  325   8.922  29.769   8.720  1.00  19.94
ATOM   962  C    PRO  325  11.756  29.190   7.559  1.00  23.10
ATOM   963  O    PRO  325  12.008  30.396   7.486  1.00  23.30
ATOM   964  N    PRO  326  12.159  28.319   6.609  1.00  23.99
ATOM   965  CD   PRO  326  12.034  26.849   6.583  1.00  23.51
ATOM   966  CA   PRO  326  12.908  28.793   5.437  1.00  23.61
ATOM   967  CB   PRO  326  12.949  27.553   4.544  1.00  22.60
ATOM   968  CG   PRO  326  13.058  26.456   5.545  1.00  22.79
ATOM   969  C    PRO  326  12.245  29.985   4.740  1.00  22.55
ATOM   970  O    PRO  326  11.019  30.087   4.696  1.00  23.41
ATOM   971  N    GLY  327  13.070  30.901   4.249  1.00  20.16
ATOM   972  CA   GLY  327  12.576  32.077   3.561  1.00  20.04
ATOM   973  C    GLY  327  12.224  33.207   4.501  1.00  20.56
ATOM   974  O    GLY  327  11.681  34.216   4.075  1.00  21.64
ATOM   975  N    SER  328  12.544  33.044   5.779  1.00  22.07
ATOM   976  CA   SER  328  12.245  34.056   6.783  1.00  21.35
ATOM   977  CB   SER  328  12.379  33.466   8.189  1.00  20.72
ATOM   978  OG   SER  328  11.326  32.565   8.454  1.00  20.21
ATOM   979  C    SER  328  13.088  35.322   6.689  1.00  22.21
ATOM   980  O    SER  328  14.185  35.333   6.115  1.00  21.32
ATOM   981  N    VAL  329  12.552  36.387   7.275  1.00  21.78
```

FIGURE 1R

| ATOM | 982  | CA  | VAL | 329 | 13.207 | 37.678 | 7.325  | 1.00 | 21.67 |
|------|------|-----|-----|-----|--------|--------|--------|------|-------|
| ATOM | 983  | CB  | VAL | 329 | 12.634 | 38.651 | 6.278  | 1.00 | 21.56 |
| ATOM | 984  | CG1 | VAL | 329 | 13.039 | 38.203 | 4.867  | 1.00 | 21.42 |
| ATOM | 985  | CG2 | VAL | 329 | 11.123 | 38.747 | 6.410  | 1.00 | 19.14 |
| ATOM | 986  | C   | VAL | 329 | 12.960 | 38.192 | 8.737  | 1.00 | 21.96 |
| ATOM | 987  | O   | VAL | 329 | 12.080 | 37.683 | 9.424  | 1.00 | 21.78 |
| ATOM | 988  | N   | THR | 330 | 13.786 | 39.132 | 9.187  | 1.00 | 23.09 |
| ATOM | 989  | CA  | THR | 330 | 13.681 | 39.708 | 10.523 | 1.00 | 24.47 |
| ATOM | 990  | CB  | THR | 330 | 15.073 | 40.131 | 11.047 | 1.00 | 24.34 |
| ATOM | 991  | OG1 | THR | 330 | 15.958 | 39.009 | 10.972 | 1.00 | 25.56 |
| ATOM | 992  | CG2 | THR | 330 | 14.997 | 40.577 | 12.490 | 1.00 | 23.96 |
| ATOM | 993  | C   | THR | 330 | 12.719 | 40.888 | 10.521 | 1.00 | 25.81 |
| ATOM | 994  | O   | THR | 330 | 13.062 | 42.014 | 10.134 | 1.00 | 25.19 |
| ATOM | 995  | N   | VAL | 331 | 11.507 | 40.600 | 10.972 | 1.00 | 27.46 |
| ATOM | 996  | CA  | VAL | 331 | 10.415 | 41.558 | 11.029 | 1.00 | 29.93 |
| ATOM | 997  | CB  | VAL | 331 | 9.065  | 40.789 | 10.871 | 1.00 | 30.69 |
| ATOM | 998  | CG1 | VAL | 331 | 7.885  | 41.620 | 11.359 | 1.00 | 33.40 |
| ATOM | 999  | CG2 | VAL | 331 | 8.871  | 40.366 | 9.408  | 1.00 | 28.41 |
| ATOM | 1000 | C   | VAL | 331 | 10.431 | 42.356 | 12.330 | 1.00 | 30.66 |
| ATOM | 1001 | O   | VAL | 331 | 10.942 | 41.880 | 13.347 | 1.00 | 30.44 |
| ATOM | 1002 | N   | PRO | 332 | 9.923  | 43.601 | 12.296 | 1.00 | 31.80 |
| ATOM | 1003 | CD  | PRO | 332 | 9.525  | 44.351 | 11.088 | 1.00 | 32.94 |
| ATOM | 1004 | CA  | PRO | 332 | 9.868  | 44.471 | 13.469 | 1.00 | 32.90 |
| ATOM | 1005 | CB  | PRO | 332 | 8.882  | 45.544 | 13.029 | 1.00 | 33.03 |
| ATOM | 1006 | CG  | PRO | 332 | 9.299  | 45.772 | 11.616 | 1.00 | 32.19 |
| ATOM | 1007 | C   | PRO | 332 | 9.403  | 43.751 | 14.726 | 1.00 | 33.35 |
| ATOM | 1008 | O   | PRO | 332 | 8.539  | 42.879 | 14.673 | 1.00 | 33.22 |
| ATOM | 1009 | N   | HIS | 333 | 10.042 | 44.092 | 15.840 | 1.00 | 34.93 |
| ATOM | 1010 | CA  | HIS | 333 | 9.747  | 43.526 | 17.149 | 1.00 | 35.66 |
| ATOM | 1011 | CB  | HIS | 333 | 11.040 | 43.034 | 17.801 | 1.00 | 35.75 |
| ATOM | 1012 | CG  | HIS | 333 | 10.864 | 42.519 | 19.196 | 1.00 | 35.91 |
| ATOM | 1013 | CD2 | HIS | 333 | 11.036 | 41.281 | 19.717 | 1.00 | 37.50 |
| ATOM | 1014 | ND1 | HIS | 333 | 10.494 | 43.327 | 20.250 | 1.00 | 35.51 |
| ATOM | 1015 | CE1 | HIS | 333 | 10.448 | 42.610 | 21.359 | 1.00 | 35.57 |
| ATOM | 1016 | NE2 | HIS | 333 | 10.774 | 41.366 | 21.063 | 1.00 | 37.41 |
| ATOM | 1017 | C   | HIS | 333 | 9.152  | 44.666 | 17.967 | 1.00 | 36.79 |
| ATOM | 1018 | O   | HIS | 333 | 9.616  | 45.804 | 17.878 | 1.00 | 37.38 |
| ATOM | 1019 | N   | PRO | 334 | 8.174  | 44.362 | 18.833 | 1.00 | 37.08 |
| ATOM | 1020 | CD  | PRO | 334 | 7.664  | 43.006 | 19.111 | 1.00 | 36.74 |
| ATOM | 1021 | CA  | PRO | 334 | 7.509  | 45.364 | 19.680 | 1.00 | 37.36 |
| ATOM | 1022 | CB  | PRO | 334 | 6.622  | 44.508 | 20.589 | 1.00 | 38.15 |
| ATOM | 1023 | CG  | PRO | 334 | 6.344  | 43.286 | 19.753 | 1.00 | 38.80 |
| ATOM | 1024 | C   | PRO | 334 | 8.458  | 46.225 | 20.521 | 1.00 | 37.12 |
| ATOM | 1025 | O   | PRO | 334 | 8.426  | 47.448 | 20.447 | 1.00 | 37.73 |
| ATOM | 1026 | N   | ASN | 335 | 9.283  | 45.564 | 21.330 | 1.00 | 36.19 |
| ATOM | 1027 | CA  | ASN | 335 | 10.231 | 46.226 | 22.228 | 1.00 | 35.31 |
| ATOM | 1028 | CB  | ASN | 335 | 10.616 | 45.294 | 23.385 | 1.00 | 36.70 |
| ATOM | 1029 | CG  | ASN | 335 | 9.433  | 44.782 | 24.146 | 1.00 | 38.17 |
| ATOM | 1030 | OD1 | ASN | 335 | 8.393  | 45.429 | 24.192 | 1.00 | 41.02 |
| ATOM | 1031 | ND2 | ASN | 335 | 9.579  | 43.602 | 24.751 | 1.00 | 37.75 |
| ATOM | 1032 | C   | ASN | 335 | 11.547 | 46.676 | 21.640 | 1.00 | 33.43 |
| ATOM | 1033 | O   | ASN | 335 | 12.410 | 47.100 | 22.404 | 1.00 | 35.07 |
| ATOM | 1034 | N   | ILE | 336 | 11.732 | 46.613 | 20.325 | 1.00 | 30.99 |
| ATOM | 1035 | CA  | ILE | 336 | 13.043 | 46.972 | 19.783 | 1.00 | 27.79 |
| ATOM | 1036 | CB  | ILE | 336 | 13.771 | 45.706 | 19.242 | 1.00 | 26.56 |
| ATOM | 1037 | CG2 | ILE | 336 | 15.209 | 46.038 | 18.847 | 1.00 | 23.81 |
| ATOM | 1038 | CG1 | ILE | 336 | 13.786 | 44.609 | 20.312 | 1.00 | 24.10 |
| ATOM | 1039 | CD1 | ILE | 336 | 14.260 | 43.272 | 19.819 | 1.00 | 22.21 |

FIGURE 1S

| ATOM | 1040 | C | ILE | 336 | 13.131 | 48.077 | 18.738 | 1.00 | 28.12 |
|---|---|---|---|---|---|---|---|---|---|
| ATOM | 1041 | O | ILE | 336 | 12.731 | 47.896 | 17.588 | 1.00 | 28.53 |
| ATOM | 1042 | N | GLU | 337 | 13.694 | 49.213 | 19.128 | 1.00 | 27.62 |
| ATOM | 1043 | CA | GLU | 337 | 13.879 | 50.309 | 18.189 | 1.00 | 28.28 |
| ATOM | 1044 | CB | GLU | 337 | 14.019 | 51.634 | 18.931 | 1.00 | 29.84 |
| ATOM | 1045 | CG | GLU | 337 | 14.335 | 52.802 | 18.002 | 1.00 | 33.89 |
| ATOM | 1046 | CD | GLU | 337 | 14.754 | 54.067 | 18.730 | 1.00 | 36.64 |
| ATOM | 1047 | OE1 | GLU | 337 | 14.866 | 54.049 | 19.978 | 1.00 | 39.22 |
| ATOM | 1048 | OE2 | GLU | 337 | 14.987 | 55.084 | 18.041 | 1.00 | 38.86 |
| ATOM | 1049 | C | GLU | 337 | 15.168 | 50.031 | 17.401 | 1.00 | 27.48 |
| ATOM | 1050 | O | GLU | 337 | 16.224 | 49.807 | 17.990 | 1.00 | 27.75 |
| ATOM | 1051 | N | GLU | 338 | 15.092 | 50.053 | 16.078 | 1.00 | 26.13 |
| ATOM | 1052 | CA | GLU | 338 | 16.264 | 49.791 | 15.260 | 1.00 | 25.01 |
| ATOM | 1053 | CB | GLU | 338 | 15.939 | 48.745 | 14.200 | 1.00 | 25.16 |
| ATOM | 1054 | CG | GLU | 338 | 15.433 | 47.431 | 14.770 | 1.00 | 26.26 |
| ATOM | 1055 | CD | GLU | 338 | 15.271 | 46.355 | 13.720 | 1.00 | 25.40 |
| ATOM | 1056 | OE1 | GLU | 338 | 14.396 | 45.490 | 13.896 | 1.00 | 26.96 |
| ATOM | 1057 | OE2 | GLU | 338 | 16.020 | 46.363 | 12.723 | 1.00 | 26.71 |
| ATOM | 1058 | C | GLU | 338 | 16.794 | 51.050 | 14.594 | 1.00 | 25.30 |
| ATOM | 1059 | O | GLU | 338 | 16.033 | 51.835 | 14.033 | 1.00 | 27.51 |
| ATOM | 1060 | N | VAL | 339 | 18.103 | 51.250 | 14.646 | 1.00 | 24.09 |
| ATOM | 1061 | CA | VAL | 339 | 18.690 | 52.421 | 14.027 | 1.00 | 22.82 |
| ATOM | 1062 | CB | VAL | 339 | 18.667 | 53.653 | 14.986 | 1.00 | 22.08 |
| ATOM | 1063 | CG1 | VAL | 339 | 18.756 | 53.221 | 16.424 | 1.00 | 21.99 |
| ATOM | 1064 | CG2 | VAL | 339 | 19.763 | 54.646 | 14.637 | 1.00 | 19.75 |
| ATOM | 1065 | C | VAL | 339 | 20.064 | 52.174 | 13.411 | 1.00 | 22.67 |
| ATOM | 1066 | O | VAL | 339 | 20.951 | 51.593 | 14.027 | 1.00 | 23.55 |
| ATOM | 1067 | N | ALA | 340 | 20.189 | 52.567 | 12.150 | 1.00 | 22.35 |
| ATOM | 1068 | CA | ALA | 340 | 21.416 | 52.428 | 11.384 | 1.00 | 23.06 |
| ATOM | 1069 | CB | ALA | 340 | 21.169 | 52.877 | 9.952 | 1.00 | 20.82 |
| ATOM | 1070 | C | ALA | 340 | 22.559 | 53.240 | 11.969 | 1.00 | 23.85 |
| ATOM | 1071 | O | ALA | 340 | 22.354 | 54.337 | 12.485 | 1.00 | 25.71 |
| ATOM | 1072 | N | LEU | 341 | 23.761 | 52.686 | 11.929 | 1.00 | 23.84 |
| ATOM | 1073 | CA | LEU | 341 | 24.920 | 53.417 | 12.404 | 1.00 | 23.48 |
| ATOM | 1074 | CB | LEU | 341 | 26.069 | 52.468 | 12.729 | 1.00 | 22.83 |
| ATOM | 1075 | CG | LEU | 341 | 25.938 | 51.583 | 13.960 | 1.00 | 21.53 |
| ATOM | 1076 | CD1 | LEU | 341 | 27.012 | 50.509 | 13.925 | 1.00 | 22.65 |
| ATOM | 1077 | CD2 | LEU | 341 | 26.054 | 52.427 | 15.203 | 1.00 | 21.05 |
| ATOM | 1078 | C | LEU | 341 | 25.307 | 54.276 | 11.206 | 1.00 | 25.07 |
| ATOM | 1079 | O | LEU | 341 | 24.967 | 53.939 | 10.064 | 1.00 | 25.58 |
| ATOM | 1080 | N | SER | 342 | 25.988 | 55.388 | 11.459 | 1.00 | 25.28 |
| ATOM | 1081 | CA | SER | 342 | 26.426 | 56.272 | 10.391 | 1.00 | 25.74 |
| ATOM | 1082 | CB | SER | 342 | 25.832 | 57.680 | 10.569 | 1.00 | 25.63 |
| ATOM | 1083 | OG | SER | 342 | 26.162 | 58.252 | 11.831 | 1.00 | 26.66 |
| ATOM | 1084 | C | SER | 342 | 27.946 | 56.313 | 10.422 | 1.00 | 26.04 |
| ATOM | 1085 | O | SER | 342 | 28.588 | 55.459 | 11.030 | 1.00 | 26.02 |
| ATOM | 1086 | N | THR | 343 | 28.528 | 57.276 | 9.727 | 1.00 | 27.63 |
| ATOM | 1087 | CA | THR | 343 | 29.972 | 57.416 | 9.712 | 1.00 | 28.59 |
| ATOM | 1088 | CB | THR | 343 | 30.429 | 58.057 | 8.404 | 1.00 | 29.62 |
| ATOM | 1089 | OG1 | THR | 343 | 29.514 | 59.101 | 8.050 | 1.00 | 30.43 |
| ATOM | 1090 | CG2 | THR | 343 | 30.455 | 57.019 | 7.302 | 1.00 | 32.51 |
| ATOM | 1091 | C | THR | 343 | 30.422 | 58.275 | 10.890 | 1.00 | 28.11 |
| ATOM | 1092 | O | THR | 343 | 31.614 | 58.399 | 11.171 | 1.00 | 29.07 |
| ATOM | 1093 | N | THR | 344 | 29.459 | 58.863 | 11.583 | 1.00 | 27.10 |
| ATOM | 1094 | CA | THR | 344 | 29.767 | 59.710 | 12.714 | 1.00 | 27.21 |
| ATOM | 1095 | CB | THR | 344 | 28.729 | 60.827 | 12.825 | 1.00 | 27.65 |
| ATOM | 1096 | OG1 | THR | 344 | 28.658 | 61.514 | 11.568 | 1.00 | 28.57 |
| ATOM | 1097 | CG2 | THR | 344 | 29.100 | 61.805 | 13.924 | 1.00 | 27.24 |

FIGURE 1T

```
ATOM   1098  C    THR   344    29.842   58.908   14.008  1.00  27.63
ATOM   1099  O    THR   344    28.884   58.225   14.396  1.00  27.69
ATOM   1100  N    GLY   345    31.003   58.969   14.649  1.00  26.95
ATOM   1101  CA   GLY   345    31.211   58.260   15.890  1.00  26.75
ATOM   1102  C    GLY   345    32.688   58.168   16.189  1.00  28.21
ATOM   1103  O    GLY   345    33.512   58.276   15.285  1.00  28.29
ATOM   1104  N    GLU   346    33.023   57.926   17.451  1.00  28.51
ATOM   1105  CA   GLU   346    34.414   57.832   17.863  1.00  29.04
ATOM   1106  CB   GLU   346    34.541   58.020   19.378  1.00  30.35
ATOM   1107  CG   GLU   346    34.291   59.439   19.880  1.00  32.52
ATOM   1108  CD   GLU   346    32.888   59.926   19.593  1.00  32.87
ATOM   1109  OE1  GLU   346    31.929   59.174   19.854  1.00  32.23
ATOM   1110  OE2  GLU   346    32.747   61.057   19.086  1.00  35.06
ATOM   1111  C    GLU   346    35.084   56.523   17.479  1.00  28.20
ATOM   1112  O    GLU   346    36.283   56.502   17.218  1.00  29.40
ATOM   1113  N    ILE   347    34.321   55.431   17.457  1.00  28.52
ATOM   1114  CA   ILE   347    34.889   54.110   17.153  1.00  26.91
ATOM   1115  CB   ILE   347    34.453   53.035   18.192  1.00  27.90
ATOM   1116  CG2  ILE   347    35.250   51.776   18.005  1.00  28.31
ATOM   1117  CG1  ILE   347    34.645   53.537   19.620  1.00  29.70
ATOM   1118  CD1  ILE   347    33.400   54.194   20.186  1.00  32.81
ATOM   1119  C    ILE   347    34.551   53.550   15.781  1.00  24.52
ATOM   1120  O    ILE   347    33.392   53.258   15.490  1.00  23.00
ATOM   1121  N    PRO   348    35.559   53.398   14.914  1.00  23.86
ATOM   1122  CD   PRO   348    36.947   53.871   15.026  1.00  23.37
ATOM   1123  CA   PRO   348    35.302   52.854   13.582  1.00  24.53
ATOM   1124  CB   PRO   348    36.692   52.834   12.959  1.00  24.34
ATOM   1125  CG   PRO   348    37.338   54.030   13.588  1.00  23.28
ATOM   1126  C    PRO   348    34.759   51.449   13.786  1.00  25.57
ATOM   1127  O    PRO   348    35.290   50.696   14.606  1.00  25.45
ATOM   1128  N    PHE   349    33.677   51.118   13.084  1.00  25.89
ATOM   1129  CA   PHE   349    33.041   49.812   13.216  1.00  24.50
ATOM   1130  CB   PHE   349    31.971   49.860   14.318  1.00  23.29
ATOM   1131  CG   PHE   349    31.358   48.522   14.632  1.00  25.07
ATOM   1132  CD1  PHE   349    32.025   47.610   15.447  1.00  26.07
ATOM   1133  CD2  PHE   349    30.111   48.175   14.119  1.00  25.08
ATOM   1134  CE1  PHE   349    31.461   46.372   15.750  1.00  25.64
ATOM   1135  CE2  PHE   349    29.535   46.945   14.411  1.00  25.25
ATOM   1136  CZ   PHE   349    30.211   46.038   15.230  1.00  26.19
ATOM   1137  C    PHE   349    32.437   49.321   11.904  1.00  23.33
ATOM   1138  O    PHE   349    31.361   49.749   11.501  1.00  22.31
ATOM   1139  N    TYR   350    33.154   48.418   11.247  1.00  23.43
ATOM   1140  CA   TYR   350    32.725   47.820    9.986  1.00  23.78
ATOM   1141  CB   TYR   350    31.636   46.759   10.230  1.00  21.13
ATOM   1142  CG   TYR   350    32.133   45.531   10.967  1.00  20.42
ATOM   1143  CD1  TYR   350    32.302   45.552   12.344  1.00  19.57
ATOM   1144  CE1  TYR   350    32.794   44.440   13.028  1.00  20.40
ATOM   1145  CD2  TYR   350    32.465   44.353   10.279  1.00  21.51
ATOM   1146  CE2  TYR   350    32.963   43.224   10.958  1.00  19.67
ATOM   1147  CZ   TYR   350    33.126   43.282   12.335  1.00  20.56
ATOM   1148  OH   TYR   350    33.648   42.212   13.040  1.00  20.53
ATOM   1149  C    TYR   350    32.280   48.823    8.920  1.00  25.07
ATOM   1150  O    TYR   350    31.215   48.680    8.324  1.00  26.53
ATOM   1151  N    GLY   351    33.118   49.817    8.656  1.00  25.52
ATOM   1152  CA   GLY   351    32.789   50.802    7.644  1.00  26.67
ATOM   1153  C    GLY   351    32.054   52.000    8.205  1.00  27.75
ATOM   1154  O    GLY   351    32.097   53.088    7.624  1.00  29.56
ATOM   1155  N    LYS   352    31.332   51.788    9.300  1.00  28.35
```

FIGURE 1U

| | | | | | | | | |
|---|---|---|---|---|---|---|---|---|
| ATOM | 1156 | CA | LYS | 352 | 30.596 | 52.858 | 9.962 | 1.00 | 26.46 |
| ATOM | 1157 | CB | LYS | 352 | 29.182 | 52.405 | 10.332 | 1.00 | 26.95 |
| ATOM | 1158 | CG | LYS | 352 | 28.352 | 51.994 | 9.145 | 1.00 | 28.09 |
| ATOM | 1159 | CD | LYS | 352 | 28.138 | 53.145 | 8.186 | 1.00 | 29.10 |
| ATOM | 1160 | CE | LYS | 352 | 27.767 | 52.615 | 6.811 | 1.00 | 31.84 |
| ATOM | 1161 | NZ | LYS | 352 | 26.677 | 51.594 | 6.876 | 1.00 | 34.67 |
| ATOM | 1162 | C | LYS | 352 | 31.373 | 53.197 | 11.213 | 1.00 | 25.16 |
| ATOM | 1163 | O | LYS | 352 | 32.560 | 52.903 | 11.313 | 1.00 | 24.74 |
| ATOM | 1164 | N | ALA | 353 | 30.704 | 53.811 | 12.170 | 1.00 | 26.04 |
| ATOM | 1165 | CA | ALA | 353 | 31.353 | 54.186 | 13.407 | 1.00 | 27.08 |
| ATOM | 1166 | CB | ALA | 353 | 31.987 | 55.568 | 13.267 | 1.00 | 26.55 |
| ATOM | 1167 | C | ALA | 353 | 30.332 | 54.172 | 14.533 | 1.00 | 27.81 |
| ATOM | 1168 | O | ALA | 353 | 29.122 | 54.285 | 14.297 | 1.00 | 29.07 |
| ATOM | 1169 | N | ILE | 354 | 30.816 | 53.977 | 15.750 | 1.00 | 26.83 |
| ATOM | 1170 | CA | ILE | 354 | 29.944 | 53.949 | 16.903 | 1.00 | 26.78 |
| ATOM | 1171 | CB | ILE | 354 | 30.136 | 52.664 | 17.758 | 1.00 | 26.37 |
| ATOM | 1172 | CG2 | ILE | 354 | 29.224 | 52.705 | 18.989 | 1.00 | 23.34 |
| ATOM | 1173 | CG1 | ILE | 354 | 29.864 | 51.409 | 16.922 | 1.00 | 26.07 |
| ATOM | 1174 | CD1 | ILE | 354 | 30.151 | 50.093 | 17.660 | 1.00 | 26.73 |
| ATOM | 1175 | C | ILE | 354 | 30.269 | 55.147 | 17.770 | 1.00 | 27.53 |
| ATOM | 1176 | O | ILE | 354 | 31.446 | 55.480 | 17.980 | 1.00 | 27.83 |
| ATOM | 1177 | N | PRO | 355 | 29.231 | 55.890 | 18.172 | 1.00 | 27.07 |
| ATOM | 1178 | CD | PRO | 355 | 27.876 | 55.817 | 17.601 | 1.00 | 26.53 |
| ATOM | 1179 | CA | PRO | 355 | 29.379 | 57.069 | 19.026 | 1.00 | 27.16 |
| ATOM | 1180 | CB | PRO | 355 | 28.042 | 57.794 | 18.851 | 1.00 | 27.57 |
| ATOM | 1181 | CG | PRO | 355 | 27.507 | 57.257 | 17.531 | 1.00 | 28.35 |
| ATOM | 1182 | C | PRO | 355 | 29.521 | 56.570 | 20.463 | 1.00 | 27.80 |
| ATOM | 1183 | O | PRO | 355 | 28.665 | 55.825 | 20.951 | 1.00 | 28.66 |
| ATOM | 1184 | N | LEU | 356 | 30.602 | 56.955 | 21.133 | 1.00 | 27.31 |
| ATOM | 1185 | CA | LEU | 356 | 30.821 | 56.537 | 22.512 | 1.00 | 26.78 |
| ATOM | 1186 | CB | LEU | 356 | 32.024 | 57.269 | 23.110 | 1.00 | 27.84 |
| ATOM | 1187 | CG | LEU | 356 | 33.384 | 56.622 | 22.838 | 1.00 | 27.71 |
| ATOM | 1188 | CD1 | LEU | 356 | 34.515 | 57.553 | 23.275 | 1.00 | 27.97 |
| ATOM | 1189 | CD2 | LEU | 356 | 33.457 | 55.297 | 23.568 | 1.00 | 25.40 |
| ATOM | 1190 | C | LEU | 356 | 29.591 | 56.787 | 23.367 | 1.00 | 25.92 |
| ATOM | 1191 | O | LEU | 356 | 29.272 | 56.004 | 24.257 | 1.00 | 25.15 |
| ATOM | 1192 | N | ALA | 357 | 28.887 | 57.872 | 23.069 | 1.00 | 26.25 |
| ATOM | 1193 | CA | ALA | 357 | 27.685 | 58.241 | 23.813 | 1.00 | 26.44 |
| ATOM | 1194 | CB | ALA | 357 | 27.072 | 59.522 | 23.228 | 1.00 | 25.83 |
| ATOM | 1195 | C | ALA | 357 | 26.638 | 57.124 | 23.873 | 1.00 | 26.65 |
| ATOM | 1196 | O | ALA | 357 | 26.011 | 56.918 | 24.911 | 1.00 | 26.75 |
| ATOM | 1197 | N | VAL | 358 | 26.502 | 56.360 | 22.791 | 1.00 | 26.24 |
| ATOM | 1198 | CA | VAL | 358 | 25.506 | 55.295 | 22.758 | 1.00 | 26.40 |
| ATOM | 1199 | CB | VAL | 358 | 25.119 | 54.892 | 21.298 | 1.00 | 25.09 |
| ATOM | 1200 | CG1 | VAL | 358 | 24.714 | 56.119 | 20.511 | 1.00 | 23.26 |
| ATOM | 1201 | CG2 | VAL | 358 | 26.266 | 54.180 | 20.597 | 1.00 | 24.96 |
| ATOM | 1202 | C | VAL | 358 | 25.881 | 54.069 | 23.590 | 1.00 | 26.35 |
| ATOM | 1203 | O | VAL | 358 | 25.050 | 53.179 | 23.797 | 1.00 | 27.18 |
| ATOM | 1204 | N | ILE | 359 | 27.121 | 54.021 | 24.074 | 1.00 | 25.51 |
| ATOM | 1205 | CA | ILE | 359 | 27.567 | 52.892 | 24.893 | 1.00 | 24.89 |
| ATOM | 1206 | CB | ILE | 359 | 28.582 | 51.982 | 24.136 | 1.00 | 22.23 |
| ATOM | 1207 | CG2 | ILE | 359 | 27.857 | 51.199 | 23.029 | 1.00 | 21.17 |
| ATOM | 1208 | CG1 | ILE | 359 | 29.756 | 52.814 | 23.600 | 1.00 | 21.55 |
| ATOM | 1209 | CD1 | ILE | 359 | 30.892 | 52.026 | 22.995 | 1.00 | 17.63 |
| ATOM | 1210 | C | ILE | 359 | 28.159 | 53.308 | 26.237 | 1.00 | 25.79 |
| ATOM | 1211 | O | ILE | 359 | 28.437 | 52.459 | 27.076 | 1.00 | 25.36 |
| ATOM | 1212 | N | ALA | 360 | 28.304 | 54.616 | 26.449 | 1.00 | 29.45 |
| ATOM | 1213 | CA | ALA | 360 | 28.879 | 55.171 | 27.681 | 1.00 | 31.32 |

FIGURE 1V

```
ATOM   1214  CB   ALA  360      28.880  56.691  27.621  1.00  30.01
ATOM   1215  C    ALA  360      28.207  54.684  28.972  1.00  32.84
ATOM   1216  O    ALA  360      28.889  54.369  29.960  1.00  33.70
ATOM   1217  N    GLY  361      26.880  54.659  28.981  1.00  32.93
ATOM   1218  CA   GLY  361      26.172  54.179  30.154  1.00  32.53
ATOM   1219  C    GLY  361      25.285  53.020  29.739  1.00  32.16
ATOM   1220  O    GLY  361      24.892  52.945  28.579  1.00  33.01
ATOM   1221  N    GLY  362      24.978  52.115  30.664  1.00  31.44
ATOM   1222  CA   GLY  362      24.124  50.980  30.352  1.00  28.17
ATOM   1223  C    GLY  362      24.894  49.725  29.979  1.00  28.18
ATOM   1224  O    GLY  362      26.128  49.699  30.060  1.00  28.64
ATOM   1225  N    ARG  363      24.168  48.677  29.597  1.00  25.54
ATOM   1226  CA   ARG  363      24.762  47.404  29.196  1.00  25.19
ATOM   1227  CB   ARG  363      24.135  46.256  29.985  1.00  25.16
ATOM   1228  CG   ARG  363      23.726  46.631  31.401  1.00  26.44
ATOM   1229  CD   ARG  363      23.093  45.460  32.123  1.00  29.20
ATOM   1230  NE   ARG  363      24.075  44.760  32.935  1.00  34.10
ATOM   1231  CZ   ARG  363      24.655  43.608  32.616  1.00  35.13
ATOM   1232  NH1  ARG  363      24.358  42.977  31.494  1.00  34.77
ATOM   1233  NH2  ARG  363      25.613  43.130  33.389  1.00  36.31
ATOM   1234  C    ARG  363      24.504  47.226  27.695  1.00  24.94
ATOM   1235  O    ARG  363      23.377  47.393  27.222  1.00  24.76
ATOM   1236  N    HIS  364      25.542  46.910  26.934  1.00  24.18
ATOM   1237  CA   HIS  364      25.385  46.776  25.494  1.00  23.64
ATOM   1238  CB   HIS  364      25.891  48.048  24.830  1.00  23.19
ATOM   1239  CG   HIS  364      25.367  49.291  25.478  1.00  25.11
ATOM   1240  CD2  HIS  364      25.895  50.084  26.438  1.00  24.33
ATOM   1241  ND1  HIS  364      24.116  49.803  25.205  1.00  26.29
ATOM   1242  CE1  HIS  364      23.894  50.856  25.970  1.00  25.44
ATOM   1243  NE2  HIS  364      24.959  51.047  26.726  1.00  25.09
ATOM   1244  C    HIS  364      26.133  45.559  24.993  1.00  23.60
ATOM   1245  O    HIS  364      27.098  45.128  25.628  1.00  24.11
ATOM   1246  N    LEU  365      25.645  44.976  23.900  1.00  22.16
ATOM   1247  CA   LEU  365      26.247  43.784  23.310  1.00  21.25
ATOM   1248  CB   LEU  365      25.241  42.635  23.316  1.00  20.31
ATOM   1249  CG   LEU  365      25.667  41.278  22.749  1.00  19.06
ATOM   1250  CD1  LEU  365      26.952  40.821  23.413  1.00  18.55
ATOM   1251  CD2  LEU  365      24.562  40.252  22.966  1.00  16.61
ATOM   1252  C    LEU  365      26.672  44.079  21.883  1.00  21.19
ATOM   1253  O    LEU  365      25.836  44.377  21.031  1.00  21.03
ATOM   1254  N    ILE  366      27.966  43.978  21.615  1.00  20.98
ATOM   1255  CA   ILE  366      28.473  44.255  20.283  1.00  21.20
ATOM   1256  CB   ILE  366      29.646  45.254  20.322  1.00  21.57
ATOM   1257  CG2  ILE  366      30.113  45.572  18.911  1.00  19.27
ATOM   1258  CG1  ILE  366      29.225  46.536  21.051  1.00  21.36
ATOM   1259  CD1  ILE  366      30.303  47.607  21.078  1.00  20.61
ATOM   1260  C    ILE  366      28.925  42.974  19.605  1.00  21.06
ATOM   1261  O    ILE  366      29.825  42.296  20.093  1.00  20.15
ATOM   1262  N    PHE  367      28.274  42.635  18.495  1.00  20.98
ATOM   1263  CA   PHE  367      28.610  41.438  17.747  1.00  21.40
ATOM   1264  CB   PHE  367      27.364  40.804  17.125  1.00  20.48
ATOM   1265  CG   PHE  367      26.556  39.975  18.093  1.00  20.75
ATOM   1266  CD1  PHE  367      25.393  40.487  18.671  1.00  20.80
ATOM   1267  CD2  PHE  367      26.951  38.675  18.416  1.00  19.09
ATOM   1268  CE1  PHE  367      24.633  39.711  19.557  1.00  19.99
ATOM   1269  CE2  PHE  367      26.210  37.899  19.291  1.00  19.22
ATOM   1270  CZ   PHE  367      25.043  38.417  19.865  1.00  20.05
ATOM   1271  C    PHE  367      29.644  41.705  16.670  1.00  22.44
```

FIGURE 1W

```
ATOM   1272  O    PHE  367   29.478  42.596  15.829  1.00  21.74
ATOM   1273  N    CYS  368   30.728  40.942  16.728  1.00  22.95
ATOM   1274  CA   CYS  368   31.807  41.032  15.761  1.00  23.17
ATOM   1275  CB   CYS  368   33.126  41.385  16.464  1.00  23.99
ATOM   1276  SG   CYS  368   33.120  43.017  17.283  1.00  21.99
ATOM   1277  C    CYS  368   31.863  39.650  15.106  1.00  23.06
ATOM   1278  O    CYS  368   31.433  38.658  15.699  1.00  21.98
ATOM   1279  N    HIS  369   32.358  39.578  13.877  1.00  23.71
ATOM   1280  CA   HIS  369   32.402  38.291  13.185  1.00  24.68
ATOM   1281  CB   HIS  369   32.429  38.498  11.667  1.00  24.85
ATOM   1282  CG   HIS  369   33.754  38.951  11.138  1.00  27.37
ATOM   1283  CD2  HIS  369   34.644  38.338  10.323  1.00  28.58
ATOM   1284  ND1  HIS  369   34.306  40.175  11.452  1.00  29.21
ATOM   1285  CE1  HIS  369   35.480  40.295  10.859  1.00  29.19
ATOM   1286  NE2  HIS  369   35.708  39.194  10.168  1.00  29.69
ATOM   1287  C    HIS  369   33.550  37.372  13.606  1.00  24.39
ATOM   1288  O    HIS  369   33.440  36.153  13.506  1.00  24.00
ATOM   1289  N    SER  370   34.641  37.959  14.087  1.00  24.30
ATOM   1290  CA   SER  370   35.814  37.189  14.479  1.00  24.06
ATOM   1291  CB   SER  370   36.949  37.460  13.494  1.00  24.57
ATOM   1292  OG   SER  370   37.431  38.784  13.648  1.00  26.06
ATOM   1293  C    SER  370   36.269  37.518  15.892  1.00  23.01
ATOM   1294  O    SER  370   35.936  38.574  16.433  1.00  23.58
ATOM   1295  N    LYS  371   37.076  36.633  16.461  1.00  23.64
ATOM   1296  CA   LYS  371   37.587  36.797  17.817  1.00  25.06
ATOM   1297  CB   LYS  371   38.146  35.466  18.320  1.00  24.91
ATOM   1298  CG   LYS  371   37.086  34.372  18.306  1.00  27.06
ATOM   1299  CD   LYS  371   37.648  32.979  18.078  1.00  28.04
ATOM   1300  CE   LYS  371   38.277  32.415  19.318  1.00  28.77
ATOM   1301  NZ   LYS  371   38.642  30.999  19.107  1.00  31.47
ATOM   1302  C    LYS  371   38.625  37.904  17.877  1.00  25.64
ATOM   1303  O    LYS  371   38.689  38.650  18.849  1.00  27.42
ATOM   1304  N    LYS  372   39.379  38.061  16.795  1.00  27.32
ATOM   1305  CA   LYS  372   40.402  39.100  16.707  1.00  28.80
ATOM   1306  CB   LYS  372   41.136  39.010  15.366  1.00  29.78
ATOM   1307  CG   LYS  372   42.339  39.923  15.243  1.00  30.84
ATOM   1308  CD   LYS  372   42.976  39.812  13.866  1.00  31.69
ATOM   1309  C    LYS  372   39.729  40.455  16.842  1.00  28.53
ATOM   1310  O    LYS  372   40.095  41.255  17.696  1.00  28.67
ATOM   1311  N    LYS  373   38.720  40.688  16.008  1.00  29.86
ATOM   1312  CA   LYS  373   37.966  41.935  16.040  1.00  30.80
ATOM   1313  CB   LYS  373   36.864  41.927  14.975  1.00  32.75
ATOM   1314  CG   LYS  373   37.131  42.879  13.817  1.00  38.26
ATOM   1315  CD   LYS  373   38.427  42.514  13.101  1.00  42.40
ATOM   1316  CE   LYS  373   38.993  43.676  12.295  1.00  43.70
ATOM   1317  NZ   LYS  373   40.324  43.301  11.729  1.00  45.18
ATOM   1318  C    LYS  373   37.362  42.209  17.422  1.00  30.08
ATOM   1319  O    LYS  373   37.301  43.359  17.850  1.00  31.06
ATOM   1320  N    CYS  374   36.923  41.157  18.114  1.00  28.22
ATOM   1321  CA   CYS  374   36.334  41.310  19.438  1.00  26.08
ATOM   1322  CB   CYS  374   35.800  39.970  19.964  1.00  23.42
ATOM   1323  SG   CYS  374   34.336  39.310  19.100  1.00  23.17
ATOM   1324  C    CYS  374   37.402  41.851  20.375  1.00  27.53
ATOM   1325  O    CYS  374   37.162  42.805  21.110  1.00  25.72
ATOM   1326  N    ASP  375   38.588  41.239  20.322  1.00  29.96
ATOM   1327  CA   ASP  375   39.735  41.633  21.149  1.00  31.23
ATOM   1328  CB   ASP  375   40.945  40.738  20.860  1.00  30.10
ATOM   1329  CG   ASP  375   40.737  39.312  21.296  1.00  29.63
```

FIGURE 1X

```
ATOM   1330  OD1  ASP   375    39.996   39.076   22.274  1.00  28.42
ATOM   1331  OD2  ASP   375    41.332   38.423   20.657  1.00  30.89
ATOM   1332  C    ASP   375    40.135   43.069   20.861  1.00  31.74
ATOM   1333  O    ASP   375    40.304   43.872   21.783  1.00  33.16
ATOM   1334  N    GLU   376    40.301   43.371   19.577  1.00  31.73
ATOM   1335  CA   GLU   376    40.686   44.701   19.127  1.00  33.34
ATOM   1336  CB   GLU   376    40.848   44.715   17.603  1.00  34.63
ATOM   1337  CG   GLU   376    41.791   43.621   17.095  1.00  38.95
ATOM   1338  CD   GLU   376    42.234   43.797   15.646  1.00  40.85
ATOM   1339  OE1  GLU   376    41.453   44.311   14.813  1.00  42.74
ATOM   1340  OE2  GLU   376    43.380   43.401   15.340  1.00  42.32
ATOM   1341  C    GLU   376    39.696   45.776   19.581  1.00. 32.36
ATOM   1342  O    GLU   376    40.099   46.831   20.067  1.00  32.77
ATOM   1343  N    LEU   377    38.404   45.493   19.464  1.00  31.01
ATOM   1344  CA   LEU   377    37.398   46.456   19.871  1.00  29.80
ATOM   1345  CB   LEU   377    36.014   46.042   19.375  1.00  27.58
ATOM   1346  CG   LEU   377    34.886   47.037   19.646  1.00  25.16
ATOM   1347  CD1  LEU   377    35.306   48.433   19.220  1.00  26.04
ATOM   1348  CD2  LEU   377    33.635   46.611   18.901  1.00  24.83
ATOM   1349  C    LEU   377    37.408   46.603   21.384  1.00  31.08
ATOM   1350  O    LEU   377    37.488   47.713   21.908  1.00  32.49
ATOM   1351  N    ALA   378    37.362   45.481   22.089  1.00  31.01
ATOM   1352  CA   ALA   378    37.372   45.516   23.541  1.00  31.90
ATOM   1353  CB   ALA   378    37.518   44.102   24.109  1.00  30.31
ATOM   1354  C    ALA   378    38.532   46.398   23.990  1.00  33.00
ATOM   1355  O    ALA   378    38.350   47.303   24.800  1.00  32.23
ATOM   1356  N    ALA   379    39.703   46.171   23.399  1.00  34.63
ATOM   1357  CA   ALA   379    40.906   46.931   23.725  1.00  36.26
ATOM   1358  CB   ALA   379    42.087   46.423   22.915  1.00  36.36
ATOM   1359  C    ALA   379    40.690   48.416   23.471  1.00  37.24
ATOM   1360  O    ALA   379    40.968   49.243   24.339  1.00  38.17
ATOM   1361  N    LYS   380    40.146   48.741   22.303  1.00  38.24
ATOM   1362  CA   LYS   380    39.880   50.125   21.935  1.00  39.63
ATOM   1363  CB   LYS   380    39.184   50.196   20.565  1.00  39.82
ATOM   1364  CG   LYS   380    39.223   51.577   19.904  1.00  40.69
ATOM   1365  CD   LYS   380    38.828   51.510   18.434  1.00  40.39
ATOM   1366  CE   LYS   380    39.265   52.757   17.654  1.00  41.28
ATOM   1367  NZ   LYS   380    38.608   54.040   18.063  1.00  40.83
ATOM   1368  C    LYS   380    39.005   50.782   22.997  1.00  40.87
ATOM   1369  O    LYS   380    39.405   51.768   23.619  1.00  42.50
ATOM   1370  N    LEU   381    37.843   50.187   23.250  1.00  40.55
ATOM   1371  CA   LEU   381    36.891   50.711   24.226  1.00  40.18
ATOM   1372  CB   LEU   381    35.632   49.842   24.243  1.00  38.99
ATOM   1373  CG   LEU   381    34.870   49.610   22.940  1.00  37.56
ATOM   1374  CD1  LEU   381    33.654   48.758   23.223  1.00  35.03
ATOM   1375  CD2  LEU   381    34.464   50.938   22.331  1.00  38.01
ATOM   1376  C    LEU   381    37.458   50.801   25.642  1.00  40.57
ATOM   1377  O    LEU   381    37.302   51.822   26.323  1.00  39.48
ATOM   1378  N    VAL   382    38.096   49.721   26.083  1.00  42.00
ATOM   1379  CA   VAL   382    38.681   49.650   27.419  1.00  42.99
ATOM   1380  CB   VAL   382    39.322   48.252   27.692  1.00  42.81
ATOM   1381  CG1  VAL   382    40.811   48.255   27.390  1.00  42.57
ATOM   1382  CG2  VAL   382    39.040   47.810   29.113  1.00  40.95
ATOM   1383  C    VAL   382    39.699   50.775   27.575  1.00  44.23
ATOM   1384  O    VAL   382    39.878   51.315   28.670  1.00  45.11
ATOM   1385  N    ALA   383    40.322   51.158   26.462  1.00  44.34
ATOM   1386  CA   ALA   383    41.293   52.244   26.468  1.00  44.39
ATOM   1387  CB   ALA   383    42.115   52.238   25.181  1.00  44.85
```

FIGURE 1Y

```
ATOM   1388  C    ALA  383   40.556  53.574  26.626  1.00  43.71
ATOM   1389  O    ALA  383   41.035  54.481  27.312  1.00  46.22
ATOM   1390  N    LEU  384   39.378  53.679  26.018  1.00  40.83
ATOM   1391  CA   LEU  384   38.578  54.895  26.099  1.00  38.30
ATOM   1392  CB   LEU  384   37.633  54.988  24.899  1.00  39.47
ATOM   1393  CG   LEU  384   38.227  54.865  23.491  1.00  41.58
ATOM   1394  CD1  LEU  384   37.102  54.745  22.468  1.00  42.20
ATOM   1395  CD2  LEU  384   39.130  56.052  23.168  1.00  42.42
ATOM   1396  C    LEU  384   37.771  54.952  27.404  1.00  36.79
ATOM   1397  O    LEU  384   36.787  55.688  27.505  1.00  36.24
ATOM   1398  N    GLY  385   38.164  54.147  28.385  1.00  35.50
ATOM   1399  CA   GLY  385   37.475  54.145  29.664  1.00  33.80
ATOM   1400  C    GLY  385   36.171  53.364  29.713  1.00  33.33
ATOM   1401  O    GLY  385   35.474  53.391  30.728  1.00  34.28
ATOM   1402  N    ILE  386   35.825  52.668  28.633  1.00  31.60
ATOM   1403  CA   ILE  386   34.590  51.890  28.604  1.00  28.68
ATOM   1404  CB   ILE  386   34.121  51.649  27.152  1.00  27.72
ATOM   1405  CG2  ILE  386   32.933  50.698  27.124  1.00  28.20
ATOM   1406  CG1  ILE  386   33.749  52.967  26.486  1.00  25.89
ATOM   1407  CD1  ILE  386   32.566  53.650  27.126  1.00  27.25
ATOM   1408  C    ILE  386   34.810  50.535  29.282  1.00  28.13
ATOM   1409  O    ILE  386   35.838  49.890  29.061  1.00  26.54
ATOM   1410  N    ASN  387   33.844  50.098  30.092  1.00  27.35
ATOM   1411  CA   ASN  387   33.944  48.800  30.771  1.00  26.98
ATOM   1412  CB   ASN  387   33.020  48.745  31.997  1.00  26.31
ATOM   1413  CG   ASN  387   33.080  47.404  32.715  1.00  26.76
ATOM   1414  OD1  ASN  387   34.130  46.749  32.741  1.00  27.49
ATOM   1415  ND2  ASN  387   31.960  46.993  33.306  1.00  23.98
ATOM   1416  C    ASN  387   33.579  47.697  29.780  1.00  25.60
ATOM   1417  O    ASN  387   32.509  47.090  29.867  1.00  25.99
ATOM   1418  N    ALA  388   34.465  47.470  28.817  1.00  24.50
ATOM   1419  CA   ALA  388   34.241  46.474  27.780  1.00  24.38
ATOM   1420  CB   ALA  388   34.692  47.012  26.430  1.00  20.14
ATOM   1421  C    ALA  388   34.945  45.167  28.088  1.00  24.87
ATOM   1422  O    ALA  388   36.080  45.156  28.559  1.00  27.09
ATOM   1423  N    VAL  389   34.269  44.059  27.829  1.00  25.51
ATOM   1424  CA   VAL  389   34.842  42.750  28.076  1.00  25.75
ATOM   1425  CB   VAL  389   34.277  42.094  29.368  1.00  27.61
ATOM   1426  CG1  VAL  389   34.659  42.918  30.586  1.00  27.58
ATOM   1427  CG2  VAL  389   32.772  41.946  29.293  1.00  30.47
ATOM   1428  C    VAL  389   34.540  41.896  26.873  1.00  24.33
ATOM   1429  O    VAL  389   33.464  41.989  26.300  1.00  24.05
ATOM   1430  N    ALA  390   35.520  41.119  26.444  1.00  25.42
ATOM   1431  CA   ALA  390   35.345  40.253  25.285  1.00  26.04
ATOM   1432  CB   ALA  390   36.674  40.083  24.531  1.00  23.07
ATOM   1433  C    ALA  390   34.794  38.888  25.667  1.00  26.03
ATOM   1434  O    ALA  390   34.959  38.416  26.799  1.00  25.70
ATOM   1435  N    TYR  391   34.076  38.286  24.732  1.00  26.60
ATOM   1436  CA   TYR  391   33.565  36.952  24.940  1.00  26.52
ATOM   1437  CB   TYR  391   32.235  36.903  25.691  1.00  25.87
ATOM   1438  CG   TYR  391   31.857  35.459  25.965  1.00  27.47
ATOM   1439  CD1  TYR  391   32.555  34.713  26.915  1.00  28.87
ATOM   1440  CE1  TYR  391   32.306  33.360  27.087  1.00  29.43
ATOM   1441  CD2  TYR  391   30.886  34.802  25.199  1.00  27.70
ATOM   1442  CE2  TYR  391   30.630  33.446  25.368  1.00  26.82
ATOM   1443  CZ   TYR  391   31.344  32.737  26.312  1.00  28.58
ATOM   1444  OH   TYR  391   31.097  31.405  26.511  1.00  30.59
ATOM   1445  C    TYR  391   33.422  36.195  23.645  1.00  26.74
```

FIGURE 1Z

```
ATOM  1446  O    TYR  391  32.853  36.685  22.675  1.00  25.62
ATOM  1447  N    TYR  392  33.981  34.997  23.646  1.00  28.03
ATOM  1448  CA   TYR  392  33.906  34.095  22.522  1.00  30.93
ATOM  1449  CB   TYR  392  34.803  34.551  21.377  1.00  31.00
ATOM  1450  CG   TYR  392  36.167  35.043  21.778  1.00  30.91
ATOM  1451  CD1  TYR  392  37.158  34.157  22.202  1.00  30.94
ATOM  1452  CE1  TYR  392  38.436  34.609  22.509  1.00  29.59
ATOM  1453  CD2  TYR  392  36.492  36.394  21.678  1.00  29.43
ATOM  1454  CE2  TYR  392  37.757  36.846  21.982  1.00  29.05
ATOM  1455  CZ   TYR  392  38.720  35.949  22.396  1.00  27.90
ATOM  1456  OH   TYR  392  39.964  36.401  22.718  1.00  29.68
ATOM  1457  C    TYR  392  34.262  32.706  23.026  1.00  33.17
ATOM  1458  O    TYR  392  34.577  32.547  24.204  1.00  33.99
ATOM  1459  N    ARG  393  34.163  31.706  22.154  1.00  35.69
ATOM  1460  CA   ARG  393  34.450  30.324  22.528  1.00  36.12
ATOM  1461  CB   ARG  393  34.221  29.383  21.344  1.00  40.66
ATOM  1462  CG   ARG  393  34.624  27.931  21.595  1.00  45.96
ATOM  1463  CD   ARG  393  34.246  27.040  20.406  1.00  50.06
ATOM  1464  NE   ARG  393  32.903  26.481  20.602  1.00  53.83
ATOM  1465  CZ   ARG  393  32.668  25.370  21.300  1.00  55.97
ATOM  1466  NH1  ARG  393  31.415  24.957  21.475  1.00  57.63
ATOM  1467  NH2  ARG  393  33.682  24.619  21.738  1.00  57.66
ATOM  1468  C    ARG  393  35.862  30.178  23.071  1.00  34.84
ATOM  1469  O    ARG  393  36.833  30.615  22.448  1.00  33.70
ATOM  1470  N    GLY  394  35.946  29.572  24.253  1.00  33.32
ATOM  1471  CA   GLY  394  37.211  29.374  24.929  1.00  32.50
ATOM  1472  C    GLY  394  37.360  30.280  26.141  1.00  31.93
ATOM  1473  O    GLY  394  38.203  30.031  27.005  1.00  33.23
ATOM  1474  N    LEU  395  36.552  31.336  26.205  1.00  30.71
ATOM  1475  CA   LEU  395  36.601  32.281  27.317  1.00  29.49
ATOM  1476  CB   LEU  395  36.238  33.695  26.869  1.00  26.83
ATOM  1477  CG   LEU  395  37.160  34.324  25.830  1.00  25.83
ATOM  1478  CD1  LEU  395  37.126  35.822  26.000  1.00  25.35
ATOM  1479  CD2  LEU  395  38.586  33.824  25.988  1.00  25.20
ATOM  1480  C    LEU  395  35.712  31.868  28.470  1.00  29.64
ATOM  1481  O    LEU  395  35.046  30.833  28.415  1.00  30.33
ATOM  1482  N    ASP  396  35.700  32.691  29.510  1.00  30.84
ATOM  1483  CA   ASP  396  34.912  32.411  30.697  1.00  32.76
ATOM  1484  CB   ASP  396  35.813  32.527  31.936  1.00  33.42
ATOM  1485  CG   ASP  396  35.194  31.932  33.187  1.00  32.63
ATOM  1486  OD1  ASP  396  33.996  31.567  33.191  1.00  32.81
ATOM  1487  OD2  ASP  396  35.932  31.823  34.180  1.00  34.06
ATOM  1488  C    ASP  396  33.731  33.376  30.790  1.00  33.30
ATOM  1489  O    ASP  396  33.900  34.569  31.070  1.00  33.42
ATOM  1490  N    VAL  397  32.529  32.842  30.605  1.00  33.00
ATOM  1491  CA   VAL  397  31.327  33.658  30.650  1.00  33.17
ATOM  1492  CB   VAL  397  30.145  32.937  29.985  1.00  34.45
ATOM  1493  CG1  VAL  397  29.618  31.827  30.898  1.00  34.59
ATOM  1494  CG2  VAL  397  29.052  33.945  29.604  1.00  33.81
ATOM  1495  C    VAL  397  30.913  34.130  32.047  1.00  32.83
ATOM  1496  O    VAL  397  30.157  35.099  32.176  1.00  33.92
ATOM  1497  N    SER  398  31.419  33.478  33.089  1.00  31.28
ATOM  1498  CA   SER  398  31.060  33.865  34.445  1.00  30.65
ATOM  1499  CB   SER  398  31.390  32.741  35.424  1.00  31.52
ATOM  1500  OG   SER  398  32.755  32.370  35.345  1.00  33.10
ATOM  1501  C    SER  398  31.714  35.166  34.910  1.00  30.89
ATOM  1502  O    SER  398  31.368  35.702  35.966  1.00  31.87
ATOM  1503  N    VAL  399  32.668  35.673  34.140  1.00  30.49
```

FIGURE 1A-1

```
ATOM   1504  CA   VAL   399    33.326  36.907  34.529  1.00  29.65
ATOM   1505  CB   VAL   399    34.793  36.976  34.008  1.00  29.94
ATOM   1506  CG1  VAL   399    35.501  35.636  34.242  1.00  29.09
ATOM   1507  CG2  VAL   399    34.841  37.372  32.552  1.00  29.84
ATOM   1508  C    VAL   399    32.512  38.122  34.076  1.00  29.51
ATOM   1509  O    VAL   399    32.753  39.245  34.530  1.00  30.22
ATOM   1510  N    ILE   400    31.534  37.889  33.202  1.00  27.63
ATOM   1511  CA   ILE   400    30.682  38.961  32.695  1.00  26.65
ATOM   1512  CB   ILE   400    29.877  38.489  31.457  1.00  26.73
ATOM   1513  CG2  ILE   400    29.017  39.627  30.912  1.00  24.30
ATOM   1514  CG1  ILE   400    30.836  37.966  30.381  1.00  27.93
ATOM   1515  CD1  ILE   400    30.161  37.431  29.132  1.00  27.24
ATOM   1516  C    ILE   400    29.717  39.357  33.808  1.00  26.54
ATOM   1517  O    ILE   400    28.987  38.521  34.320  1.00  25.84
ATOM   1518  N    PRO   401    29.720  40.637  34.213  1.00  27.05
ATOM   1519  CD   PRO   401    30.441  41.786  33.632  1.00  26.21
ATOM   1520  CA   PRO   401    28.816  41.069  35.281  1.00  27.20
ATOM   1521  CB   PRO   401    29.191  42.537  35.469  1.00  26.22
ATOM   1522  CG   PRO   401    29.597  42.959  34.085  1.00  25.90
ATOM   1523  C    PRO   401    27.339  40.903  34.906  1.00  29.40
ATOM   1524  O    PRO   401    26.945  41.134  33.773  1.00  29.57
ATOM   1525  N    THR   402    26.551  40.447  35.871  1.00  30.54
ATOM   1526  CA   THR   402    25.123  40.231  35.727  1.00  30.29
ATOM   1527  CB   THR   402    24.663  39.255  36.825  1.00  31.76
ATOM   1528  OG1  THR   402    25.063  37.929  36.462  1.00  35.36
ATOM   1529  CG2  THR   402    23.168  39.308  37.059  1.00  34.23
ATOM   1530  C    THR   402    24.373  41.557  35.835  1.00  29.90
ATOM   1531  O    THR   402    23.246  41.695  35.357  1.00  29.95
ATOM   1532  N    SER   403    24.997  42.532  36.474  1.00  29.98
ATOM   1533  CA   SER   403    24.385  43.839  36.624  1.00  30.57
ATOM   1534  CB   SER   403    23.655  43.927  37.961  1.00  30.45
ATOM   1535  OG   SER   403    24.372  43.219  38.954  1.00  34.50
ATOM   1536  C    SER   403    25.451  44.917  36.499  1.00  30.16
ATOM   1537  O    SER   403    26.650  44.628  36.581  1.00  30.53
ATOM   1538  N    GLY   404    25.008  46.146  36.265  1.00  29.14
ATOM   1539  CA   GLY   404    25.924  47.257  36.119  1.00  27.59
ATOM   1540  C    GLY   404    26.336  47.472  34.675  1.00  26.53
ATOM   1541  O    GLY   404    26.237  46.563  33.852  1.00  26.16
ATOM   1542  N    ASP   405    26.796  48.685  34.381  1.00  25.54
ATOM   1543  CA   ASP   405    27.241  49.067  33.049  1.00  23.74
ATOM   1544  CB   ASP   405    27.837  50.468  33.062  1.00  23.03
ATOM   1545  CG   ASP   405    26.838  51.530  33.392  1.00  24.18
ATOM   1546  OD1  ASP   405    25.636  51.217  33.568  1.00  22.99
ATOM   1547  OD2  ASP   405    27.277  52.698  33.480  1.00  24.90
ATOM   1548  C    ASP   405    28.324  48.156  32.543  1.00  23.67
ATOM   1549  O    ASP   405    29.292  47.873  33.259  1.00  25.75
ATOM   1550  N    VAL   406    28.211  47.774  31.279  1.00  23.25
ATOM   1551  CA   VAL   406    29.210  46.926  30.656  1.00  22.78
ATOM   1552  CB   VAL   406    29.259  45.506  31.291  1.00  23.65
ATOM   1553  CG1  VAL   406    27.978  44.730  30.983  1.00  25.24
ATOM   1554  CG2  VAL   406    30.505  44.741  30.809  1.00  23.18
ATOM   1555  C    VAL   406    28.916  46.807  29.181  1.00  21.61
ATOM   1556  O    VAL   406    27.767  46.920  28.760  1.00  23.02
ATOM   1557  N    VAL   407    29.973  46.672  28.392  1.00  20.28
ATOM   1558  CA   VAL   407    29.842  46.490  26.960  1.00  17.52
ATOM   1559  CB   VAL   407    30.487  47.639  26.159  1.00  15.18
ATOM   1560  CG1  VAL   407    30.314  47.406  24.675  1.00  11.58
ATOM   1561  CG2  VAL   407    29.852  48.966  26.549  1.00  15.21
```

FIGURE 1A-2

```
ATOM   1562  C    VAL   407    30.548   45.178   26.659  1.00  17.42
ATOM   1563  O    VAL   407    31.753   45.060   26.806  1.00  18.03
ATOM   1564  N    VAL   408    29.773   44.155   26.351  1.00  17.67
ATOM   1565  CA   VAL   408    30.340   42.868   26.025  1.00  18.23
ATOM   1566  CB   VAL   408    29.371   41.733   26.449  1.00  19.02
ATOM   1567  CG1  VAL   408    29.885   40.373   26.012  1.00  18.33
ATOM   1568  CG2  VAL   408    29.178   41.757   27.947  1.00  17.66
ATOM   1569  C    VAL   408    30.572   42.860   24.509  1.00  18.78
ATOM   1570  O    VAL   408    29.686   43.231   23.742  1.00  18.45
ATOM   1571  N    VAL   409    31.800   42.568   24.093  1.00  17.88
ATOM   1572  CA   VAL   409    32.137   42.483   22.679  1.00  17.88
ATOM   1573  CB   VAL   409    33.418   43.249   22.359  1.00  17.72
ATOM   1574  CG1  VAL   409    33.718   43.135   20.884  1.00  19.24
ATOM   1575  CG2  VAL   409    33.264   44.719   22.749  1.00  17.08
ATOM   1576  C    VAL   409    32.308   40.978   22.435  1.00  18.24
ATOM   1577  O    VAL   409    33.267   40.360   22.909  1.00  16.84
ATOM   1578  N    ALA   410    31.392   40.397   21.668  1.00  18.77
ATOM   1579  CA   ALA   410    31.400   38.958   21.473  1.00  18.14
ATOM   1580  CB   ALA   410    30.431   38.351   22.486  1.00  18.34
ATOM   1581  C    ALA   410    31.054   38.426   20.089  1.00  17.88
ATOM   1582  O    ALA   410    30.686   39.176   19.181  1.00  18.45
ATOM   1583  N    THR   411    31.194   37.109   19.950  1.00  16.99
ATOM   1584  CA   THR   411    30.827   36.404   18.738  1.00  17.24
ATOM   1585  CB   THR   411    31.821   35.299   18.361  1.00  16.51
ATOM   1586  OG1  THR   411    31.863   34.331   19.409  1.00  18.59
ATOM   1587  CG2  THR   411    33.204   35.852   18.101  1.00  18.00
ATOM   1588  C    THR   411    29.504   35.711   19.103  1.00  19.33
ATOM   1589  O    THR   411    28.972   35.889   20.204  1.00  20.25
ATOM   1590  N    ASP   412    29.016   34.851   18.221  1.00  21.45
ATOM   1591  CA   ASP   412    27.768   34.145   18.473  1.00  22.15
ATOM   1592  CB   ASP   412    27.239   33.567   17.166  1.00  19.65
ATOM   1593  CG   ASP   412    26.783   34.635   16.221  1.00  15.73
ATOM   1594  OD1  ASP   412    26.071   35.534   16.684  1.00  16.40
ATOM   1595  OD2  ASP   412    27.137   34.591   15.031  1.00  16.44
ATOM   1596  C    ASP   412    27.868   33.064   19.549  1.00  24.32
ATOM   1597  O    ASP   412    26.888   32.380   19.848  1.00  23.10
ATOM   1598  N    ALA   413    29.055   32.920   20.125  1.00  28.20
ATOM   1599  CA   ALA   413    29.284   31.937   21.168  1.00  31.95
ATOM   1600  CB   ALA   413    30.724   31.974   21.611  1.00  31.34
ATOM   1601  C    ALA   413    28.371   32.172   22.360  1.00  35.40
ATOM   1602  O    ALA   413    27.812   31.222   22.905  1.00  38.88
ATOM   1603  N    LEU   414    28.207   33.434   22.755  1.00  38.48
ATOM   1604  CA   LEU   414    27.368   33.772   23.911  1.00  40.49
ATOM   1605  CB   LEU   414    27.411   35.292   24.203  1.00  40.58
ATOM   1606  CG   LEU   414    26.880   35.779   25.570  1.00  39.61
ATOM   1607  CD1  LEU   414    27.734   35.225   26.691  1.00  39.02
ATOM   1608  CD2  LEU   414    26.855   37.290   25.652  1.00  38.26
ATOM   1609  C    LEU   414    25.923   33.298   23.721  1.00  41.04
ATOM   1610  O    LEU   414    25.586   32.246   24.309  1.00  41.21
ATOM   1611  CB   PHE   418    23.962   34.889   28.719  1.00  49.92
ATOM   1612  CG   PHE   418    24.665   35.936   29.554  1.00  49.95
ATOM   1613  CD1  PHE   418    25.107   35.639   30.844  1.00  48.64
ATOM   1614  CD2  PHE   418    24.847   37.228   29.063  1.00  49.25
ATOM   1615  CE1  PHE   418    25.716   36.613   31.632  1.00  48.52
ATOM   1616  CE2  PHE   418    25.457   38.212   29.846  1.00  49.33
ATOM   1617  CZ   PHE   418    25.890   37.905   31.131  1.00  48.87
ATOM   1618  C    PHE   418    21.732   35.511   29.710  1.00  48.72
ATOM   1619  O    PHE   418    21.041   36.066   28.842  1.00  48.37
```

FIGURE 1A-3

```
ATOM   1620  N    PHE   418    22.021   33.365   28.442  1.00  50.78
ATOM   1621  CA   PHE   418    22.670   34.351   29.353  1.00  49.76
ATOM   1622  N    THR   419    21.697   35.856   30.994  1.00  46.61
ATOM   1623  CA   THR   419    20.872   36.956   31.471  1.00  45.71
ATOM   1624  CB   THR   419    20.577   36.801   32.970  1.00  48.47
ATOM   1625  OG1  THR   419    21.767   36.364   33.654  1.00  51.07
ATOM   1626  CG2  THR   419    19.463   35.785   33.182  1.00  48.87
ATOM   1627  C    THR   419    21.628   38.257   31.213  1.00  43.14
ATOM   1628  O    THR   419    22.191   38.865   32.124  1.00  42.27
ATOM   1629  N    GLY   420    21.651   38.662   29.950  1.00  41.16
ATOM   1630  CA   GLY   420    22.362   39.862   29.568  1.00  37.36
ATOM   1631  C    GLY   420    21.732   41.160   30.017  1.00  35.27
ATOM   1632  O    GLY   420    22.436   42.091   30.376  1.00  34.05
ATOM   1633  N    ASP   421    20.407   41.238   29.972  1.00  34.00
ATOM   1634  CA   ASP   421    19.705   42.454   30.365  1.00  31.58
ATOM   1635  CB   ASP   421    19.751   42.629   31.886  1.00  33.33
ATOM   1636  CG   ASP   421    18.986   43.842   32.350  1.00  36.90
ATOM   1637  OD1  ASP   421    17.869   44.063   31.838  1.00  37.58
ATOM   1638  OD2  ASP   421    19.510   44.586   33.212  1.00  39.50
ATOM   1639  C    ASP   421    20.376   43.626   29.654  1.00  29.23
ATOM   1640  O    ASP   421    20.784   44.614   30.274  1.00  27.56
ATOM   1641  N    PHE   422    20.510   43.480   28.340  1.00  27.41
ATOM   1642  CA   PHE   422    21.148   44.485   27.495  1.00  25.64
ATOM   1643  CB   PHE   422    21.792   43.818   26.269  1.00  21.10
ATOM   1644  CG   PHE   422    22.973   42.955   26.601  1.00  17.18
ATOM   1645  CD1  PHE   422    22.951   41.595   26.328  1.00  14.50
ATOM   1646  CD2  PHE   422    24.111   43.504   27.190  1.00  15.37
ATOM   1647  CE1  PHE   422    24.049   40.787   26.638  1.00  14.66
ATOM   1648  CE2  PHE   422    25.214   42.711   27.503  1.00  14.24
ATOM   1649  CZ   PHE   422    25.185   41.353   27.229  1.00  12.70
ATOM   1650  C    PHE   422    20.236   45.626   27.044  1.00  24.93
ATOM   1651  O    PHE   422    19.110   45.409   26.605  1.00  24.73
ATOM   1652  N    ASP   423    20.740   46.846   27.167  1.00  24.37
ATOM   1653  CA   ASP   423    20.010   48.033   26.752  1.00  24.05
ATOM   1654  CB   ASP   423    20.607   49.285   27.398  1.00  24.07
ATOM   1655  CG   ASP   423    20.341   49.339   28.870  1.00  23.88
ATOM   1656  OD1  ASP   423    19.159   49.417   29.246  1.00  27.21
ATOM   1657  OD2  ASP   423    21.294   49.268   29.658  1.00  24.16
ATOM   1658  C    ASP   423    20.048   48.147   25.239  1.00  23.57
ATOM   1659  O    ASP   423    19.154   48.747   24.638  1.00  23.30
ATOM   1660  N    SER   424    21.086   47.585   24.626  1.00  21.30
ATOM   1661  CA   SER   424    21.182   47.611   23.182  1.00  20.49
ATOM   1662  CB   SER   424    21.644   48.981   22.691  1.00  21.66
ATOM   1663  OG   SER   424    23.054   49.075   22.716  1.00  22.36
ATOM   1664  C    SER   424    22.110   46.538   22.633  1.00  20.13
ATOM   1665  O    SER   424    22.919   45.950   23.369  1.00  18.98
ATOM   1666  N    VAL   425    21.940   46.272   21.339  1.00  18.97
ATOM   1667  CA   VAL   425    22.751   45.319   20.588  1.00  16.27
ATOM   1668  CB   VAL   425    21.916   44.096   20.052  1.00  15.46
ATOM   1669  CG1  VAL   425    22.703   43.332   18.999  1.00  12.48
ATOM   1670  CG2  VAL   425    21.560   43.148   21.177  1.00  11.79
ATOM   1671  C    VAL   425    23.259   46.094   19.382  1.00  15.96
ATOM   1672  O    VAL   425    22.501   46.848   18.767  1.00  15.96
ATOM   1673  N    ILE   426    24.556   46.003   19.115  1.00  15.81
ATOM   1674  CA   ILE   426    25.139   46.644   17.947  1.00  16.74
ATOM   1675  CB   ILE   426    26.251   47.640   18.304  1.00  18.60
ATOM   1676  CG2  ILE   426    26.805   48.275   17.022  1.00  18.26
ATOM   1677  CG1  ILE   426    25.697   48.710   19.254  1.00  17.67
```

FIGURE 1A-4

```
ATOM   1678  CD1  ILE  426  26.635  49.857  19.531  1.00  19.38
ATOM   1679  C    ILE  426  25.669  45.434  17.199  1.00  17.81
ATOM   1680  O    ILE  426  26.385  44.611  17.774  1.00  18.67
ATOM   1681  N    ASP  427  25.295  45.318  15.931  1.00  18.83
ATOM   1682  CA   ASP  427  25.625  44.158  15.110  1.00  18.61
ATOM   1683  CB   ASP  427  24.284  43.525  14.711  1.00  19.39
ATOM   1684  CG   ASP  427  24.405  42.146  14.094  1.00  18.80
ATOM   1685  OD1  ASP  427  25.516  41.611  13.922  1.00  17.99
ATOM   1686  OD2  ASP  427  23.337  41.592  13.774  1.00  19.23
ATOM   1687  C    ASP  427  26.417  44.516  13.870  1.00  18.42
ATOM   1688  O    ASP  427  26.077  45.479  13.185  1.00  19.02
ATOM   1689  N    CYS  428  27.454  43.728  13.570  1.00  17.93
ATOM   1690  CA   CYS  428  28.277  43.944  12.375  1.00  18.18
ATOM   1691  CB   CYS  428  29.628  43.247  12.502  1.00  18.00
ATOM   1692  SG   CYS  428  29.549  41.453  12.475  1.00  19.71
ATOM   1693  C    CYS  428  27.555  43.423  11.135  1.00  18.32
ATOM   1694  O    CYS  428  27.944  43.708  10.011  1.00  21.01
ATOM   1695  N    ASN  429  26.530  42.609  11.351  1.00  18.21
ATOM   1696  CA   ASN  429  25.713  42.055  10.272  1.00  18.70
ATOM   1697  CB   ASN  429  25.054  43.180   9.462  1.00  18.15
ATOM   1698  CG   ASN  429  24.271  44.152  10.336  1.00  18.71
ATOM   1699  OD1  ASN  429  24.504  45.356  10.294  1.00  19.89
ATOM   1700  ND2  ASN  429  23.358  43.633  11.147  1.00  17.96
ATOM   1701  C    ASN  429  26.386  41.043   9.352  1.00  18.76
ATOM   1702  O    ASN  429  25.867  40.732   8.283  1.00  18.71
ATOM   1703  N    THR  430  27.517  40.492   9.781  1.00  19.72
ATOM   1704  CA   THR  430  28.226  39.486   8.996  1.00  19.58
ATOM   1705  CB   THR  430  29.527  40.044   8.377  1.00  18.32
ATOM   1706  OG1  THR  430  30.433  40.441   9.413  1.00  18.44
ATOM   1707  CG2  THR  430  29.215  41.241   7.505  1.00  16.13
ATOM   1708  C    THR  430  28.532  38.291   9.893  1.00  20.27
ATOM   1709  O    THR  430  28.475  38.399  11.112  1.00  20.61
ATOM   1710  N    CME  431  28.829  37.144   9.300  1.00  21.71
ATOM   1711  CA   CME  431  29.118  35.958  10.088  1.00  23.49
ATOM   1712  C    CME  431  30.100  35.064   9.351  1.00  23.26
ATOM   1713  O    CME  431  30.117  35.024   8.124  1.00  24.03
ATOM   1714  CB   CME  431  27.822  35.191  10.390  1.00  24.65
ATOM   1715  SG   CME  431  26.882  34.701   8.908  1.00  28.78
ATOM   1716  2SG  CME  431  25.080  34.061   9.615  1.00  30.80
ATOM   1717  2CB  CME  431  25.261  32.249   9.685  1.00  32.16
ATOM   1718  2CA  CME  431  26.230  31.721  10.742  1.00  34.08
ATOM   1719  OG   CME  431  26.088  32.402  11.978  1.00  36.06
ATOM   1720  N    VAL  432  30.949  34.393  10.112  1.00  23.66
ATOM   1721  CA   VAL  432  31.952  35.489   9.569  1.00  25.04
ATOM   1722  CB   VAL  432  33.212  33.429  10.487  1.00  26.14
ATOM   1723  CG1  VAL  432  34.215  32.412   9.968  1.00  25.89
ATOM   1724  CG2  VAL  432  33.860  34.811  10.587  1.00  26.03
ATOM   1725  C    VAL  432  31.295  32.135   9.552  1.00  24.44
ATOM   1726  O    VAL  432  30.594  31.780  10.493  1.00  24.47
ATOM   1727  N    THR  433  31.486  31.390   8.474  1.00  25.86
ATOM   1728  CA   THR  433  30.890  30.062   8.374  1.00  26.89
ATOM   1729  CB   THR  433  29.443  30.140   7.829  1.00  26.52
ATOM   1730  OG1  THR  433  28.812  28.859   7.968  1.00  28.69
ATOM   1731  CG2  THR  433  29.438  30.564   6.362  1.00  24.41
ATOM   1732  C    THR  433  31.718  29.093   7.527  1.00  26.04
ATOM   1733  O    THR  433  32.543  29.504   6.709  1.00  24.26
ATOM   1734  N    GLN  434  31.519  27.802   7.774  1.00  27.85
ATOM   1735  CA   GLN  434  32.221  26.750   7.052  1.00  28.61
```

FIGURE 1A-5

```
ATOM   1736  CB   GLN  434   32.034  25.402   7.745  1.00  31.09
ATOM   1737  CG   GLN  434   32.787  25.245   9.044  1.00  35.42
ATOM   1738  CD   GLN  434   34.249  24.893   8.853  1.00  37.94
ATOM   1739  OE1  GLN  434   34.643  23.759   9.081  1.00  44.05
ATOM   1740  NE2  GLN  434   35.057  25.853   8.428  1.00  37.21
ATOM   1741  C    GLN  434   31.701  26.657   5.628  1.00  27.68
ATOM   1742  O    GLN  434   30.494  26.673   5.387  1.00  26.87
ATOM   1743  N    THR  435   32.619  26.503   4.692  1.00  26.85
ATOM   1744  CA   THR  435   32.246  26.416   3.305  1.00  27.23
ATOM   1745  CB   THR  435   32.334  27.804   2.651  1.00  29.34
ATOM   1746  OG1  THR  435   31.794  27.751   1.323  1.00  33.86
ATOM   1747  CG2  THR  435   33.792  28.265   2.593  1.00  29.75
ATOM   1748  C    THR  435   33.184  25.433   2.609  1.00  25.74
ATOM   1749  O    THR  435   34.350  25.287   3.001  1.00  24.92
ATOM   1750  N    VAL  436   32.658  24.734   1.608  1.00  23.49
ATOM   1751  CA   VAL  436   33.447  23.774   0.858  1.00  22.57
ATOM   1752  CB   VAL  436   32.712  22.391   0.684  1.00  21.11
ATOM   1753  CG1  VAL  436   31.389  22.557  -0.029  1.00  19.30
ATOM   1754  CG2  VAL  436   33.602  21.399  -0.061  1.00  17.28
ATOM   1755  C    VAL  436   33.800  24.370  -0.493  1.00  22.79
ATOM   1756  O    VAL  436   33.029  25.129  -1.071  1.00  23.69
ATOM   1757  N    ASP  437   35.009  24.084  -0.951  1.00  23.38
ATOM   1758  CA   ASP  437   35.470  24.562  -2.237  1.00  23.03
ATOM   1759  CB   ASP  437   36.593  25.582  -2.043  1.00  25.16
ATOM   1760  CG   ASP  437   37.087  26.176  -3.358  1.00  27.57
ATOM   1761  OD1  ASP  437   36.421  26.006  -4.408  1.00  28.15
ATOM   1762  OD2  ASP  437   38.156  26.820  -3.332  1.00  30.89
ATOM   1763  C    ASP  437   35.976  23.344  -2.991  1.00  22.31
ATOM   1764  O    ASP  437   36.949  22.724  -2.581  1.00  23.36
ATOM   1765  N    PHE  438   35.257  22.948  -4.031  1.00  22.10
ATOM   1766  CA   PHE  438   35.646  21.804  -4.849  1.00  24.52
ATOM   1767  CB   PHE  438   34.444  21.329  -5.676  1.00  24.50
ATOM   1768  CG   PHE  438   33.252  20.944  -4.833  1.00  27.22
ATOM   1769  CD1  PHE  438   32.162  21.800  -4.713  1.00  27.14
ATOM   1770  CD2  PHE  438   33.242  19.739  -4.123  1.00  27.35
ATOM   1771  CE1  PHE  438   31.079  21.466  -3.897  1.00  27.93
ATOM   1772  CE2  PHE  438   32.166  19.394  -3.305  1.00  26.72
ATOM   1773  CZ   PHE  438   31.084  20.257  -3.191  1.00  28.20
ATOM   1774  C    PHE  438   36.784  22.298  -5.741  1.00  25.20
ATOM   1775  O    PHE  438   36.655  22.372  -6.964  1.00  27.05
ATOM   1776  N    SER  439   37.905  22.609  -5.094  1.00  25.29
ATOM   1777  CA   SER  439   39.087  23.167  -5.732  1.00  24.15
ATOM   1778  CB   SER  439   39.928  23.886  -4.682  1.00  24.18
ATOM   1779  OG   SER  439   39.975  23.146  -3.471  1.00  24.29
ATOM   1780  C    SER  439   39.978  22.302  -6.614  1.00  24.46
ATOM   1781  O    SER  439   40.881  22.834  -7.266  1.00  24.35
ATOM   1782  N    LEU  440   39.766  20.988  -6.615  1.00  24.35
ATOM   1783  CA   LEU  440   40.553  20.083  -7.460  1.00  26.08
ATOM   1784  CB   LEU  440   40.122  20.254  -8.923  1.00  25.16
ATOM   1785  CG   LEU  440   38.607  20.230  -9.120  1.00  26.05
ATOM   1786  CD1  LEU  440   38.242  20.519 -10.563  1.00  25.63
ATOM   1787  CD2  LEU  440   38.072  18.879  -8.673  1.00  26.91
ATOM   1788  C    LEU  440   42.069  20.314  -7.341  1.00  26.71
ATOM   1789  O    LEU  440   42.786  20.331  -8.341  1.00  28.25
ATOM   1790  N    ASP  441   42.551  20.455  -6.111  1.00  26.91
ATOM   1791  CA   ASP  441   43.966  20.705  -5.858  1.00  25.13
ATOM   1792  CB   ASP  441   44.167  22.197  -5.573  1.00  25.06
ATOM   1793  CG   ASP  441   43.347  22.691  -4.367  1.00  27.62
```

FIGURE 1A-6

```
ATOM  1794  OD1  ASP  441  42.462  21.954  -3.863  1.00  26.35
ATOM  1795  OD2  ASP  441  43.605  23.821  -3.905  1.00  26.72
ATOM  1796  C    ASP  441  44.471  19.883  -4.669  1.00  24.82
ATOM  1797  O    ASP  441  45.123  20.420  -3.781  1.00  24.32
ATOM  1798  N    PRO  442  44.328  18.548  -4.718  1.00  24.11
ATOM  1799  CD   PRO  442  44.909  17.709  -3.650  1.00  23.78
ATOM  1800  CA   PRO  442  43.750  17.712  -5.773  1.00  24.26
ATOM  1801  CB   PRO  442  44.505  16.401  -5.588  1.00  23.48
ATOM  1802  CG   PRO  442  44.562  16.289  -4.100  1.00  23.95
ATOM  1803  C    PRO  442  42.250  17.450  -5.747  1.00  24.59
ATOM  1804  O    PRO  442  41.674  17.082  -6.778  1.00  26.09
ATOM  1805  N    THR  443  41.608  17.664  -4.601  1.00  25.49
ATOM  1806  CA   THR  443  40.183  17.360  -4.465  1.00  23.89
ATOM  1807  CB   THR  443  40.014  16.138  -3.532  1.00  23.42
ATOM  1808  OG1  THR  443  40.674  16.405  -2.291  1.00  24.59
ATOM  1809  CG2  THR  443  40.643  14.905  -4.145  1.00  22.83
ATOM  1810  C    THR  443  39.269  18.502  -3.996  1.00  23.35
ATOM  1811  O    THR  443  38.669  19.197  -4.818  1.00  22.91
ATOM  1812  N    PHE  444  39.125  18.666  -2.684  1.00  22.01
ATOM  1813  CA   PHE  444  38.271  19.713  -2.141  1.00  21.72
ATOM  1814  CB   PHE  444  36.883  19.159  -1.748  1.00  20.61
ATOM  1815  CG   PHE  444  36.910  18.077  -0.693  1.00  18.78
ATOM  1816  CD1  PHE  444  36.849  18.399   0.659  1.00  19.13
ATOM  1817  CD2  PHE  444  36.954  16.731  -1.053  1.00  18.82
ATOM  1818  CE1  PHE  444  36.827  17.394   1.640  1.00  18.38
ATOM  1819  CE2  PHE  444  36.933  15.723  -0.081  1.00  16.79
ATOM  1820  CZ   PHE  444  36.869  16.052   1.261  1.00  16.58
ATOM  1821  C    PHE  444  38.931  20.432  -0.971  1.00  21.99
ATOM  1822  O    PHE  444  39.983  19.998  -0.481  1.00  22.62
ATOM  1823  N    THR  445  38.333  21.548  -0.558  1.00  22.06
ATOM  1824  CA   THR  445  38.834  22.353   0.552  1.00  22.10
ATOM  1825  CB   THR  445  39.519  23.642   0.040  1.00  22.17
ATOM  1826  OG1  THR  445  40.542  23.311  -0.903  1.00  24.33
ATOM  1827  CG2  THR  445  40.132  24.423   1.187  1.00  20.65
ATOM  1828  C    THR  445  37.682  22.795   1.452  1.00  21.98
ATOM  1829  O    THR  445  36.674  23.298   0.971  1.00  21.81
ATOM  1830  N    ILE  446  37.806  22.555   2.745  1.00  23.22
ATOM  1831  CA   ILE  446  36.789  22.998   3.684  1.00  26.55
ATOM  1832  CB   ILE  446  36.318  21.874   4.652  1.00  25.92
ATOM  1833  CG2  ILE  446  35.603  22.461   5.858  1.00  25.60
ATOM  1834  CG1  ILE  446  35.346  20.939   3.929  1.00  22.35
ATOM  1835  CD1  ILE  446  35.814  19.552   3.909  1.00  21.01
ATOM  1836  C    ILE  446  37.474  24.125   4.437  1.00  28.48
ATOM  1837  O    ILE  446  38.516  23.921   5.065  1.00  30.14
ATOM  1838  N    GLU  447  36.943  25.330   4.276  1.00  29.02
ATOM  1839  CA   GLU  447  37.494  26.509   4.916  1.00  28.87
ATOM  1840  CB   GLU  447  38.245  27.325   3.867  1.00  29.79
ATOM  1841  CG   GLU  447  37.433  27.601   2.611  1.00  31.68
ATOM  1842  CD   GLU  447  38.282  28.042   1.435  1.00  33.86
ATOM  1843  OE1  GLU  447  39.496  28.280   1.609  1.00  35.31
ATOM  1844  OE2  GLU  447  37.733  28.133   0.317  1.00  37.54
ATOM  1845  C    GLU  447  36.340  27.310   5.520  1.00  29.27
ATOM  1846  O    GLU  447  35.330  26.731   5.919  1.00  29.04
ATOM  1847  N    THR  448  36.497  28.625   5.633  1.00  28.51
ATOM  1848  CA   THR  448  35.431  29.453   6.167  1.00  29.44
ATOM  1849  CB   THR  448  35.720  29.947   7.596  1.00  29.38
ATOM  1850  OG1  THR  448  36.836  30.841   7.584  1.00  30.76
ATOM  1851  CG2  THR  448  36.019  28.797   8.514  1.00  30.09
```

FIGURE 1A-7

```
ATOM   1852  C    THR  448   35.267  30.657   5.261  1.00  29.41
ATOM   1853  O    THR  448   36.198  31.027   4.549  1.00  29.33
ATOM   1854  N    THR  449   34.059  31.213   5.228  1.00  29.92
ATOM   1855  CA   THR  449   33.773  32.390   4.421  1.00  29.42
ATOM   1856  CB   THR  449   32.943  32.047   3.174  1.00  28.46
ATOM   1857  OG1  THR  449   33.623  31.047   2.417  1.00  29.99
ATOM   1858  CG2  THR  449   32.770  33.272   2.294  1.00  28.99
ATOM   1859  C    THR  449   32.976  33.363   5.276  1.00  29.18
ATOM   1860  O    THR  449   32.068  32.953   6.006  1.00  28.97
ATOM   1861  N    THR  450   33.380  34.628   5.256  1.00  27.76
ATOM   1862  CA   THR  450   32.668  35.638   6.008  1.00  26.60
ATOM   1863  CB   THR  450   33.600  36.759   6.469  1.00  27.00
ATOM   1864  OG1  THR  450   34.613  36.202   7.324  1.00  26.73
ATOM   1865  CG2  THR  450   32.812  37.819   7.247  1.00  25.31
ATOM   1866  C    THR  450   31.578  36.145   5.076  1.00  26.94
ATOM   1867  O    THR  450   31.856  36.685   4.003  1.00  26.91
ATOM   1868  N    LEU  451   30.333  35.896   5.464  1.00  26.50
ATOM   1869  CA   LEU  451   29.184  36.267   4.661  1.00  25.37
ATOM   1870  CB   LEU  451   28.401  35.007   4.294  1.00  25.61
ATOM   1871  CG   LEU  451   29.076  33.801   3.662  1.00  26.81
ATOM   1872  CD1  LEU  451   28.101  32.649   3.739  1.00  27.81
ATOM   1873  CD2  LEU  451   29.459  34.096   2.220  1.00  26.32
ATOM   1874  C    LEU  451   28.215  37.168   5.399  1.00  24.26
ATOM   1875  O    LEU  451   28.287  37.313   6.622  1.00  23.50
ATOM   1876  N    PRO  452   27.324  37.834   4.646  1.00  22.96
ATOM   1877  CD   PRO  452   27.281  37.930   3.174  1.00  23.01
ATOM   1878  CA   PRO  452   26.328  38.707  15.252  1.00  21.34
ATOM   1879  CB   PRO  452   25.528  39.189   4.045  1.00  22.18
ATOM   1880  CG   PRO  452   26.545  39.213   2.957  1.00  23.73
ATOM   1881  C    PRO  452   25.490  37.742   6.069  1.00  20.41
ATOM   1882  O    PRO  452   25.315  36.587   5.674  1.00  20.81
ATOM   1883  N    GLN  453   24.983  38.197   7.201  1.00  19.57
ATOM   1884  CA   GLN  453   24.179  37.334   8.053  1.00  18.59
ATOM   1885  CB   GLN  453   23.888  38.047   9.364  1.00  18.03
ATOM   1886  CG   GLN  453   22.915  39.183   9.194  1.00  16.29
ATOM   1887  CD   GLN  453   22.857  40.088  10.384  1.00  17.25
ATOM   1888  OE1  GLN  453   22.521  41.259  10.244  1.00  18.98
ATOM   1889  NE2  GLN  453   23.184  39.565  11.571  1.00  12.28
ATOM   1890  C    GLN  453   22.861  37.023   7.368  1.00  19.31
ATOM   1891  O    GLN  453   22.451  37.735   6.445  1.00  19.70
ATOM   1892  N    ASP  454   22.215  35.939   7.786  1.00  19.47
ATOM   1893  CA   ASP  454   20.915  35.592   7.225  1.00  20.05
ATOM   1894  CB   ASP  454   20.831  34.095   6.866  1.00  20.04
ATOM   1895  CG   ASP  454   20.782  33.200   8.086  1.00  22.40
ATOM   1896  OD1  ASP  454   21.568  33.406   9.032  1.00  22.31
ATOM   1897  OD2  ASP  454   19.926  32.296   8.103  1.00  25.12
ATOM   1898  C    ASP  454   19.883  36.001   8.281  1.00  19.45
ATOM   1899  O    ASP  454   20.250  36.566   9.309  1.00  19.72
ATOM   1900  N    ALA  455   18.607  35.720   8.041  1.00  20.44
ATOM   1901  CA   ALA  455   17.544  36.083   8.986  1.00  20.48
ATOM   1902  CB   ALA  455   16.178  35.765   8.390  1.00  17.68
ATOM   1903  C    ALA  455   17.662  35.469  10.380  1.00  19.73
ATOM   1904  O    ALA  455   17.265  36.091  11.368  1.00  22.40
ATOM   1905  N    VAL  456   18.147  34.234  10.462  1.00  20.09
ATOM   1906  CA   VAL  456   18.295  33.564  11.754  1.00  19.00
ATOM   1907  CB   VAL  456   18.746  32.099  11.578  1.00  19.21
ATOM   1908  CG1  VAL  456   19.143  31.485  12.933  1.00  17.42
ATOM   1909  CG2  VAL  456   17.636  31.293  10.917  1.00  16.27
```

FIGURE 1A-8

```
ATOM   1910  C    VAL  456    19.316  34.319  12.594  1.00  17.87
ATOM   1911  O    VAL  456    19.062  34.642  13.744  1.00  18.04
ATOM   1912  N    SER  457    20.438  34.660  11.972  1.00  19.53
ATOM   1913  CA   SER  457    21.517  35.392  12.630  1.00  19.10
ATOM   1914  CB   SER  457    22.673  35.589  11.644  1.00  17.70
ATOM   1915  OG   SER  457    23.631  36.508  12.143  1.00  20.26
ATOM   1916  C    SER  457    21.049  36.745  13.157  1.00  18.37
ATOM   1917  O    SER  457    21.246  37.063  14.324  1.00  18.88
ATOM   1918  N    ARG  458    20.402  37.519  12.292  1.00  18.67
ATOM   1919  CA   ARG  458    19.916  38.851  12.636  1.00  18.34
ATOM   1920  CB   ARG  458    19.356  39.551  11.389  1.00  15.93
ATOM   1921  CG   ARG  458    19.049  41.042  11.573  1.00  15.45
ATOM   1922  CD   ARG  458    18.892  41.721  10.220  1.00  13.63
ATOM   1923  NE   ARG  458    18.931  43.176  10.303  1.00  14.59
ATOM   1924  CZ   ARG  458    19.865  43.935   9.733  1.00  16.49
ATOM   1925  NH1  ARG  458    19.816  45.257   9.859  1.00  18.89
ATOM   1926  NH2  ARG  458    20.871  43.377   9.062  1.00  17.85
ATOM   1927  C    ARG  458    18.863  38.798  13.723  1.00  18.62
ATOM   1928  O    ARG  458    18.924  39.562  14.674  1.00  18.82
ATOM   1929  N    THR  459    17.900  37.896  13.580  1.00  20.47
ATOM   1930  CA   THR  459    16.831  37.759  14.571  1.00  22.62
ATOM   1931  CB   THR  459    15.759  36.708  14.120  1.00  23.54
ATOM   1932  OG1  THR  459    15.175  37.109  12.872  1.00  23.92
ATOM   1933  CG2  THR  459    14.655  36.566  15.168  1.00  23.27
ATOM   1934  C    THR  459    17.395  37.354  15.939  1.00  22.25
ATOM   1935  O    THR  459    16.988  37.896  16.974  1.00  22.42
ATOM   1936  N    GLN  460    18.324  36.400  15.945  1.00  21.83
ATOM   1937  CA   GLN  460    18.913  35.943  17.196  1.00  23.58
ATOM   1938  CB   GLN  460    19.575  34.574  17.022  1.00  28.20
ATOM   1939  CG   GLN  460    18.532  33.481  16.700  1.00  34.19
ATOM   1940  CD   GLN  460    19.106  32.076  16.567  1.00  38.92
ATOM   1941  OE1  GLN  460    18.389  31.140  16.174  1.00  41.47
ATOM   1942  NE2  GLN  460    20.386  31.910  16.903  1.00  41.20
ATOM   1943  C    GLN  460    19.847  36.972  17.814  1.00  21.76
ATOM   1944  O    GLN  460    19.841  37.167  19.024  1.00  22.18
ATOM   1945  N    ARG  461    20.601  37.677  16.983  1.00  20.55
ATOM   1946  CA   ARG  461    21.490  38.710  17.485  1.00  19.90
ATOM   1947  CB   ARG  461    22.460  39.178  16.398  1.00  18.96
ATOM   1948  CG   ARG  461    23.810  38.533  16.562  1.00  18.17
ATOM   1949  CD   ARG  461    24.341  37.840  15.337  1.00  20.30
ATOM   1950  NE   ARG  461    25.088  38.742  14.479  1.00  21.22
ATOM   1951  CZ   ARG  461    26.196  38.426  13.812  1.00  20.58
ATOM   1952  NH1  ARG  461    26.740  37.220  13.886  1.00  18.60
ATOM   1953  NH2  ARG  461    26.716  39.316  12.992  1.00  23.17
ATOM   1954  C    ARG  461    20.661  39.855  18.042  1.00  20.36
ATOM   1955  O    ARG  461    20.824  40.229  19.201  1.00  21.32
ATOM   1956  N    ARG  462    19.724  40.366  17.247  1.00  20.67
ATOM   1957  CA   ARG  462    18.847  41.453  17.685  1.00  20.84
ATOM   1958  CB   ARG  462    17.857  41.820  16.574  1.00  21.40
ATOM   1959  CG   ARG  462    16.931  42.969  16.941  1.00  22.08
ATOM   1960  CD   ARG  462    15.792  43.156  15.944  1.00  21.34
ATOM   1961  NE   ARG  462    14.830  42.062  16.007  1.00  21.80
ATOM   1962  CZ   ARG  462    13.742  41.978  15.247  1.00  21.21
ATOM   1963  NH1  ARG  462    12.935  40.937  15.371  1.00  22.57
ATOM   1964  NH2  ARG  462    13.459  42.929  14.367  1.00  18.74
ATOM   1965  C    ARG  462    18.056  41.018  18.926  1.00  21.55
ATOM   1966  O    ARG  462    17.801  41.822  19.833  1.00  21.69
ATOM   1967  N    GLY  463    17.711  39.731  18.965  1.00  21.00
```

FIGURE 1A-9

```
ATOM   1968  CA   GLY   463    16.950   39.173   20.064  1.00  21.40
ATOM   1969  C    GLY   463    17.594   39.194   21.434  1.00  23.27
ATOM   1970  O    GLY   463    16.951   38.847   22.420  1.00  25.42
ATOM   1971  N    ARG   464    18.856   39.586   21.522  1.00  24.33
ATOM   1972  CA   ARG   464    19.530   39.644   22.814  1.00  25.08
ATOM   1973  CB   ARG   464    21.044   39.714   22.620  1.00  25.94
ATOM   1974  CG   ARG   464    21.632   38.564   21.823  1.00  28.27
ATOM   1975  CD   ARG   464    21.511   37.237   22.554  1.00  31.16
ATOM   1976  NE   ARG   464    22.670   36.393   22.274  1.00  35.52
ATOM   1977  CZ   ARG   464    22.887   35.766   21.119  1.00  39.25
ATOM   1978  NH1  ARG   464    23.987   35.031   20.963  1.00  40.53
ATOM   1979  NH2  ARG   464    21.991   35.828   20.132  1.00  39.41
ATOM   1980  C    ARG   464    19.042   40.848   23.634  1.00  25.24
ATOM   1981  O    ARG   464    19.297   40.933   24.843  1.00  24.97
ATOM   1982  N    THR   465    18.360   41.784   22.975  1.00  25.46
ATOM   1983  CA   THR   465    17.821   42.970   23.651  1.00  25.46
ATOM   1984  CB   THR   465    18.428   44.286   23.081  1.00  22.61
ATOM   1985  OG1  THR   465    18.181   45.357   23.993  1.00  21.95
ATOM   1986  CG2  THR   465    17.831   44.644   21.731  1.00  19.47
ATOM   1987  C    THR   465    16.285   42.987   23.545  1.00  27.08
ATOM   1988  O    THR   465    15.697   42.133   22.874  1.00  27.65
ATOM   1989  N    GLY   466    15.644   43.931   24.230  1.00  28.70
ATOM   1990  CA   GLY   466    14.194   44.025   24.192  1.00  30.14
ATOM   1991  C    GLY   466    13.486   42.861   24.871  1.00  31.44
ATOM   1992  O    GLY   466    12.354   42.508   24.512  1.00  32.18
ATOM   1993  N    ARG   467    14.135   42.280   25.875  1.00  32.23
ATOM   1994  CA   ARG   467    13.578   41.143   26.600  1.00  32.05
ATOM   1995  CB   ARG   467    14.679   40.144   26.937  1.00  29.85
ATOM   1996  CG   ARG   467    15.369   39.574   25.734  1.00  28.91
ATOM   1997  CD   ARG   467    16.432   38.620   26.174  1.00  30.63
ATOM   1998  NE   ARG   467    17.122   38.018   25.044  1.00  33.36
ATOM   1999  CZ   ARG   467    17.549   36.760   25.027  1.00  35.37
ATOM   2000  NH1  ARG   467    18.173   36.275   23.959  1.00  36.51
ATOM   2001  NH2  ARG   467    17.370   35.987   26.088  1.00  36.08
ATOM   2002  C    ARG   467    12.858   41.567   27.873  1.00  33.30
ATOM   2003  O    ARG   467    13.431   41.573   28.963  1.00  34.17
ATOM   2004  N    GLY   468    11.583   41.898   27.732  1.00  34.55
ATOM   2005  CA   GLY   468    10.808   42.314   28.882  1.00  34.38
ATOM   2006  C    GLY   468    10.967   43.791   29.163  1.00  34.53
ATOM   2007  O    GLY   468    10.558   44.274   30.213  1.00  36.37
ATOM   2008  N    LYS   469    11.590   44.503   28.237  1.00  33.19
ATOM   2009  CA   LYS   469    11.787   45.932   28.379  1.00  32.67
ATOM   2010  CB   LYS   469    12.797   46.258   29.491  1.00  34.53
ATOM   2011  CG   LYS   469    14.257   45.905   29.206  1.00  35.53
ATOM   2012  CD   LYS   469    15.157   46.408   30.336  1.00  35.50
ATOM   2013  CE   LYS   469    16.634   46.384   29.961  1.00  36.18
ATOM   2014  NZ   LYS   469    17.508   46.793   31.106  1.00  33.86
ATOM   2015  C    LYS   469    12.291   46.417   27.045  1.00  31.65
ATOM   2016  O    LYS   469    12.765   45.627   26.234  1.00  32.31
ATOM   2017  N    PRO   470    12.164   47.717   26.778  1.00  30.75
ATOM   2018  CD   PRO   470    11.491   48.754   27.580  1.00  30.88
ATOM   2019  CA   PRO   470    12.626   48.255   25.500  1.00  28.89
ATOM   2020  CB   PRO   470    12.238   49.731   25.597  1.00  29.64
ATOM   2021  CG   PRO   470    11.044   49.721   26.519  1.00  30.22
ATOM   2022  C    PRO   470    14.130   48.089   25.298  1.00  27.83
ATOM   2023  O    PRO   470    14.910   48.069   26.256  1.00  28.38
ATOM   2024  N    GLY   471    14.525   47.975   24.040  1.00  25.46
ATOM   2025  CA   GLY   471    15.923   47.834   23.701  1.00  22.38
```

FIGURE 1A-10

```
ATOM   2026  C    GLY  471   16.164  48.513  22.373  1.00  20.97
ATOM   2027  O    GLY  471   15.216  48.887  21.668  1.00  20.48
ATOM   2028  N    ILE  472   17.431  48.715  22.043  1.00  20.35
ATOM   2029  CA   ILE  472   17.803  49.344  20.792  1.00  19.19
ATOM   2030  CB   ILE  472   18.500  50.710  21.018  1.00  19.31
ATOM   2031  CG2  ILE  472   18.916  51.317  19.697  1.00  19.60
ATOM   2032  CG1  ILE  472   17.534  51.680  21.706  1.00  20.42
ATOM   2033  CD1  ILE  472   18.101  53.048  21.989  1.00  20.47
ATOM   2034  C    ILE  472   18.727  48.400  20.045  1.00  20.13
ATOM   2035  O    ILE  472   19.509  47.650  20.651  1.00  18.96
ATOM   2036  N    TYR  473   18.593  48.402  18.726  1.00  20.53
ATOM   2037  CA   TYR  473   19.406  47.562  17.865  1.00  20.24
ATOM   2038  CB   TYR  473   18.527  46.504  17.184  1.00  17.07
ATOM   2039  CG   TYR  473   19.236  45.657  16.154  1.00  16.23
ATOM   2040  CD1  TYR  473   20.183  44.704  16.537  1.00  16.38
ATOM   2041  CE1  TYR  473   20.844  43.918  15.594  1.00  15.97
ATOM   2042  CD2  TYR  473   18.961  45.809  14.792  1.00  15.90
ATOM   2043  CE2  TYR  473   19.615  45.033  13.830  1.00  17.92
ATOM   2044  CZ   TYR  473   20.561  44.085  14.236  1.00  19.05
ATOM   2045  OH   TYR  473   21.232  43.322  13.292  1.00  16.03
ATOM   2046  C    TYR  473   20.054  48.481  16.839  1.00  20.38
ATOM   2047  O    TYR  473   19.372  49.235  16.156  1.00  21.81
ATOM   2048  N    ARG  474   21.377  48.486  16.795  1.00  21.07
ATOM   2049  CA   ARG  474   22.087  49.311  15.833  1.00  21.12
ATOM   2050  CB   ARG  474   23.092  50.217  16.535  1.00  22.36
ATOM   2051  CG   ARG  474   22.454  51.054  17.627  1.00  24.18
ATOM   2052  CD   ARG  474   23.444  51.980  18.304  1.00  25.34
ATOM   2053  NE   ARG  474   22.844  52.571  19.493  1.00  26.57
ATOM   2054  CZ   ARG  474   21.960  53.562  19.476  1.00  26.60
ATOM   2055  NH1  ARG  474   21.468  54.026  20.615  1.00  25.83
ATOM   2056  NH2  ARG  474   21.580  54.105  18.327  1.00  27.33
ATOM   2057  C    ARG  474   22.766  48.354  14.876  1.00  21.22
ATOM   2058  O    ARG  474   23.282  47.310  15.281  1.00  21.04
ATOM   2059  N    PHE  475   22.740  48.699  13.599  1.00  22.21
ATOM   2060  CA   PHE  475   23.306  47.849  12.575  1.00  23.28
ATOM   2061  CB   PHE  475   22.170  47.148  11.815  1.00  25.19
ATOM   2062  CG   PHE  475   21.164  48.103  11.199  1.00  26.26
ATOM   2063  CD1  PHE  475   20.079  48.570  11.941  1.00  25.75
ATOM   2064  CD2  PHE  475   21.307  48.537   9.878  1.00  26.21
ATOM   2065  CE1  PHE  475   19.156  49.452  11.374  1.00  24.75
ATOM   2066  CE2  PHE  475   20.390  49.417   9.306  1.00  24.17
ATOM   2067  CZ   PHE  475   19.314  49.873  10.060  1.00  23.51
ATOM   2068  C    PHE  475   24.151  48.638  11.598  1.00  23.82
ATOM   2069  O    PHE  475   23.960  49.843  11.428  1.00  25.90
ATOM   2070  N    VAL  476   25.082  47.946  10.955  1.00  23.60
ATOM   2071  CA   VAL  476   25.957  48.545   9.959  1.00  22.75
ATOM   2072  CB   VAL  476   27.299  47.772   9.898  1.00  23.15
ATOM   2073  CG1  VAL  476   28.178  48.292   8.773  1.00  22.36
ATOM   2074  CG2  VAL  476   28.019  47.881  11.227  1.00  23.76
ATOM   2075  C    VAL  476   25.263  48.440   8.594  1.00  21.91
ATOM   2076  O    VAL  476   25.323  49.353   7.774  1.00  22.30
ATOM   2077  N    ALA  477   24.590  47.320   8.371  1.00  21.29
ATOM   2078  CA   ALA  477   23.919  47.066   7.111  1.00  21.64
ATOM   2079  CB   ALA  477   24.658  45.974   6.328  1.00  21.38
ATOM   2080  C    ALA  477   22.454  46.696   7.301  1.00  21.13
ATOM   2081  O    ALA  477   22.091  45.962   8.218  1.00  20.40
ATOM   2082  N    PRO  478   21.598  47.195   6.403  1.00  21.02
ATOM   2083  CD   PRO  478   21.990  48.162   5.360  1.00  21.21
```

FIGURE 1A-11

```
ATOM   2084  CA   PRO   478    20.152   46.976    6.400  1.00  23.06
ATOM   2085  CB   PRO   478    19.648   48.180    5.601  1.00  23.71
ATOM   2086  CG   PRO   478    20.722   48.326    4.561  1.00  23.74
ATOM   2087  C    PRO   478    19.669   45.653    5.791  1.00  21.67
ATOM   2088  O    PRO   478    18.532   45.226    6.028  1.00  21.26
ATOM   2089  N    GLY   479    20.515   45.021    4.992  1.00  19.99
ATOM   2090  CA   GLY   479    20.118   43.779    4.368  1.00  19.25
ATOM   2091  C    GLY   479    20.473   42.550    5.166  1.00  19.67
ATOM   2092  O    GLY   479    21.255   42.611    6.117  1.00  19.75
ATOM   2093  N    GLU   480    19.892   41.430    4.762  1.00  18.74
ATOM   2094  CA   GLU   480    20.135   40.145    5.395  1.00  19.62
ATOM   2095  CB   GLU   480    19.266   39.994    6.641  1.00  19.51
ATOM   2096  CG   GLU   480    17.798   39.867    6.293  1.00  20.84
ATOM   2097  CD   GLU   480    16.907   39.754    7.487  1.00  20.69
ATOM   2098  OE1  GLU   480    15.720   40.123    7.353  1.00  21.54
ATOM   2099  OE2  GLU   480    17.383   39.300    8.547  1.00  20.24
ATOM   2100  C    GLU   480    19.713   39.095    4.373  1.00  20.25
ATOM   2101  O    GLU   480    18.875   39.368    3.508  1.00  21.34
ATOM   2102  N    ARG   481    20.297   37.908    4.442  1.00  19.33
ATOM   2103  CA   ARG   481    19.916   36.858    3.515  1.00  18.50
ATOM   2104  CB   ARG   481    21.063   35.868    3.302  1.00  18.20
ATOM   2105  CG   ARG   481    22.241   36.404    2.523  1.00  15.86
ATOM   2106  CD   ARG   481    23.287   35.325    2.421  1.00  15.43
ATOM   2107  NE   ARG   481    23.964   35.096    3.694  1.00  14.91
ATOM   2108  CZ   ARG   481    23.950   33.946    4.367  1.00  15.54
ATOM   2109  NH1  ARG   481    23.279   32.903    3.897  1.00  15.94
ATOM   2110  NH2  ARG   481    24.642   33.826    5.495  1.00  11.48
ATOM   2111  C    ARG   481    18.744   36.118    4.118  1.00  19.75
ATOM   2112  O    ARG   481    18.698   35.898    5.332  1.00  19.19
ATOM   2113  N    PRO   482    17.726   35.814    3.303  1.00  21.15
ATOM   2114  CD   PRO   482    17.480   36.254    1.914  1.00  21.49
ATOM   2115  CA   PRO   482    16.577   35.081    3.848  1.00  21.68
ATOM   2116  CB   PRO   482    15.704   34.858    2.611  1.00  21.74
ATOM   2117  CG   PRO   482    15.976   36.100    1.785  1.00  22.13
ATOM   2118  C    PRO   482    17.096   33.749    4.422  1.00  21.37
ATOM   2119  O    PRO   482    18.049   33.166    3.896  1.00  21.05
ATOM   2120  N    SER   483    16.502   33.288    5.513  1.00  21.11
ATOM   2121  CA   SER   483    16.942   32.048    6.133  1.00  21.78
ATOM   2122  CB   SER   483    16.247   31.868    7.487  1.00  21.27
ATOM   2123  OG   SER   483    14.868   31.562    7.331  1.00  19.02
ATOM   2124  C    SER   483    16.591   30.860    5.251  1.00  22.57
ATOM   2125  O    SER   483    15.780   30.983    4.343  1.00  22.97
ATOM   2126  N    GLY   484    17.213   29.714    5.502  1.00  24.13
ATOM   2127  CA   GLY   484    16.835   28.539    4.747  1.00  26.14
ATOM   2128  C    GLY   484    17.833   27.793    3.904  1.00  27.18
ATOM   2129  O    GLY   484    17.500   26.727    3.387  1.00  28.70
ATOM   2130  N    MET   485    19.028   28.337    3.722  1.00  27.71
ATOM   2131  CA   MET   485    20.027   27.653    2.913  1.00  27.75
ATOM   2132  CB   MET   485    20.517   28.557    1.782  1.00  30.73
ATOM   2133  CG   MET   485    19.436   29.106    0.850  1.00  36.02
ATOM   2134  SD   MET   485    18.683   27.861   -0.207  1.00  42.25
ATOM   2135  CE   MET   485    20.139   26.751   -0.591  1.00  41.08
ATOM   2136  C    MET   485    21.221   27.259    3.759  1.00  25.81
ATOM   2137  O    MET   485    21.559   27.941    4.726  1.00  23.50
ATOM   2138  N    PHE   486    21.812   26.116    3.443  1.00  25.36
ATOM   2139  CA   PHE   486    23.018   25.693    4.138  1.00  25.36
ATOM   2140  CB   PHE   486    22.746   24.797    5.359  1.00  23.40
ATOM   2141  CG   PHE   486    22.193   23.445    5.035  1.00  24.70
```

FIGURE 1A-12

```
ATOM   2142  CD1  PHE   486    23.048   22.371    4.795  1.00  25.53
ATOM   2143  CD2  PHE   486    20.822   23.226    5.034  1.00  23.72
ATOM   2144  CE1  PHE   486    22.549   21.098    4.564  1.00  25.73
ATOM   2145  CE2  PHE   486    20.311   21.959    4.804  1.00  25.05
ATOM   2146  CZ   PHE   486    21.174   20.887    4.569  1.00  25.77
ATOM   2147  C    PHE   486    24.004   25.089    3.141  1.00  24.60
ATOM   2148  O    PHE   486    23.616   24.599    2.075  1.00  22.55
ATOM   2149  N    ASP   487    25.282   25.232    3.465  1.00  25.33
ATOM   2150  CA   ASP   487    26.392   24.769    2.639  1.00  25.56
ATOM   2151  CB   ASP   487    27.674   25.435    3.150  1.00  25.82
ATOM   2152  CG   ASP   487    28.810   25.337    2.174  1.00  25.43
ATOM   2153  OD1  ASP   487    28.767   26.041    1.155  1.00  26.83
ATOM   2154  OD2  ASP   487    29.752   24.568    2.421  1.00  26.93
ATOM   2155  C    ASP   487    26.590   23.244    2.582  1.00  26.12
ATOM   2156  O    ASP   487    26.323   22.518    3.548  1.00  26.16
ATOM   2157  N    SER   488    27.134   22.781    1.462  1.00  26.57
ATOM   2158  CA   SER   488    27.421   21.365    1.244  1.00  26.60
ATOM   2159  CB   SER   488    27.972   21.165   -0.173  1.00  28.61
ATOM   2160  OG   SER   488    28.173   19.795   -0.481  1.00  31.93
ATOM   2161  C    SER   488    28.421   20.838    2.286  1.00  26.05
ATOM   2162  O    SER   488    28.447   19.639    2.583  1.00  26.13
ATOM   2163  N    SER   489    29.227   21.728    2.861  1.00  24.66
ATOM   2164  CA   SER   489    30.185   21.301    3.864  1.00  22.91
ATOM   2165  CB   SER   489    31.078   22.459    4.300  1.00  21.25
ATOM   2166  OG   SER   489    30.310   23.551    4.768  1.00  21.37
ATOM   2167  C    SER   489    29.422   20.737    5.062  1.00  23.17
ATOM   2168  O    SER   489    29.978   19.963    5.846  1.00  24.42
ATOM   2169  N    VAL   490    28.156   21.129    5.216  1.00  21.89
ATOM   2170  CA   VAL   490    27.363   20.620    6.324  1.00  21.05
ATOM   2171  CB   VAL   490    26.038   21.396    6.522  1.00  21.77
ATOM   2172  CG1  VAL   490    25.220   20.725    7.598  1.00  20.51
ATOM   2173  CG2  VAL   490    26.314   22.853    6.931  1.00  20.48
ATOM   2174  C    VAL   490    27.088   19.147    6.051  1.00  20.91
ATOM   2175  O    VAL   490    27.114   18.341    6.973  1.00  22.47
ATOM   2176  N    LEU   491    26.879   18.793    4.779  1.00  21.01
ATOM   2177  CA   LEU   491    26.636   17.397    4.390  1.00  21.10
ATOM   2178  CB   LEU   491    26.283   17.289    2.909  1.00  20.22
ATOM   2179  CG   LEU   491    25.006   18.026    2.505  1.00  22.49
ATOM   2180  CD1  LEU   491    24.743   17.853    1.014  1.00  20.45
ATOM   2181  CD2  LEU   491    23.829   17.495    3.329  1.00  21.46
ATOM   2182  C    LEU   491    27.900   16.594    4.686  1.00  20.78
ATOM   2183  O    LEU   491    27.843   15.522    5.292  1.00  22.36
ATOM   2184  N    CYS   492    29.046   17.138    4.291  1.00  19.79
ATOM   2185  CA   CYS   492    30.317   16.491    4.556  1.00  19.65
ATOM   2186  CB   CYS   492    31.468   17.390    4.092  1.00  18.82
ATOM   2187  SG   CYS   492    33.106   16.704    4.401  1.00  20.38
ATOM   2188  C    CYS   492    30.413   16.274    6.067  1.00  19.87
ATOM   2189  O    CYS   492    30.801   15.205    6.537  1.00  20.08
ATOM   2190  N    GLU   493    29.997   17.289    6.817  1.00  21.33
ATOM   2191  CA   GLU   493    30.028   17.262    8.274  1.00  22.71
ATOM   2192  CB   GLU   493    29.724   18.648    8.830  1.00  24.31
ATOM   2193  CG   GLU   493    30.165   18.820   10.269  1.00  28.02
ATOM   2194  CD   GLU   493    30.042   20.247   10.763  1.00  29.49
ATOM   2195  OE1  GLU   493    29.269   21.030   10.166  1.00  31.62
ATOM   2196  OE2  GLU   493    30.720   20.585   11.758  1.00  32.33
ATOM   2197  C    GLU   493    29.074   16.229    8.862  1.00  21.21
ATOM   2198  O    GLU   493    29.344   15.663    9.925  1.00  21.52
ATOM   2199  N    CYS   494    27.975   15.969    8.161  1.00  20.48
```

FIGURE 1A-13

```
ATOM  2200  CA   CYS  494  27.008  14.970   8.611  1.00  20.92
ATOM  2201  CB   CYS  494  25.690  15.097   7.830  1.00  20.47
ATOM  2202  SG   CYS  494  24.630  16.512   8.329  1.00  19.52
ATOM  2203  C    CYS  494  27.616  13.565   8.471  1.00  20.64
ATOM  2204  O    CYS  494  27.548  12.750   9.404  1.00  21.39
ATOM  2205  N    TYR  495  28.240  13.296   7.324  1.00  18.97
ATOM  2206  CA   TYR  495  28.886  12.008   7.092  1.00  20.35
ATOM  2207  CB   TYR  495  29.372  11.918   5.645  1.00  19.37
ATOM  2208  CG   TYR  495  28.260  11.676   4.653  1.00  19.50
ATOM  2209  CD1  TYR  495  27.606  12.740   4.038  1.00  19.12
ATOM  2210  CE1  TYR  495  26.557  12.524   3.146  1.00  18.63
ATOM  2211  CD2  TYR  495  27.840  10.378   4.348  1.00  18.29
ATOM  2212  CE2  TYR  495  26.794  10.154   3.461  1.00  18.31
ATOM  2213  CZ   TYR  495  26.158  11.229   2.866  1.00  18.52
ATOM  2214  OH   TYR  495  25.114  11.014   1.997  1.00  22.20
ATOM  2215  C    TYR  495  30.060  11.804   8.059  1.00  20.52
ATOM  2216  O    TYR  495  30.287  10.708   8.572  1.00  20.61
ATOM  2217  N    ASP  496  30.804  12.874   8.302  1.00  21.88
ATOM  2218  CA   ASP  496  31.934  12.834   9.212  1.00  23.32
ATOM  2219  CB   ASP  496  32.631  14.204   9.212  1.00  25.74
ATOM  2220  CG   ASP  496  33.981  14.190   9.928  1.00  28.22
ATOM  2221  OD1  ASP  496  35.028  14.310   9.252  1.00  27.49
ATOM  2222  OD2  ASP  496  33.995  14.083  11.172  1.00  29.66
ATOM  2223  C    ASP  496  31.433  12.459  10.613  1.00  24.14
ATOM  2224  O    ASP  496  32.051  11.639  11.302  1.00  24.65
ATOM  2225  N    ALA  497  30.291  13.023  11.007  1.00  25.27
ATOM  2226  CA   ALA  497  29.685  12.758  12.322  1.00  25.04
ATOM  2227  CB   ALA  497  28.555  13.746  12.592  1.00  26.49
ATOM  2228  C    ALA  497  29.169  11.327  12.464  1.00  25.23
ATOM  2229  O    ALA  497  29.274  10.718  13.540  1.00  24.69
ATOM  2230  N    GLY  498  28.571  10.807  11.397  1.00  24.53
ATOM  2231  CA   GLY  498  28.077   9.443  11.433  1.00  25.39
ATOM  2232  C    GLY  498  29.231   8.490  11.695  1.00  25.40
ATOM  2233  O    GLY  498  29.164   7.619  12.567  1.00  24.85
ATOM  2234  N    CME  499  30.314   8.708  10.960  1.00  25.32
ATOM  2235  CA   CME  499  31.527   7.908  11.068  1.00  25.32
ATOM  2236  C    CME  499  32.278   8.088  12.377  1.00  23.75
ATOM  2237  O    CME  499  32.746   7.116  12.958  1.00  23.80
ATOM  2238  CB   CME  499  32.475   8.244   9.917  1.00  25.58
ATOM  2239  SG   CME  499  31.828   7.806   8.284  1.00  25.23
ATOM  2240  2SG  CME  499  31.898   5.788   8.347  1.00  25.26
ATOM  2241  2CB  CME  499  33.623   5.432   7.900  1.00  22.20
ATOM  2242  2CA  CME  499  33.954   5.815   6.487  1.00  20.21
ATOM  2243  OG   CME  499  33.382   4.900   5.576  1.00  20.89
ATOM  2244  N    ALA  500  32.397   9.329  12.835  1.00  23.46
ATOM  2245  CA   ALA  500  33.126   9.619  14.068  1.00  23.38
ATOM  2246  CB   ALA  500  33.626  11.066  14.060  1.00  22.52
ATOM  2247  C    ALA  500  32.359   9.351  15.349  1.00  25.43
ATOM  2248  O    ALA  500  32.889   8.739  16.279  1.00  25.86
ATOM  2249  N    TRP  501  31.102   9.781  15.392  1.00  27.22
ATOM  2250  CA   TRP  501  30.303   9.623  16.601  1.00  28.60
ATOM  2251  CB   TRP  501  29.788  10.983  17.057  1.00  27.51
ATOM  2252  CG   TRP  501  30.851  11.978  17.305  1.00  25.74
ATOM  2253  CD2  TRP  501  31.598  12.149  18.510  1.00  23.93
ATOM  2254  CE2  TRP  501  32.450  13.254  18.319  1.00  24.45
ATOM  2255  CE3  TRP  501  31.631  11.477  19.732  1.00  23.70
ATOM  2256  CD1  TRP  501  31.270  12.947  16.450  1.00  25.45
ATOM  2257  NE1  TRP  501  32.230  13.725  17.052  1.00  26.50
```

FIGURE 1A-14

```
ATOM   2258  CZ2  TRP  501   33.319  13.706  19.304  1.00  24.88
ATOM   2259  CZ3  TRP  501   32.498  11.924  20.712  1.00  24.31
ATOM   2260  CH2  TRP  501   33.331  13.028  20.493  1.00  25.27
ATOM   2261  C    TRP  501   29.116   8.675  16.639  1.00  29.45
ATOM   2262  O    TRP  501   28.799   8.155  17.708  1.00  31.24
ATOM   2263  N    TYR  502   28.452   8.442  15.512  1.00  29.45
ATOM   2264  CA   TYR  502   27.244   7.623  15.556  1.00  28.83
ATOM   2265  CB   TYR  502   26.064   8.418  14.987  1.00  26.77
ATOM   2266  CG   TYR  502   25.962   9.775  15.638  1.00  26.30
ATOM   2267  CD1  TYR  502   26.177  10.940  14.907  1.00  25.61
ATOM   2268  CE1  TYR  502   26.215  12.178  15.534  1.00  26.43
ATOM   2269  CD2  TYR  502   25.768   9.888  17.019  1.00  25.72
ATOM   2270  CE2  TYR  502   25.804  11.118  17.655  1.00  26.34
ATOM   2271  CZ   TYR  502   26.031  12.258  16.908  1.00  26.72
ATOM   2272  OH   TYR  502   26.103  13.475  17.541  1.00  29.21
ATOM   2273  C    TYR  502   27.268   6.226  15.004  1.00  29.90
ATOM   2274  O    TYR  502   26.218   5.623  14.808  1.00  30.51
ATOM   2275  N    GLU  503   28.459   5.688  14.795  1.00  30.61
ATOM   2276  CA   GLU  503   28.585   4.337  14.272  1.00  31.76
ATOM   2277  CB   GLU  503   28.115   3.320  15.300  1.00  33.16
ATOM   2278  CG   GLU  503   28.959   3.248  16.531  1.00  37.65
ATOM   2279  CD   GLU  503   28.810   1.913  17.218  1.00  42.70
ATOM   2280  OE1  GLU  503   27.654   1.459  17.415  1.00  44.39
ATOM   2281  OE2  GLU  503   29.854   1.304  17.541  1.00  46.49
ATOM   2282  C    GLU  503   27.781   4.150  13.008  1.00  30.99
ATOM   2283  O    GLU  503   27.274   3.062  12.740  1.00  32.02
ATOM   2284  N    LEU  504   27.670   5.212  12.224  1.00  31.39
ATOM   2285  CA   LEU  504   26.905   5.147  10.992  1.00  29.95
ATOM   2286  CB   LEU  504   25.963   6.351  10.864  1.00  26.33
ATOM   2287  CG   LEU  504   24.920   6.570  11.959  1.00  24.35
ATOM   2288  CD1  LEU  504   24.128   7.804  11.624  1.00  24.54
ATOM   2289  CD2  LEU  504   24.006   5.375  12.084  1.00  22.44
ATOM   2290  C    LEU  504   27.752   5.034   9.736  1.00  31.09
ATOM   2291  O    LEU  504   28.750   5.747   9.556  1.00  32.06
ATOM   2292  N    THR  505   27.323   4.116   8.883  1.00  29.82
ATOM   2293  CA   THR  505   27.918   3.847   7.590  1.00  28.87
ATOM   2294  CB   THR  505   27.336   2.520   7.067  1.00  29.51
ATOM   2295  OG1  THR  505   27.897   1.429   7.806  1.00  32.11
ATOM   2296  CG2  THR  505   27.595   2.337   5.612  1.00  31.82
ATOM   2297  C    THR  505   27.475   4.989   6.672  1.00  27.43
ATOM   2298  O    THR  505   26.390   5.542   6.857  1.00  28.06
ATOM   2299  N    PRO  506   28.302   5.367   5.680  1.00  26.19
ATOM   2300  CD   PRO  506   29.680   4.930   5.378  1.00  25.34
ATOM   2301  CA   PRO  506   27.895   6.456   4.784  1.00  24.28
ATOM   2302  CB   PRO  506   29.007   6.460   3.734  1.00  24.62
ATOM   2303  CG   PRO  506   30.212   6.083   4.533  1.00  23.11
ATOM   2304  C    PRO  506   26.529   6.153   4.165  1.00  24.09
ATOM   2305  O    PRO  506   25.705   7.046   3.990  1.00  22.93
ATOM   2306  N    ALA  507   26.291   4.880   3.855  1.00  24.47
ATOM   2307  CA   ALA  507   25.018   4.448   3.283  1.00  23.40
ATOM   2308  CB   ALA  507   25.079   2.968   2.912  1.00  22.03
ATOM   2309  C    ALA  507   23.871   4.715   4.269  1.00  23.01
ATOM   2310  O    ALA  507   22.786   5.133   3.866  1.00  22.45
ATOM   2311  N    GLU  508   24.123   4.488   5.555  1.00  22.85
ATOM   2312  CA   GLU  508   23.125   4.724   6.596  1.00  25.62
ATOM   2313  CB   GLU  508   23.593   4.149   7.936  1.00  26.13
ATOM   2314  CG   GLU  508   23.710   2.638   7.941  1.00  30.10
ATOM   2315  CD   GLU  508   24.322   2.069   9.217  1.00  32.11
```

FIGURE 1A-15

| | | | | | | | | | |
|---|---|---|---|---|---|---|---|---|---|
| ATOM | 2316 | OE1 | GLU | 508 | 24.722 | 2.840 | 10.110 | 1.00 | 34.14 |
| ATOM | 2317 | OE2 | GLU | 508 | 24.406 | 0.828 | 9.323 | 1.00 | 35.16 |
| ATOM | 2318 | C | GLU | 508 | 22.849 | 6.222 | 6.743 | 1.00 | 26.03 |
| ATOM | 2319 | O | GLU | 508 | 21.694 | 6.635 | 6.843 | 1.00 | 26.78 |
| ATOM | 2320 | N | THR | 509 | 23.912 | 7.025 | 6.773 | 1.00 | 25.74 |
| ATOM | 2321 | CA | THR | 509 | 23.785 | 8.474 | 6.882 | 1.00 | 24.39 |
| ATOM | 2322 | CB | THR | 509 | 25.168 | 9.148 | 6.907 | 1.00 | 23.11 |
| ATOM | 2323 | OG1 | THR | 509 | 25.853 | 8.790 | 8.113 | 1.00 | 20.57 |
| ATOM | 2324 | CG2 | THR | 509 | 25.035 | 10.659 | 6.828 | 1.00 | 22.40 |
| ATOM | 2325 | C | THR | 509 | 22.973 | 9.000 | 5.692 | 1.00 | 25.46 |
| ATOM | 2326 | O | THR | 509 | 22.129 | 9.886 | 5.853 | 1.00 | 27.07 |
| ATOM | 2327 | N | THR | 510 | 23.193 | 8.421 | 4.513 | 1.00 | 24.22 |
| ATOM | 2328 | CA | THR | 510 | 22.471 | 8.825 | 3.314 | 1.00 | 23.80 |
| ATOM | 2329 | CB | THR | 510 | 22.992 | 8.074 | 2.087 | 1.00 | 23.34 |
| ATOM | 2330 | OG1 | THR | 510 | 24.355 | 8.443 | 1.855 | 1.00 | 26.59 |
| ATOM | 2331 | CG2 | THR | 510 | 22.193 | 8.429 | 0.870 | 1.00 | 22.93 |
| ATOM | 2332 | C | THR | 510 | 20.961 | 8.624 | 3.457 | 1.00 | 23.48 |
| ATOM | 2333 | O | THR | 510 | 20.174 | 9.456 | 3.013 | 1.00 | 23.82 |
| ATOM | 2334 | N | VAL | 511 | 20.565 | 7.529 | 4.098 | 1.00 | 24.04 |
| ATOM | 2335 | CA | VAL | 511 | 19.157 | 7.216 | 4.321 | 1.00 | 23.83 |
| ATOM | 2336 | CB | VAL | 511 | 19.019 | 5.872 | 5.072 | 1.00 | 25.13 |
| ATOM | 2337 | CG1 | VAL | 511 | 17.577 | 5.644 | 5.509 | 1.00 | 24.67 |
| ATOM | 2338 | CG2 | VAL | 511 | 19.480 | 4.729 | 4.168 | 1.00 | 24.94 |
| ATOM | 2339 | C | VAL | 511 | 18.482 | 8.329 | 5.122 | 1.00 | 22.86 |
| ATOM | 2340 | O | VAL | 511 | 17.391 | 8.783 | 4.783 | 1.00 | 23.35 |
| ATOM | 2341 | N | ARG | 512 | 19.160 | 8.779 | 6.168 | 1.00 | 22.63 |
| ATOM | 2342 | CA | ARG | 512 | 18.663 | 9.843 | 7.028 | 1.00 | 22.06 |
| ATOM | 2343 | CB | ARG | 512 | 19.465 | 9.846 | 8.325 | 1.00 | 20.58 |
| ATOM | 2344 | CG | ARG | 512 | 19.312 | 8.538 | 9.080 | 1.00 | 21.48 |
| ATOM | 2345 | CD | ARG | 512 | 20.435 | 8.307 | 10.076 | 1.00 | 22.08 |
| ATOM | 2346 | NE | ARG | 512 | 20.375 | 6.949 | 10.602 | 1.00 | 22.43 |
| ATOM | 2347 | CZ | ARG | 512 | 20.475 | 6.631 | 11.889 | 1.00 | 24.44 |
| ATOM | 2348 | NH1 | ARG | 512 | 20.401 | 5.361 | 12.262 | 1.00 | 24.03 |
| ATOM | 2349 | NH2 | ARG | 512 | 20.666 | 7.574 | 12.804 | 1.00 | 26.08 |
| ATOM | 2350 | C | ARG | 512 | 18.693 | 11.222 | 6.348 | 1.00 | 22.38 |
| ATOM | 2351 | O | ARG | 512 | 17.727 | 11.990 | 6.424 | 1.00 | 20.41 |
| ATOM | 2352 | N | LEU | 513 | 19.788 | 11.524 | 5.657 | 1.00 | 23.97 |
| ATOM | 2353 | CA | LEU | 513 | 19.907 | 12.802 | 4.970 | 1.00 | 23.82 |
| ATOM | 2354 | CB | LEU | 513 | 21.351 | 13.042 | 4.511 | 1.00 | 23.01 |
| ATOM | 2355 | CG | LEU | 513 | 22.412 | 13.142 | 5.619 | 1.00 | 22.43 |
| ATOM | 2356 | CD1 | LEU | 513 | 23.758 | 13.482 | 5.030 | 1.00 | 20.55 |
| ATOM | 2357 | CD2 | LEU | 513 | 22.027 | 14.191 | 6.637 | 1.00 | 21.42 |
| ATOM | 2358 | C | LEU | 513 | 18.923 | 12.860 | 3.800 | 1.00 | 23.93 |
| ATOM | 2359 | O | LEU | 513 | 18.388 | 13.917 | 3.481 | 1.00 | 26.02 |
| ATOM | 2360 | N | ARG | 514 | 18.641 | 11.714 | 3.196 | 1.00 | 23.65 |
| ATOM | 2361 | CA | ARG | 514 | 17.697 | 11.653 | 2.086 | 1.00 | 23.31 |
| ATOM | 2362 | CB | ARG | 514 | 17.726 | 10.259 | 1.461 | 1.00 | 24.64 |
| ATOM | 2363 | CG | ARG | 514 | 16.779 | 10.063 | 0.294 | 1.00 | 27.95 |
| ATOM | 2364 | CD | ARG | 514 | 17.055 | 11.033 | -0.848 | 1.00 | 31.79 |
| ATOM | 2365 | NE | ARG | 514 | 18.388 | 10.876 | -1.430 | 1.00 | 34.83 |
| ATOM | 2366 | CZ | ARG | 514 | 19.048 | 11.847 | -2.057 | 1.00 | 35.11 |
| ATOM | 2367 | NH1 | ARG | 514 | 20.251 | 11.608 | -2.561 | 1.00 | 36.73 |
| ATOM | 2368 | NH2 | ARG | 514 | 18.523 | 13.067 | -2.154 | 1.00 | 34.98 |
| ATOM | 2369 | C | ARG | 514 | 16.289 | 11.997 | 2.595 | 1.00 | 23.18 |
| ATOM | 2370 | O | ARG | 514 | 15.598 | 12.822 | 2.010 | 1.00 | 23.43 |
| ATOM | 2371 | N | ALA | 515 | 15.892 | 11.396 | 3.714 | 1.00 | 22.98 |
| ATOM | 2372 | CA | ALA | 515 | 14.585 | 11.648 | 4.319 | 1.00 | 23.14 |
| ATOM | 2373 | CB | ALA | 515 | 14.434 | 10.836 | 5.587 | 1.00 | 22.55 |

FIGURE 1A-16

```
ATOM   2374  C    ALA   515     14.430  13.135   4.630  1.00  23.92
ATOM   2375  O    ALA   515     13.382  13.721   4.379  1.00  23.30
ATOM   2376  N    TYR   516     15.483  13.734   5.181  1.00  24.72
ATOM   2377  CA   TYR   516     15.493  15.157   5.505  1.00  24.73
ATOM   2378  CB   TYR   516     16.860  15.537   6.077  1.00  20.83
ATOM   2379  CG   TYR   516     16.997  16.989   6.481  1.00  21.19
ATOM   2380  CD1  TYR   516     16.811  17.385   7.805  1.00  19.78
ATOM   2381  CE1  TYR   516     16.966  18.717   8.189  1.00  18.78
ATOM   2382  CD2  TYR   516     17.340  17.971   5.545  1.00  20.90
ATOM   2383  CE2  TYR   516     17.493  19.308   5.924  1.00  20.29
ATOM   2384  CZ   TYR   516     17.305  19.662   7.246  1.00  18.46
ATOM   2385  OH   TYR   516     17.473  20.960   7.626  1.00  21.53
ATOM   2386  C    TYR   516     15.213  15.963   4.226  1.00  26.41
ATOM   2387  O    TYR   516     14.390  16.883   4.218  1.00  26.36
ATOM   2388  N    MET   517     15.893  15.594   3.146  1.00  27.82
ATOM   2389  CA   MET   517     15.736  16.268   1.868  1.00  29.62
ATOM   2390  CB   MET   517     16.897  15.910   0.929  1.00  32.52
ATOM   2391  CG   MET   517     18.257  16.449   1.415  1.00  36.99
ATOM   2392  SD   MET   517     19.641  16.357   0.240  1.00  42.11
ATOM   2393  CE   MET   517     19.692  18.060  -0.335  1.00  41.79
ATOM   2394  C    MET   517     14.394  15.971   1.215  1.00  30.17
ATOM   2395  O    MET   517     13.863  16.793   0.484  1.00  31.65
ATOM   2396  N    ASN   518     13.824  14.813   1.507  1.00  30.49
ATOM   2397  CA   ASN   518     12.543  14.455   0.926  1.00  31.49
ATOM   2398  CB   ASN   518     12.338  12.941   0.965  1.00  33.77
ATOM   2399  CG   ASN   518     12.983  12.236  -0.210  1.00  35.89
ATOM   2400  OD1  ASN   518     13.269  12.852  -1.245  1.00  36.28
ATOM   2401  ND2  ASN   518     13.204  10.929  -0.065  1.00  35.87
ATOM   2402  C    ASN   518     11.359  15.146   1.585  1.00  32.06
ATOM   2403  O    ASN   518     10.242  15.100   1.059  1.00  33.11
ATOM   2404  N    THR   519     11.568  15.770   2.740  1.00  31.41
ATOM   2405  CA   THR   519     10.453  16.441   3.389  1.00  29.95
ATOM   2406  CB   THR   519     10.353  16.087   4.881  1.00  30.80
ATOM   2407  OG1  THR   519     11.403  16.723   5.606  1.00  36.48
ATOM   2408  CG2  THR   519     10.477  14.588   5.069  1.00  32.01
ATOM   2409  C    THR   519     10.435  17.955   3.166  1.00  28.51
ATOM   2410  O    THR   519     11.380  18.678   3.509  1.00  27.20
ATOM   2411  N    PRO   520      9.361  18.447   2.528  1.00  27.84
ATOM   2412  CD   PRO   520      8.275  17.657   1.919  1.00  27.48
ATOM   2413  CA   PRO   520      9.185  19.869   2.236  1.00  25.32
ATOM   2414  CB   PRO   520      7.850  19.891   1.491  1.00  25.57
ATOM   2415  CG   PRO   520      7.812  18.568   0.806  1.00  25.28
ATOM   2416  C    PRO   520      9.117  20.740   3.482  1.00  24.11
ATOM   2417  O    PRO   520      8.695  20.294   4.544  1.00  24.19
ATOM   2418  N    GLY   521      9.553  21.985   3.341  1.00  23.43
ATOM   2419  CA   GLY   521      9.491  22.931   4.437  1.00  23.18
ATOM   2420  C    GLY   521     10.708  23.045   5.313  1.00  23.53
ATOM   2421  O    GLY   521     10.690  23.813   6.279  1.00  23.92
ATOM   2422  N    LEU   522     11.744  22.267   5.010  1.00  23.75
ATOM   2423  CA   LEU   522     12.985  22.293   5.783  1.00  21.75
ATOM   2424  CB   LEU   522     13.448  20.860   6.099  1.00  20.22
ATOM   2425  CG   LEU   522     12.696  20.053   7.166  1.00  19.37
ATOM   2426  CD1  LEU   522     13.320  18.681   7.255  1.00  18.45
ATOM   2427  CD2  LEU   522     12.754  20.739   8.521  1.00  17.70
ATOM   2428  C    LEU   522     14.076  23.051   5.029  1.00  19.66
ATOM   2429  O    LEU   522     13.898  23.398   3.867  1.00  19.67
ATOM   2430  N    PRO   523     15.157  23.439   5.725  1.00  18.95
ATOM   2431  CD   PRO   523     15.328  23.445   7.187  1.00  16.62
```

FIGURE 1A-17

```
ATOM   2432  CA   PRO   523   16.255  24.159   5.073  1.00  20.39
ATOM   2433  CB   PRO   523   17.270  24.305   6.208  1.00  19.00
ATOM   2434  CG   PRO   523   16.387  24.512   7.380  1.00  19.06
ATOM   2435  C    PRO   523   16.814  23.317   3.912  1.00  22.86
ATOM   2436  O    PRO   523   16.822  22.083   3.981  1.00  23.38
ATOM   2437  N    VAL   524   17.302  23.973   2.862  1.00  25.30
ATOM   2438  CA   VAL   524   17.819  23.250   1.707  1.00  27.02
ATOM   2439  CB   VAL   524   16.986  23.556   0.438  1.00  27.40
ATOM   2440  CG1  VAL   524   15.537  23.193   0.671  1.00  26.10
ATOM   2441  CG2  VAL   524   17.098  25.016   0.066  1.00  29.26
ATOM   2442  C    VAL   524   19.302  23.426   1.391  1.00  27.30
ATOM   2443  O    VAL   524   19.912  24.461   1.674  1.00  27.05
ATOM   2444  N    CYS   525   19.866  22.377   0.809  1.00  28.81
ATOM   2445  CA   CYS   525   21.260  22.331   0.397  1.00  30.97
ATOM   2446  CB   CYS   525   22.095  21.541   1.401  1.00  32.28
ATOM   2447  SG   CYS   525   21.430  19.886   1.803  1.00  38.03
ATOM   2448  C    CYS   525   21.285  21.617  -0.948  1.00  31.93
ATOM   2449  O    CYS   525   20.280  21.019  -1.365  1.00  31.91
ATOM   2450  N    GLN   526   22.416  21.699  -1.639  1.00  32.52
ATOM   2451  CA   GLN   526   22.557  21.053  -2.932  1.00  33.47
ATOM   2452  CB   GLN   526   23.831  21.525  -3.622  1.00  36.06
ATOM   2453  CG   GLN   526   23.797  22.989  -4.028  1.00  39.05
ATOM   2454  CD   GLN   526   25.143  23.497  -4.519  1.00  43.09
ATOM   2455  OE1  GLN   526   26.181  22.863  -4.302  1.00  44.20
ATOM   2456  NE2  GLN   526   25.134  24.648  -5.181  1.00  45.25
ATOM   2457  C    GLN   526   22.588  19.553  -2.709  1.00  32.95
ATOM   2458  O    GLN   526   23.203  19.070  -1.757  1.00  33.73
ATOM   2459  N    ASP   527   21.915  18.816  -3.580  1.00  32.09
ATOM   2460  CA   ASP   527   21.857  17.372  -3.459  1.00  31.50
ATOM   2461  CB   ASP   527   20.800  16.819  -4.421  1.00  33.07
ATOM   2462  CG   ASP   527   20.444  15.364  -4.145  1.00  34.64
ATOM   2463  OD1  ASP   527   19.441  14.898  -4.729  1.06  37.28
ATOM   2464  OD2  ASP   527   21.152  14.684  -3.363  1.00  36.58
ATOM   2465  C    ASP   527   23.220  16.747  -3.740  1.00  30.96
ATOM   2466  O    ASP   527   23.507  16.370  -4.877  1.00  30.98
ATOM   2467  N    HIS   528   24.070  16.673  -2.716  1.00  29.78
ATOM   2468  CA   HIS   528   25.408  16.079  -2.856  1.00  28.64
ATOM   2469  CB   HIS   528   26.500  17.060  -2.445  1.00  26.18
ATOM   2470  CG   HIS   528   26.610  18.248  -3.333  1.00  23.97
ATOM   2471  CD2  HIS   528   25.951  18.579  -4.468  1.00  23.60
ATOM   2472  ND1  HIS   528   27.483  19.281  -3.077  1.00  23.80
ATOM   2473  CE1  HIS   528   27.357  20.202  -4.015  1.00  24.23
ATOM   2474  NE2  HIS   528   26.433  19.801  -4.870  1.00  25.47
ATOM   2475  C    HIS   528   25.556  14.840  -1.997  1.00  28.65
ATOM   2476  O    HIS   528   26.657  14.516  -1.557  1.00  28.39
ATOM   2477  N    LEU   529   24.453  14.137  -1.776  1.00  29.34
ATOM   2478  CA   LEU   529   24.478  12.947  -0.942  1.00  29.62
ATOM   2479  CB   LEU   529   23.047  12.479  -0.645  1.00  29.60
ATOM   2480  CG   LEU   529   22.188  13.506   0.109  1.00  27.75
ATOM   2481  CD1  LEU   529   20.849  12.898   0.483  1.00  26.93
ATOM   2482  CD2  LEU   529   22.917  13.973   1.356  1.00  24.19
ATOM   2483  C    LEU   529   25.326  11.827  -1.540  1.00  29.38
ATOM   2484  O    LEU   529   26.158  11.237  -0.847  1.00  28.82
ATOM   2485  N    ALA   530   25.140  11.564  -2.830  1.00  29.06
ATOM   2486  CA   ALA   530   25.904  10.519  -3.508  1.00  29.34
ATOM   2487  CB   ALA   530   25.415  10.343  -4.951  1.00  29.19
ATOM   2488  C    ALA   530   27.394  10.856  -3.489  1.00  28.63
ATOM   2489  O    ALA   530   28.236   9.991  -3.217  1.00  29.57
```

FIGURE 1A-18

```
ATOM   2490  N    PHE   531    27.709   12.125   -3.731   1.00   26.99
ATOM   2491  CA   PHE   531    29.094   12.553   -3.735   1.00   25.83
ATOM   2492  CB   PHE   531    29.232   14.024   -4.124   1.00   25.62
ATOM   2493  CG   PHE   531    30.621   14.553   -3.938   1.00   26.14
ATOM   2494  CD1  PHE   531    31.652   14.139   -4.778   1.00   26.59
ATOM   2495  CD2  PHE   531    30.918   15.398   -2.883   1.00   25.50
ATOM   2496  CE1  PHE   531    32.962   14.556   -4.564   1.00   25.76
ATOM   2497  CE2  PHE   531    32.222   15.820   -2.659   1.00   27.06
ATOM   2498  CZ   PHE   531    33.249   15.396   -3.502   1.00   26.12
ATOM   2499  C    PHE   531    29.769   12.325   -2.395   1.00   24.62
ATOM   2500  O    PHE   531    30.763   11.617   -2.328   1.00   26.66
ATOM   2501  N    TRP   532    29.222   12.900   -1.327   1.00   22.70
ATOM   2502  CA   TRP   532    29.824   12.758   -0.002   1.00   21.65
ATOM   2503  CB   TRP   532    29.145   13.682    1.006   1.00   20.94
ATOM   2504  CG   TRP   532    29.451   15.121    0.742   1.00   20.29
ATOM   2505  CD2  TRP   532    30.739   15.758    0.824   1.00   21.51
ATOM   2506  CE2  TRP   532    30.557   17.112    0.462   1.00   21.80
ATOM   2507  CE3  TRP   532    32.027   15.315    1.162   1.00   20.31
ATOM   2508  CD1  TRP   532    28.573   16.082    0.351   1.00   20.68
ATOM   2509  NE1  TRP   532    29.228   17.281    0.180   1.00   21.58
ATOM   2510  CZ2  TRP   532    31.618   18.037    0.428   1.00   21.77
ATOM   2511  CZ3  TRP   532    33.080   16.230    1.130   1.00   22.10
ATOM   2512  CH2  TRP   532    32.866   17.579    0.763   1.00   21.20
ATOM   2513  C    TRP   532    29.865   11.328    0.496   1.00   21.68
ATOM   2514  O    TRP   532    30.800   10.925    1.206   1.00   20.01
ATOM   2515  N    GLU   533    28.848   10.561    0.122   1.00   22.69
ATOM   2516  CA   GLU   533    28.787    9.159    0.488   1.00   23.84
ATOM   2517  CB   GLU   533    27.455    8.553    0.058   1.00   26.03
ATOM   2518  CG   GLU   533    27.279    7.129    0.543   1.00   26.87
ATOM   2519  CD   GLU   533    26.055    6.468   -0.018   1.00   27.26
ATOM   2520  OE1  GLU   533    25.058    7.165   -0.302   1.00   26.87
ATOM   2521  OE2  GLU   533    26.103    5.238   -0.185   1.00   30.58
ATOM   2522  C    GLU   533    29.926    8.450   -0.245   1.00   23.94
ATOM   2523  O    GLU   533    30.584    7.569    0.319   1.00   24.95
ATOM   2524  N    GLY   534    30.149    8.832   -1.502   1.00   23.38
ATOM   2525  CA   GLY   534    31.227    8.236   -2.277   1.00   23.87
ATOM   2526  C    GLY   534    32.555    8.469   -1.569   1.00   23.44
ATOM   2527  O    GLY   534    33.263    7.517   -1.214   1.00   22.74
ATOM   2528  N    VAL   535    32.829    9.739   -1.269   1.00   22.38
ATOM   2529  CA   VAL   535    34.050   10.147   -0.584   1.00   22.30
ATOM   2530  CB   VAL   535    34.037   11.674   -0.254   1.00   21.82
ATOM   2531  CG1  VAL   535    35.184   12.033    0.702   1.00   17.86
ATOM   2532  CG2  VAL   535    34.124   12.491   -1.541   1.00   17.05
ATOM   2533  C    VAL   535    34.312    9.351    0.696   1.00   22.60
ATOM   2534  O    VAL   535    35.324    8.655    0.799   1.00   23.81
ATOM   2535  N    PHE   536    33.381    9.411    1.645   1.00   22.80
ATOM   2536  CA   PHE   536    33.548    8.710    2.916   1.00   21.82
ATOM   2537  CB   PHE   536    32.496    9.169    3.931   1.00   21.01
ATOM   2538  CG   PHE   536    32.793   10.514    4.529   1.00   18.99
ATOM   2539  CD1  PHE   536    32.371   11.677    3.901   1.00   15.68
ATOM   2540  CD2  PHE   536    33.555   10.616    5.687   1.00   16.90
ATOM   2541  CE1  PHE   536    32.708   12.921    4.410   1.00   16.35
ATOM   2542  CE2  PHE   536    33.893   11.861    6.204   1.00   17.77
ATOM   2543  CZ   PHE   536    33.469   13.019    5.561   1.00   14.57
ATOM   2544  C    PHE   536    33.598    7.192    2.817   1.00   23.73
ATOM   2545  O    PHE   536    34.253    6.535    3.632   1.00   22.08
ATOM   2546  N    THR   537    32.941    6.633    1.805   1.00   26.19
ATOM   2547  CA   THR   537    32.952    5.189    1.619   1.00   28.54
```

FIGURE 1A-19

| | | | | | | | | |
|---|---|---|---|---|---|---|---|---|
| ATOM | 2548 | CB | THR | 537 | 31.998 | 4.771 | 0.490 | 1.00 | 29.40 |
| ATOM | 2549 | OG1 | THR | 537 | 30.649 | 5.019 | 0.905 | 1.00 | 31.40 |
| ATOM | 2550 | CG2 | THR | 537 | 32.148 | 3.287 | 0.174 | 1.00 | 29.35 |
| ATOM | 2551 | C | THR | 537 | 34.380 | 4.686 | 1.342 | 1.00 | 29.80 |
| ATOM | 2552 | O | THR | 537 | 34.741 | 3.566 | 1.722 | 1.00 | 30.70 |
| ATOM | 2553 | N | GLY | 538 | 35.201 | 5.537 | 0.733 | 1.00 | 29.84 |
| ATOM | 2554 | CA | GLY | 538 | 36.567 | 5.151 | 0.437 | 1.00 | 28.99 |
| ATOM | 2555 | C | GLY | 538 | 37.549 | 5.377 | 1.573 | 1.00 | 28.25 |
| ATOM | 2556 | O | GLY | 538 | 38.678 | 4.892 | 1.523 | 1.00 | 28.81 |
| ATOM | 2557 | N | LEU | 539 | 37.132 | 6.094 | 2.606 | 1.00 | 27.46 |
| ATOM | 2558 | CA | LEU | 539 | 38.020 | 6.375 | 3.720 | 1.00 | 27.32 |
| ATOM | 2559 | CB | LEU | 539 | 37.655 | 7.707 | 4.378 | 1.00 | 26.09 |
| ATOM | 2560 | CG | LEU | 539 | 37.583 | 8.951 | 3.481 | 1.00 | 24.55 |
| ATOM | 2561 | CD1 | LEU | 539 | 37.394 | 10.159 | 4.367 | 1.00 | 23.67 |
| ATOM | 2562 | CD2 | LEU | 539 | 38.843 | 9.108 | 2.645 | 1.00 | 24.83 |
| ATOM | 2563 | C | LEU | 539 | 37.963 | 5.248 | 4.725 | 1.00 | 28.87 |
| ATOM | 2564 | O | LEU | 539 | 37.689 | 5.458 | 5.909 | 1.00 | 30.15 |
| ATOM | 2565 | N | THR | 540 | 38.259 | 4.047 | 4.250 | 1.00 | 29.75 |
| ATOM | 2566 | CA | THR | 540 | 38.224 | 2.872 | 5.098 | 1.00 | 30.28 |
| ATOM | 2567 | CB | THR | 540 | 37.875 | 1.625 | 4.277 | 1.00 | 30.11 |
| ATOM | 2568 | OG1 | THR | 540 | 38.931 | 1.351 | 3.352 | 1.00 | 30.87 |
| ATOM | 2569 | CG2 | THR | 540 | 36.591 | 1.858 | 3.492 | 1.00 | 31.21 |
| ATOM | 2570 | C | THR | 540 | 39.533 | 2.652 | 5.857 | 1.00 | 30.76 |
| ATOM | 2571 | O | THR | 540 | 40.573 | 3.203 | 5.509 | 1.00 | 30.52 |
| ATOM | 2572 | N | HIS | 541 | 39.452 | 1.859 | 6.921 | 1.00 | 31.78 |
| ATOM | 2573 | CA | HIS | 541 | 40.603 | 1.524 | 7.757 | 1.00 | 31.88 |
| ATOM | 2574 | CB | HIS | 541 | 41.605 | 0.652 | 6.969 | 1.00 | 31.23 |
| ATOM | 2575 | C | HIS | 541 | 41.295 | 2.741 | 8.365 | 1.00 | 30.69 |
| ATOM | 2576 | O | HIS | 541 | 42.461 | 2.992 | 8.097 | 1.00 | 33.64 |
| ATOM | 2577 | N | ILE | 542 | 40.581 | 3.483 | 9.202 | 1.00 | 29.88 |
| ATOM | 2578 | CA | ILE | 542 | 41.149 | 4.661 | 9.852 | 1.00 | 29.84 |
| ATOM | 2579 | CB | ILE | 542 | 40.032 | 5.650 | 10.323 | 1.00 | 28.82 |
| ATOM | 2580 | CG2 | ILE | 542 | 39.306 | 5.107 | 11.560 | 1.00 | 27.39 |
| ATOM | 2581 | CG1 | ILE | 542 | 40.622 | 7.021 | 10.661 | 1.00 | 26.39 |
| ATOM | 2582 | CD1 | ILE | 542 | 39.573 | 8.090 | 10.915 | 1.00 | 22.88 |
| ATOM | 2583 | C | ILE | 542 | 41.912 | 4.172 | 11.068 | 1.00 | 31.23 |
| ATOM | 2584 | O | ILE | 542 | 41.687 | 3.052 | 11.523 | 1.00 | 32.59 |
| ATOM | 2585 | N | ASP | 543 | 42.833 | 4.978 | 11.583 | 1.00 | 32.70 |
| ATOM | 2586 | CA | ASP | 543 | 43.558 | 4.580 | 12.778 | 1.00 | 33.07 |
| ATOM | 2587 | CB | ASP | 543 | 44.882 | 5.326 | 12.906 | 1.00 | 32.63 |
| ATOM | 2588 | CG | ASP | 543 | 45.667 | 4.909 | 14.136 | 1.00 | 34.41 |
| ATOM | 2589 | OD1 | ASP | 543 | 46.261 | 3.815 | 14.106 | 1.00 | 37.12 |
| ATOM | 2590 | OD2 | ASP | 543 | 45.698 | 5.666 | 15.135 | 1.00 | 35.50 |
| ATOM | 2591 | C | ASP | 543 | 42.636 | 4.978 | 13.914 | 1.00 | 34.38 |
| ATOM | 2592 | O | ASP | 543 | 42.306 | 6.160 | 14.067 | 1.00 | 34.89 |
| ATOM | 2593 | N | ALA | 544 | 42.206 | 3.997 | 14.702 | 1.00 | 34.33 |
| ATOM | 2594 | CA | ALA | 544 | 41.307 | 4.260 | 15.820 | 1.00 | 34.13 |
| ATOM | 2595 | CB | ALA | 544 | 40.876 | 2.956 | 16.460 | 1.00 | 34.20 |
| ATOM | 2596 | C | ALA | 544 | 41.873 | 5.212 | 16.876 | 1.00 | 34.61 |
| ATOM | 2597 | O | ALA | 544 | 41.133 | 5.998 | 17.463 | 1.00 | 34.47 |
| ATOM | 2598 | N | HIS | 545 | 43.180 | 5.159 | 17.113 | 1.00 | 36.16 |
| ATOM | 2599 | CA | HIS | 545 | 43.782 | 6.035 | 18.111 | 1.00 | 36.63 |
| ATOM | 2600 | CB | HIS | 545 | 45.216 | 5.635 | 18.445 | 1.00 | 38.84 |
| ATOM | 2601 | CG | HIS | 545 | 45.902 | 6.604 | 19.362 | 1.00 | 41.47 |
| ATOM | 2602 | CD2 | HIS | 545 | 47.105 | 7.221 | 19.272 | 1.00 | 41.80 |
| ATOM | 2603 | ND1 | HIS | 545 | 45.320 | 7.068 | 20.523 | 1.00 | 42.23 |
| ATOM | 2604 | CE1 | HIS | 545 | 46.136 | 7.927 | 21.110 | 1.00 | 42.36 |
| ATOM | 2605 | NE2 | HIS | 545 | 47.225 | 8.039 | 20.371 | 1.00 | 42.08 |

FIGURE 1A-20

```
ATOM   2606  C    HIS   545    43.773    7.491   17.709   1.00   36.37
ATOM   2607  O    HIS   545    43.606    8.358   18.561   1.00   37.33
ATOM   2608  N    PHE   546    44.043    7.767   16.437   1.00   35.97
ATOM   2609  CA   PHE   546    44.044    9.148   15.958   1.00   36.04
ATOM   2610  CB   PHE   546    44.565    9.232   14.520   1.00   35.63
ATOM   2611  CG   PHE   546    46.052    9.084   14.405   1.00   35.41
ATOM   2612  CD1  PHE   546    46.890    9.545   15.411   1.00   35.87
ATOM   2613  CD2  PHE   546    46.618    8.471   13.292   1.00   36.70
ATOM   2614  CE1  PHE   546    48.264    9.397   15.310   1.00   35.65
ATOM   2615  CE2  PHE   546    47.996    8.317   13.183   1.00   34.51
ATOM   2616  CZ   PHE   546    48.817    8.779   14.192   1.00   35.18
ATOM   2617  C    PHE   546    42.632    9.713   16.041   1.00   35.77
ATOM   2618  O    PHE   546    42.435   10.845   16.486   1.00   34.76
ATOM   2619  N    LEU   547    41.655    8.898   15.643   1.00   36.27
ATOM   2620  CA   LEU   547    40.244    9.287   15.673   1.00   36.99
ATOM   2621  CB   LEU   547    39.365    8.134   15.188   1.00   35.89
ATOM   2622  CG   LEU   547    37.856    8.399   15.168   1.00   35.86
ATOM   2623  CD1  LEU   547    37.535    9.650   14.342   1.00   34.64
ATOM   2624  CD2  LEU   547    37.143    7.178   14.609   1.00   35.41
ATOM   2625  C    LEU   547    39.824    9.718   17.075   1.00   37.45
ATOM   2626  O    LEU   547    39.218   10.776   17.253   1.00   36.59
ATOM   2627  N    SER   548    40.176    8.906   18.066   1.00   38.91
ATOM   2628  CA   SER   548    39.855    9.212   19.454   1.00   40.88
ATOM   2629  CB   SER   548    40.258    8.050   20.375   1.00   42.68
ATOM   2630  OG   SER   548    41.228    7.208   19.763   1.00   46.74
ATOM   2631  C    SER   548    40.534   10.505   19.902   1.00   40.49
ATOM   2632  O    SER   548    40.013   11.231   20.747   1.00   41.69
ATOM   2633  N    GLN   549    41.691   10.802   19.328   1.00   39.68
ATOM   2634  CA   GLN   549    42.395   12.015   19.686   1.00   39.49
ATOM   2635  CB   GLN   549    43.845   11.956   19.218   1.00   41.25
ATOM   2636  CG   GLN   549    44.736   11.018   20.006   1.00   42.18
ATOM   2637  CD   GLN   549    46.209   11.238   19.706   1.00   42.98
ATOM   2638  OE1  GLN   549    46.922   10.300   19.363   1.00   44.07
ATOM   2639  NE2  GLN   549    46.674   12.479   19.847   1.00   42.49
ATOM   2640  C    GLN   549    41.723   13.222   19.063   1.00   40.07
ATOM   2641  O    GLN   549    41.451   14.213   19.741   1.00   39.72
ATOM   2642  N    THR   550    41.437   13.124   17.770   1.00   41.21
ATOM   2643  CA   THR   550    40.824   14.222   17.036   1.00   43.02
ATOM   2644  CB   THR   550    40.714   13.920   15.515   1.00   43.79
ATOM   2645  OG1  THR   550    40.200   12.595   15.307   1.00   44.92
ATOM   2646  CG2  THR   550    42.069   14.041   14.857   1.00   43.92
ATOM   2647  C    THR   550    39.469   14.641   17.575   1.00   43.65
ATOM   2648  O    THR   550    39.197   15.836   17.716   1.00   43.09
ATOM   2649  N    LYS   551    38.611   13.671   17.871   1.00   45.05
ATOM   2650  CA   LYS   551    37.301   14.027   18.391   1.00   46.81
ATOM   2651  CB   LYS   551    36.265   12.922   18.145   1.00   45.60
ATOM   2652  CG   LYS   551    36.584   11.534   18.617   1.00   44.11
ATOM   2653  CD   LYS   551    35.523   10.578   18.052   1.00   42.52
ATOM   2654  CE   LYS   551    35.569    9.206   18.706   1.00   41.73
ATOM   2655  NZ   LYS   551    34.474    8.315   18.244   1.00   39.62
ATOM   2656  C    LYS   551    37.345   14.523   19.837   1.00   47.87
ATOM   2657  O    LYS   551    36.420   15.198   20.304   1.00   48.23
ATOM   2658  N    GLN   552    38.473   14.275   20.499   1.00   49.00
ATOM   2659  CA   GLN   552    38.699   14.719   21.870   1.00   49.66
ATOM   2660  CB   GLN   552    39.705   13.800   22.555   1.00   51.22
ATOM   2661  CG   GLN   552    40.070   14.232   23.961   1.00   55.28
ATOM   2662  CD   GLN   552    41.365   13.612   24.435   1.00   57.87
ATOM   2663  OE1  GLN   552    41.518   12.388   24.443   1.00   59.24
```

FIGURE 1A-21

```
ATOM   2664  NE2  GLN  552   42.315  14.457  24.827  1.00  59.52
ATOM   2665  C    GLN  552   39.250  16.150  21.837  1.00  50.06
ATOM   2666  O    GLN  552   39.060  16.930  22.776  1.00  49.38
ATOM   2667  N    SER  553   39.944  16.479  20.748  1.00  50.55
ATOM   2668  CA   SER  553   40.532  17.802  20.560  1.00  50.62
ATOM   2669  CB   SER  553   41.660  17.742  19.514  1.00  50.03
ATOM   2670  OG   SER  553   41.169  17.575  18.189  1.00  47.69
ATOM   2671  C    SER  553   39.494  18.833  20.129  1.00  51.44
ATOM   2672  O    SER  553   39.792  20.024  20.048  1.00  52.81
ATOM   2673  N    GLY  554   38.282  18.375  19.840  1.00  52.03
ATOM   2674  CA   GLY  554   37.240  19.282  19.397  1.00  52.43
ATOM   2675  C    GLY  554   37.401  19.638  17.924  1.00  52.57
ATOM   2676  O    GLY  554   36.778  20.581  17.426  1.00  53.51
ATOM   2677  N    GLU  555   38.231  18.874  17.221  1.00  51.69
ATOM   2678  CA   GLU  555   38.470  19.103  15.802  1.00  50.16
ATOM   2679  CB   GLU  555   39.399  18.011  15.259  1.00  51.56
ATOM   2680  CG   GLU  555   40.415  18.498  14.237  1.00  53.15
ATOM   2681  CD   GLU  555   41.455  19.438  14.830  1.00  53.99
ATOM   2682  OE1  GLU  555   42.325  18.955  15.595  1.00  54.91
ATOM   2683  OE2  GLU  555   41.406  20.652  14.521  1.00  53.02
ATOM   2684  C    GLU  555   37.136  19.099  15.047  1.00  47.60
ATOM   2685  O    GLU  555   36.346  18.171  15.193  1.00  48.20
ATOM   2686  N    ASN  556   36.916  20.125  14.226  1.00  45.50
ATOM   2687  CA   ASN  556   35.683  20.303  13.439  1.00  42.96
ATOM   2688  CB   ASN  556   35.796  21.560  12.573  1.00  44.24
ATOM   2689  CG   ASN  556   34.507  22.366  12.529  1.00  45.63
ATOM   2690  OD1  ASN  556   34.544  23.589  12.485  1.00  46.71
ATOM   2691  ND2  ASN  556   33.366  21.687  12.533  1.00  46.27
ATOM   2692  C    ASN  556   35.240  19.117  12.564  1.00  40.45
ATOM   2693  O    ASN  556   34.038  18.830  12.448  1.00  41.36
ATOM   2694  N    PHE  557   36.188  18.477  11.894  1.00  35.01
ATOM   2695  CA   PHE  557   35.874  17.321  11.056  1.00  30.51
ATOM   2696  CB   PHE  557   36.141  17.617   9.575  1.00  26.25
ATOM   2697  CG   PHE  557   35.119  18.516   8.936  1.00  24.10
ATOM   2698  CD1  PHE  557   35.093  19.878   9.212  1.00  23.27
ATOM   2699  CD2  PHE  557   34.184  18.001   8.050  1.00  21.00
ATOM   2700  CE1  PHE  557   34.150  20.710   8.612  1.00  20.85
ATOM   2701  CE2  PHE  557   33.243  18.825   7.450  1.00  18.34
ATOM   2702  CZ   PHE  557   33.225  20.174   7.731  1.00  20.74
ATOM   2703  C    PHE  557   36.809  16.228  11.535  1.00  29.61
ATOM   2704  O    PHE  557   37.739  15.845  10.825  1.00  30.80
ATOM   2705  N    PRO  558   36.557  15.687  12.738  1.00  28.44
ATOM   2706  CD   PRO  558   35.338  15.899  13.535  1.00  27.55
ATOM   2707  CA   PRO  558   37.378  14.633  13.341  1.00  27.40
ATOM   2708  CB   PRO  558   36.580  14.244  14.586  1.00  27.92
ATOM   2709  CG   PRO  558   35.178  14.573  14.212  1.00  28.58
ATOM   2710  C    PRO  558   37.715  13.434  12.459  1.00  25.97
ATOM   2711  O    PRO  558   38.848  12.948  12.490  1.00  25.27
ATOM   2712  N    TYR  559   36.763  12.977  11.652  1.00  23.97
ATOM   2713  CA   TYR  559   37.039  11.836  10.796  1.00  23.89
ATOM   2714  CB   TYR  559   35.753  11.193  10.258  1.00  21.95
ATOM   2715  CG   TYR  559   35.984   9.781   9.769  1.00  21.57
ATOM   2716  CD1  TYR  559   35.891   8.685  10.639  1.00  24.12
ATOM   2717  CE1  TYR  559   36.204   7.389  10.207  1.00  22.12
ATOM   2718  CD2  TYR  559   36.382   9.541   8.461  1.00  22.30
ATOM   2719  CE2  TYR  559   36.696   8.261   8.024  1.00  22.08
ATOM   2720  CZ   TYR  559   36.610   7.199   8.895  1.00  22.68
ATOM   2721  OH   TYR  559   36.966   5.958   8.437  1.00  28.01
```

FIGURE 1A-22

| | | | | | | | | |
|---|---|---|---|---|---|---|---|---|
| ATOM | 2722 | C | TYR | 559 | 38.002 | 12.202 | 9.661 | 1.00 | 23.70 |
| ATOM | 2723 | O | TYR | 559 | 38.932 | 11.451 | 9.360 | 1.00 | 25.56 |
| ATOM | 2724 | N | LEU | 560 | 37.819 | 13.366 | 9.053 | 1.00 | 23.40 |
| ATOM | 2725 | CA | LEU | 560 | 38.716 | 13.756 | 7.965 | 1.00 | 22.40 |
| ATOM | 2726 | CB | LEU | 560 | 38.184 | 14.979 | 7.203 | 1.00 | 19.29 |
| ATOM | 2727 | CG | LEU | 560 | 36.905 | 14.744 | 6.387 | 1.00 | 19.21 |
| ATOM | 2728 | CD1 | LEU | 560 | 36.621 | 15.965 | 5.524 | 1.00 | 17.94 |
| ATOM | 2729 | CD2 | LEU | 560 | 37.023 | 13.499 | 5.508 | 1.00 | 16.77 |
| ATOM | 2730 | C | LEU | 560 | 40.133 | 14.007 | 8.475 | 1.00 | 21.57 |
| ATOM | 2731 | O | LEU | 560 | 41.096 | 13.511 | 7.896 | 1.00 | 22.32 |
| ATOM | 2732 | N | VAL | 561 | 40.247 | 14.730 | 9.587 | 1.00 | 21.43 |
| ATOM | 2733 | CA | VAL | 561 | 41.543 | 15.049 | 10.175 | 1.00 | 20.86 |
| ATOM | 2734 | CB | VAL | 561 | 41.404 | 15.990 | 11.397 | 1.00 | 20.24 |
| ATOM | 2735 | CG1 | VAL | 561 | 42.761 | 16.265 | 12.011 | 1.00 | 22.08 |
| ATOM | 2736 | CG2 | VAL | 561 | 40.789 | 17.309 | 10.972 | 1.00 | 20.07 |
| ATOM | 2737 | C | VAL | 561 | 42.276 | 13.774 | 10.566 | 1.00 | 21.69 |
| ATOM | 2738 | O | VAL | 561 | 43.384 | 13.537 | 10.103 | 1.00 | 22.16 |
| ATOM | 2739 | N | ALA | 562 | 41.634 | 12.936 | 11.379 | 1.00 | 22.88 |
| ATOM | 2740 | CA | ALA | 562 | 42.210 | 11.672 | 11.831 | 1.00 | 22.13 |
| ATOM | 2741 | CB | ALA | 562 | 41.248 | 10.966 | 12.728 | 1.00 | 20.52 |
| ATOM | 2742 | C | ALA | 562 | 42.580 | 10.763 | 10.663 | 1.00 | 23.28 |
| ATOM | 2743 | O | ALA | 562 | 43.571 | 10.031 | 10.728 | 1.00 | 24.95 |
| ATOM | 2744 | N | TYR | 563 | 41.787 | 10.792 | 9.596 | 1.00 | 23.47 |
| ATOM | 2745 | CA | TYR | 563 | 42.083 | 9.952 | 8.443 | 1.00 | 24.18 |
| ATOM | 2746 | CB | TYR | 563 | 40.887 | 9.861 | 7.496 | 1.00 | 24.43 |
| ATOM | 2747 | CG | TYR | 563 | 40.962 | 8.633 | 6.631 | 1.00 | 25.76 |
| ATOM | 2748 | CD1 | TYR | 563 | 40.645 | 7.376 | 7.151 | 1.00 | 26.28 |
| ATOM | 2749 | CE1 | TYR | 563 | 40.789 | 6.222 | 6.386 | 1.00 | 27.58 |
| ATOM | 2750 | CD2 | TYR | 563 | 41.418 | 8.708 | 5.315 | 1.00 | 26.40 |
| ATOM | 2751 | CE2 | TYR | 563 | 41.566 | 7.560 | 4.538 | 1.00 | 27.19 |
| ATOM | 2752 | CZ | TYR | 563 | 41.251 | 6.322 | 5.081 | 1.00 | 27.76 |
| ATOM | 2753 | OH | TYR | 563 | 41.391 | 5.193 | 4.314 | 1.00 | 29.58 |
| ATOM | 2754 | C | TYR | 563 | 43.345 | 10.426 | 7.701 | 1.00 | 23.93 |
| ATOM | 2755 | O | TYR | 563 | 44.206 | 9.612 | 7.341 | 1.00 | 23.21 |
| ATOM | 2756 | N | GLN | 564 | 43.452 | 11.736 | 7.478 | 1.00 | 23.24 |
| ATOM | 2757 | CA | GLN | 564 | 44.631 | 12.298 | 6.825 | 1.00 | 22.78 |
| ATOM | 2758 | CB | GLN | 564 | 44.510 | 13.825 | 6.675 | 1.00 | 21.93 |
| ATOM | 2759 | CG | GLN | 564 | 45.804 | 14.539 | 6.222 | 1.00 | 21.73 |
| ATOM | 2760 | CD | GLN | 564 | 46.209 | 14.241 | 4.781 | 1.00 | 21.45 |
| ATOM | 2761 | OE1 | GLN | 564 | 45.773 | 14.928 | 3.846 | 1.00 | 21.98 |
| ATOM | 2762 | NE2 | GLN | 564 | 47.055 | 13.231 | 4.595 | 1.00 | 18.62 |
| ATOM | 2763 | C | GLN | 564 | 45.843 | 11.951 | 7.689 | 1.00 | 22.24 |
| ATOM | 2764 | O | GLN | 564 | 46.898 | 11.598 | 7.170 | 1.00 | 22.24 |
| ATOM | 2765 | N | ALA | 565 | 45.671 | 12.015 | 9.006 | 1.00 | 22.72 |
| ATOM | 2766 | CA | ALA | 565 | 46.749 | 11.700 | 9.938 | 1.00 | 24.32 |
| ATOM | 2767 | CB | ALA | 565 | 46.330 | 12.008 | 11.362 | 1.00 | 23.28 |
| ATOM | 2768 | C | ALA | 565 | 47.138 | 10.232 | 9.803 | 1.00 | 25.85 |
| ATOM | 2769 | O | ALA | 565 | 48.324 | 9.890 | 9.830 | 1.00 | 26.02 |
| ATOM | 2770 | N | THR | 566 | 46.138 | 9.377 | 9.607 | 1.00 | 26.56 |
| ATOM | 2771 | CA | THR | 566 | 46.359 | 7.939 | 9.446 | 1.00 | 27.00 |
| ATOM | 2772 | CB | THR | 566 | 45.007 | 7.215 | 9.330 | 1.00 | 25.94 |
| ATOM | 2773 | OG1 | THR | 566 | 44.338 | 7.276 | 10.593 | 1.00 | 26.58 |
| ATOM | 2774 | CG2 | THR | 566 | 45.184 | 5.770 | 8.926 | 1.00 | 25.45 |
| ATOM | 2775 | C | THR | 566 | 47.228 | 7.647 | 8.212 | 1.00 | 26.39 |
| ATOM | 2776 | O | THR | 566 | 48.239 | 6.951 | 8.288 | 1.00 | 26.71 |
| ATOM | 2777 | N | VAL | 567 | 46.823 | 8.205 | 7.082 | 1.00 | 26.66 |
| ATOM | 2778 | CA | VAL | 567 | 47.533 | 8.047 | 5.824 | 1.00 | 25.23 |
| ATOM | 2779 | CB | VAL | 567 | 46.777 | 8.804 | 4.704 | 1.00 | 24.80 |

FIGURE 1A-23

```
ATOM   2780  CG1  VAL  567  47.633   8.941   3.480  1.00  24.37
ATOM   2781  CG2  VAL  567  45.473   8.053   4.362  1.00  24.95
ATOM   2782  C    VAL  567  48.989   8.519   5.947  1.00  24.66
ATOM   2783  O    VAL  567  49.903   7.867   5.438  1.00  24.50
ATOM   2784  N    CYS  568  49.202   9.622   6.656  1.00  24.76
ATOM   2785  CA   CYS  568  50.544  10.156   6.861  1.00  25.31
ATOM   2786  CB   CYS  568  50.490  11.529   7.546  1.00  24.87
ATOM   2787  SG   CYS  568  49.934  12.883   6.493  1.00  23.18
ATOM   2788  C    CYS  568  51.357   9.188   7.717  1.00  26.58
ATOM   2789  O    CYS  568  52.460   8.797   7.351  1.00  26.47
ATOM   2790  N    ALA  569  50.794   8.776   8.843  1.00  27.17
ATOM   2791  CA   ALA  569  51.484   7.862   9.726  1.00  28.58
ATOM   2792  CB   ALA  560  50.601   7.502  10.904  1.00  28.99
ATOM   2793  C    ALA  569  51.899   6.607   8.967  1.00  30.34
ATOM   2794  O    ALA  569  53.086   6.270   8.921  1.00  31.47
ATOM   2795  N    ARG  570  50.938   5.961   8.308  1.00  30.52
ATOM   2796  CA   ARG  570  51.210   4.732   7.567  1.00  30.59
ATOM   2797  CB   ARG  570  49.918   4.143   6.992  1.00  30.69
ATOM   2798  CG   ARG  570  48.997   3.561   8.054  1.00  30.15
ATOM   2799  CD   ARG  570  47.765   2.913   7.458  1.00  29.12
ATOM   2800  NE   ARG  570  46.828   2.506   8.507  1.00  30.17
ATOM   2801  CZ   ARG  570  45.516   2.374   8.336  1.00  27.42
ATOM   2802  NH1  ARG  570  44.748   1.995   9.347  1.00  29.10
ATOM   2803  NH2  ARG  570  44.966   2.638   7.163  1.00  27.47
ATOM   2804  C    ARG  570  52.253   4.890   6.469  1.00  31.40
ATOM   2805  O    ARG  570  52.902   3.923   6.084  1.00  33.32
ATOM   2806  N    ALA  571  52.390   6.103   5.944  1.00  31.42
ATOM   2807  CA   ALA  571  53.370   6.380   4.901  1.00  29.19
ATOM   2808  CB   ALA  571  52.795   7.363   3.905  1.00  26.97
ATOM   2809  C    ALA  571  54.636   6.960   5.536  1.00  30.02
ATOM   2810  O    ALA  571  55.630   7.179   4.859  1.00  31.04
ATOM   2811  N    GLN  572  54.609   7.157   6.850  1.00  31.02
ATOM   2812  CA   GLN  572  55.727   7.753   7.568  1.00  31.99
ATOM   2813  CB   GLN  572  56.946   6.842   7.579  1.00  35.87
ATOM   2814  CG   GLN  572  56.830   5.689   8.542  1.00  41.94
ATOM   2815  CD   GLN  572  58.170   5.040   8.801  1.00  45.72
ATOM   2816  OE1  GLN  572  58.562   4.819   9.954  1.00  47.02
ATOM   2817  NE2  GLN  572  58.894   4.740   7.726  1.00  48.15
ATOM   2818  C    GLN  572  56.071   9.093   6.935  1.00  30.48
ATOM   2819  O    GLN  572  57.235   9.489   6.880  1.00  30.24
ATOM   2820  N    ALA  573  55.029   9.765   6.451  1.00  28.34
ATOM   2821  CA   ALA  573  55.114  11.072   5.814  1.00  26.25
ATOM   2822  CB   ALA  573  54.253  11.084   4.537  1.00  24.36
ATOM   2823  C    ALA  573  54.601  12.113   6.822  1.00  25.50
ATOM   2824  O    ALA  573  53.844  11.783   7.744  1.00  24.77
ATOM   2825  N    PRO  574  55.049  13.370   6.699  1.00  24.64
ATOM   2826  CD   PRO  574  56.068  13.892   5.771  1.00  24.05
ATOM   2827  CA   PRO  574  54.595  14.404   7.633  1.00  24.57
ATOM   2828  CB   PRO  574  55.675  15.471   7.500  1.00  25.21
ATOM   2829  CG   PRO  574  56.036  15.383   6.042  1.00  26.61
ATOM   2830  C    PRO  574  53.227  14.957   7.253  1.00  25.52
ATOM   2831  O    PRO  574  52.784  14.813   6.107  1.00  25.99
ATOM   2832  N    PRO  575  52.525  15.580   8.212  1.00  25.30
ATOM   2833  CD   PRO  575  52.893  15.792   9.622  1.00  24.49
ATOM   2834  CA   PRO  575  51.202  16.146   7.926  1.00  25.44
ATOM   2835  CB   PRO  575  50.717  16.584   9.309  1.00  25.55
ATOM   2836  CG   PRO  575  51.989  16.927  10.022  1.00  25.38
ATOM   2837  C    PRO  575  51.327  17.324   6.955  1.00  25.27
```

FIGURE 1A-24

```
ATOM   2838  O    PRO  575   52.439  17.751   6.630  1.00  24.04
ATOM   2839  N    PRO  576   50.190  17.827   6.440  1.00  25.82
ATOM   2840  CD   PRO  576   48.829  17.300   6.637  1.00  24.51
ATOM   2841  CA   PRO  576   50.171  18.952   5.501  1.00  26.20
ATOM   2842  CB   PRO  576   48.686  19.236   5.357  1.00  24.96
ATOM   2843  CG   PRO  576   48.099  17.876   5.460  1.00  25.27
ATOM   2844  C    PRO  576   50.935  20.158   6.031  1.00  27.89
ATOM   2845  O    PRO  576   51.529  20.921   5.262  1.00  28.06
ATOM   2846  N    SER  577   50.893  20.333   7.345  1.00  29.44
ATOM   2847  CA   SER  577   51.599  21.415   8.012  1.00  30.58
ATOM   2848  CB   SER  577   50.800  22.720   7.946  1.00  29.32
ATOM   2849  OG   SER  577   49.630  22.650   8.739  1.00  29.45
ATOM   2850  C    SER  577   51.777  20.963   9.452  1.00  32.15
ATOM   2851  O    SER  577   51.410  19.839   9.801  1.00  31.77
ATOM   2852  N    TRP  578   52.371  21.819  10.276  1.00  34.52
ATOM   2853  CA   TRP  578   52.580  21.500  11.680  1.00  35.77
ATOM   2854  CB   TRP  578   54.069  21.540  12.040  1.00  36.18
ATOM   2855  CG   TRP  578   54.784  20.303  11.588  1.00  36.28
ATOM   2856  CD2  TRP  578   54.612  18.983  12.111  1.00  36.36
ATOM   2857  CE2  TRP  578   55.441  18.121  11.353  1.00  35.89
ATOM   2858  CE3  TRP  578   53.835  18.443  13.148  1.00  35.12
ATOM   2859  CD1  TRP  578   55.691  20.196  10.564  1.00  35.71
ATOM   2860  NE1  TRP  578   56.086  18.887  10.418  1.00  35.51
ATOM   2861  CZ2  TRP  578   55.513  16.746  11.599  1.00  35.54
ATOM   2862  CZ3  TRP  578   53.907  17.078  13.391  1.00  35.54
ATOM   2863  CH2  TRP  578   54.741  16.244  12.619  1.00  36.06
ATOM   2864  C    TRP  578   51.761  22.431  12.555  1.00  35.97
ATOM   2865  O    TRP  578   52.179  22.832  13.635  1.00  36.76
ATOM   2866  N    ASP  579   50.595  22.800  12.051  1.00  36.49
ATOM   2867  CA   ASP  579   49.694  23.656  12.786  1.00  38.09
ATOM   2868  CB   ASP  579   48.710  24.314  11.819  1.00  41.72
ATOM   2869  CG   ASP  579   49.409  25.243  10.817  1.00  45.89
ATOM   2870  OD1  ASP  579   49.175  25.102   9.595  1.00  48.85
ATOM   2871  OD2  ASP  579   50.197  26.119  11.248  1.00  48.08
ATOM   2872  C    ASP  579   48.999  22.742  13.792  1.00  37.56
ATOM   2873  O    ASP  579   48.998  21.528  13.606  1.00  38.03
ATOM   2874  N    ALA  580   48.419  23.316  14.847  1.00  36.79
ATOM   2875  CA   ALA  580   47.748  22.552  15.915  1.00  35.50
ATOM   2876  CB   ALA  580   46.956  23.496  16.810  1.00  36.40
ATOM   2877  C    ALA  580   46.856  21.391  15.470  1.00  34.02
ATOM   2878  O    ALA  580   46.700  20.404  16.188  1.00  32.85
ATOM   2879  N    MET  581   46.272  21.520  14.285  1.00  33.63
ATOM   2880  CA   MET  581   45.401  20.492  13.740  1.00  32.54
ATOM   2881  CB   MET  581   44.908  20.902  12.348  1.00  32.51
ATOM   2882  CG   MET  581   44.043  19.857  11.656  1.00  31.86
ATOM   2883  SD   MET  581   43.448  20.404  10.057  1.00  33.21
ATOM   2884  CE   MET  581   42.419  21.765  10.534  1.00  34.37
ATOM   2885  C    MET  581   46.119  19.158  13.636  1.00  32.20
ATOM   2886  O    MET  581   45.470  18.113  13.609  1.00  33.12
ATOM   2887  N    TRP  582   47.450  19.194  13.591  1.00  30.73
ATOM   2888  CA   TRP  582   48.246  17.979  13.455  1.00  29.56
ATOM   2889  CB   TRP  582   49.078  18.060  12.172  1.00  25.83
ATOM   2890  CG   TRP  582   48.252  18.490  10.972  1.00  22.26
ATOM   2891  CD2  TRP  582   47.205  17.743  10.330  1.00  19.39
ATOM   2892  CE2  TRP  582   46.672  18.563   9.319  1.00  18.29
ATOM   2893  CE3  TRP  582   46.666  16.461  10.515  1.00  18.37
ATOM   2894  CD1  TRP  582   48.312  19.690  10.331  1.00  19.79
ATOM   2895  NE1  TRP  582   47.367  19.744   9.345  1.00  19.82
```

FIGURE 1A-25

```
ATOM   2896  CZ2  TRP   582   45.620   18.148    8.490  1.00  16.85
ATOM   2897  CZ3  TRP   582   45.623   16.047    9.693  1.00  16.11
ATOM   2898  CH2  TRP   582   45.111   16.891    8.694  1.00  17.32
ATOM   2899  C    TRP   582   49.121   17.630   14.661  1.00  31.31
ATOM   2900  O    TRP   582   50.215   17.097   14.519  1.00  31.41
ATOM   2901  N    ALA   583   48.589   17.866   15.856  1.00  34.62
ATOM   2902  CA   ALA   583   49.285   17.575   17.107  1.00  34.61
ATOM   2903  CB   ALA   583   48.493   18.145   18.283  1.00  34.87
ATOM   2904  C    ALA   583   49.496   16.075   17.295  1.00  34.99
ATOM   2905  O    ALA   583   50.489   15.646   17.877  1.00  35.31
ATOM   2906  N    CYS   584   48.560   15.282   16.788  1.00  37.04
ATOM   2907  CA   CYS   584   48.610   13.815   16.893  1.00  38.08
ATOM   2908  CB   CYS   584   47.396   13.199   16.182  1.00  37.55
ATOM   2909  SG   CYS   584   47.130   13.868   14.512  1.00  40.22
ATOM   2910  C    CYS   584   49.886   13.200   16.317  1.00  37.89
ATOM   2911  O    CYS   584   50.375   12.178   16.809  1.00  37.62
ATOM   2912  N    LEU   585   50.422   13.835   15.279  1.00  37.89
ATOM   2913  CA   LEU   585   51.616   13.339   14.604  1.00  37.24
ATOM   2914  CB   LEU   585   51.506   13.590   13.099  1.00  34.72
ATOM   2915  CG   LEU   585   50.359   12.817   12.447  1.00  33.11
ATOM   2916  CD1  LEU   585   50.194   13.205   10.994  1.00  32.42
ATOM   2917  CD2  LEU   585   50.624   11.328   12.586  1.00  33.32
ATOM   2918  C    LEU   585   52.913   13.916   15.122  1.00  37.69
ATOM   2919  O    LEU   585   53.967   13.659   14.549  1.00  38.68
ATOM   2920  N    ILE   586   52.844   14.667   16.215  1.00  38.37
ATOM   2921  CA   ILE   566   54.033   15.286   16.776  1.00  39.55
ATOM   2922  CB   ILE   586   53.675   16.366   17.816  1.00  38.52
ATOM   2923  CG2  ILE   586   54.915   16.799   18.593  1.00  37.57
ATOM   2924  CG1  ILE   586   53.067   17.575   17.101  1.00  38.01
ATOM   2925  CD1  ILE   586   52.671   18.705   18.018  1.00  37.82
ATOM   2926  C    ILE   586   55.015   14.277   17.355  1.00  41.37
ATOM   2927  O    ILE   586   56.191   14.274   16.985  1.00  42.88
ATOM   2928  N    ALA   587   54.528   13.391   18.215  1.00  41.55
ATOM   2929  CA   ALA   587   55.381   12.390   18.832  1.00  41.50
ATOM   2930  CB   ALA   587   54.544   11.442   19.665  1.00  42.38
ATOM   2931  C    ALA   587   56.214   11.606   17.810  1.00  42.23
ATOM   2932  O    ALA   587   57.358   11.236   18.089  1.00  43.74
ATOM   2933  N    LEU   588   55.644   11.375   16.628  1.00  41.27
ATOM   2934  CA   LEU   588   56.315   10.627   15.561  1.00  39.52
ATOM   2935  CB   LEU   588   55.270    9.940   14.678  1.00  39.86
ATOM   2936  CG   LEU   588   54.315    8.889   15.240  1.00  38.47
ATOM   2937  CD1  LEU   588   53.206    8.640   14.235  1.00  36.97
ATOM   2938  CD2  LEU   588   55.072    7.609   15.545  1.00  37.35
ATOM   2939  C    LEU   588   57.190   11.497   14.656  1.00  39.04
ATOM   2940  O    LEU   588   58.020   10.984   13.912  1.00  36.99
ATOM   2941  N    LYS   589   56.999   12.809   14.742  1.00  40.00
ATOM   2942  CA   LYS   589   57.701   13.800   13.922  1.00  42.08
ATOM   2943  CB   LYS   589   57.711   15.158   14.635  1.00  40.84
ATOM   2944  CG   LYS   589   58.259   16.282   13.795  1.00  41.90
ATOM   2945  CD   LYS   589   57.780   17.626   14.304  1.00  43.78
ATOM   2946  CE   LYS   589   58.264   18.756   13.414  1.00  44.18
ATOM   2947  NZ   LYS   589   57.675   20.058   13.824  1.00  46.71
ATOM   2948  C    LYS   589   59.099   13.460   13.368  1.00  43.12
ATOM   2949  O    LYS   589   59.343   13.595   12.162  1.00  43.36
ATOM   2950  N    PRO   590   60.026   13.013   14.230  1.00  43.51
ATOM   2951  CD   PRO   590   59.933   12.911   15.698  1.00  44.56
ATOM   2952  CA   PRO   590   61.378   12.672   13.778  1.00  42.92
ATOM   2953  CB   PRO   590   62.039   12.177   15.059  1.00  44.20
```

FIGURE 1A-26

| | | | | | | | | |
|---|---|---|---|---|---|---|---|---|
| ATOM | 2954 | CG | PRO | 590 | 61.380 | 13.008 | 16.112 | 1.00 | 44.80 |
| ATOM | 2955 | C | PRO | 590 | 61.432 | 11.598 | 12.700 | 1.00 | 42.62 |
| ATOM | 2956 | O | PRO | 590 | 62.368 | 11.558 | 11.901 | 1.00 | 44.16 |
| ATOM | 2957 | N | THR | 591 | 60.443 | 10.716 | 12.697 | 1.00 | 40.90 |
| ATOM | 2958 | CA | THR | 591 | 60.386 | 9.625 | 11.735 | 1.00 | 38.82 |
| ATOM | 2959 | CB | THR | 591 | 59.742 | 8.390 | 12.393 | 1.00 | 40.84 |
| ATOM | 2960 | OG1 | THR | 591 | 58.390 | 8.691 | 12.775 | 1.00 | 41.16 |
| ATOM | 2961 | CG2 | THR | 591 | 60.531 | 7.999 | 13.643 | 1.00 | 40.40 |
| ATOM | 2962 | C | THR | 591 | 59.637 | 9.953 | 10.441 | 1.00 | 36.37 |
| ATOM | 2963 | O | THR | 591 | 59.770 | 9.249 | 9.438 | 1.00 | 35.64 |
| ATOM | 2964 | N | LEU | 592 | 58.844 | 11.016 | 10.467 | 1.00 | 35.52 |
| ATOM | 2965 | CA | LEU | 592 | 58.054 | 11.415 | 9.308 | 1.00 | 32.95 |
| ATOM | 2966 | CB | LEU | 592 | 56.904 | 12.330 | 9.737 | 1.00 | 31.23 |
| ATOM | 2967 | CG | LEU | 592 | 55.935 | 11.656 | 10.719 | 1.00 | 30.46 |
| ATOM | 2968 | CD1 | LEU | 592 | 54.765 | 12.565 | 11.025 | 1.00 | 30.71 |
| ATOM | 2969 | CD2 | LEU | 592 | 55.438 | 10.341 | 10.145 | 1.00 | 28.34 |
| ATOM | 2970 | C | LEU | 592 | 58.945 | 12.090 | 8.293 | 1.00 | 32.65 |
| ATOM | 2971 | O | LEU | 592 | 59.561 | 13.116 | 8.579 | 1.00 | 31.57 |
| ATOM | 2972 | N | HIS | 593 | 58.998 | 11.508 | 7.100 | 1.00 | 33.01 |
| ATOM | 2973 | CA | HIS | 593 | 59.840 | 12.005 | 6.016 | 1.00 | 33.45 |
| ATOM | 2974 | CB | HIS | 593 | 61.103 | 11.140 | 5.916 | 1.00 | 36.56 |
| ATOM | 2975 | CG | HIS | 593 | 60.814 | 9.677 | 5.743 | 1.00 | 40.30 |
| ATOM | 2976 | CD2 | HIS | 593 | 60.734 | 8.908 | 4.632 | 1.00 | 41.91 |
| ATOM | 2977 | ND1 | HIS | 593 | 60.502 | 8.849 | 6.801 | 1.00 | 42.01 |
| ATOM | 2978 | CE1 | HIS | 593 | 60.239 | 7.634 | 6.351 | 1.00 | 41.87 |
| ATOM | 2979 | NE2 | HIS | 593 | 60.371 | 7.643 | 5.037 | 1.00 | 42.34 |
| ATOM | 2980 | C | HIS | 593 | 59.133 | 11.968 | 4.670 | 1.00 | 31.17 |
| ATOM | 2981 | O | HIS | 593 | 58.321 | 11.084 | 4.398 | 1.00 | 30.16 |
| ATOM | 2982 | N | GLY | 594 | 59.478 | 12.925 | 3.821 | 1.00 | 30.14 |
| ATOM | 2983 | CA | GLY | 594 | 58.907 | 12.975 | 2.490 | 1.00 | 27.59 |
| ATOM | 2984 | C | GLY | 594 | 57.747 | 13.918 | 2.282 | 1.00 | 24.95 |
| ATOM | 2985 | O | GLY | 594 | 57.465 | 14.775 | 3.123 | 1.00 | 26.12 |
| ATOM | 2986 | N | PRO | 595 | 57.093 | 13.815 | 1.119 | 1.00 | 22.45 |
| ATOM | 2987 | CD | PRO | 595 | 57.443 | 12.914 | 0.005 | 1.00 | 21.56 |
| ATOM | 2988 | CA | PRO | 595 | 55.951 | 14.652 | 0.776 | 1.00 | 21.39 |
| ATOM | 2989 | CB | PRO | 595 | 55.888 | 14.516 | -0.739 | 1.00 | 21.51 |
| ATOM | 2990 | CG | PRO | 595 | 56.283 | 13.091 | -0.953 | 1.00 | 21.07 |
| ATOM | 2991 | C | PRO | 595 | 54.684 | 14.117 | 1.443 | 1.00 | 21.15 |
| ATOM | 2992 | O | PRO | 595 | 54.562 | 12.927 | 1.741 | 1.00 | 21.34 |
| ATOM | 2993 | N | THR | 596 | 53.752 | 15.017 | 1.695 | 1.00 | 20.85 |
| ATOM | 2994 | CA | THR | 596 | 52.489 | 14.685 | 2.314 | 1.00 | 19.78 |
| ATOM | 2995 | CB | THR | 596 | 51.855 | 15.958 | 2.914 | 1.00 | 18.44 |
| ATOM | 2996 | OG1 | THR | 596 | 52.742 | 16.520 | 3.890 | 1.00 | 18.54 |
| ATOM | 2997 | CG2 | THR | 596 | 50.512 | 15.640 | 3.552 | 1.00 | 17.29 |
| ATOM | 2998 | C | THR | 596 | 51.499 | 14.121 | 1.304 | 1.00 | 19.38 |
| ATOM | 2999 | O | THR | 596 | 51.308 | 14.712 | 0.233 | 1.00 | 19.92 |
| ATOM | 3000 | N | PRO | 597 | 50.977 | 12.901 | 1.551 | 1.00 | 19.28 |
| ATOM | 3001 | CD | PRO | 597 | 51.461 | 11.862 | 2.478 | 1.00 | 18.63 |
| ATOM | 3002 | CA | PRO | 597 | 49.997 | 12.351 | 0.607 | 1.00 | 19.90 |
| ATOM | 3003 | CB | PRO | 597 | 49.972 | 10.863 | 0.970 | 1.00 | 19.83 |
| ATOM | 3004 | CG | PRO | 597 | 50.380 | 10.840 | 2.410 | 1.00 | 19.57 |
| ATOM | 3005 | C | PRO | 597 | 48.671 | 13.092 | 0.927 | 1.00 | 20.50 |
| ATOM | 3006 | O | PRO | 597 | 47.891 | 12.680 | 1.790 | 1.00 | 20.99 |
| ATOM | 3007 | N | LEU | 598 | 48.501 | 14.252 | 0.294 | 1.00 | 18.90 |
| ATOM | 3008 | CA | LEU | 598 | 47.355 | 15.120 | 0.510 | 1.00 | 17.83 |
| ATOM | 3009 | CB | LEU | 598 | 47.614 | 16.493 | -0.128 | 1.00 | 17.96 |
| ATOM | 3010 | CG | LEU | 598 | 46.722 | 17.655 | 0.314 | 1.00 | 18.91 |
| ATOM | 3011 | CD1 | LEU | 598 | 46.948 | 17.896 | 1.792 | 1.00 | 16.89 |

FIGURE 1A-27

```
ATOM   3012  CD2  LEU  598  47.011  18.916  -0.490  1.00  16.71
ATOM   3013  C    LEU  598  46.037  14.542   0.010  1.00  17.19
ATOM   3014  O    LEU  598  45.862  14.285  -1.187  1.00  17.59
ATOM   3015  N    LEU  599  45.097  14.378   0.935  1.00  15.70
ATOM   3016  CA   LEU  599  43.801  13.823   0.598  1.00  15.41
ATOM   3017  CB   LEU  599  43.236  13.034   1.782  1.00  14.25
ATOM   3018  CG   LEU  599  44.071  11.861   2.304  1.00  14.47
ATOM   3019  CD1  LEU  599  43.268  11.092   3.331  1.00  11.46
ATOM   3020  CD2  LEU  599  44.500  10.944   1.165  1.00  12.30
ATOM   3021  C    LEU  599  42.832  14.907   0.188  1.00  15.60
ATOM   3022  O    LEU  599  42.063  14.739   0.743  1.00  14.98
ATOM   3023  N    TYR  600  42.889  16.022   0.902  1.00  16.33
ATOM   3024  CA   TYR  600  42.025  17.178   0.675  1.00  16.87
ATOM   3025  CB   TYR  600  40.607  16.876   1.177  1.00  16.11
ATOM   3026  CG   TYR  600  40.567  15.864   2.303  1.00  15.17
ATOM   3027  CD1  TYR  600  41.172  16.124   3.536  1.00  15.04
ATOM   3028  CE1  TYR  600  41.198  15.163   4.546  1.00  15.31
ATOM   3029  CD2  TYR  600  39.980  14.622   2.112  1.00  15.05
ATOM   3030  CE2  TYR  600  39.997  13.657   3.112  1.00  16.28
ATOM   3031  CZ   TYR  600  40.607  13.931   4.323  1.00  15.83
ATOM   3032  OH   TYR  600  40.623  12.953   5.295  1.00  18.80
ATOM   3033  C    TYR  600  42.644  18.279   1.516  1.00  16.31
ATOM   3034  O    TYR  600  43.624  18.025   2.212  1.00  17.03
ATOM   3035  N    ARG  601  42.083  19.485   1.480  1.00  17.91
ATOM   3036  CA   ARG  601  42.623  20.578   2.287  1.00  19.15
ATOM   3037  CB   ARG  601  42.991  21.775   1.407  1.00  19.16
ATOM   3038  CG   ARG  601  43.949  21.415   0.298  1.00  21.99
ATOM   3039  CD   ARG  601  44.411  22.615  -0.487  1.00  24.32
ATOM   3040  NE   ARG  601  45.189  22.200  -1.649  1.00  27.46
ATOM   3041  CZ   ARG  601  46.317  22.783  -2.052  1.00  29.91
ATOM   3042  NH1  ARG  601  46.954  22.328  -3.127  1.00  29.79
ATOM   3043  NH2  ARG  601  46.813  23.819  -1.385  1.00  29.28
ATOM   3044  C    ARG  601  41.688  21.004   3.420  1.00  20.23
ATOM   3045  O    ARG  601  40.501  21.273   3.208  1.00  20.27
ATOM   3046  N    LEU  602  42.237  21.035   4.630  1.00  21.19
ATOM   3047  CA   LEU  602  41.496  21.427   5.821  1.00  22.38
ATOM   3048  CB   LEU  602  41.437  20.264   6.809  1.00  22.22
ATOM   3049  CG   LEU  602  40.807  18.965   6.306  1.00  23.52
ATOM   3050  CD1  LEU  602  40.914  17.913   7.390  1.00  22.77
ATOM   3051  CD2  LEU  602  39.349  19.186   5.895  1.00  23.14
ATOM   3052  C    LEU  602  42.228  22.594   6.468  1.00  23.77
ATOM   3053  O    LEU  602  41.820  23.108   7.511  1.00  24.94
ATOM   3054  N    GLY  603  43.318  23.003   5.830  1.00  25.45
ATOM   3055  CA   GLY  603  44.131  24.087   6.330  1.00  25.21
ATOM   3056  C    GLY  603  45.240  24.352   5.339  1.00  26.57
ATOM   3057  O    GLY  603  45.160  23.924   4.183  1.00  26.29
ATOM   3058  N    ALA  604  46.293  25.021   5.796  1.00  27.24
ATOM   3059  CA   ALA  604  47.417  25.362   4.934  1.00  27.36
ATOM   3060  CB   ALA  604  48.215  26.499   5.554  1.00  27.18
ATOM   3061  C    ALA  604  48.315  24.164   4.684  1.00  26.80
ATOM   3062  O    ALA  604  48.598  23.395   5.603  1.00  26.71
ATOM   3063  N    VAL  605  48.728  23.990   3.431  1.00  28.18
ATOM   3064  CA   VAL  605  49.615  22.892   3.059  1.00  29.48
ATOM   3065  CB   VAL  605  49.089  22.064   1.812  1.00  28.74
ATOM   3066  CG1  VAL  605  47.642  21.658   2.015  1.00  28.64
ATOM   3067  CG2  VAL  605  49.221  22.825   0.518  1.00  29.95
ATOM   3068  C    VAL  605  51.000  23.487   2.821  1.00  30.10
ATOM   3069  O    VAL  605  51.255  24.133   1.807  1.00  30.89
```

FIGURE 1A-28

| | | | | | | | | | |
|---|---|---|---|---|---|---|---|---|---|
| ATOM | 3070 | N | GLN | 606 | 51.863 | 23.357 | 3.818 | 1.00 | 31.14 |
| ATOM | 3071 | CA | GLN | 606 | 53.213 | 23.897 | 3.720 | 1.00 | 32.44 |
| ATOM | 3072 | CB | GLN | 606 | 53.627 | 24.481 | 5.068 | 1.00 | 34.05 |
| ATOM | 3073 | CG | GLN | 606 | 52.846 | 25.750 | 5.412 | 1.00 | 38.82 |
| ATOM | 3074 | CD | GLN | 606 | 52.595 | 25.915 | 6.899 | 1.00 | 41.93 |
| ATOM | 3075 | OE1 | GLN | 606 | 51.501 | 26.294 | 7.316 | 1.00 | 44.45 |
| ATOM | 3076 | NE2 | GLN | 606 | 53.605 | 25.625 | 7.710 | 1.00 | 43.43 |
| ATOM | 3077 | C | GLN | 606 | 54.249 | 22.900 | 3.200 | 1.00 | 31.71 |
| ATOM | 3078 | O | GIN | 606 | 55.117 | 23.251 | 2.399 | 1.00 | 32.38 |
| ATOM | 3079 | N | ASN | 607 | 54.143 | 21.652 | 3.636 | 1.00 | 30.92 |
| ATOM | 3080 | CA | ASN | 607 | 55.074 | 20.616 | 3.208 | 1.00 | 29.53 |
| ATOM | 3081 | CB | ASN | 607 | 54.861 | 19.351 | 4.047 | 1.00 | 31.91 |
| ATOM | 3082 | CG | ASN | 607 | 55.911 | 18.281 | 3.778 | 1.00 | 34.41 |
| ATOM | 3083 | OD1 | ASN | 607 | 57.109 | 18.580 | 3.692 | 1.00 | 35.38 |
| ATOM | 3084 | ND2 | ASN | 607 | 55.471 | 17.035 | 3.626 | 1.00 | 33.25 |
| ATOM | 3085 | C | ASN | 607 | 54.892 | 20.287 | 1.728 | 1.00 | 28.03 |
| ATOM | 3086 | O | ASN | 607 | 53.937 | 20.733 | 1.089 | 1.00 | 27.96 |
| ATOM | 3087 | N | GLU | 608 | 55.852 | 19.566 | 1.164 | 1.00 | 26.45 |
| ATOM | 3088 | CA | GLU | 608 | 55.755 | 19.146 | -0.227 | 1.00 | 25.62 |
| ATOM | 3089 | CB | GLU | 608 | 57.023 | 18.420 | -0.663 | 1.00 | 28.49 |
| ATOM | 3090 | CG | GLU | 608 | 58.214 | 19.314 | -0.845 | 1.00 | 33.96 |
| ATOM | 3091 | CD | GLU | 608 | 59.497 | 18.528 | -0.996 | 1.00 | 38.84 |
| ATOM | 3092 | OE1 | GLU | 608 | 59.482 | 17.495 | -1.711 | 1.00 | 40.73 |
| ATOM | 3093 | OE2 | GLU | 608 | 60.515 | 18.941 | -0.388 | 1.00 | 40.03 |
| ATOM | 3094 | C | GLU | 608 | 54.604 | 18.168 | -0.242 | 1.00 | 22.39 |
| ATOM | 3095 | O | GLU | 608 | 54.364 | 17.499 | 0.754 | 1.00 | 22.12 |
| ATOM | 3096 | N | VAL | 609 | 53.947 | 18.036 | -1.384 | 1.00 | 21.16 |
| ATOM | 3097 | CA | VAL | 609 | 52.803 | 17.147 | -1.525 | 1.00 | 19.97 |
| ATOM | 3098 | CB | VAL | 609 | 51.526 | 17.971 | -1.943 | 1.00 | 18.69 |
| ATOM | 3099 | CG1 | VAL | 609 | 50.343 | 17.049 | -2.263 | 1.00 | 18.90 |
| ATOM | 3100 | CG2 | VAL | 609 | 51.136 | 18.937 | -0.851 | 1.00 | 17.99 |
| ATOM | 3101 | C | VAL | 609 | 53.020 | 16.099 | -2.607 | 1.00 | 19.62 |
| ATOM | 3102 | O | VAL | 609 | 53.767 | 16.337 | -3.560 | 1.00 | 19.53 |
| ATOM | 3103 | N | THR | 610 | 52.413 | 14.926 | -2.419 | 1.00 | 19.46 |
| ATOM | 3104 | CA | THR | 610 | 52.412 | 13.872 | -3.430 | 1.00 | 20.82 |
| ATOM | 3105 | CB | THR | 610 | 53.156 | 12.556 | -3.003 | 1.00 | 21.42 |
| ATOM | 3106 | OG1 | THR | 610 | 53.151 | 11.639 | -4.108 | 1.00 | 21.70 |
| ATOM | 3107 | CG2 | THR | 610 | 52.507 | 11.877 | -1.806 | 1.00 | 20.08 |
| ATOM | 3108 | C | THR | 610 | 50.917 | 13.607 | -3.657 | 1.00 | 21.22 |
| ATOM | 3109 | O | THR | 610 | 50.105 | 13.807 | -2.743 | 1.00 | 22.98 |
| ATOM | 3110 | N | LEU | 611 | 50.541 | 13.278 | -4.890 | 1.00 | 21.98 |
| ATOM | 3111 | CA | LEU | 611 | 49.145 | 12.981 | -5.239 | 1.00 | 21.98 |
| ATOM | 3112 | CB | LEU | 611 | 48.648 | 13.895 | -6.369 | 1.00 | 20.70 |
| ATOM | 3113 | CG | LEU | 611 | 48.629 | 15.415 | -6.175 | 1.00 | 22.00 |
| ATOM | 3114 | CD1 | LEU | 611 | 47.817 | 16.058 | -7.299 | 1.00 | 20.18 |
| ATOM | 3115 | CD2 | LEU | 611 | 48.018 | 15.759 | -4.815 | 1.00 | 22.59 |
| ATOM | 3116 | C | LEU | 611 | 49.030 | 11.528 | -5.700 | 1.00 | 22.41 |
| ATOM | 3117 | O | LEU | 611 | 48.086 | 11.155 | -6.389 | 1.00 | 24.23 |
| ATOM | 3118 | N | THR | 612 | 49.997 | 10.709 | -5.321 | 1.00 | 23.19 |
| ATOM | 3119 | CA | THR | 612 | 50.002 | 9.319 | -5.732 | 1.00 | 25.23 |
| ATOM | 3120 | CB | THR | 612 | 51.449 | 8.834 | -5.995 | 1.00 | 27.01 |
| ATOM | 3121 | OG1 | THR | 612 | 52.242 | 8.995 | -4.805 | 1.00 | 29.09 |
| ATOM | 3122 | CG2 | THR | 612 | 52.079 | 9.633 | -7.127 | 1.00 | 27.28 |
| ATOM | 3123 | C | THR | 612 | 49.331 | 8.350 | -4.765 | 1.00 | 24.95 |
| ATOM | 3124 | O | THR | 612 | 49.217 | 7.168 | -5.072 | 1.00 | 25.66 |
| ATOM | 3125 | N | HIS | 613 | 48.904 | 8.816 | -3.595 | 1.00 | 24.14 |
| ATOM | 3126 | CA | HIS | 613 | 48.283 | 7.898 | -2.653 | 1.00 | 23.56 |
| ATOM | 3127 | CB | HIS | 613 | 48.080 | 8.555 | -1.292 | 1.00 | 21.38 |

FIGURE 1A-29

```
ATOM   3128  CG   HIS   613    47.870    7.579   -0.171   1.00   21.58
ATOM   3129  CD2  HIS   613    48.699    7.162    0.814   1.00   21.05
ATOM   3130  ND1  HIS   613    46.680    6.909    0.026   1.00   20.95
ATOM   3131  CE1  HIS   613    46.788    6.118    1.080   1.00   18.99
ATOM   3132  NE2  HIS   613    48.002    6.255    1.577   1.00   19.71
ATOM   3133  C    HIS   613    46.962    7.381   -3.225   1.00   24.95
ATOM   3134  O    HIS   613    46.211    8.132   -3.855   1.00   24.56
ATOM   3135  N    PRO   614    46.683    6.074   -3.047   1.00   25.96
ATOM   3136  CD   PRO   614    47.577    5.083   -2.412   1.00   25.46
ATOM   3137  CA   PRO   614    45.455    5.430   -3.537   1.00   25.84
ATOM   3138  CB   PRO   614    45.526    4.051   -2.884   1.00   25.79
ATOM   3139  CG   PRO   614    46.989    3.774   -2.849   1.00   26.21
ATOM   3140  C    PRO   614    44.168    6.182   -3.137   1.00   26.01
ATOM   3141  O    PRO   614    43.253    6.346   -3.946   1.00   26.99
ATOM   3142  N    ILE   615    44.114    6.643   -1.890   1.00   25.62
ATOM   3143  CA   ILE   615    42.959    7.379   -1.383   1.00   25.23
ATOM   3144  CB   ILE   615    43.075    7.635    0.132   1.00   26.29
ATOM   3145  CG2  ILE   615    41.823    8.358    0.644   1.00   25.16
ATOM   3146  CG1  ILE   615    43.264    6.306    0.873   1.00   24.79
ATOM   3147  CD1  ILE   615    42.158    5.291    0.603   1.00   25.74
ATOM   3148  C    ILE   615    42.766    8.699   -2.127   1.00   25.02
ATOM   3149  O    ILE   615    41.641    9.075   -2.449   1.00   24.98
ATOM   3150  N    THR   616    43.870    9.388   -2.409   1.00   24.97
ATOM   3151  CA   THR   616    43.838   10.654   -3.142   1.00   24.03
ATOM   3152  CB   THR   616    45.268   11.208   -1.307   1.00   21.36
ATOM   3153  OG1  THR   616    45.880   11.313   -2.023   1.00   19.82
ATOM   3154  CG2  THR   616    45.255   12.573   -3.946   1.00   22.30
ATOM   3155  C    THR   616    43.234   10.403   -4.531   1.00   25.54
ATOM   3156  O    THR   616    42.312   11.107   -4.970   1.00   25.06
ATOM   3157  N    LYS   617    43.745    9.374   -5.205   1.00   26.21
ATOM   3158  CA   LYS   617    43.268    9.013   -6.532   1.00   26.68
ATOM   3159  CB   LYS   617    44.103    7.865   -7.106   1.00   29.57
ATOM   3160  CG   LYS   617    45.601    8.150   -7.174   1.00   32.92
ATOM   3161  CD   LYS   617    46.125    8.036   -8.593   1.00   36.18
ATOM   3162  CE   LYS   617    45.459    9.068   -9.512   1.00   39.50
ATOM   3163  NZ   LYS   617    45.780    8.867  -10.963   1.00   39.79
ATOM   3164  C    LYS   617    41.789    8.630   -6.469   1.00   25.76
ATOM   3165  O    LYS   617    41.023    8.968   -7.375   1.00   23.91
ATOM   3166  N    TYR   618    41.401    7.935   -5.397   1.00   25.82
ATOM   3167  CA   TYR   618    40.010    7.518   -5.180   1.00   26.33
ATOM   3168  CB   TYR   618    39.884    6.701   -3.883   1.00   28.26
ATOM   3169  CG   TYR   618    38.441    6.394   -3.504   1.00   32.04
ATOM   3170  CD1  TYR   618    37.768    5.307   -4.081   1.00   33.48
ATOM   3171  CE1  TYR   618    36.423    5.049   -3.804   1.00   32.78
ATOM   3172  CD2  TYR   618    37.725    7.221   -2.624   1.00   31.35
ATOM   3173  CE2  TYR   618    36.372    6.971   -2.339   1.00   31.99
ATOM   3174  CZ   TYR   618    35.735    5.880   -2.938   1.00   33.67
ATOM   3175  OH   TYR   618    34.421    5.588   -2.668   1.00   34.74
ATOM   3176  C    TYR   618    39.091    8.740   -5.086   1.00   26.08
ATOM   3177  O    TYR   618    38.135    8.871   -5.850   1.00   24.27
ATOM   3178  N    ILE   619    39.395    9.637   -4.148   1.00   26.53
ATOM   3179  CA   ILE   619    38.592   10.840   -3.952   1.00   26.78
ATOM   3180  CB   ILE   619    39.110   11.696   -2.771   1.00   26.09
ATOM   3181  CG2  ILE   619    38.201   12.890   -2.554   1.00   27.00
ATOM   3182  CG1  ILE   619    39.114   10.868   -1.484   1.00   24.87
ATOM   3183  CD1  ILE   619    39.696   11.585   -0.275   1.00   23.06
ATOM   3184  C    ILE   619    38.531   11.669   -5.232   1.00   27.63
ATOM   3185  O    ILE   619    37.510   12.299   -5.517   1.00   28.56
```

FIGURE 1A-30

```
ATOM   3186  N    MET  620   39.603  11.635   -6.020  1.00  28.31
ATOM   3187  CA   MET  620   39.642  12.367   -7.281  1.00  29.16
ATOM   3188  CB   MET  620   41.047  12.339   -7.888  1.00  30.86
ATOM   3189  CG   MET  620   42.068  13.180   -7.133  1.00  31.31
ATOM   3190  SD   MET  620   43.700  13.152   -7.887  1.00  33.66
ATOM   3191  CE   MET  620   43.745  14.717   -8.555  1.00  34.32
ATOM   3192  C    MET  620   38.625  11.813   -8.274  1.00  29.85
ATOM   3193  O    MET  620   38.040  12.563   -9.048  1.00  29.99
ATOM   3194  N    THR  621   38.397  10.504   -8.248  1.00  31.58
ATOM   3195  CA   THR  621   37.412   9.909   -9.146  1.00  33.23
ATOM   3196  CB   THR  621   37.505   8.351   -9.182  1.00  34.83
ATOM   3197  OG1  THR  621   37.348   7.801   -7.865  1.00  34.63
ATOM   3198  CG2  THR  621   38.853   7.918   -9.741  1.00  34.93
ATOM   3199  C    THR  621   36.008  10.355   -8.727  1.00  33.69
ATOM   3200  O    THR  621   35.089  10.387   -9.539  1.00  32.60
KTOM   3201  N    CYS  622   35.860  10.705   -7.449  1.00  35.29
ATOM   3202  CA   CYS  622   34.582  11.166   -6.915  1.00  36.11
ATOM   3203  CB   CYS  622   34.584  11.148   -5.379  1.00  34.25
ATOM   3204  SG   CYS  622   34.541   9.474   -4.630  1.00  34.81
ATOM   3205  C    CYS  622   34.282  12.565   -7.434  1.00  37.34
ATOM   3206  O    CYS  622   33.124  12.980   -7.498  1.00  38.25
ATOM   3207  N    MET  623   35.329  13.284   -7.823  1.00  38.28
ATOM   3208  CA   MET  623   35.161  14.626   -8.352  1.00  40.10
ATOM   3209  CB   MET  623   36.477  15.399   -8.297  1.00  38.66
ATOM   3210  CG   MET  623   37.160  15.447   -6.952  1.00  38.37
ATOM   3211  SD   MET  623   36.295  16.417   -5.730  1.00  38.37
ATOM   3212  CE   MET  623   36.561  15.423   -4.310  1.00  38.68
ATOM   3213  C    MET  623   34.701  14.559   -9.809  1.00  42.69
ATOM   3214  O    MET  623   33.953  15.425  -10.263  1.00  44.25
ATOM   3215  N    SER  624   35.169  13.544  -10.539  1.00  44.54
ATOM   3216  CA   SER  624   34.843  13.373  -11.959  1.00  45.95
ATOM   3217  CB   SER  624   35.862  12.432  -12.624  1.00  46.09
ATOM   3218  OG   SER  624   36.043  11.237  -11.879  1.00  45.68
ATOM   3219  C    SER  624   33.408  12.937  -12.294  1.00  46.50
ATOM   3220  O    SER  624   32.901  11.984  -11.658  1.00  48.12

SULFATE ION COORDINATES

Atom
            Type  Resid    #       X        Y        Z     OCC    B
ATOM   3221  S    SO4   1001    8.646   28.709   22.190  1.00  32.01
ATOM   3222  O1   SO4   1001    9.006   27.263   22.094  1.00  35.92
ATOM   3223  O2   SO4   1001    8.328   28.982   23.610  1.00  33.43
ATOM   3224  O3   SO4   1001    9.821   29.520   21.744  1.00  33.54
ATOM   3225  O4   SO4   1001    7.429   28.930   21.367  1.00  32.87

DNA COORDINATES

Atom
            Type  Resid    #       X        Y        Z     OCC    B
ATOM   3226  O3'  THY    2    37.257   37.479    7.626  1.00  62.88
ATOM   3227  P    THY    3    38.537   37.587    8.598  1.00  64.59
ATOM   3228  O1P  THY    3    39.744   37.500    7.737  1.00  65.36
ATOM   3229  O2P  THY    3    38.349   38.772    9.478  1.00  64.52
ATOM   3230  O5'  THY    3    38.465   36.284    9.516  1.00  61.39
ATOM   3231  C2'  THY    3    39.582   33.841   11.157  1.00  57.22
```

FIGURE 1A-31

| | | | | | | | | |
|---|---|---|---|---|---|---|---|---|
| ATOM | 3232 | C5' | THY | 3 | 37.215 | 35.787 | 9.985 | 1.00 58.94 |
| ATOM | 3233 | C4' | THY | 3 | 37.364 | 34.359 | 10.454 | 1.00 57.48 |
| ATOM | 3234 | O4' | THY | 3 | 38.036 | 33.610 | 9.411 | 1.00 57.98 |
| ATOM | 3235 | C1' | THY | 3 | 39.244 | 33.059 | 9.901 | 1.00 57.84 |
| ATOM | 3236 | C3' | THY | 3 | 38.209 | 34.160 | 11.712 | 1.00 55.51 |
| ATOM | 3237 | O3' | THY | 3 | 37.714 | 33.032 | 12.440 | 1.00 53.32 |
| ATOM | 3238 | P | THY | 4 | 37.453 | 33.144 | 14.024 | 1.00 51.06 |
| ATOM | 3239 | O1P | THY | 4 | 38.284 | 32.114 | 14.682 | 1.00 52.62 |
| ATOM | 3240 | O2P | THY | 4 | 37.572 | 34.555 | 14.460 | 1.00 52.47 |
| ATOM | 3241 | O5' | THY | 4 | 35.934 | 32.695 | 14.174 | 1.00 51.46 |
| ATOM | 3242 | N1 | THY | 4 | 33.007 | 29.972 | 13.415 | 1.00 46.84 |
| ATOM | 3243 | C6 | THY | 4 | 34.293 | 29.767 | 12.965 | 1.00 47.09 |
| ATOM | 3244 | C2 | THY | 4 | 31.944 | 29.300 | 12.868 | 1.00 45.86 |
| ATOM | 3245 | O2 | THY | 4 | 30.796 | 29.449 | 13.234 | 1.00 45.89 |
| ATOM | 3246 | N3 | THY | 4 | 32.280 | 28.434 | 11.866 | 1.00 46.41 |
| ATOM | 3247 | C4 | THY | 4 | 33.542 | 28.179 | 11.371 | 1.00 47.33 |
| ATOM | 3248 | O4 | THY | 4 | 33.690 | 27.380 | 10.465 | 1.00 49.11 |
| ATOM | 3249 | C5 | THY | 4 | 34.610 | 28.916 | 11.991 | 1.00 47.24 |
| ATOM | 3250 | C2' | THY | 4 | 33.891 | 30.788 | 15.545 | 1.00 50.03 |
| ATOM | 3251 | C5' | THY | 4 | 34.879 | 33.651 | 14.170 | 1.00 50.28 |
| ATOM | 3252 | C4' | THY | 4 | 33.674 | 33.079 | 14.873 | 1.00 49.97 |
| ATOM | 3253 | O4' | THY | 4 | 32.919 | 32.228 | 13.976 | 1.00 48.97 |
| ATOM | 3254 | C1' | THY | 4 | 32.790 | 30.920 | 14.512 | 1.00 47.73 |
| ATOM | 3255 | C3' | THY | 4 | 34.075 | 32.202 | 16.056 | 1.00 50.49 |
| ATOM | 3256 | O3' | THY | 4 | 33.236 | 32.403 | 17.179 | 1.00 50.67 |
| ATOM | 3257 | P | THY | 5 | 33.285 | 31.347 | 18.371 | 1.00 47.87 |
| ATOM | 3258 | O1P | THY | 5 | 34.541 | 30.575 | 18.215 | 1.00 48.85 |
| ATOM | 3259 | O2P | THY | 5 | 33.015 | 32.074 | 19.631 | 1.00 48.56 |
| ATOM | 3260 | O5' | THY | 5 | 32.072 | 30.374 | 18.051 | 1.00 49.19 |
| ATOM | 3261 | N1 | THY | 5 | 31.213 | 27.155 | 16.419 | 1.00 58.66 |
| ATOM | 3262 | C6 | THY | 5 | 32.482 | 27.691 | 16.481 | 1.00 59.82 |
| ATOM | 3263 | C2 | TRY | 5 | 30.878 | 26.224 | 15.460 | 1.00 60.12 |
| ATOM | 3264 | O2 | THY | 5 | 29.775 | 25.706 | 15.384 | 1.00 61.69 |
| ATOM | 3265 | N3 | THY | 5 | 31.896 | 25.911 | 14.590 | 1.00 60.92 |
| ATOM | 3266 | C4 | THY | 5 | 33.180 | 26.422 | 14.589 | 1.00 60.86 |
| ATOM | 3267 | O4 | THY | 5 | 33.980 | 26.063 | 13.733 | 1.00 62.48 |
| ATOM | 3268 | C5 | THY | 5 | 33.467 | 27.375 | 15.633 | 1.00 60.58 |
| ATOM | 3269 | C2' | THY | 5 | 30.746 | 27.746 | 18.796 | 1.00 54.89 |
| ATOM | 3270 | C5' | THY | 5 | 30.759 | 30.895 | 17.870 | 1.00 52.14 |
| ATOM | 3271 | C4' | THY | 5 | 29.741 | 29.807 | 18.097 | 1.00 53.54 |
| ATOM | 3272 | O4' | THY | 5 | 29.757 | 28.886 | 16.980 | 1.00 54.95 |
| ATOM | 3273 | C1' | THY | 5 | 30.192 | 27.595 | 17.387 | 1.00 56.51 |
| ATOM | 3274 | C3' | THY | 5 | 30.042 | 28.976 | 19.338 | 1.00 53.67 |
| ATOM | 3275 | O3' | THY | 5 | 28.841 | 28.640 | 20.011 | 1.00 53.59 |
| ATOM | 3276 | P | THY | 6 | 28.902 | 27.677 | 21.286 | 1.00 55.49 |
| ATOM | 3277 | O1P | THY | 6 | 30.314 | 27.643 | 21.757 | 1.00 54.73 |
| ATOM | 3278 | O2P | THY | 6 | 27.825 | 28.072 | 22.235 | 1.00 56.13 |
| ATOM | 3279 | O5' | THY | 6 | 28.517 | 26.262 | 20.665 | 1.00 56.29 |
| ATOM | 3280 | N1 | THY | 6 | 29.855 | 23.122 | 18.173 | 1.00 60.63 |
| ATOM | 3281 | C6 | THY | 6 | 30.949 | 23.677 | 18.806 | 1.00 61.06 |
| ATOM | 3282 | C2 | THY | 6 | 29.949 | 22.610 | 16.902 | 1.00 61.67 |
| ATOM | 3283 | O2 | THY | 6 | 28.995 | 22.152 | 16.291 | 1.00 61.78 |
| ATOM | 3284 | N3 | THY | 6 | 31.212 | 22.658 | 16.363 | 1.00 63.46 |
| ATOM | 3285 | C4 | THY | 6 | 32.355 | 23.175 | 16.950 | 1.00 63.98 |
| ATOM | 3286 | O4 | THY | 6 | 33.427 | 23.132 | 16.348 | 1.00 66.37 |
| ATOM | 3287 | C5 | THY | 6 | 32.171 | 23.732 | 18.268 | 1.00 62.56 |
| ATOM | 3288 | C2' | THY | 6 | 28.701 | 23.043 | 20.380 | 1.00 58.18 |
| ATOM | 3289 | C5' | THY | 6 | 27.266 | 26.086 | 19.995 | 1.00 55.60 |

FIGURE 1A-32

| | | | | | | | | |
|---|---|---|---|---|---|---|---|---|
| ATOM | 3290 | C4' | THY | 6 | 27.031 | 24.624 | 19.695 | 1.00 56.65 |
| ATOM | 3291 | O4' | THY | 6 | 27.827 | 24.224 | 18.554 | 1.00 57.17 |
| ATOM | 3292 | C1' | THY | 6 | 28.559 | 23.051 | 18.868 | 1.00 58.86 |
| ATOM | 3293 | C3' | THY | 6 | 27.402 | 23.677 | 20.838 | 1.00 57.43 |
| ATOM | 3294 | O3' | THY | 6 | 26.423 | 22.658 | 21.005 | 1.00 57.14 |
| ATOM | 3295 | P | THY | 7 | 26.118 | 22.092 | 22.476 | 1.00 55.41 |
| ATOM | 3296 | O1P | THY | 7 | 27.388 | 21.574 | 23.052 | 1.00 55.46 |
| ATOM | 3297 | O2P | THY | 7 | 25.341 | 23.126 | 23.212 | 1.00 55.42 |
| ATOM | 3298 | O5' | THY | 7 | 25.155 | 20.856 | 22.209 | 1.00 54.29 |
| ATOM | 3299 | N1 | THY | 7 | 28.804 | 18.991 | 19.952 | 1.00 50.01 |
| ATOM | 3300 | C6 | THY | 7 | 29.541 | 19.632 | 20.927 | 1.00 49.74 |
| ATOM | 3301 | C2 | THY | 7 | 29.235 | 18.962 | 18.632 | 1.00 49.72 |
| ATOM | 3302 | O2 | THY | 7 | 28.630 | 18.401 | 17.735 | 1.00 49.11 |
| ATOM | 3303 | N3 | THY | 7 | 30.418 | 19.620 | 18.403 | 1.00 49.95 |
| ATOM | 3304 | C4 | THY | 7 | 31.199 | 20.284 | 19.331 | 1.00 50.77 |
| ATOM | 3305 | O4 | THY | 7 | 32.238 | 20.836 | 18.973 | 1.00 52.95 |
| ATOM | 3306 | C5 | THY | 7 | 30.695 | 20.267 | 20.688 | 1.00 50.49 |
| ATOM | 3307 | C2' | THY | 7 | 27.275 | 18.299 | 21.813 | 1.00 49.16 |
| ATOM | 3308 | C5' | THY | 7 | 24.826 | 20.456 | 20.880 | 1.00 51.47 |
| ATOM | 3309 | C4' | THY | 7 | 25.318 | 19.048 | 20.636 | 1.00 49.37 |
| ATOM | 3310 | O4' | THY | 7 | 26.467 | 19.074 | 19.756 | 1.00 49.04 |
| ATOM | 3311 | C1' | THY | 7 | 27.533 | 18.322 | 20.317 | 1.00 49.64 |
| ATOM | 3312 | C3' | THY | 7 | 25.759 | 18.341 | 21.914 | 1.00 48.18 |
| ATOM | 3313 | O3' | THY | 7 | 25.208 | 17.033 | 22.016 | 1.00 45.69 |
| ATOM | 3314 | P | THY | 8 | 25.223 | 16.282 | 23.434 | 1.00 43.16 |
| ATOM | 3315 | O1P | THY | 8 | 26.128 | 17.012 | 24.351 | 1.00 44.74 |
| ATOM | 3316 | O2P | THY | 8 | 23.837 | 16.004 | 23.867 | 1.00 44.40 |
| ATOM | 3317 | O5' | THY | 8 | 25.923 | 14.895 | 23.096 | 1.00 45.67 |
| ATOM | 3318 | N1 | THY | 8 | 29.550 | 14.234 | 20.725 | 1.00 45.65 |
| ATOM | 3319 | C6 | THY | 8 | 30.514 | 14.642 | 21.618 | 1.00 44.74 |
| ATOM | 3320 | C2 | THY | 8 | 29.464 | 14.791 | 19.469 | 1.00 46.33 |
| ATOM | 3321 | O2 | THY | 8 | 28.611 | 14.482 | 18.661 | 1.00 48.73 |
| ATOM | 3322 | N3 | THY | 8 | 30.418 | 15.737 | 19.193 | 1.00 46.38 |
| ATOM | 3323 | C4 | THY | 8 | 31.416 | 16.183 | 20.035 | 1.00 45.35 |
| ATOM | 3324 | O4 | THY | 8 | 32.203 | 17.041 | 19.650 | 1.00 44.96 |
| ATOM | 3325 | C5 | THY | 8 | 31.435 | 15.573 | 21.343 | 1.00 45.22 |
| ATOM | 3326 | C2' | THY | 8 | 28.573 | 12.869 | 22.592 | 1.00 46.80 |
| ATOM | 3327 | C5' | THY | 8 | 25.331 | 13.994 | 22.171 | 1.00 46.20 |
| ATOM | 3328 | C4' | THY | 8 | 26.346 | 12.982 | 21.695 | 1.00 46.45 |
| ATOM | 3329 | O4' | THY | 8 | 27.289 | 13.613 | 20.792 | 1.00 45.83 |
| ATOM | 3330 | C1' | THY | 8 | 28.598 | 13.170 | 21.103 | 1.00 46.11 |
| ATOM | 3331 | C3' | THY | 8 | 27.170 | 12.324 | 22.806 | 1.00 46.52 |
| ATOM | 3332 | O3' | THY | 8 | 27.137 | 10.893 | 22.783 | 1.00 46.89 |

WATER MOLECULE COORDINATES

| | | Atom Type | Resid | # | X | Y | Z | OCC | B |
|---|---|---|---|---|---|---|---|---|---|
| ATOM | 3333 | OH2 | TIP3 | 1 | -0.245 | 23.385 | 32.975 | 1.00 | 19.18 |
| ATOM | 3334 | OH2 | TIP3 | 2 | 22.305 | 18.313 | 19.597 | 1.00 | 27.90 |
| ATOM | 3335 | OH2 | TIP3 | 3 | 16.363 | 43.283 | 27.772 | 1.00 | 24.59 |
| ATOM | 3336 | OH2 | TIP3 | 4 | 36.537 | 45.914 | 31.680 | 1.00 | 20.59 |
| ATOM | 3337 | OH2 | TIP3 | 5 | 17.542 | 27.937 | 8.465 | 1.00 | 18.37 |
| ATOM | 3338 | OH2 | TIP3 | 6 | 35.726 | 50.776 | 9.824 | 1.00 | 31.71 |
| ATOM | 3339 | OH2 | TIP3 | 7 | 20.453 | 38.335 | 27.173 | 1.00 | 47.06 |
| ATOM | 3340 | OH2 | TIP3 | 8 | 15.332 | 19.267 | 24.557 | 1.00 | 25.04 |
| ATOM | 3341 | OH2 | TIP3 | 9 | 31.258 | 50.983 | 30.493 | 1.00 | 29.38 |

FIGURE 1A-33

```
ATOM   3342  OH2  TIP3   10     28.501    7.997    7.807  1.00  21.94
ATOM   3343  OH2  TIP3   11     24.624   24.205   25.328  1.00  24.23
ATOM   3344  OH2  TIP3   12     14.538   39.417   17.207  1.00  26.71
ATOM   3345  OH2  TIP3   13     19.304   29.672    7.885  1.00  17.01
ATOM   3346  OH2  TIP3   14      9.539   36.215    8.250  1.00  19.38
ATOM   3347  OH2  TIP3   15     22.976   93.935   15.769  1.00  19.99
ATOM   3348  OH2  TIP3   16     11.332   38.883   13.163  1.00  41.21
ATOM   3349  OH2  TIP3   17     44.389   17.456    4.710  1.00  25.71
ATOM   3350  OH2  TIP3   18     18.217   51.026   25.327  1.00  21.08
ATOM   3351  OH2  TIP3   19     52.875    8.529    0.460  1.00  38.69
ATOM   3352  OH2  TIP3   20     49.464    5.589    3.749  1.00  29.49
ATOM   3353  OH2  TIP3   21     18.312   39.750   29.166  1.00  35.93
ATOM   3354  OH2  TIP3   22     45.019   20.106    S.017  1.00  21.12
ATOM   3355  OH2  TIP3   23      0.745   18.945   33.170  1.00  25.64
ATOM   3356  OH2  TIP3   24     43.077    1.470    3.086  1.00  41.57
ATOM   3357  OH2  TIP3   25     32.242   40.177   37.162  1.00  30.45
ATOM   3358  OH2  TIP3   26     22.005   19.740   17.116  1.00  23.05
ATOM   3359  OH2  TIP3   27     23.883   51.464   21.877  1.00  39.16
ATOM   3360  OH2  TIP3   28     23.231   34.878   17.602  1.00  27.32
ATOM   3361  OH2  TIP3   29     16.275   41.943   30.227  1.00  44.09
ATOM   3362  OH2  TIP3   31     24.393   23.198   -0.349  1.00  34.79
ATOM   3363  OH2  TIP3   32     55.138   10.008    1.356  1.00  34.91
ATOM   3364  OH2  TIP3   33      8.529   32.844    5.639  1.00  48.78
ATOM   3365  OH2  TIP3   35     13.937   52.763   22.191  1.00  34.84
ATOM   3366  OH2  TIP3   36     17.459    5.667    9.998  1.00  37.45
ATOM   3367  OH2  TIP3   37     42.199   25.099   -1.836  1.00  37.69
ATOM   3368  OH2  TIP3   38      7.460   11.207   37.359  1.00  41.26
ATOM   3369  OH2  TIP3   39     24.315   32.263   19.069  1.00  27.49
ATOM   3370  OH2  TIP3   40     17.157   21.378   10.360  1.00  29.71
ATOM   3371  OH2  TIP3   41     13.157    9.144   28.767  1.00  32.39
ATOM   3372  OH2  TIP3   42     12.931   38.890   19.337  1.00  35.82
ATOM   3373  OH2  TIP3   43     38.696   43.515   31.888  1.00  28.12
ATOM   3374  OH2  TIP3   44     29.294   19.356   13.799  1.00  43.11
ATOM   3375  OH2  TIP3   45      9.044    7.812    9.252  1.00  19.18
ATOM   3376  OH2  TIP3   46     21.324   52.606   27.604  1.00  54.59
ATOM   3377  OH2  TIP3   47     30.914   34.967   12.824  1.00  25.06
ATOM   3378  OH2  TIP3   48     13.454    2.315   10.562  1.00  34.40
ATOM   3379  OH2  TIP3   49     28.876   32.558   13.029  1.00  51.94
ATOM   3380  OH2  TIP3   50      1.840   14.917   35.047  1.00  25.56
ATOM   3381  OH2  TIP3   51     20.036    5.057    8.439  1.00  38.71
ATOM   3382  OH2  TIP3   52     21.989   31.348   10.718  1.00  34.34
ATOM   3383  OH2  TIP3   53     22.314   46.201   35.658  1.00  33.59
ATOM   3384  OH2  TIP3   54     26.721   19.845   14.781  1.00  29.32
ATOM   3385  OH2  TIP3   55     21.199    6.956   15.517  1.00  31.86
ATOM   3386  OH2  TIP3   56     24.460   56.129   15.361  1.00  47.79
ATOM   3387  OH2  TIP3   57     24.841   34.491   13.673  1.00  35.87
ATOM   3388  OH2  TIP3   58     34.366   27.984   -0.318  1.00  26.26
ATOM   3389  OH2  TIP3   59     48.536    3.488   11.538  1.00  36.52
ATOM   3390  OH2  TIP3   60      2.038   28.386   33.590  1.00  32.11
ATOM   3391  OH2  TIP3   61     18.422   25.811   21.407  1.00  26.96
ATOM   3392  OH2  TIP3   62     12.957   44.530   11.249  1.00  28.06
ATOM   3393  OH2  TIP3   63     47.339    3.540    3.822  1.00  42.83
ATOM   3394  OH2  TIP3   64     11.061   26.825   19.834  1.00  26.76
ATOM   3395  OH2  TIP3   65     15.719    9.453   30.418  1.00  33.97
ATOM   3396  OH2  TIP3   66     45.394   -0.086    3.586  1.00  37.65
ATOM   3397  OH2  TIP3   67     33.010   41.548    8.551  1.00  53.15
ATOM   3398  OH2  TIP3   68      5.850   48.967   10.652  1.00  54.79
ATOM   3399  OH2  TIP3   69     27.164   56.234   13.872  1.00  23.47
```

FIGURE 1A-34

```
ATOM   3400  OH2  TIP3   70    30.776   23.190   13.426  1.00  35.94
ATOM   3401  OH2  TIP3   71    39.550    3.505   -0.797  1.00  44.89
ATOM   3402  OH2  TIP3   72    11.418   30.014   18.681  1.00  37.07
ATOM   3403  OH2  TIP3   73    12.592   28.999   20.880  1.00  37.53
ATOM   3404  OH2  TIP3   74    54.478    6.360   11.185  1.00  42.03
ATOM   3405  OH2  TIP3   75    12.086    2.791   12.915  1.00  29.59
ATOM   3406  OH2  TIP3   76    18.225   19.519   33.978  1.00  33.10
ATOM   3407  OH2  TIP3   77    11.677   36.171   12.007  1.00  56.16
ATOM   3408  OH2  TIP3   78    11.319   35.115   15.313  1.00  35.91
ATOM   3409  OH2  TIP3   79    49.775    4.145   -0.325  1.00  63.48
ATOM   3410  OH2  TIP3   80    46.373   21.363    6.807  1.00  26.12
ATOM   3411  OH2  TIP3   81    18.126   35.806   20.605  1.00  29.66
ATOM   3412  OH2  TIP3   82    28.293    3.447    0.583  1.00  21.79
ATOM   3413  OH2  TIP3   83    20.086    4.628   14.855  1.00  44.92
ATOM   3414  OH2  TIP3   85    19.694   33.413    0.806  1.00  34.26
ATOM   3415  OH2  TIP3   87    17.814    5.041   25.621  1.00  45.94
ATOM   3416  OH2  TIP3   88     9.151   35.189   12.200  1.00  50.30
ATOM   3417  OH2  TIP3   89    28.063   25.834    6.403  1.00  47.14
ATOM   3418  OH2  TIP3   90    23.930   54.835   27.010  1.00  36.48
ATOM   3419  OH2  TIP3   91     8.080   25.210    6.084  1.00  33.01
ATOM   3420  OH2  TIP3   92    25.675   26.853    5.755  1.00  39.86
ATOM   3421  OH2  TIP3   93    36.215   33.769    7.228  1.00  24.13
ATOM   3422  OH2  TIP3   94    44.576    4.479    5.203  1.00  49.35
ATOM   3423  OH2  TIP3   95     8.686   33.376    8.329  1.00  28.75
ATOM   3424  OH2  TIP3   96    16.567   43.764   11.647  1.00  37.52
ATOM   3425  OH2  TIP3   97    18.639   37.102   28.670  1.00  34.49
ATOM   3426  OH2  TIP3   98    11.850   38.492   15.839  1.00  58.36
ATOM   3427  OH2  TIP3   99     1.757   17.697   30.552  1.00  30.16
ATOM   3428  OH2  TIP3  100    38.062   41.239   27.946  1.00  17.16
ATOM   3429  OH2  TIP3  101    27.889   50.445   37.057  1.00  48.61
ATOM   3430  OH2  TIP3  102    47.875    2.606    1.215  1.00  45.89
ATOM   3431  OH2  TIP3  103    57.882   18.168    8.130  1.00  45.09
ATOM   3432  OH2  TIP3  104    21.556   43.776   35.255  1.00  33.42
ATOM   3433  OH2  TIP3  105    22.140   30.473    5.457  1.00  39.79
ATOM   3434  OH2  TIP3  106    32.336    8.468   23.760  1.00  73.89
ATOM   3435  OH2  TIP3  107    51.548    8.278   -1.912  1.00  28.27
ATOM   3436  OH2  TIP3  108     8.860   13.655   39.162  1.00  33.15
ATOM   3437  OH2  TIP3  109     6.700    4.449   19.242  1.00  51.28
ATOM   3438  OH2  TIP3  110    33.801   29.559   25.988  1.00  53.24
ATOM   3439  OH2  TIP3  I11    42.999    2.893   -1.302  1.00  46.52
ATOM   3440  OH2  TIP3  112    31.945   15.930   15.358  1.00  47.42
ATOM   3441  OH2  TIP3  113    22.230   16.440   -7.612  1.00  56.68
ATOM   3442  OH2  TIP3  115    13.726   39.997   22.208  1.00  31.56
ATOM   3443  OH2  TIP3  116    23.251   37.041   24.987  1.00  53.40
ATOM   3444  OH2  TIP3  117    23.611   32.166   12.751  1.00  38.21
ATOM   3445  OH2  TIP3  118    30.487   26.338   -0.700  1.00  31.83
ATOM   3446  OH2  TIP3  119    19.447    2.060   15.121  1.00  39.28
ATOM   3447  OH2  TIP3  120    24.042   51.710    8.456  1.00  39.94
ATOM   3448  OH2  TIP3  121    47.391   -0.070    5.383  1.00  37.69
ATOM   3449  OH2  TIP3  122    59.581   21.821    1.048  1.00  54.95
ATOM   3450  OH2  TIP3  123     9.207   34.806   16.904  1.00  31.85
ATOM   3451  OH2  TIP3  124     3.401    4.534   13.008  1.00  53.38
ATOM   3452  OH2  TIP3  125    21.114   48.341   33.295  1.00  43.92
ATOM   3453  OH2  TIP3  126    20.174   32.741   20.466  1.00  66.24
ATOM   3454  OH2  TIP3  128    16.410   45.812   26.424  1.00  35.46
ATOM   3455  OH2  TIP3  129    32.863   61.435   29.648  1.00  66.85
ATOM   3456  OH2  TIP3  130    33.387   55.608    7.433  1.00  64.07
ATOM   3457  OH2  TIP3  131    28.167   51.328   29.584  1.00  27.99
```

FIGURE 1A-35

| | | | | | | | | |
|---|---|---|---|---|---|---|---|---|
| ATOM | 3458 | OH2 | TIP3 | 132 | 16.147 | 45.753 | 6.715 | 1.00 | 54.98 |
| ATOM | 3459 | OH2 | TIP3 | 133 | 20.658 | 52.304 | 24.938 | 1.00 | 25.99 |
| ATOM | 3460 | OH2 | TIP3 | 134 | 44.627 | 9.499 | -13.307 | 1.00 | 44.79 |
| ATOM | 3461 | OH2 | TIP3 | 135 | 64.095 | 6.945 | 12.329 | 1.00 | 44.41 |
| ATOM | 3462 | OH2 | TIP3 | 136 | 18.514 | 41.737 | 27.310 | 1.00 | 19.89 |
| ATOM | 3463 | OH2 | TIP3 | 137 | 42.275 | 19.609 | -2.298 | 1.00 | 15.25 |
| ATOM | 3464 | OH2 | TIP3 | 139 | 14.970 | 49.971 | 28.272 | 1.00 | 35.15 |
| ATOM | 3465 | OH2 | TIP3 | 140 | 15.165 | 8.029 | 3.479 | 1.00 | 38.41 |
| ATOM | 3466 | OH2 | TIP3 | 141 | 17.347 | 7.548 | 21.016 | 1.00 | 36.09 |
| ATOM | 3467 | OH2 | TIP3 | 142 | 21.921 | 4.401 | 1.631 | 1.00 | 39.46 |
| ATOM | 3468 | OH2 | TIP3 | 143 | 23.711 | 49.091 | 33.933 | 1.00 | 39.80 |
| ATOM | 3469 | OH2 | TIP3 | 144 | 21.398 | 56.732 | 11.465 | 1.00 | 30.74 |
| ATOM | 3470 | OH2 | TIP3 | 145 | 15.424 | 25.910 | 28.153 | 1.00 | 28.23 |
| ATOM | 3471 | OH2 | TIP3 | 146 | 30.399 | 11.030 | -7.068 | 1.00 | 50.79 |
| ATOM | 3472 | OH2 | TIP3 | 147 | 12.734 | 29.004 | 16.438 | 1.00 | 22.08 |
| ATOM | 3473 | OH2 | TIP3 | 148 | 53.920 | 5.003 | 16.906 | 1.00 | 54.39 |
| ATOM | 3474 | OH2 | TIP3 | 149 | 7.523 | 36.343 | 15.403 | 1.00 | 44.62 |
| ATOM | 3475 | OH2 | TIP3 | 150 | 14.223 | 30.953 | 15.400 | 1.00 | 37.15 |
| ATOM | 3476 | OH2 | TIP3 | 151 | 28.644 | 2.628 | 3.023 | 1.00 | 31.14 |
| ATOM | 3477 | OH2 | TIP3 | 152 | 15.963 | 9.043 | 22.893 | 1.00 | 26.75 |
| ATOM | 3478 | OH2 | TIP3 | 153 | 17.823 | 10.746 | 23.731 | 1.00 | 20.71 |
| ATOM | 3479 | OH2 | TIP3 | 154 | 29.179 | 54.461 | 32.613 | 1.00 | 68.03 |
| ATOM | 3480 | OH2 | TIP3 | 155 | 35.993 | 37.805 | 29.152 | 1.00 | 20.17 |
| ATOM | 3481 | OH2 | TIP3 | 156 | 53.831 | 24.063 | 9.859 | 1.00 | 49.86 |
| ATOM | 3482 | OH2 | TIP3 | 157 | 20.267 | 46.970 | 30.983 | 1.00 | 34.93 |
| ATOM | 3483 | OH2 | TIP3 | 158 | 32.383 | 43.988 | 6.930 | 1.00 | 39.67 |
| ATOM | 3484 | OH2 | TIP3 | 159 | 2.201 | 6.263 | 18.618 | 1.00 | 35.49 |
| ATOM | 3485 | OH2 | TIP3 | 160 | 48.626 | 11.397 | -2.343 | 1.00 | 32.41 |
| ATOM | 3486 | OH2 | TIP3 | 161 | 21.594 | 8.868 | -2.657 | 1.00 | 47.49 |
| ATOM | 3487 | OH2 | TIP3 | 162 | 21.981 | 51.645 | 6.828 | 1.00 | 36.67 |
| ATOM | 3488 | OH2 | TIP3 | 163 | 41.875 | 36.089 | 18.851 | 1.00 | 38.83 |
| ATOM | 3489 | OH2 | TIP3 | 164 | 39.302 | 39.590 | 11.776 | 1.00 | 50.01 |
| ATOM | 3490 | OH2 | TIP3 | 165 | 40.112 | 35.572 | 14.944 | 1.00 | 47.69 |
| ATOM | 3491 | OH2 | TIP3 | 166 | 39.529 | 30.929 | 22.535 | 1.00 | 41.91 |

FIGURE 8

```
                                         β1                  α1
                                       |←——→|          |←————————→|
          mVDFIPVENLETTMRSPVFTDNSSPPAVPQSFQVAHLHAPTGSGKSTKVPAAYAA   220
         β2           α2              β3    β4     β5     α3
       |←—→|. |←————————————→|      |←→|  |←→|    |←→| |←——→|
       QGYKVLVLNPSVAATLGFGAYMSKAHGVDPNIRTGVRTITTGSPITYSTYGKFLADGGCS  280
          β6            α4         α4A     β7                β1'
        |←→|       |←————————→|   |↔|   |←—→|              |←→|.
       GGAYDIICDECHSTDATSILGIGTVLDQAETAGARLVVLATATPPGSVTVPHPNIEEVA   340
          β1A' β1B'  α1'     β2'            α2'            β3'
        |↔|  |↔|  |←→|.  |←———→|      |←————————→|       |←—→|
       LSTTGEIPFYGKAIPLEVIKGGRHLIFCHSKKKCDELAAKLVALGINAVAYYRGLDVSVI   400
            β5'              β6'     β6A'           β6B'         α4'
          |←→|           |←→|     |←—→|         |←——→|        |←—————
       PTSGDVVVVATDALMTGFTGDFDSVIDCNTCVTQTVDFSLPTFTIETTTLPQDAVSRTQ   460
              β7'       β8         α5                    α6
        →|  |←→|.     |↔| |←————→|             |←————————→|
       RRGRTGRGKPGIYRFVAPGERPSGMFDSSVLCECYDAGCAWYELTPAETTVRLRAYMNTP   520
         β9         α7            α8                 α9
        |↔|      |←———→|.      |←——→|           |←————————→|
       GLPVCQDHLEFWEGVFTGLTHIDAHFLSQTKQSGENFPYLVAYQATVCARAQAPPPSWDQ   580
                             α10
                          |←———→|
       MWKCLIRLKPTLHGPTPLLYRLGAVQNEVTLTHPITKYIMTCMSADLEVVTgsgshhhhhh 641
```

FIGURE 9A

|  | | I | | Ia | | II | | III |
|---|---|---|---|---|---|---|---|---|
| NS3 | 204 | APTGSGKSTK | (13) | VLNPSVAATLGF | (40) | DECHSTD | (25) | TATPPGSVTVPHPN |
| NPH-II | 185 | GGTGVGKTSQ | (28) | VILSLPRIALVR | (60) | DEVHEHD | (23) | TATLEDDRERLKVF |
| EIF-4A | 63 | AQSTGKTGT | (19) | MLAPTRELALQI | (63) | DEADEML | (24) | SATMPNDVLEVTTK |
| PcrA | 31 | AGAGSGKTRV | (20) | AITFTNKAAREM | (150) | DEYQDTN | (19) | VGDADQSIYRWRGA |
| UvrD | 30 | AGAGSGKTRV | (20) | AVTFTNKAAREM | (150) | DEFQDTN | (19) | VGDDDQSIYGWRGA |
| Rep | 22 | AGAGSGKTRV | (20) | AVTFTNKAAAEM | (150) | DEYQDTN | (19) | VGDDDQSIYSWRGA |

|  | | IV? | | V | | VI | |
|---|---|---|---|---|---|---|---|
| NS3 | 365 | LIFCHSKKK | (36) | ATDALMTGFTGDFE | (32) | VSRTQRRGRTGRG | |
| NPH-II | 397 | IVFVASVAQ | (43) | STPYLESSVTIRNV | (24) | SMRDQRKGRVGRV | |
| EIF-4A | 263 | VIFCNTRRK | (43) | STDLLARGIDVQQV | (12) | EERRLAYVGITRA | |
| PcrA | 280 | ILLEQNYRS | (273) | MTLHAAKGLEFPVV | (23) | EERRLAYVGITRA | |
| UvrD | 278 | IRLEQNYRS | (271) | MTLHSAKGLEFPQV | (23) | EERRLAYVGVTRA | |
| Rep | 272 | IKLEQNYRS | (275) | MTLHASKGLEFPYV | (22) | EERRLAYVGITRA | |

HEPATITIS C VIRUS HELICASE CRYSTALS AND COORDINATES THAT DEFINE HELICASE BINDING POCKETS

CROSS-REFERENCE TO PRIOR APPLICATION

This application is a continuation-in-part of now abandoned U.S. provisional patent application Ser. No. 60/055,772, filed Aug. 13, 1997.

TECHNICAL FIELD OF THE INVENTION

The invention relates to the X-ray crystal structure of the hepatitis C virus helicase domain. More specifically, the invention relates to crystallized complexes of HCV helicase and an oligonucleotide, to crystallizable compositions of HCV helicase and an oligonucleotide and to methods of crystallizing an HCV helicase-oligonucleotide complex. The invention further relates to a computer programmed with the structure coordinates of the HCV helicase oligonucleotide binding pocket or the HCV helicase nucleotide triphosphate pocket wherein said computer is capable of displaying a three-dimensional representation of that binding pocket.

BACKGROUND OF THE INVENTION

Infection by the hepatitis C virus (HCV) is responsible for most transfusion-associated cases of non-A, non-B hepatitis and also accounts for a significant proportion of community-acquired hepatitis cases worldwide. Relatively few HCV infected individuals experience acute hepatitis, but up to 85% appear to develop persistent infection that often leads to chronic hepatitis and liver cirrhosis, eventually predisposing them to hepatocellular carcinoma. At present, vaccines are unavailable and no broadly effective therapies exist for this viral disease. Consequently, much research has focused on the HCV replicative enzymes as targets for more effective therapies.

HCV contains an approximately 9.6 kb single-stranded positive sense RNA genome classified as its own genus in the Flaviviridae family of animal viruses, which also includes the flavivirus and pestivirus genera. Its genome consists of a conserved 5' nontranslated sequence that serves as an internal ribosome entry site, a single open reading frame that encodes a polyprotein of >3000 amino acids, and a 3' nontranslated region. The 3' nontranslated region contains tracts of poly(U)$_n$ and poly(UC)$_n$ followed by a novel conserved 98 nucleotide sequence.

Proteolytic processing of the HCV polyprotein by virally-encoded proteases generates several nonstructural (NS) proteins with enzymatic activities essential for the replicative cycle of the virus [P. Neddermann et al., Biol. Chem., 378, pp. 469–476 (1997)]. NS2 encodes a presumed metalloprotease, NS5B is a RNA-dependent RNA polymerase, and NS3 is a bifunctional enzyme with a serine protease localized to the N-terminal 181 residues of the protein and a RNA helicase in the C-terminal 465 amino acids. The NS3 protease performs an intramolecular cleavage at the NS3/NS4A junction to form a tight noncovalent NS3-NS4A complex necessary for efficient processing of the remaining polyprotein [C. Failla et al., J. Virol., 69, pp. 1769–1777 (1995); R. Bartenschlager et al., J. Virol., 69, pp. 7519–7528 (1995); Y. Tanji et al., J. Virol., 69, pp. 1575–1581 (1995)]. To date, no evidence exists to suggest that the serine protease and helicase domains are separated by proteolytic processing of NS3 in vivo. This may reflect economical packaging of these enzymatic components, or could imply a functional interdependence between the two domains.

Numerous studies have demonstrated that the serine protease [J. L. Kim et al., Cell, 87, pp. 343–355 (1996); W. Markland et al., J. Gen. Virol., 78, pp. 39–43(1997).; C. Steinkuhler et al., J. Virol., 70, pp. 6694–6700 (1996)] and RNA helicase domains [J. A. Suzich et al., J. Virol., 67, pp. 6152–6158 (1993); C. L. Tai et al., J. Virol., 70, pp. 8477–8484 (1996); L. Jin et al., Arch. Biochem. Biophys., 323, pp. 47–53 (1995); and F. Preugschat et al., J. Biol. Chem., 271, pp. 24449–24457 (1996)] of NS3 can be expressed independently and isolated as catalytically active species. However, emerging evidence suggests that the NS3 protease and helicase domains may contact one another and modulate NS3 catalytic activities. Examples include apparent differences in pH optima of ATPase and RNA unwinding activities between a contiguous NS3 protein complexed with the NS4A cofactor [K. A Morgenstern et al., J. Virol., 71, pp. 3767–3775 (1997); Z. Hong et al., J. Virol., 70, pp. 4261–4268 (1996)] and an isolated NS3 helicase domain [C. L. Tai et al., J. Virol., (1996), supra; L. Jin et al., Arch. Biochem. Biophys., (1995), supra; F. Preugschat et al., J. Biol. Chem., (1996), supra; and Y. Gwack et al., Biochem. Biophys. Res. Commun., 225, pp. 654–659 (1996)]. Similarly, the ATPase activities of both proteins differ in their sensitivity to polynucleotide stimulation. Contiguous NS3 appears to have a lower apparent dissociation constant for poly(U) than does the helicase domain [J. A. Suzich et al., J. Virol., (1993), supra; F. Preugschat et al., J. Biol. Chem., (1996), supra; K. A. Morgenstern et al., J. Virol., (1997), supra; A. Kanai et al., FEBS Lett., 376, pp. 221–224 (1995)]. Aside from these differences, both proteins display nearly indistinguishable kinetic parameters for NTP hydrolysis when stimulated with saturating polynucleotide [J. A. Suzich et al., J. Virol., (1993), supra; K. A. Morgenstern et al., J. Virol., (1997), supra], both display 3'-5' directionality for translocation along a polynucleotide substrate, and the helicases of both proteins effectively unwind duplex RNA:RNA substrates [C. L. Tai et al., J. Virol., (1996), supra; Z. Hong et al., J. Virol., (1996), supra].

In addition to HCV, all flavi- and pestiviruses sequenced to date contain conserved helicase sequence motifs in their homologous NS3 proteins, suggesting that this enzyme plays an important role in the HCV replicative cycle [R. H. Miller et al., Proc. Natl. Acad. Sci. USA, 87, pp. 2057–2061 (1990)]. Consistent with this possibility, helicase encoding sequences have been identified in other viruses and helicases are suggested to catalyze the separation of double-stranded nucleic acid structures during transcription and genome replication [G. Kadare et al., J. Virol., 71, pp. 2583–2590 (1997)]. Previous studies with poliovirus, a positive-stranded RNA virus of the Picornaviridae family, show that mutation of conserved sequence motifs in the 2C elicase inhibits virus replication and proliferation [C. Mirzayan et al., Virology, 189, pp. 547–555 (1992)]. Similar mutational studies on the helicases encoded by herpes simplex virus type 1 and bovine papilloma virus also show that these enzymes are critical for virus replication [P. MacPherson et al., Virology, 204, pp. 403–408 (1994); R. Martinez et al., J. Virol., 66, pp. 6735–6746 (1992)]. Thus, the ability to inhibit helicase activity in HCV may provide an avenue for the therapeutic treatment of HCV infection.

Unfortunately, little is known about the details of how ATP binding and hydrolysis leads to DNA or RNA strand unwinding by the helicase. Two structures of helicases crystallized in the absence of polynucleotide, but, unfortunately, they have not yielded the critical information needed to extrapolate to an enzyme mechanism [N. Yao et al., Nat. Struct. Biol., 4, pp. 463–467 (1997); H. S. Subramanya et al., Nature, 384, pp. 379–383 (1996)].

Thus, there is a great need to solve the crystal structure of the helicase complexed with an oligonucleotide and, in particular, to delineate the oligonucleotide and nucleotide triphosphate (NTP) binding pockets of that enzyme. With this information, computer models of these binding sites can be created and potential inhibitors of HCV helicase can be rationally designed.

SUMMARY OF THE INVENTION

Applicants have solved this problem by providing a crystallized complex of the NS3 helicase domain of HCV and a single stranded oligonucleotide. That crystal has been solved by X-ray crystallography to a resolution of 2.2 Å. Based upon that crystal structure, applicants have identified the key amino acid residues that make up the oligonucleotide binding pocket of the helicase.

Thus, the invention relates to a crystallized complex comprising the NS3 helicase domain of hepatitis C virus or mutants thereof and an oligonucleotide.

The invention also relates to crystallizable compositions comprising the NS3 helicase domain, either as an isolated polypeptide or as part of the full length NS3 HCV protein, or single amino acid mutants thereof, and an oligonucleotide. And it relates to methods of using such compositions to produce the aforementioned crystals.

The invention also provides the X-ray structure coordinates of an NS3 helicase-oligonucleotide complex. Those coordinates, or at least the portion that define the oligonucleotide binding pocket or the NTP binding pocket are useful in methods for designing inhibitors of the NS3 helicase, which in turn may be useful in treating HCV infection. This is another aspect of the present invention.

In a related aspect, the invention provides a computer programmed with the coordinates of the NS3 helicase oligonucleotide binding pocket or the NTP binding pocket and with a program capable of converting those coordinates into a three-dimensional representation of the binding pocket on a display connected to the computer.

Finally, the invention provides a computer which, when programmed with at least a portion of the structural coordinates of HCV NS3 helicase and an X-ray diffraction data set of a different molecule or molecular complex, performs a Fourier transform of these structural coordinates of the helicase coordinates and then processes the X-ray diffraction data into structure coordinates of the different molecule or molecular complex via the process of molecular replacement.

BRIEF DESCRIPTION OF THE DRAWINGS

FIGS. 1A through 1Z and FIGS. 1A-1 through 1A-35 list the atomic structure coordinates for NS3 helicase in complex with $dU_8$ as derived by X-ray diffraction from a crystal of that complex. The following abbreviations are used in FIG. 1:

"Atom type" refers to the element whose coordinates are measured. The first letter in the column defines the element.

"X, Y, Z" crystallographically define the atomic position of the element measured.

"B" is a thermal factor that measures movement of the atom around its atomic center.

"Occ" is an occupancy factor that refers to the fraction of the molecules in which each atom occupies the position specified by the coordinates. A value of "1" indicates that each atom has the same conformation, i.e., the same position, in all molecules of the crystal.

Figure 2:
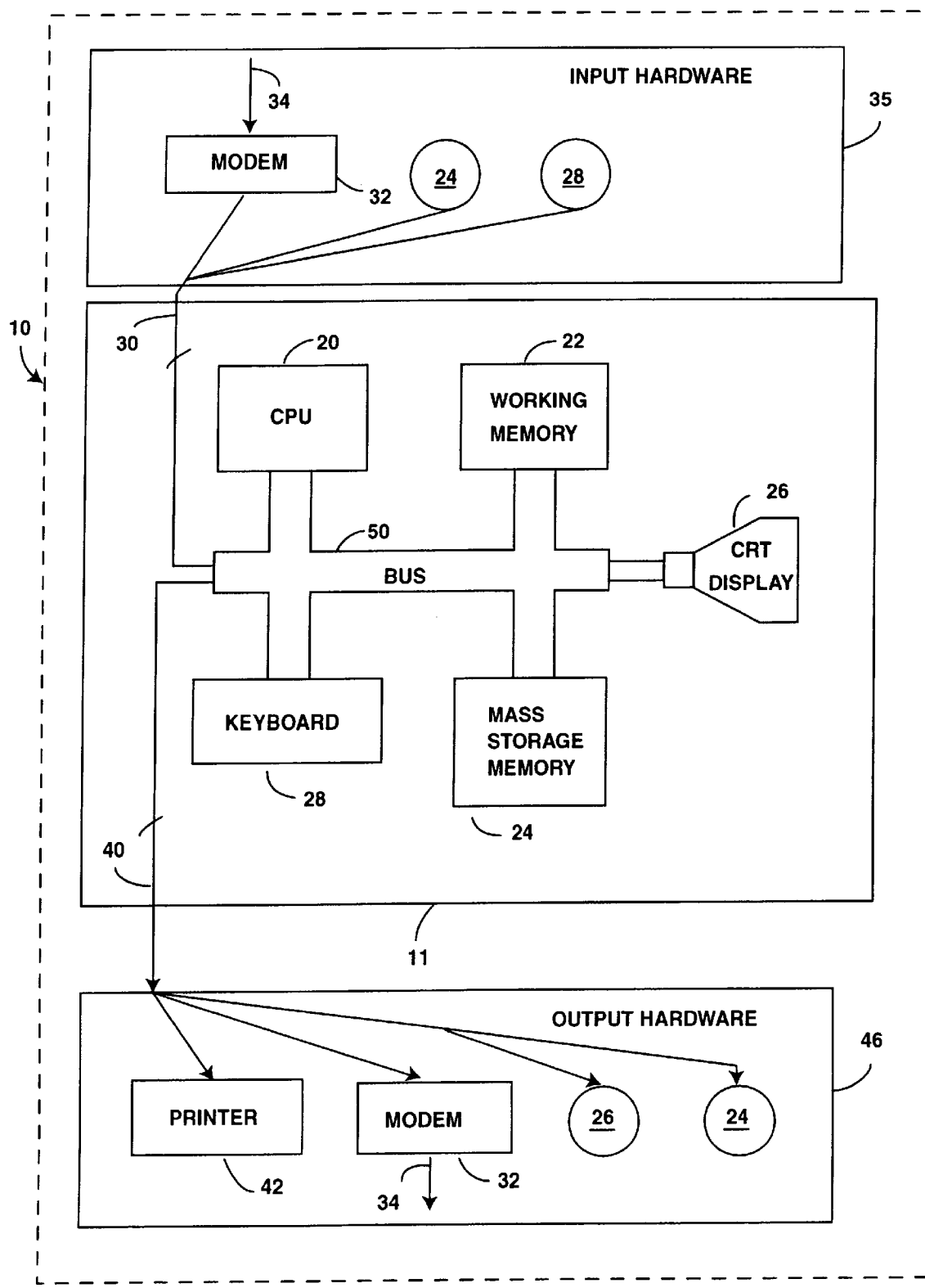

FIG. 2 shows a diagram of a computer used to generate a three-dimensional graphical representation of a molecule or molecular complex according to this invention.

Figure 3:
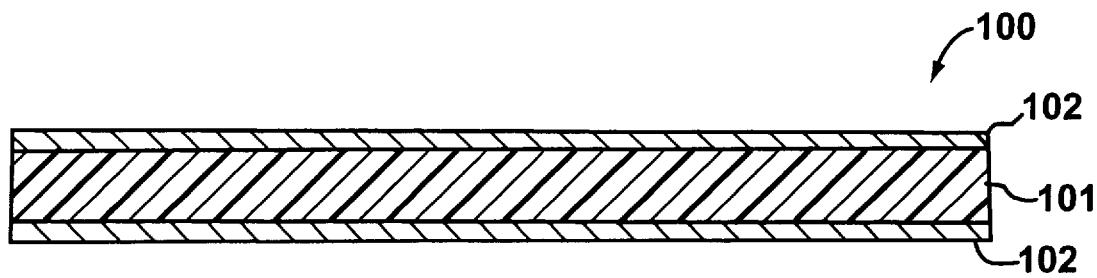

FIG. 3 shows a cross section of a magnetic storage medium.

Figure 4:
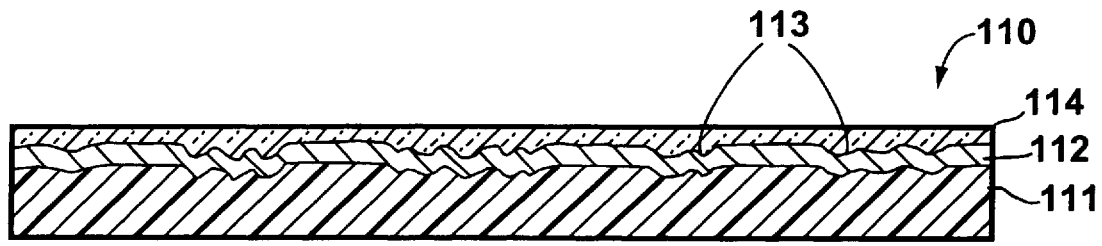

FIG. 4 shows a cross section of a optically-readable data storage medium.

Figure 5:

FIG. 5 depicts a stereo ribbon diagram of the overall fold of the NS3 helicase with bound $d(U)_8$. Domain 1 is colored blue, domain 2 red, and domain 3 green. The sulfate and DNA are colored yellow.

Figure 6:
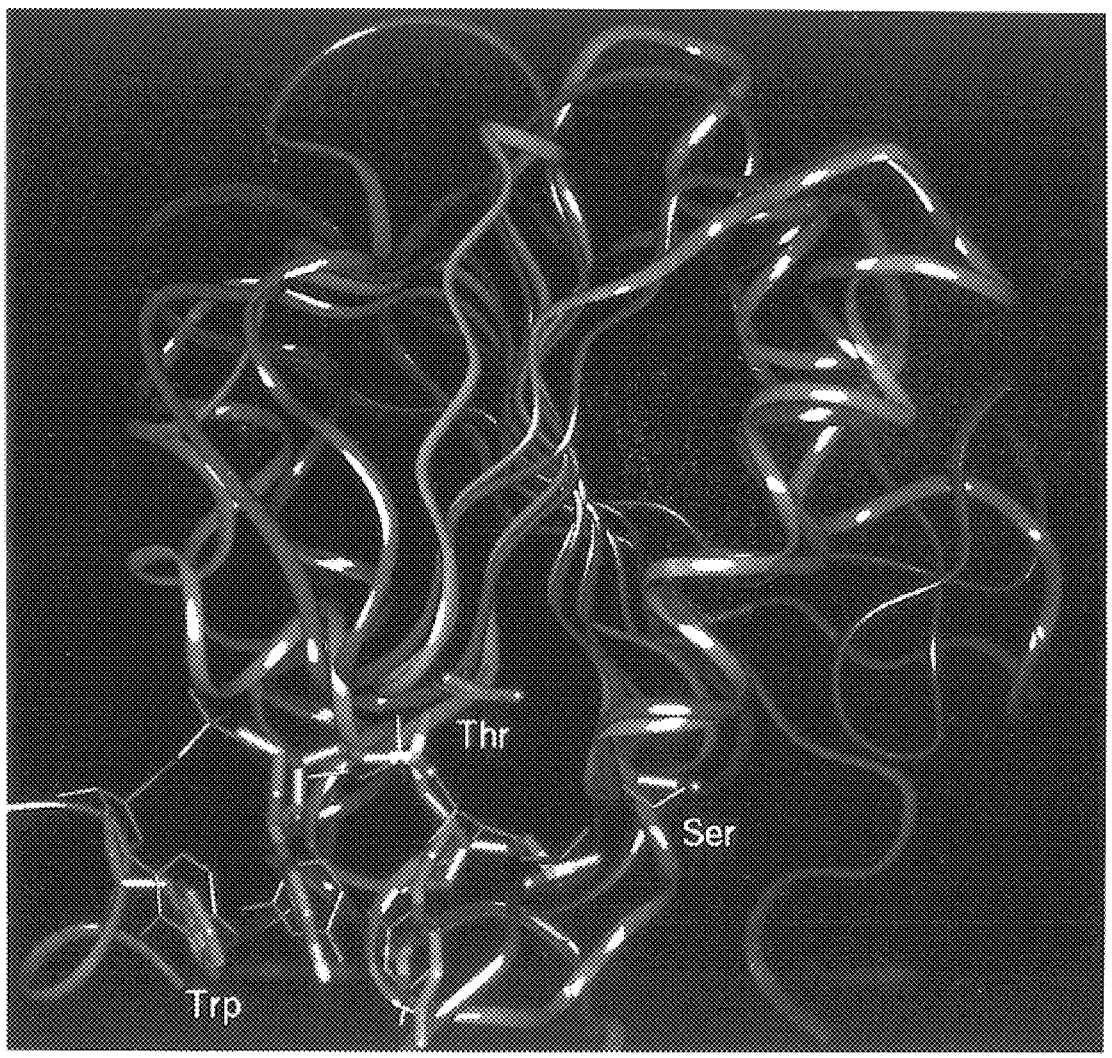

FIG. 6 depicts a superposition of domains 1 (blue) and 2 (red) of NS3 helicase based on conserved secondary structure motifs with a 2.0 Å C-alpha RMS deviation over 78 residues. Residues corresponding to binding to the 3' end of the oligonucleotide are depicted as thick lines. Also shown is the location of Trp-501.

Figure 7A:
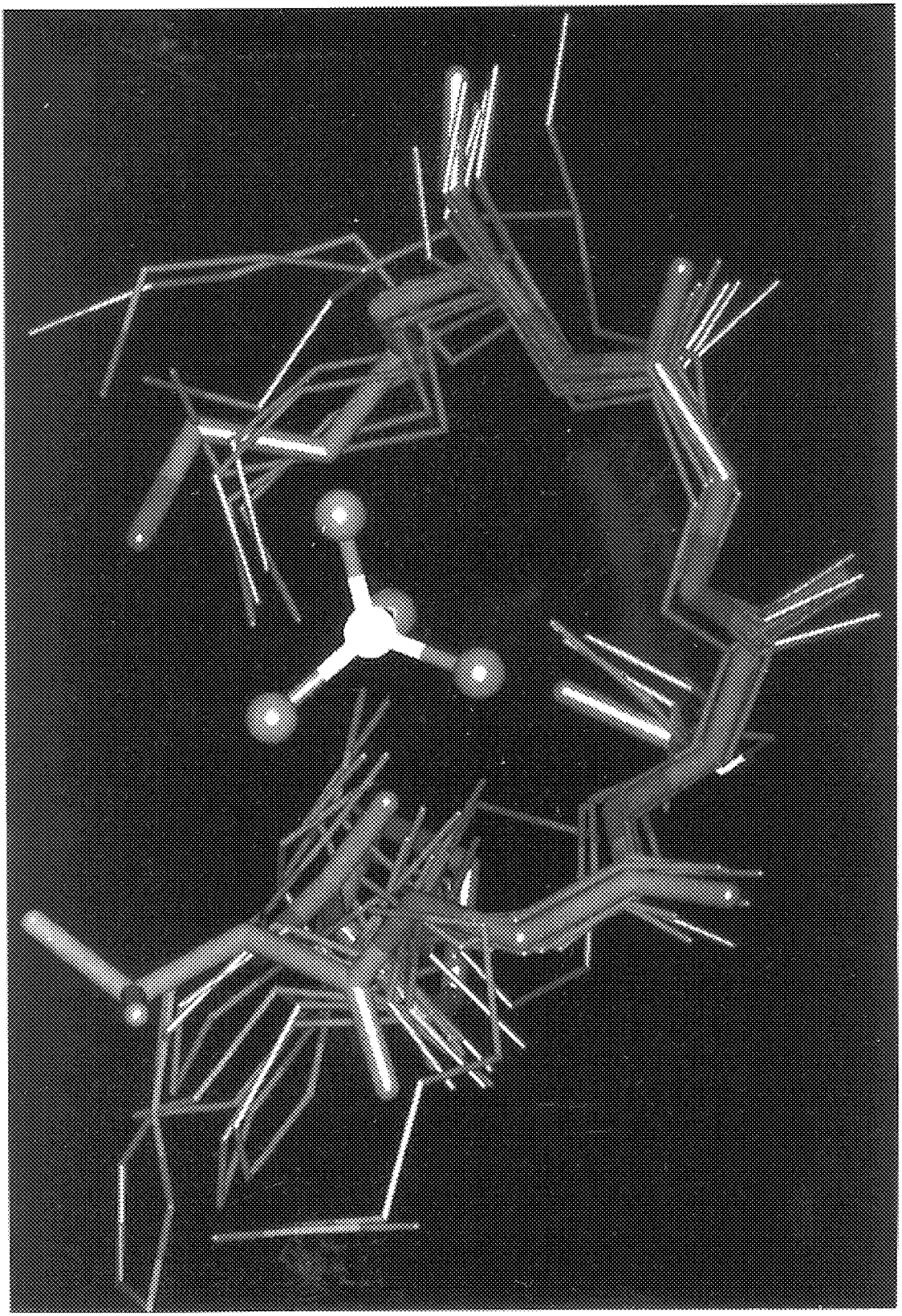

FIG. 7A depicts the residues surrounding the bound sulfate superimposed on the phosphate binding loops of eight deoxynucleoside monophosphate kinases.

Figure 7B:
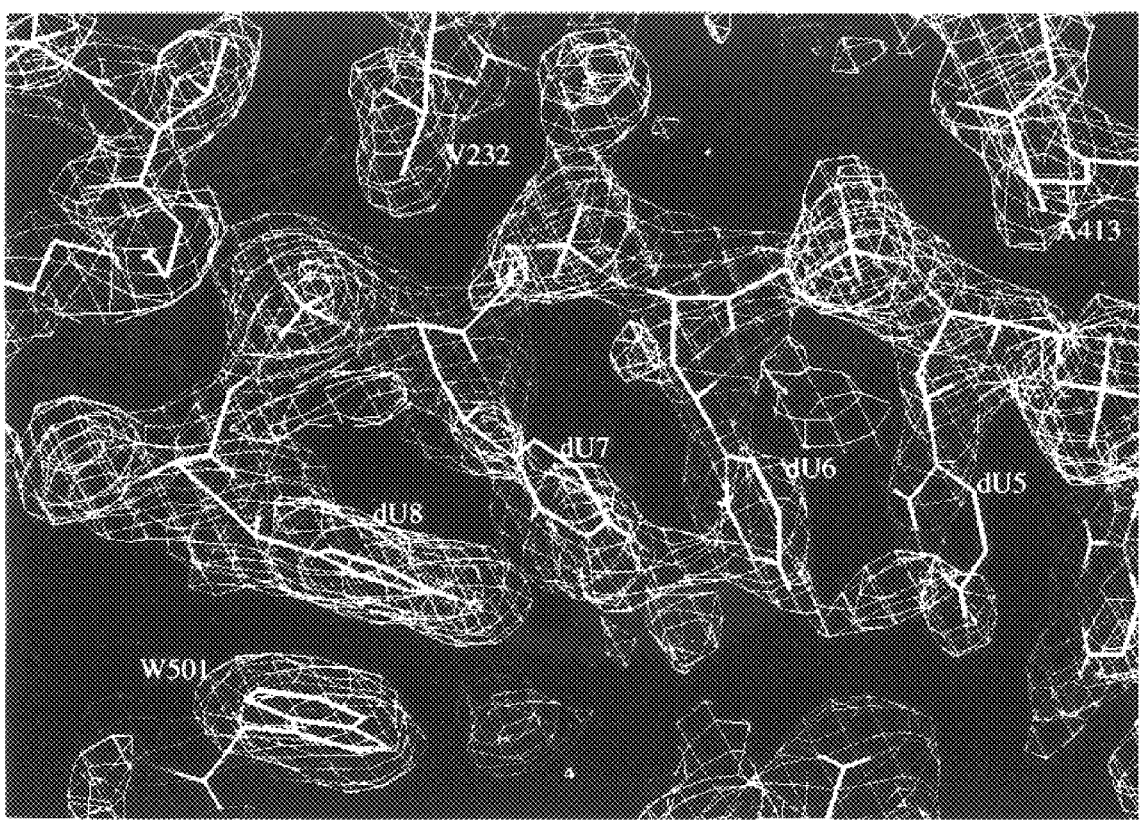

FIG. 7B depicts the electron density encompassing the bound DNA substrate. The orange color depicts the difference Fourier $(F_o-F_c)$ electron density map calculated before DNA or water molecules were built into the model. The blue color depicts the final $2F_o-F_c$ electron density map calculated at 2.2 Å resolution using the refined model.

FIG. 8 depicts the secondary structure of HCV NS3 helicase (indicated above the sequence). The conserved sequence motifs are underscored. The non-HCV N-terminal and C-terminal residues which were added during cloning are depicted in lower case. No density was observed for residues in italics. The residues are numbered based on their location in the NS3 protein.

FIG. 9A depicts aligned sequences of conserved motifs from other helicases. The motifs are colored similar to what was previously reported for the PcrA helicase to aid in comparison of the structures of enzymes from superfamilies I and II. Panel B depicts the location of conserved motifs.

Figure 10:
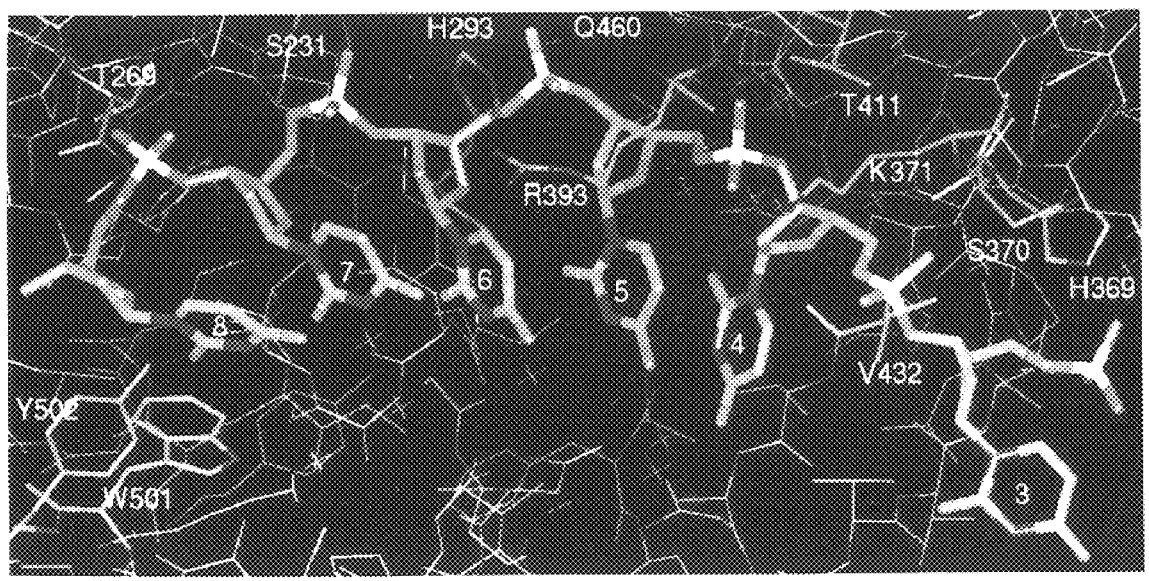

FIG. 10 depicts a view into the central binding cleft of the NS3 helicase domain.

Figure 11A:
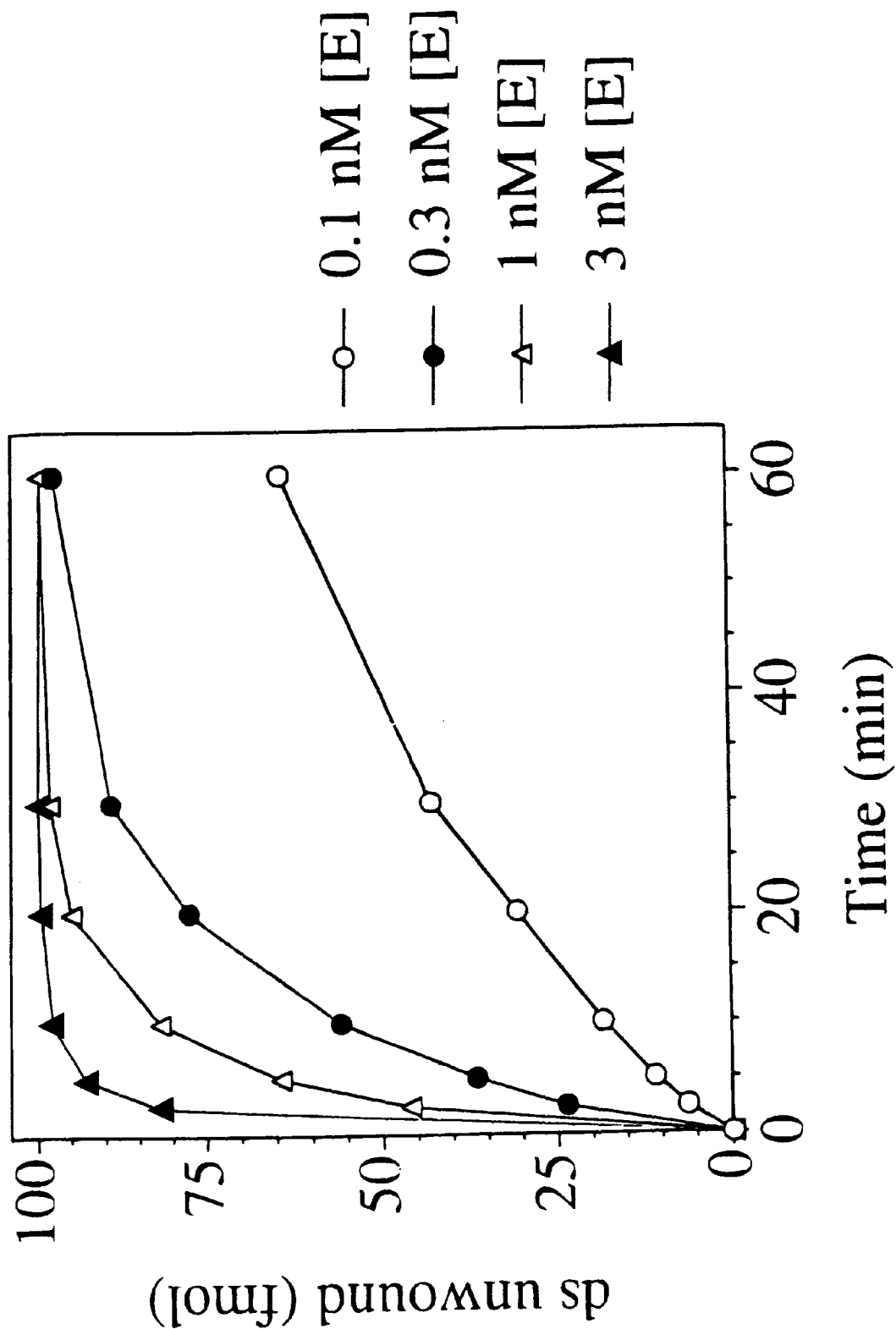

FIG. 11A depicts the effect of enzyme concentration and incubation time on HCV NS3 helicase.

Figure 11B:
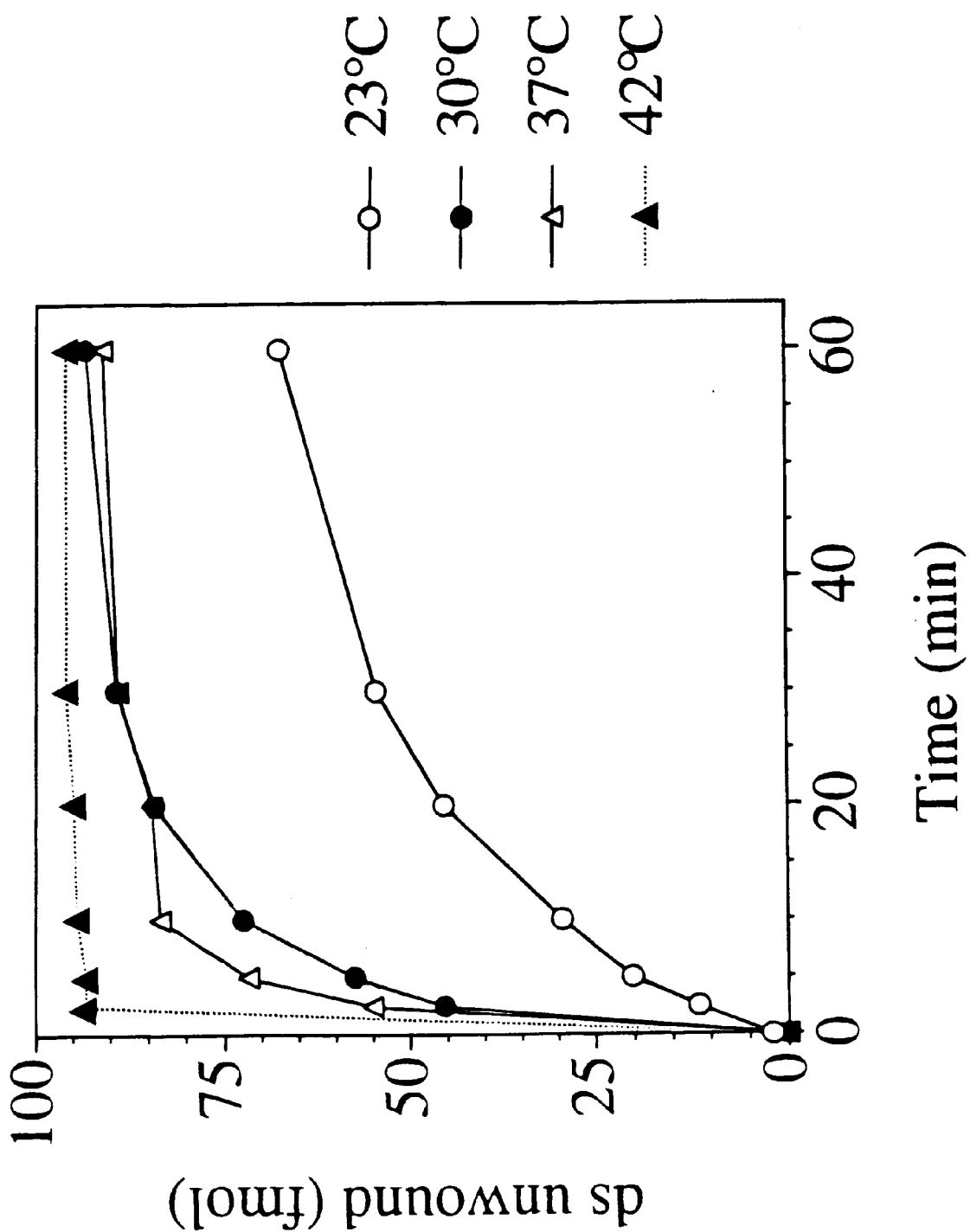

FIG. 11B depicts the effect of incubation temperature on helicase activity.

Figure 11C:
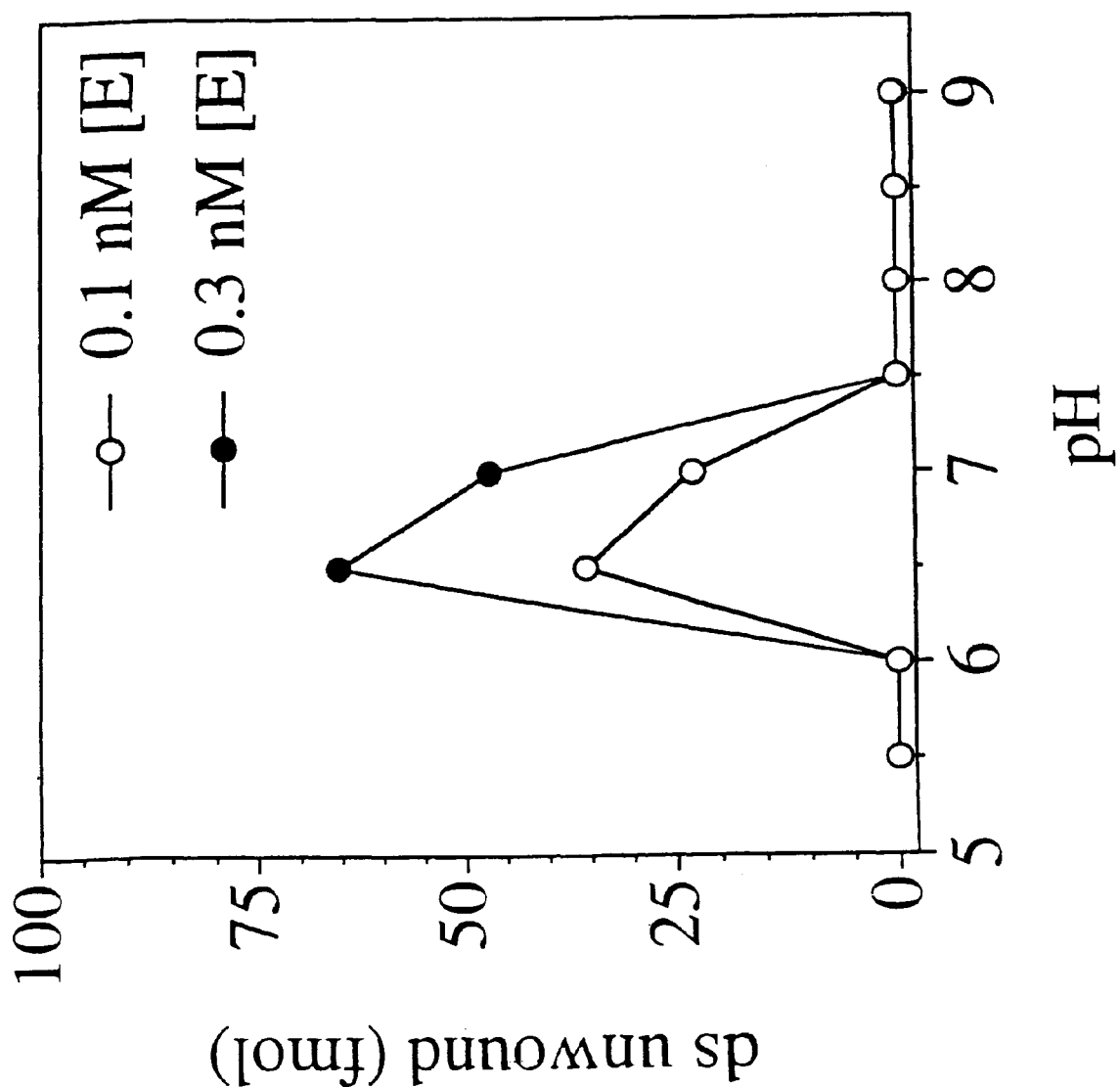

FIG. 11C depicts the effect of pH on helicase activity.

Figure 11D:
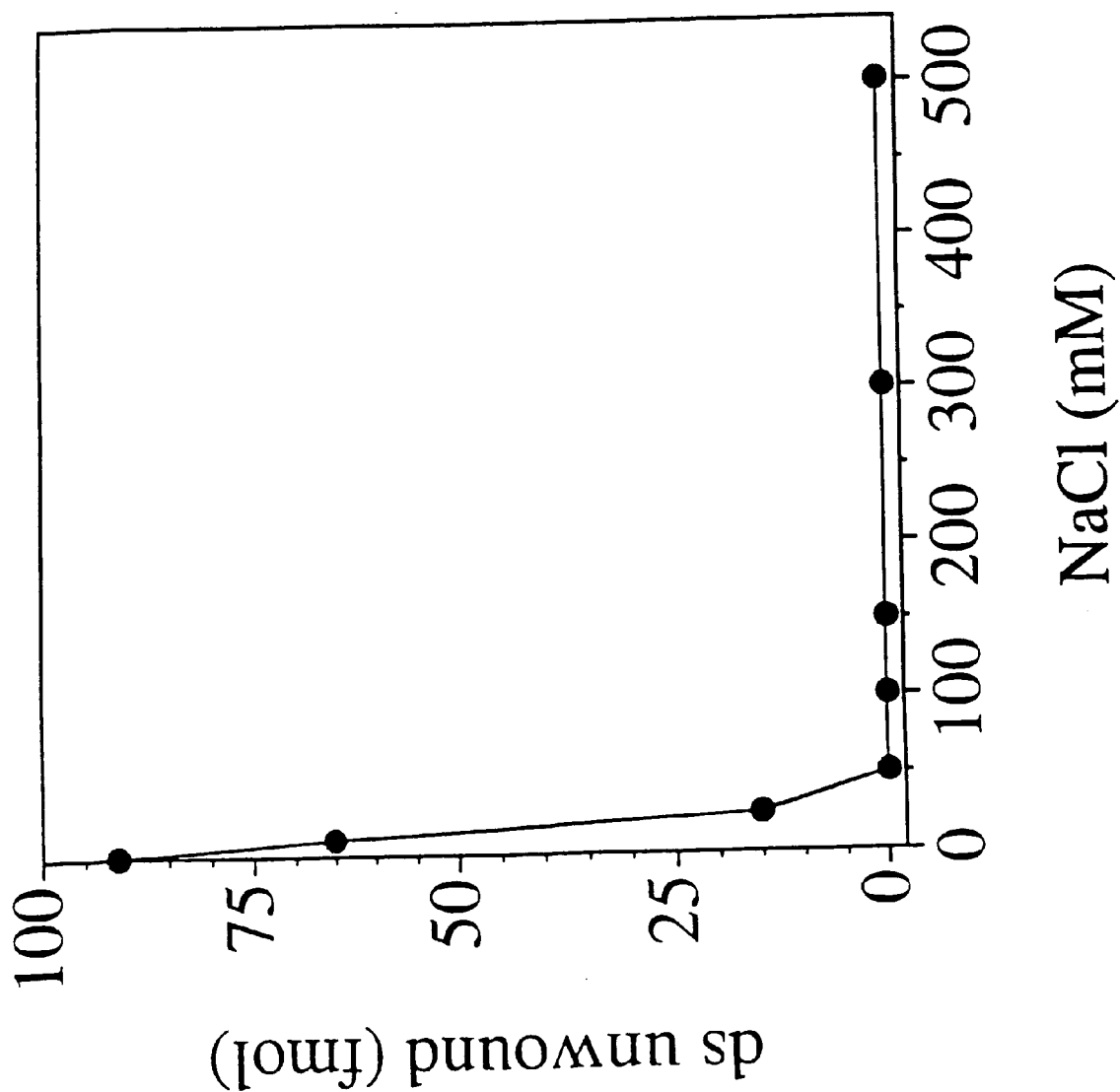

FIG. 11D depicts the effect of monovalent cations on helicase activity.

Figure 11E:
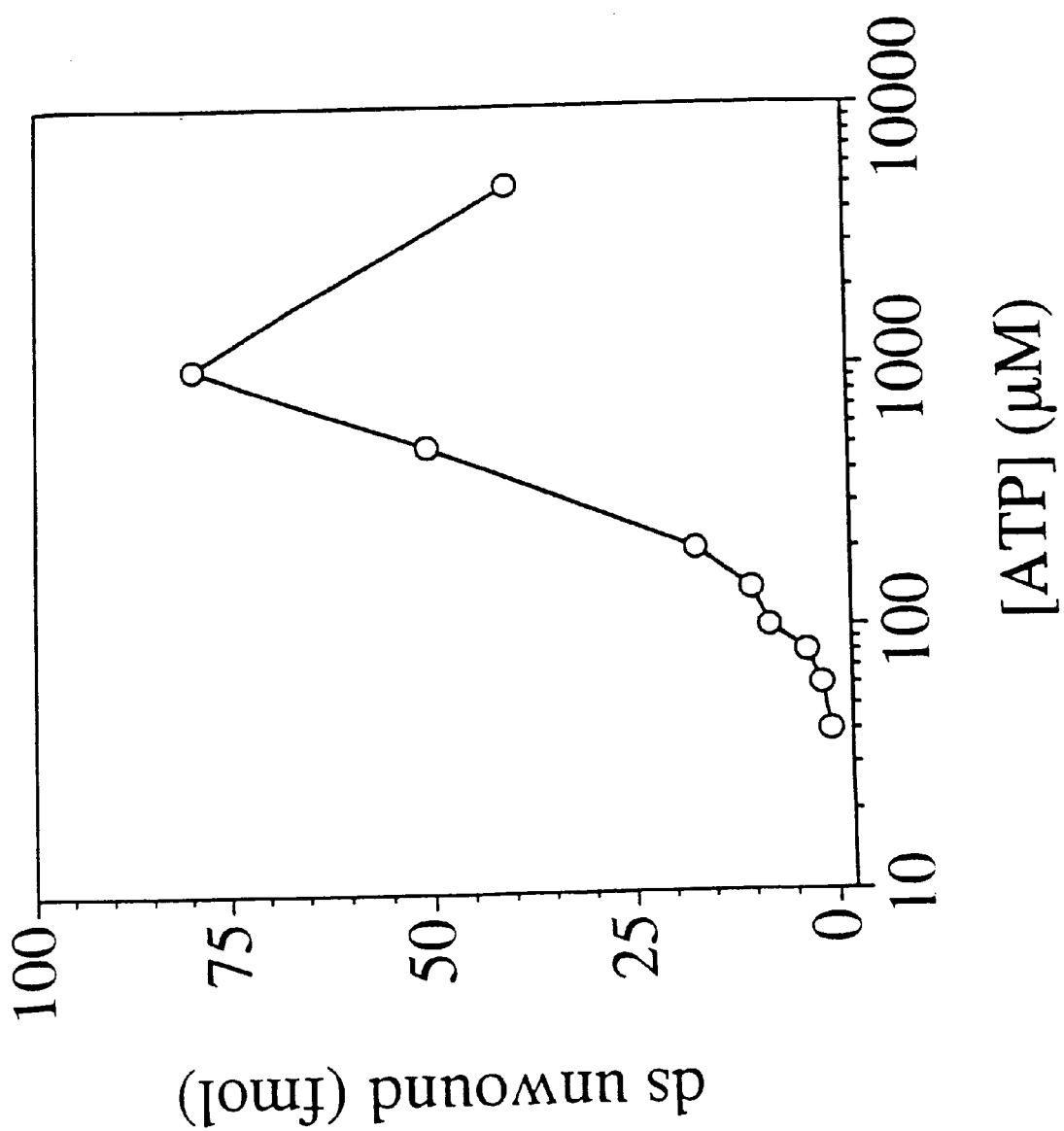

FIG. 11E depicts the effect of ATP on helicase activity.

Figure 11F:
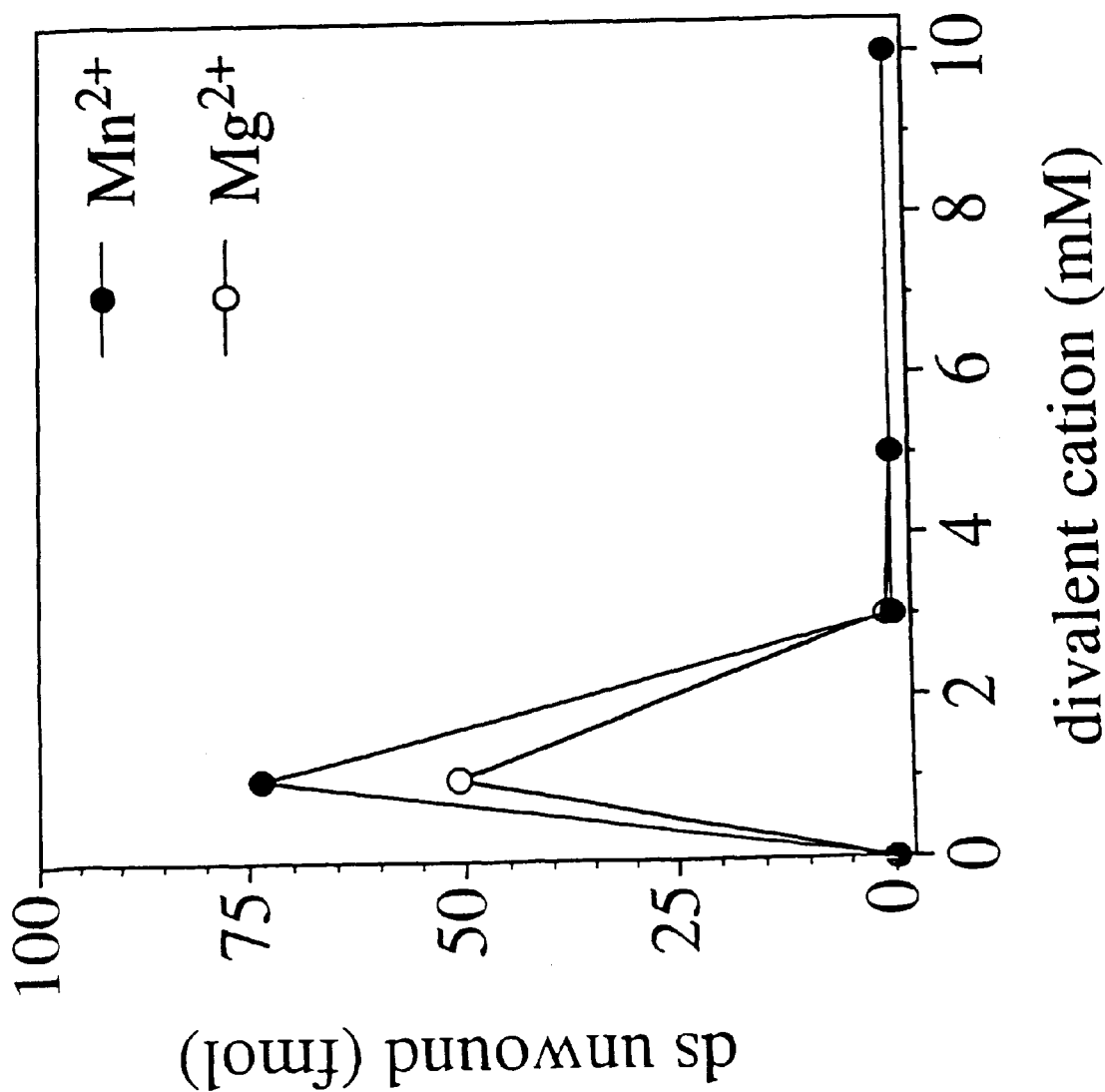

FIG. 11F depicts the effect of divalent cations on enzyme activity.

Figure 12A:
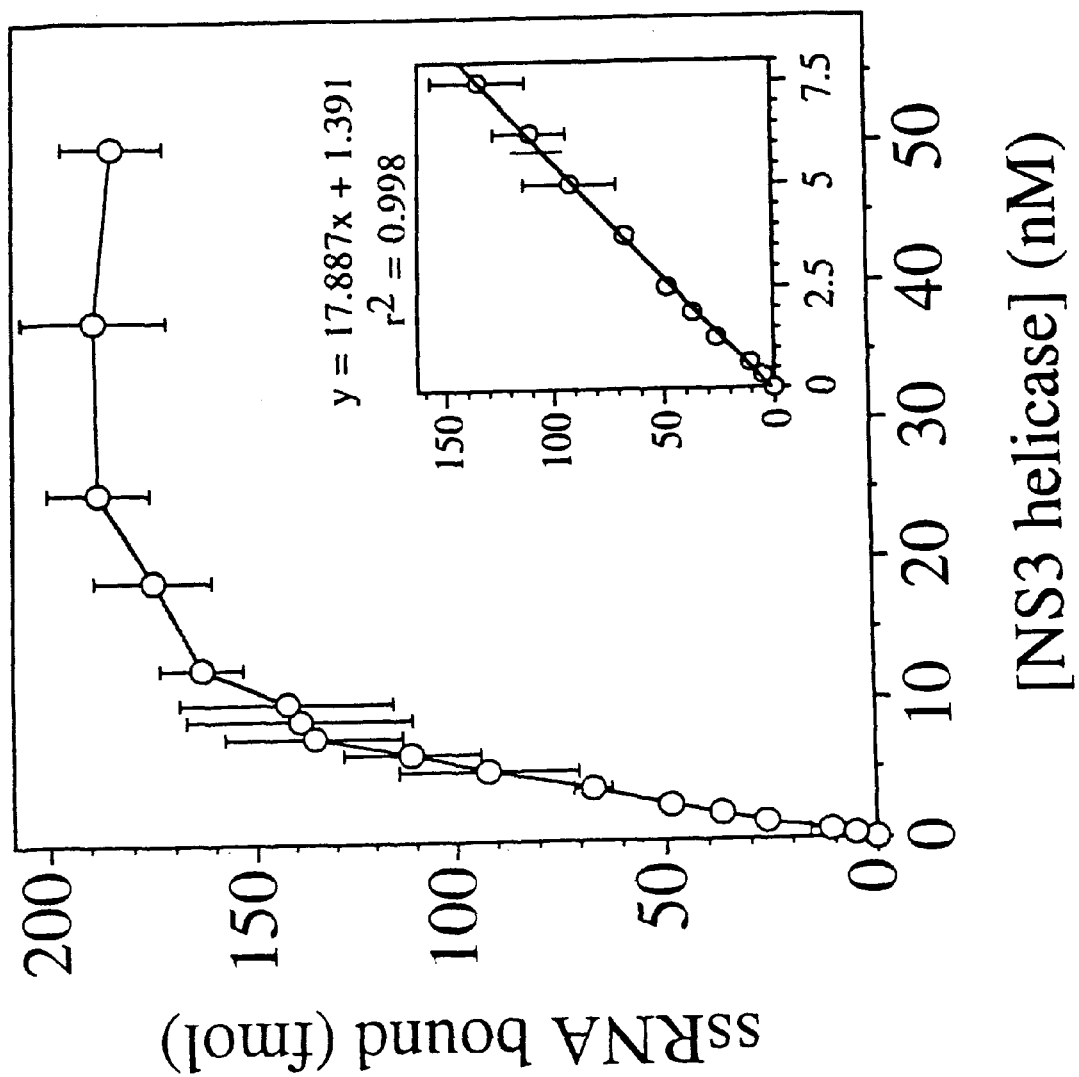

FIG. 12A depicts the effect of enzyme concentration on the binding of [$^{32}$P]-ssRNA substrate to HCV NS3 helicase.

Figure 12B:
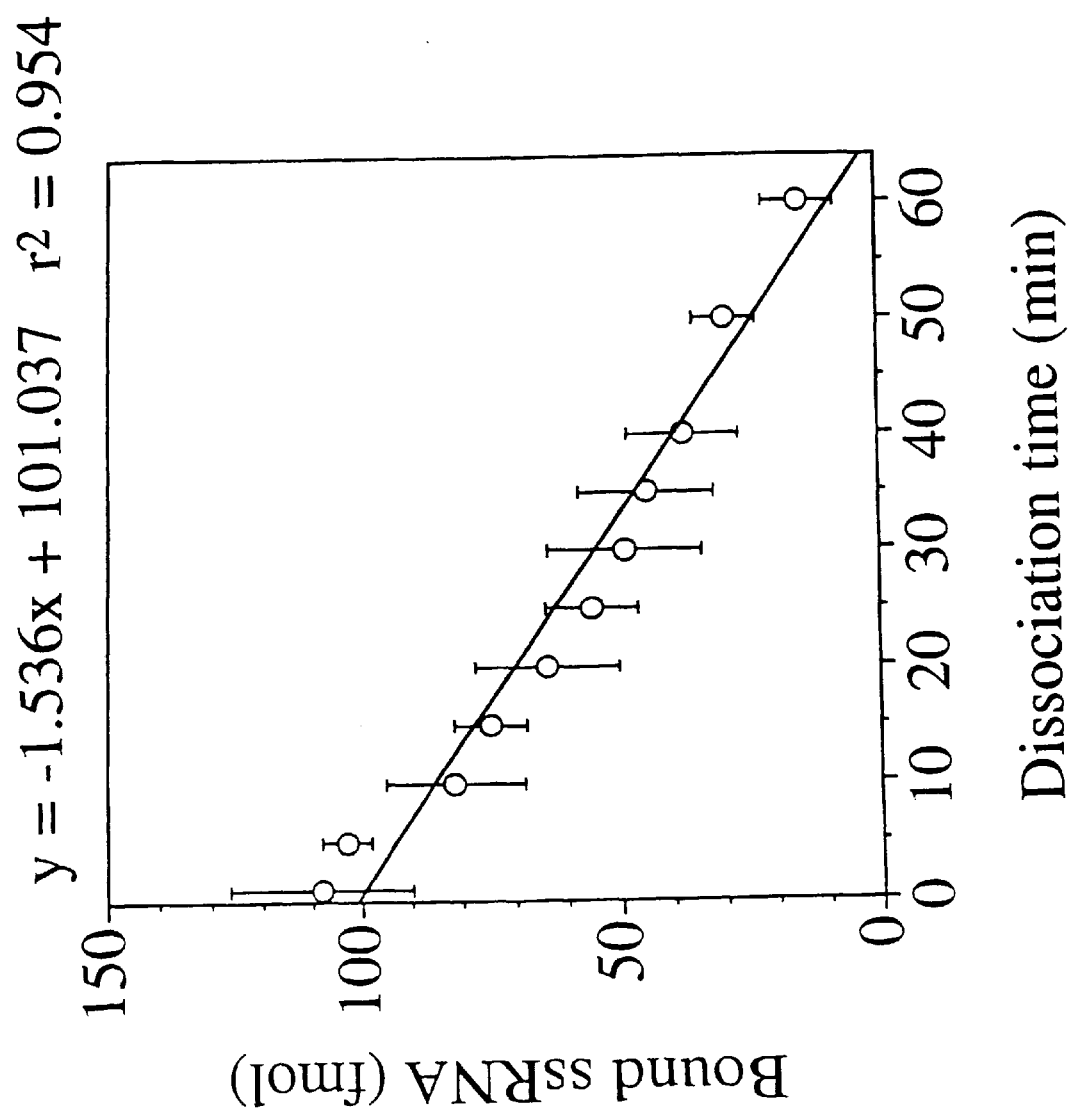

FIG. 12B depicts the dissociation of pre-formed NS3 helicase/[$^{32}$P]-labeled ssRNA complex by [$^3$H]-labeled ssRNA over time.

Figure 12C:
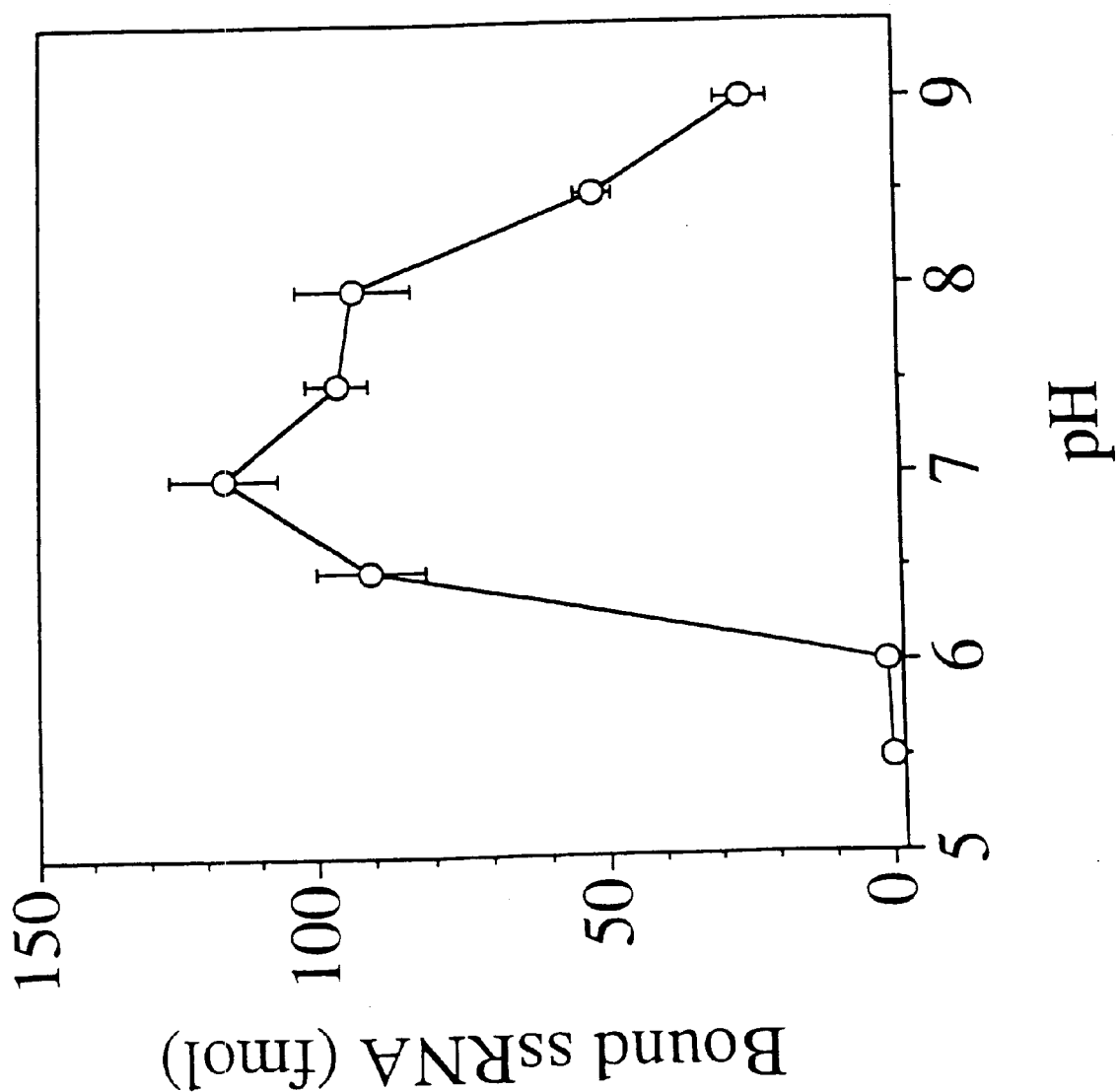

FIG. 12C depicts the effect of pH on the binding of ssRNA to helicase.

Figure 12D:
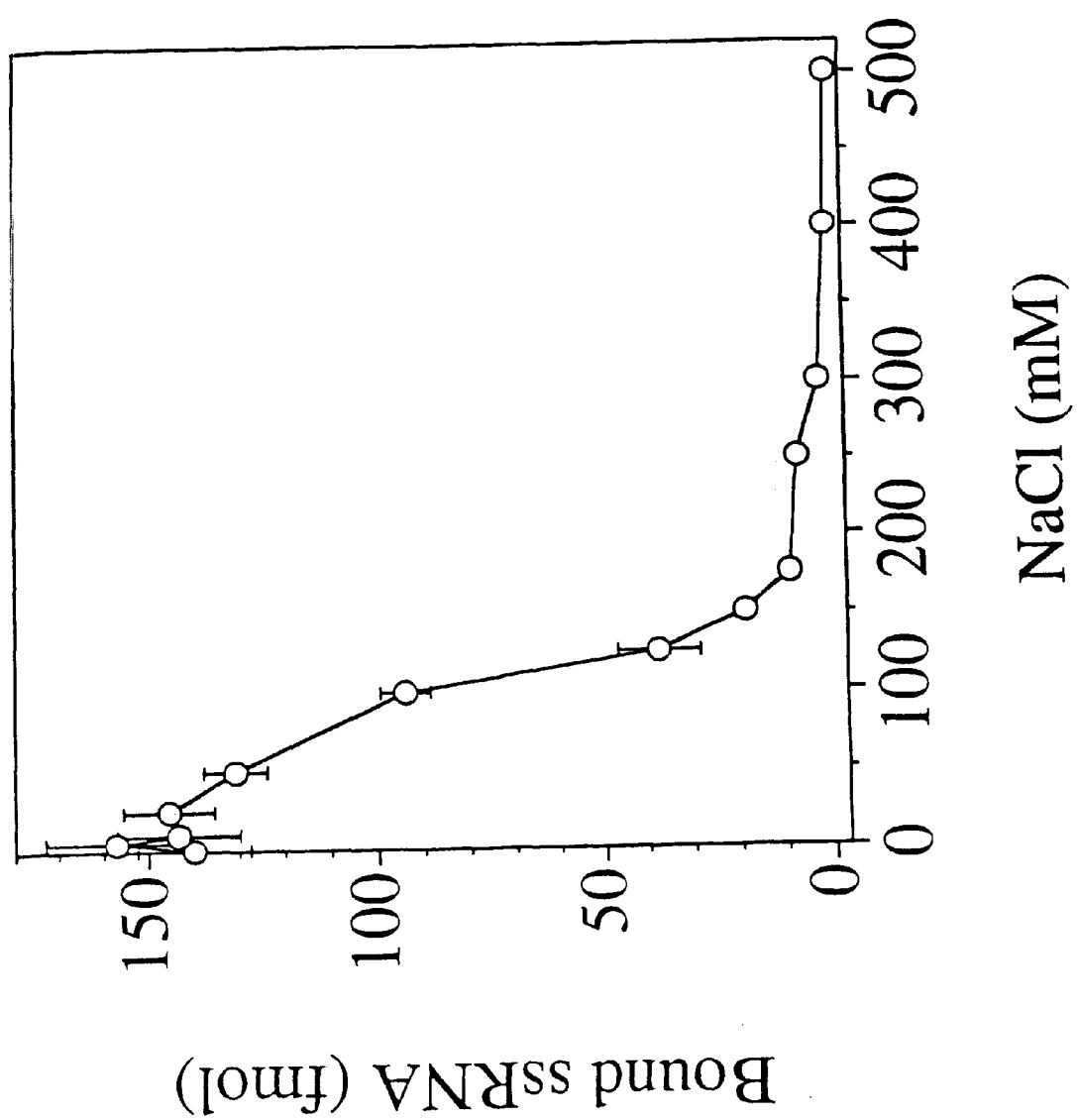

FIG. 12D depicts the effect of monovalent cation on ssRNA binding to helicase.

Figure 12E:
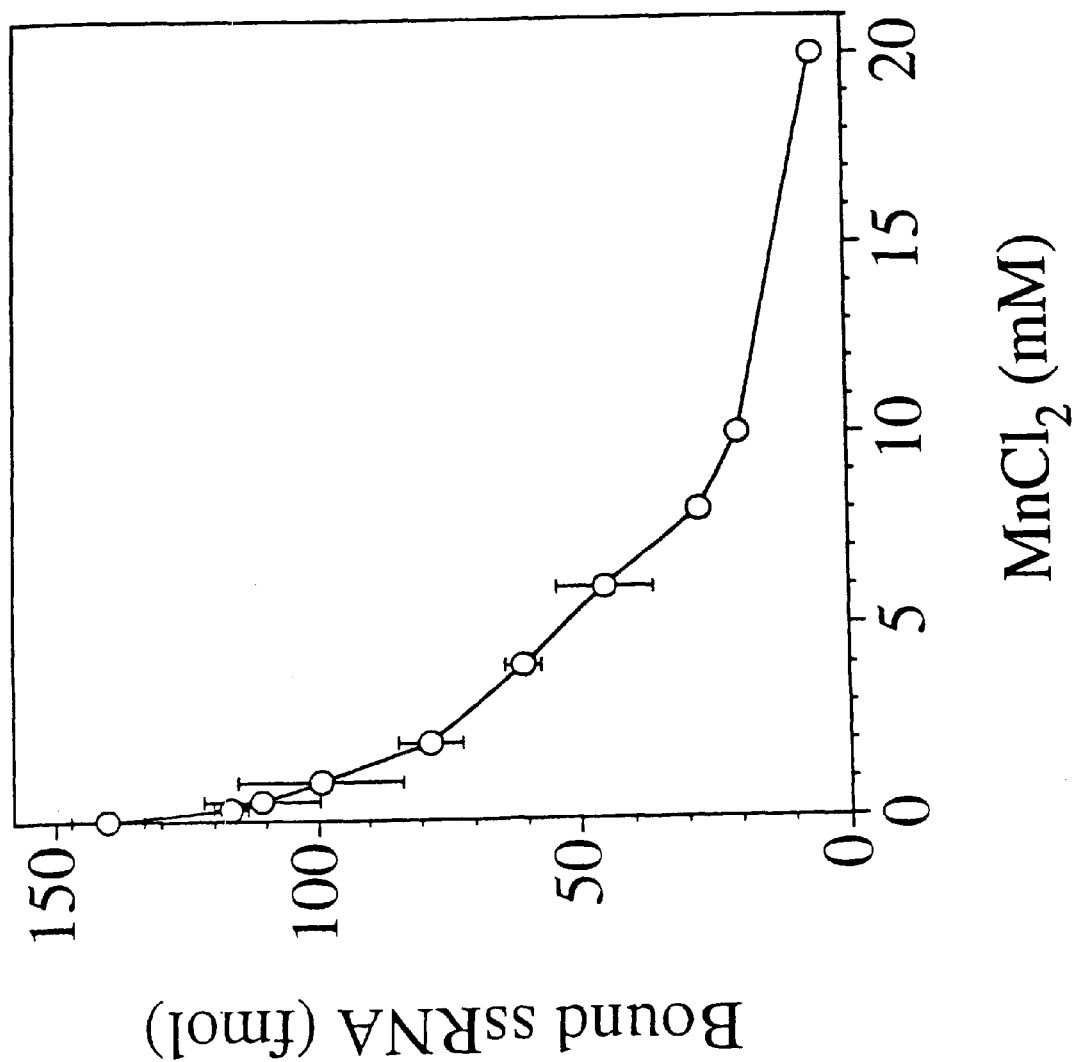

FIG. 12E depicts the effect of divalent cations on ssRNA binding to helicase.

Figure 13A:
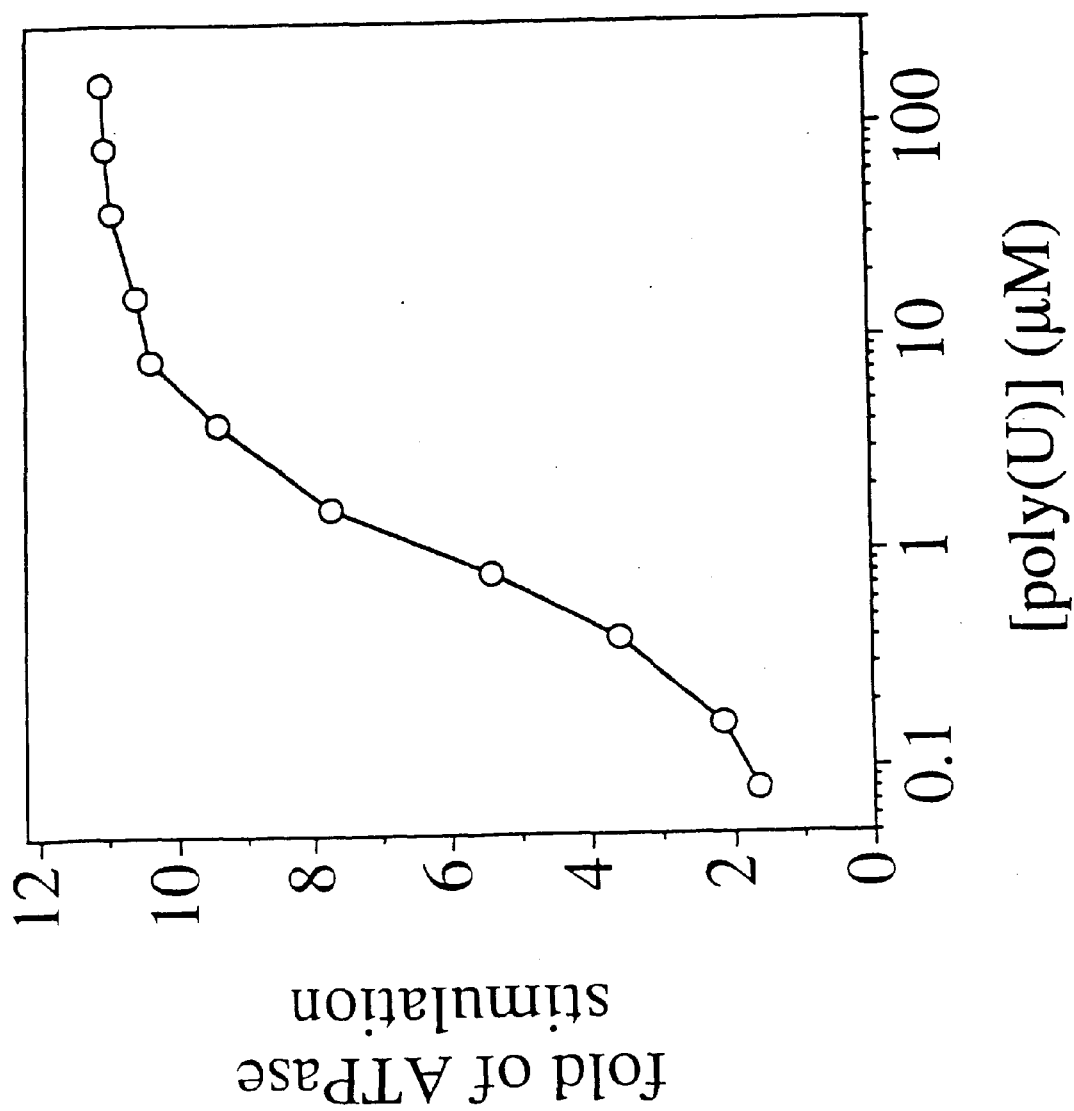

FIG. 13A depicts the effect of poly (U) on the ATPase activity of HCV NS3 helicase.

Figure 13B:
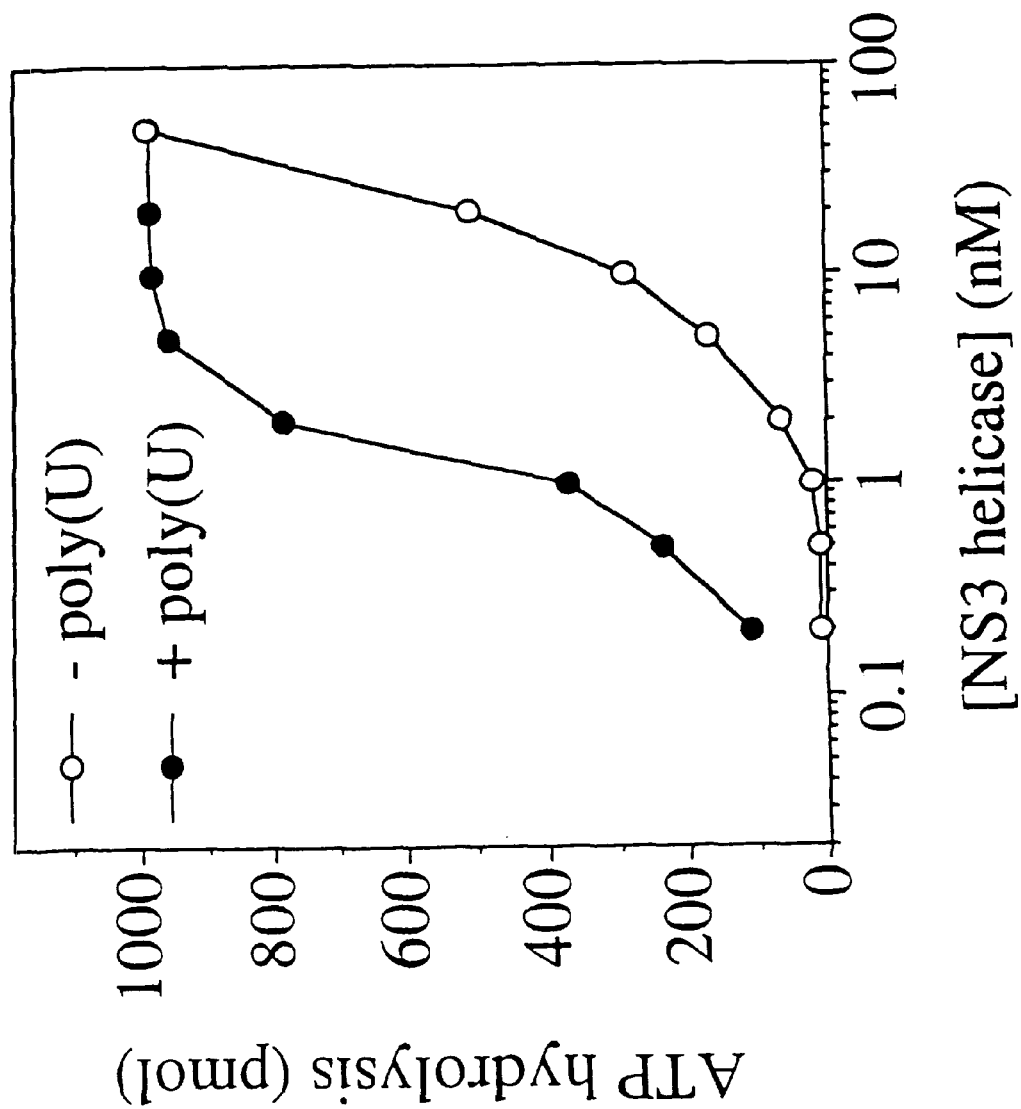

FIG. 13B depicts the effect of enzyme concentration on ATPase activity in the presence or absence of poly (U).

DETAILED DESCRIPTION OF THE INVENTION

In order that the invention described herein may be more fully understood, the following detailed description is set forth.

According to one embodiment, the invention provides a crystallizable composition comprising NS3 helicase and an oligonucleotide.

The NS3 helicase protein in the crystallizable complexes of this invention is selected from the isolated helicase domain from any strain or the consensus sequence of the HCV NS3 protein (e.g., amino acids 167–631 of SEQ ID NO:2); the entire NS3 protein from any strain of HCV or the consensus sequence of that protein (e.g., SEQ ID NO:2); any portion of the NS3 protein that contains a functional helicase domain, which has been indicated to be amino acids 183–582 by C. Hyun-Soo et al., *J. Biol. Chem.*, 273, pp. 15045–15052 (1998), from any strain of HCV or the consensus sequence of that protein (e.g., amino acids 183–582 of SEQ ID NO:2, amino acids 167–631 of SEQ ID NO:2, amino acids 183–631 of SEQ ID NO:2) and amino acid mutants of any of the above (including, but not limited to, SEQ ID NO:2 or any portion thereof that includes amino acids 183–582 of SEQ ID NO:2 and contains one or more of the following single amino acid replacements: Ser231-to-Ala, Thr269-to-Ala, Ser370-to-Ala, Thr411-to-Ala, Trp501-to-Phe, Trp501-to-Leu or Trp501-to-Ala, Gln460-to-Ala, Arg461-to-Ala, Arg462-to-Ala, Arg464-to-Ala, or Arg467-to-Ala).

The NS3 protein utilized in the crystallizable compositions of this invention may also contain additional amino acids at the N- and/or C-terminus which may be useful in purifying the protein when produced recombinantly. For example, we have found that a polyhistidine tag at the C-terminus is useful in purifying NS3 proteins produced in recombinant host cells through the use of appropriate resins, such as Q-Sepharose (Pharmacia, Piscataway, N.J.). Such tags may also be useful in increasing the solubility of the NS3 protein.

The second component in these compositions is an oligonucleotide. Preferably, the oligonucleotide is single-stranded, although double-stranded oligonucleotides may be used and subsequently dissociated prior to crystallization. Preferably, the oligonucleotide is a polynucleotide of between about 6 and 20 bases. More preferably, the oligonucleotide is between about 6 and 12 bases. Most preferably, the oligonucleotide is polyuracil 8 nucleotides long ($dU_8$).

The molar ratio of NS3 helicase to oligonucleotide should be about 1:1, although ranges between 1:5 and 5:1 are acceptable.

The buffers and other reagents present in the crystallizable compositions of this application may be any components that promote crystallization and/or are compatible with crystallization conditions. An example of such a buffer condition is 15 mM MES (pH 6.5), 2.5 mM β-mercaptoethanol.

The invention also relates to crystals of NS3 helicase complexed with an oligonucleotide. Both the NS3 helicase component and the oligonucleotide component are the same as those described above for crystallizable compositions. These crystals are obtained from the above described compositions by standard crystallization protocols, such as the protocol exemplified in the Example section below.

The invention also relates to a method of making NS3 helicase-containing crystals. Such methods comprise the steps of:
 a) obtaining a crystallizable composition comprising an NS3 helicase protein and an oligonucleotide in a molar ratio of between 1:5 and 5:1; and
 b) subjecting said composition to conditions which promote crystallization.

Again, the choice for the NS3 helicase protein and the oligonucleotide utilized in the above crystallization method are the same as those set forth above for crystallizable compositions.

As mentioned above, applicants have solved the three-dimensional X-ray crystal structure of an NS3 helicase-$dU_8$ complex. The atomic coordinate data is presented in FIG. 1.

In order to use the structure coordinates generated for the NS3 helicase-$dU_8$ complex or its NTP or oligonucleotide binding pockets or portions or homologues thereof, it is often times necessary to convert them into a three-dimensional shape. This is achieved through the use of commercially available software that is capable of generating three-dimensional graphical representations of molecules or portions thereof from a set of structure coordinates.

Binding pockets, also referred to as binding sites in the present invention, are of significant utility in fields such as drug discovery. The association of natural ligands or substrates with the binding pockets of their corresponding receptors or enzymes is the basis of many biological mechanisms of action. Similarly, many drugs exert their biological effects through association with the binding pockets of receptors and enzymes. Such associations may occur with all or any parts of the binding pocket. An understanding of such associations will help lead to the design of drugs having more favorable associations with their target receptor or enzyme, and thus, improved biological effects. Therefore, this information is valuable in designing potential inhibitors of the binding sites of biologically important targets.

The term "binding pocket", as used herein, refers to a region of a molecule or molecular complex, that, as a result of its shape, favorably associates with another chemical entity or compound.

Applicants have identified three binding pockets which are good targets for designing inhibitors. Two of these binding pockets reside in the region of the helicase where an oligonucleotide binds. These pockets are designated U4 and U8, based upon the nucleotide of $dU_8$ that lies in this pocket in an NS3 helicase-dU8 complex. The third binding pocket is the NTP binding pocket. While this binding pocket has been partially described by others [T. Yao et al., *Nat. Struct. Biol.*, 4, pp. 463–467 (1997)], applicants have further defined this pocket in a way that was not derivable from what was known in the art.

The terms "U4-, U8- and NTP-like binding pocket", as used herein, refer to a portion of a molecule or molecular complex whose shape is sufficiently similar to the NS3 helicase U4, U8 and NTP binding pocket, so as to bind common ligands. These commonalties of shape are defined by a root mean square deviation from the structure coordinates of the backbone atoms of the amino acids that make up these binding pockets in the NS3 helicase structure (as set forth in FIG. 1) of not more than 1.5 Å. The method of performing this calculation is described below.

In resolving the crystal structure of NS3 helicase in complex with an oligonucleotide, applicants have determined that NS3 amino acids Val232, Thr254, Gly255, Thr269, Gly271, Lys272, Ala275, Trp501 and Tyr502 form close contacts (<4 Å) with U8 of $dU_8$ in the NS3 helicase-$dU_8$ complex. Thus, a binding pocket defined by the structural coordinates of those amino acids, as set forth in FIG. 1; or a binding pocket whose root mean square deviation from the structure coordinates of the backbone atoms of those amino acids of not more than 1.5 Å is considered a U8-like binding pocket of this invention.

Applicants have also determined that in addition to the NS3 amino acids set forth above, Pro230, Val256, Thr298, Ala497, Lys551, Gln552, Gly554, Glu555, Asn556 and Pro558 are within 8 Å of U8 of the bound oligonucleotide and therefore are also close enough to interact with that substrate. Thus, in a preferred embodiment, a binding pocket defined by the structural coordinates of the amino acids that are within 8 Å of U8 of the bound oligonucleotide, as set forth in FIG. 1; or a binding pocket whose root mean square deviation from the structure coordinates of the backbone atoms of those amino acids is not more than 1.5 Å is considered a preferred NS3 helicase U8-like binding pocket of this invention.

Applicants have further determined that the NS3 helicase amino acids that define the shape of the U4 oligonucleotide binding pocket are: His369, Ser370, Lys371, Tyr392, Arg393, Thr411, Asp412, Ala413, Cys431, Val432, Gln434, Ile446, Thr448, Arg461, Glu493, Glu555, Asn556 and Phe557. Thus, a binding pocket defined by the structural coordinates of these amino acids, as set forth in FIG. 1; or a binding pocket whose root mean square deviation from the structure coordinates of the backbone atoms of these amino acids is not more than 1.5 Å is considered a NS3 helicase U4-like binding pocket of this invention.

Applicants have also more completely determined, as compared to the prior art, the NS3 helicase amino acids that define the shape of the NTP binding pocket. Those amino acids are: Pro205, Thr206, Gly207, Ser208, Gly209, Lys210, Ser211, Thr212, Lys213. Asn229, Ala234, Gly237, Phe238, Tyr241, Asp290, Glu291, His293, Thr322, Ala323, Thr324, Gln460, Gly463, Arg464 and Arg467. Thus, a binding pocket defined by the structural coordinates of these amino acids, as set forth in FIG. 1; or a binding pocket whose root mean square deviation from the structure coordinates of the backbone atoms of these amino acids is not more than 1.5 Å is considered a NS3 helicase NTP-like binding pocket of this invention.

It will be readily apparent to those of skill in the art that the numbering of amino acids in other isoforms of NS3 may be different than that set forth for herein. Corresponding amino acids in other isoforms of NS3 are easily identified by visual inspection of the amino acid sequences or by using commercially available homology software programs.

Each of those amino acids of NS3 helicase is defined by a set of structure coordinates set forth in FIG. 1. The term "structure coordinates" refers to Cartesian coordinates derived from mathematical equations related to the patterns obtained on diffraction of a monochromatic beam of X-rays by the atoms (scattering centers) of a protein or protein-ligand complex in crystal form. The diffraction data are used to calculate an electron density map of the repeating unit of the crystal. The electron density maps are then used to establish the positions of the individual atoms of the enzyme or enzyme complex.

Those of skill in the art understand that a set of structure coordinates for an enzyme or an enzyme-complex or a portion thereof, is a relative set of points that define a shape in three dimensions. Thus, it is possible that an entirely different set of coordinates could define a similar or identical shape. Moreover, slight variations in the individual coordinates will have little effect on overall shape. In terms of binding pockets, these variations would not be expected to significantly alter the nature of ligands that could associate with those pockets.

The term "associating with" refers to a condition of proximity between a chemical entity or compound, or portions thereof, and a binding pocket or binding site on a protein. The association may be non-covalent—wherein the juxtaposition is energetically favored by hydrogen bonding or van der Waals or electrostatic interactions—or it may be covalent.

The variations in coordinates discussed above may be generated because of mathematical manipulations of the NS3 helicase-oligonucleotide complex structure coordinates. For example, the structure coordinates set forth in FIG. 1 could be manipulated by crystallographic permutations of the structure coordinates, fractionalization of the structure coordinates, integer additions or subtractions to sets of the structure coordinates, inversion of the structure coordinates or any combination of the above.

Alternatively, modifications in the crystal structure due to mutations, additions, substitutions, and/or deletions of amino acids, or other changes in any of the components that make up the crystal could also account for variations in structure coordinates. If such variations are within an acceptable standard error as compared to the original coordinates, the resulting three-dimensional shape is considered to be the same. Thus, for example, a ligand that bound to the oligonucleotide binding pocket of NS3 helicase would also be expected to bind to another binding pocket whose structure coordinates defined a shape that fell within the acceptable error.

Various computational analyses are therefore necessary to determine whether a molecule or the binding pocket portion thereof is sufficiently similar to the NS3 helicase binding pockets described above. Such analyses may be carried out in well known software applications, such as the Molecular Similarity application of QUANTA (Molecular Simulations Inc., San Diego, Calif.) version 4.1, and as described in the accompanying User's Guide.

The Molecular Similarity application permits comparisons between different structures, different conformations of the same structure, and different parts of the same structure. The procedure used in Molecular Similarity to compare structures is divided into four steps: 1) load the structures to be compared; 2) define the atom equivalences in these structures; 3) perform a fitting operation; and 4) analyze the results.

Each structure is identified by a name. One structure is identified as the target (i.e., the fixed structure); all remaining structures are working structures (i.e., moving structures). Since atom equivalency within QUANTA is defined by user input, for the purpose of this invention we will define equivalent atoms as protein backbone atoms (N, Cα, C and O) for all conserved residues between the two structures being compared. We will also consider only rigid fitting operations.

When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atom is an absolute minimum. This number, given in angstroms, is reported by QUANTA.

For the purpose of this invention, any molecule or molecular complex or binding pocket thereof that has a root mean square deviation of conserved residue backbone atoms (N, Cα, C, O) of less than 1.5 Å when superimposed on the relevant backbone atoms described by structure coordinates listed in FIG. 1 are considered identical. More preferably, the root mean square deviation is less than 1.0 Å.

The term "root mean square deviation" means the square root of the arithmetic mean of the squares of the deviations from the mean. It is a way to express the deviation or variation from a trend or object. For purposes of this invention, the "root mean square deviation" defines the variation in the backbone of a protein from the backbone of NS3 helicase or a binding pocket portion thereof, as defined by the structure coordinates of NS3 helicase described herein.

Therefore, according to another embodiment of this invention is provided a computer for producing:
- a) a three-dimensional representation of a molecule or molecular complex, wherein said molecule or molecular complex comprises a binding pocket defined by structure coordinates of NS3 amino acids Val232, Thr254, Gly255, Thr269, Gly271, Lys272, Ala275, Trp501 and Tyr502 according to FIG. 1; or
- b) a three-dimensional representation of a homologue of said molecule or molecular complex, wherein said homologue comprises a binding pocket that has a root mean square deviation from the backbone atoms of said amino acids of not more than 1.5 Å, wherein said computer comprises:
  - (i) a machine-readable data storage medium comprising a data storage material encoded with machine-readable data, wherein said data comprises the structure coordinates of NS3 amino acids Val232, Thr254, Gly255, Thr269, Gly271, Lys272, Ala275, Trp501 and Tyr502 according to FIG. 1;
  - (ii) a working memory for storing instructions for processing said machine-readable data;
  - (iii) a central-processing unit coupled to said working memory and to said machine-readable data storage medium for processing said machine readable data into said three-dimensional representation; and
  - (iv) a display coupled to said central-processing unit for displaying said three-dimensional representation.

According to a preferred embodiment, the computer produces a three-dimensional representation of:
- a) a molecule or molecular complex comprising a binding pocket defined by the structure coordinates of NS3 helicase amino acids Val232, Thr254, Gly255, Thr269, Gly271, Lys272, Ala275, Trp501, Tyr502, Pro230, Val256, Thr298, Ala497, Lys551, Gln552, Gly554, Glu555, Asn556 and Pro558, according to FIG. 1; or
- b) a homologue of said molecule or molecular complex, wherein said homologue comprises a binding pocket that has a root mean square deviation from the backbone atoms of said amino acids of not more than 1.5 Å.

In that preferred embodiment, the machine readable data comprises the structure coordinates of NS3 amino acids Val232, Thr254, Gly255, Thr269, Gly271, Lys272, Ala275, Trp501, Tyr502, Pro230, Val256, Thr298, Ala497, Lys551, Gln552, Gly554, Glu555, Asn556 and Pro558, according to FIG. 1.

In the above two embodiments, the computer is producing a three-dimensional graphical structure of a molecule or a molecular complex which comprises a NS3 helicase U8-like binding pocket.

In an alternate embodiment, the computer produces a three-dimensional representation of:
- a) a molecule or molecular complex comprising a binding pocket defined by the structure coordinates of NS3 helicase amino acids His369, Ser370, Lys371, Tyr392, Arg393, Thr411, Asp412, Ala413, Cys431, Val432, Gln434, Ile446, Thr448, Arg461, Glu493, Glu555, Asn556 and Phe557, according to FIG. 1; or
- b) a homologue of said molecule or molecular complex, wherein said homologue comprises a binding pocket that has a root mean square deviation from the backbone atoms of said amino acids of not more than 1.5 Å.

In this alternate embodiment, the machine readable data comprises the structure coordinates of NS3 amino acids His369, Ser370, Lys371, Tyr392, Arg393, Thr411, Asp412, Ala413, Cys431, Val432, Gln434, Ile446, Thr448, Arg461, Glu493, Glu555, Asn556 and Phe557, according to FIG. 1.

In this embodiment, the computer is producing a three-dimensional graphical structure of a molecule or a molecular complex which comprises a NS3 helicase U4-like binding pocket.

In yet another alternate embodiment, the computer produces a three-dimensional representation of:
- a) a molecule or molecular complex comprising a binding pocket defined by the structure coordinates of NS3 helicase amino acids Pro205, Thr206, Gly207, Ser208, Gly209, Lys210, Ser211, Thr212, Lys213Asn229, Ala234, Gly237, Phe238, Tyr241, Asp290, Glu291, His293, Thr322, Ala323, Thr324, Gln460, Gly463, Arg464 and Arg467, according to FIG. 1; or
- b) a homologue of said molecule or molecular complex, wherein said homologue comprises a binding pocket that has a root mean square deviation from the backbone atoms of said amino acids of not more than 1.5 Å.

In this alternate embodiment, the machine readable data comprises the structure coordinates of NS3 amino acids Pro205, Thr206, Gly207, Ser208, Gly209, Lys210, Ser211, Thr212, Lys213, Asn229, Ala234, Gly237, Phe238, Tyr241, Asp290, Glu291, His293, Thr322, Ala323, Thr324, Gln460, Gly463, Arg464 and Arg467, according to FIG. 1.

In this embodiment, the computer is producing a three-dimensional graphical structure of a molecule or a molecular complex which comprises a NS3 helicase NTP-like binding pocket.

Even more preferred is a computer for producing a three-dimensional representation of a molecule or molecular complex defined by structure coordinates of all of the NS3 amino acids set forth in FIG. 1, or a three-dimensional representation of a homologue of said molecule or molecular complex, wherein said homologue comprises a binding pocket that has a root mean square deviation from the backbone atoms of said amino acids of not more than 1.5 Å. In this embodiment, the machined readable data contains the coordinates of all of the NS3 According to an alternate embodiment, the invention provides a computer for determining at least a portion of the structure coordinates corresponding to X-ray diffraction data obtained from a molecule or molecular complex, wherein said computer comprises:
- (a) a machine-readable data storage medium comprising a data storage material encoded with machine-readable data, wherein said data comprises at least a portion of the structural coordinates of NS3 helicase according to FIG. 1;
- (b) a machine-readable data storage medium comprising a data storage material encoded with machine-readable data, wherein said data comprises X-ray diffraction data from said molecule or molecular complex;
- (c) a working memory for storing instructions for processing said machine-readable data of (a) and (b);
- (d) a central-processing unit coupled to said working memory and to said machine-readable data storage medium of (a) and (b) for performing a Fourier transform of the machine readable data of (a) and for processing said machine readable data of (b) into structure coordinates; and
- (e) a display coupled to said central-processing unit for displaying said structure coordinates of said molecule or molecular complex.

For example, the Fourier transform of the structure coordinates set forth in FIG. 1 may be used to determine at least a portion of the structure coordinates of other helicases.

FIG. 2 demonstrates one version of these embodiments. System 10 includes a computer 11 comprising a central processing unit ("CPU") 20, a working memory 22 which may be, e.g., RAM (random-access memory) or "core" memory, mass storage memory 24 (such as one or more disk drives or CD-ROM drives), one or more cathode-ray tube ("CRT") display terminals 26, one or more keyboards 28, one or more input lines 30, and one or more output lines 40, all of which are interconnected by a conventional bi-directional system bus 50.

Input hardware 36, coupled to computer 11 by input lines 30, may be implemented in a variety of ways. Machine-readable data of this invention may be inputted via the use of a modem or modems 32 connected by a telephone line or dedicated data line 34. Alternatively or additionally, the input hardware 36 may comprise CD-ROM drives or disk drives 24. In conjunction with display terminal 26, keyboard 28 may also be used as an input device.

Output hardware 46, coupled to computer 11 by output lines 40, may similarly be implemented by conventional devices. By way of example, output hardware 46 may include CRT display terminal 26 for displaying a graphical representation of a binding pocket of this invention using a program such as QUANTA as described herein. Output hardware might also include a printer 42, so that hard copy output may be produced, or a disk drive 24, to store system output for later use.

In operation, CPU 20 coordinates the use of the various input and output devices 36, 46, coordinates data accesses from mass storage 24 and accesses to and from working memory 22, and determines the sequence of data processing steps. A number of programs may be used to process the machine-readable data of this invention. Such programs are discussed in reference to the computational methods of drug discovery as described herein. Specific references to components of the hardware system 10 are included as appropriate throughout the following description of the data storage medium.

FIG. 3 shows a cross section of a magnetic data storage medium 100 which can be encoded with a machine-readable data that can be carried out by a system such as system 10 of FIG. 2. Medium 100 can be a conventional floppy diskette or hard disk, having a suitable substrate 101, which may be conventional, and a suitable coating 102, which may be conventional, on one or both sides, containing magnetic domains (not visible) whose polarity or orientation can be altered magnetically. Medium 100 may also have an opening (not shown) for receiving the spindle of a disk drive or other data storage device 24.

The magnetic domains of coating 102 of medium 100 are polarized or oriented so as to encode in manner which may be conventional, machine readable data such as that described herein, for execution by a system such as system 10 of FIG. 2.

FIG. 4 shows a cross section of an optically-readable data storage medium 110 which also can be encoded with such a machine-readable data, or set of instructions, which can be carried out by a system such as system 10 of FIG. 2. Medium 110 can be a conventional compact disk read only memory (CD-ROM) or a rewritable medium such as a magneto-optical disk which is optically readable and magneto-optically writable. Medium 100 preferably has a suitable substrate 111, which may be conventional, and a suitable coating 112, which may be conventional, usually of one side of substrate 111.

In the case of CD-ROM, as is well known, coating 112 is reflective and is impressed with a plurality of pits 113 to encode the machine-readable data. The arrangement of pits is read by reflecting laser light off the surface of coating 112. A protective coating 114, which preferably is substantially transparent, is provided on top of coating 112.

In the case of a magneto-optical disk, as is well known, coating 112 has no pits 113, but has a plurality of magnetic domains whose polarity or orientation can be changed magnetically when heated above a certain temperature, as by a laser (not shown). The orientation of the domains can be read by measuring the polarization of laser light reflected from coating 112. The arrangement of the domains encodes the data as described above.

Thus, in accordance with the present invention, X-ray coordinate data capable of being processed into a three dimensional graphical display of a molecule or molecular complex which comprises a NS3 helicase-like binding pocket is stored in a machine-readable storage medium.

The NS3 helicase X-ray coordinate data, when used in conjunction with a computer programmed with software to translate those coordinates into the 3-dimensional structure of a molecule or molecular complex comprising a NS3 helicase-like binding pocket may be used for a variety of purposes, such as drug discovery.

For example, the structure encoded by the data may be computationally evaluated for its ability to associate with chemical entities. Chemical entities that associate with NS3 helicase may inhibit that enzyme, and are potential drug candidates. Alternatively, the structure encoded by the data may be displayed in a graphical three-dimensional representation on a computer screen. This allows visual inspection of the structure, as well as visual inspection of the structure's association with chemical entities.

Thus, according to another embodiment, the invention relates to a method for evaluating the potential of a chemical entity to associate with a) a molecule or molecular complex comprising a binding pocket defined by structure coordinates of NS3 helicase amino acids Val232, Thr254, Gly255, Thr269, Gly271, Lys272, Ala275, Trp501 and Tyr502 according to FIG. 1, or b) a homologue of said molecule or molecular complex, wherein said homologue comprises a binding pocket that has a root mean square deviation from the backbone atoms of said amino acids of not more than 1.5 Å.

This method comprises the steps of:

i) employing computational means to perform a fitting operation between the chemical entity and a binding pocket of the molecule or molecular complex; and ii) analyzing the results of said fitting operation to quantify the association between the chemical entity and the binding pocket.

The term "chemical entity", as used herein, refers to chemical compounds, complexes of at least two chemical compounds, and fragments of such compounds or complexes.

Preferably, the method evaluates the potential of a chemical entity to associate with a) a molecule or molecular complex comprising a binding pocket defined by structure coordinates of NS3 helicase amino acids Val232, Thr254, Gly255, Thr269, Gly271, Lys272, Ala275, Trp501, Tyr502, Pro230, Val256, Thr298, Ala497, Lys551, Gln552, Gly554, Glu555, Asn556 and Pro558 according to FIG. 1, or b) a homologue of said molecule or molecular complex, wherein said homologue comprises a binding pocket that has a root mean square deviation from the backbone atoms of said amino acids of not more than 1.5 Å. These embodiments relate to evaluating the potential of a chemical entity to associate with a NS3 helicase U8-like binding pocket.

In an alternate embodiment, the same steps indicated above are used in a method for evaluating the potential of a chemical entity to associate with a) a molecule or molecular complex comprising a binding pocket defined by structure coordinates of NS3 helicase amino acids His369, Ser370, Lys371, Tyr392, Arg393, Thr411, Asp412, Ala413, Cys431, Val432, Gln434, Ile446, Thr448, Arg461, Glu493, Glu555, Asn556 and Phe557 according to FIG. 1, or b) a homologue of said molecule or molecular complex, wherein said homologue comprises a binding pocket that has a root mean square deviation from the backbone atoms of said amino acids of not more than 1.5 Å.

These embodiments relate to evaluating the potential of a chemical entity to associate with a NS3 helicase U4-like binding pocket.

In yet another alternate embodiment, the same steps indicated above are used in a method for evaluating the potential of a chemical entity to associate with a) a molecule or molecular complex comprising a binding pocket defined by structure coordinates of NS3 helicase amino acids Pro205, Thr202, Gly207, Ser208, Gly209, Lys210, Ser211, Thr212, Lys213, Asn229, Ala234, Gly237, Phe238, Tyr241, Asp290, Glu291, His293, Thr322, Ala323, Thr324, Gln460, Gly463, Arg464 and Arg467 according to FIG. 1, or b) a homologue of said molecule or molecular complex, wherein said homologue comprises a binding pocket that has a root mean square deviation from the backbone atoms of said amino acids of not more than 1.5 Å.

These embodiments relate to evaluating the potential of a chemical entity to associate with a NS3 helicase NTP-like binding pocket.

Even more preferably, the method evaluates the potential of a chemical entity to associate with a molecule or molecular complex defined by structure coordinates of all of the NS3 helicase amino acids, as set forth in FIG. 1, or a homologue of said molecule or molecular complex having a root mean square deviation from the backbone atoms of said amino acids of not more than 1.5 Å.

Alternatively, the structural coordinates of the NS3 helicase binding pocket can be utilized in a method for identifying a potential agonist or antagonist of a molecule comprising a NS3 helicase-like binding pocket. This method comprises the steps of:

a. using the atomic coordinates of Val232, Thr254, Gly255, Thr269, Gly271, Lys272, Ala275, Trp501 and Tyr502 according to FIG. 1 ± a root mean square deviation from the backbone atoms of said amino acids of not more than 1.5 Å, to generate a three-dimensional structure of molecule comprising a NS3 helicase-like binding pocket;

b. employing said three-dimensional structure to design or select said potential agonist or antagonist;

c. synthesizing said agonist or antagonist; and d. contacting said agonist or antagonist with said molecule to determine the ability of said potential agonist or antagonist to interact with said molecule.

More preferred is when the atomic coordinates of Val232, Thr254, Gly255, Thr269, Gly271, Lys272, Ala275, Trp501, Tyr502, Pro230, Val256, Thr298, Ala497, Lys551, Gln552, Gly554, Glu555, Asn556 and Pro558 according to FIG. 1 ± a root mean square deviation from the backbone atoms of said amino acids of not more than 1.5 Å, are used to generate a three-dimensional structure of molecule comprising a NS3 helicase-like binding pocket.

These methods are designed to identify agonists and antagonists that associate with an NS3 helicase U8-like binding pocket.

Alternatively, the atomic coordinates of the NS3 helicase U4 binding pocket—His369, Ser370, Lys371, Tyr392, Arg393, Thr411, Asp412, Ala413, Cys431, Val432, Gln434, Ile446, Thr448, Arg461, Glu493, Glu555, Asn556 and Phe557 according to FIG. 1—± a root mean square deviation from the backbone atoms of said amino acids of not more than 1.5 Å, may be used in step a), above, to generate a three-dimensional structure of molecule comprising a NS3 helicase-like binding pocket.

In another alternative embodiment, the atomic coordinates of the NS3 helicase NTP binding site—Pro205, Thr206, Gly207, Ser208, Gly209, Lys210, Ser211, Thr212, Lys213, Asn229, Ala234, Gly237, Phe238, Tyr241, Asp290, Glu291, His293, Thr322, Ala323, Thr324, Gln460, Gly463, Arg464 and Arg467 according to FIG. 1—± a root mean square deviation from the backbone atoms of said amino acids of not more than 1.5 Å, may be used in step a), above, to generate a three-dimensional structure of molecule comprising a NS3 helicase-like binding pocket.

Most preferred is when the atomic coordinates of all the amino acids of NS3 helicase according to FIG. 1 ± a root mean square deviation from the backbone atoms of said amino acids of not more than 1.5 Å, are used to generate a three-dimensional structure of molecule comprising a NS3 helicase-like binding pocket.

For the first time, the present invention permits the use of molecular design techniques to identify, select and design chemical entities, including inhibitory compounds, capable of binding to NS3 helicase-like binding pockets—in particular, the oligonucleotide binding pocket of NS3 helicase.

Applicants' elucidation of the U4 and U8 binding pockets in the oligonucleotide binding site and an expanded elucidation of the NTP binding pocket on NS3 helicase provides the necessary information for designing new chemical entities and compounds that may interact with NS3 helicase-like binding pockets, in whole or in part.

Throughout this section, discussions about the ability of an entity to bind to, associate with or inhibit a NS3 helicase-like binding pocket refers to features of the entity alone. Assays to determine if a compound binds to NS3 helicase are well known in the art and are exemplified below.

The design of compounds that bind to or inhibit NS3 helicase-like binding pockets according to this invention generally involves consideration of two factors. First, the entity must be capable of physically and structurally associating with parts or all of the NS3 helicase-like binding pockets. Non-covalent molecular interactions important in this association include hydrogen bonding, van der Waals interactions, hydrophobic interactions and electrostatic interactions.

Second, the entity must be able to assume a conformation that allows it to associate with the NS3 helicase-like binding pocket directly. Although certain portions of the entity will not directly participate in these associations, those portions of the entity may still influence the overall conformation of the molecule. This, in turn, may have a significant impact on potency. Such conformational requirements include the overall three-dimensional structure and orientation of the chemical entity in relation to all or a portion of the binding pocket, or the spacing between functional groups of an entity comprising several chemical entities that directly interact with the NS3 helicase-like binding pocket or homologues thereof.

The potential inhibitory or binding effect of a chemical entity on a NS3 helicase-like binding pocket may be analyzed prior to its actual synthesis and testing by the use of computer modeling techniques. If the theoretical structure of the given entity suggests insufficient interaction and association between it and the NS3 helicase-like binding pocket, testing of the entity is obviated. However, if computer modeling indicates a strong interaction, the molecule may then be synthesized and tested for its ability to bind to a NS3 helicase-like binding pocket. This may be achieved by testing the ability of the molecule to inhibit NS3 helicase using the assays described in Example 5. In this manner, synthesis of inoperative compounds may be avoided.

A potential inhibitor of a NS3 helicase-like binding pocket may be computationally evaluated by means of a series of steps in which chemical entities or fragments are screened and selected for their ability to associate with the NS3 helicase-like binding pockets.

One skilled in the art may use one of several methods to screen chemical entities or fragments for their ability to associate with a NS3 helicase-like binding pocket. This process may begin by visual inspection of, for example, a NS3 helicase-like binding pocket on the computer screen based on the NS3 helicase structure coordinates in FIG. 1 or other coordinates which define a similar shape generated from the machine-readable storage medium. Selected fragments or chemical entities may then be positioned in a variety of orientations, or docked, within that binding pocket as defined supra. Docking may be accomplished using software such as Quanta and Sybyl, followed by energy minimization and molecular dynamics with standard molecular mechanics force fields, such as CHARMM and AMBER.

Specialized computer programs may also assist in the process of selecting fragments or chemical entities. These include:
1. GRID (P. J. Goodford, "A Computational Procedure for Determining Energetically Favorable Binding Sites on Biologically Important Macromolecules", *J. Med. Chem.,* 28, pp. 849–857 (1985)). GRID is available from Oxford University, Oxford, UK.
2. MCSS (A. Miranker et al., "Functionality Maps of Binding Sites: A Multiple Copy Simultaneous Search Method." *Proteins: Structure, Function and Genetics,* 11, pp. 29–34 (1991)). MCSS is available from Molecular Simulations, San Diego, Calif.
3. AUTODOCK (D. S. Goodsell et al., "Automated Docking of Substrates to Proteins by Simulated Annealing", *Proteins: Structure. Function, and Genetics,* 8, pp. 195–20 (1990)). AUTODOCK is available from Scripps Research Institute, La Jolla, Calif.
4. DOCK (I. D. Kuntz et al., "A Geometric Approach to Macromolecule-Ligand Interactions", *J. Mol. Biol.,* 161, pp. 269–288 (1982)). DOCK is available from University of California, San Francisco, Calif.

Once suitable chemical entities or fragments have been selected, they can be assembled into a single compound or complex. Assembly may be preceded by visual inspection of the relationship of the fragments to each other on the three-dimensional image displayed on a computer screen in relation to the structure coordinates of NS3 helicase. This would be followed by manual model building using software such as Quanta or Sybyl [Tripos Associates, St. Louis, Mo.].

Useful programs to aid one of skill in the art in connecting the individual chemical entities or fragments include:
1. CAVEAT (P. A. Bartlett et al, "CAVEAT: A Program to Facilitate the Structure-Derived Design of Biologically Active Molecules", in *Molecular Recognition in Chemical and Biological Problems",* Special Pub., Royal Chem. Soc., 78, pp. 182–196 (1989); G. Lauri and P. A. Bartlett, "CAVEAT: a Program to Facilitate the Design of Organic Molecules", *J. Comput. Aided Mol. Des.,* 8, pp. 51–66 (1994)). CAVEAT is available from the University of California, Berkeley, Calif.
2. 3D Database systems such as ISIS (MDL Information Systems, San Leandro, Calif.). This area is reviewed in Y. C. Martin, "3D Database Searching in Drug Design", *J. Med. Chem.,* 35, pp. 2145–2154 (1992).
3. HOOK (M. B. Eisen et al, "HOOK: A Program for Finding Novel Molecular Architectures that Satisfy the Chemical and Steric Requirements of a Macromolecule Binding Site", *Proteins: Struct., Funct., Genet.,* 19, pp. 199–221 (1994). HOOK is available from Molecular Simulations, San Diego, Calif.

Instead of proceeding to build an inhibitor of a NS3 helicase-like binding pocket in a step-wise fashion one fragment or chemical entity at a time as described above, inhibitory or other NS3 helicase binding compounds may be designed as a whole or "de novo" using either an empty binding site or optionally including some portion(s) of a known inhibitor(s). There are many de novo ligand design methods including:
1. LUDI (H.-J. Bohm, "The Computer Program LUDI: A New Method for the De Novo Design of Enzyme Inhibitors", *J. Comp. Aid. Molec. Design,* 6, pp. 61–78 (1992)). LUDI is available from Molecular Simulations Incorporated, San Diego, Calif.
2. LEGEND (Y. Nishibata et al., *Tetrahedron,* 47, p. 8985 (1991)). LEGEND is available from Molecular Simulations Incorporated, San Diego, Calif.
3. LeapFrog (available from Tripos Associates, St. Louis, Mo.).
4. SPROUT (V. Gillet et al, "SPROUT: A Program for Structure Generation)", *J. Comput. Aided Mol. Design,* 7, pp. 127–153 (1993)). SPROUT is available from the University of Leeds, UK.

Other molecular modeling techniques may also be employed in accordance with this invention [see, e.g., N. C. Cohen et al., "Molecular Modeling Software and Methods for Medicinal Chemistry, *J. Med. Chem.,* 33, pp. 883–894 (1990); see also, M. A. Navia and M. A. Murcko, "The Use of Structural Information in Drug Design", *Current Opinions in Structural Biology,* 2, pp. 202–210 (1992); L. M. Balbes et al., "A Perspective of Modern Methods in Computer-Aided Drug Design", in *Reviews in Computational Chemistry, Vol.* 5, K. B. Lipkowitz and D. B. Boyd, Eds., VCH, New York, pp. 337–380 (1994); see also, W. C. Guida, "Software For Structure-Based Drug Design", *Curr. Opin. Struct. Biology,,* 4, pp. 777–781 (1994)].

Once a compound has been designed or selected by the above methods, the efficiency with which that entity may bind to an NS3 helicase binding pocket may be tested and optimized by computational evaluation. For example, an effective NS3 helicase binding pocket inhibitor must preferably demonstrate a relatively small difference in energy between its bound and free states (i.e., a small deformation energy of binding). Thus, the most efficient NS3 helicase binding pocket inhibitors should preferably be designed with a deformation energy of binding of not greater than about 10 kcal/mole, more preferably, not greater than 7 kcal/mole. NS3 helicase binding pocket inhibitors may interact with the binding pocket in more than one conformation that is similar in overall binding energy. In those cases, the deformation energy of binding is taken to be the difference between the energy of the free entity and the average energy of the conformations observed when the inhibitor binds to the protein.

An entity designed or selected as binding to an NS3 helicase binding pocket may be further computationally optimized so that in its bound state it would preferably lack repulsive electrostatic interaction with the target enzyme and with the surrounding water molecules. Such non-complementary electrostatic interactions include repulsive charge-charge, dipole—dipole and charge-dipole interactions.

Specific computer software is available in the art to evaluate compound deformation energy and electrostatic interactions. Examples of programs designed for such uses include: Gaussian 94, revision C (M. J. Frisch, Gaussian, Inc., Pittsburgh, Pa. ©1995); AMBER, version 4.1 (P. A. Kollman, University of California at San Francisco, ©1995); QUANTA/CHARMM (Molecular Simulations, Inc., San Diego, Calif. 1995); Insight II/Discover (Molecular Simulations, Inc., San Diego, Calif. ©1995); DelPhi (Molecular Simulations, Inc., San Diego, Calif. ©1995); and AMSOL (Quantum Chemistry Program Exchange, Indiana University). These programs may be implemented, for instance, using a Silicon Graphics workstation such as an Indigo$^2$ with "IMPACT" graphics. Other hardware systems and software packages will be known to those skilled in the art.

Another approach enabled by this invention, is the computational screening of small molecule databases for chemical entities or compounds that can bind in whole, or in part, to a NS3 helicase binding pocket. In this screening, the quality of fit of such entities to the binding site may be judged either by shape complementarity or by estimated interaction energy [E. C. Meng et al., *J. Comp. Chem.*, 13, pp. 505–524 (1992)].

According to another embodiment, the invention provides compounds which associate with a NS3 helicase-like binding pocket produced or identified by the method set forth above.

The structure coordinates set forth in FIG. 1 can also be used to aid in obtaining structural information about another crystallized molecule or molecular complex. This may be achieved by any of a number of well-known techniques, including molecular replacement.

Therefore, in another embodiment this invention provides a method of utilizing molecular replacement to obtain structural information about a molecule or molecular complex whose structure is unknown comprising the steps of:

a) crystallizing said molecule or molecular complex of unknown structure;

b) generating X-ray diffraction data from said crystallized molecule or molecular complex; and c) applying at least a portion of the structure coordinates set forth in FIG. 1 to the X-ray diffraction data to generate a three-dimensional electron density map of the molecule or molecular complex whose structure is unknown.

By using molecular replacement, all or part of the structure coordinates of the NS3 helicase/oligonucleotide complex as provided by this invention (and set forth in FIG. 1) can be used to determine the structure of a crystallized molecule or molecular complex whose structure is unknown more quickly and efficiently than attempting to determine such information ab initio.

Molecular replacement provides an accurate estimation of the phases for an unknown structure. Phases are a factor in equations used to solve crystal structures that can not be determined directly. obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of the NS3 helicase/oligonucleotide complex according to FIG. 1 within the unit cell of the crystal of the unknown molecule or molecular complex so as best to account for the observed X-ray diffraction data of the crystal of the molecule or molecular complex whose structure is unknown. Phases can then be calculated from this model and combined with the observed X-ray diffraction data amplitudes to generate an electron density map of the structure whose coordinates are unknown. This, in turn, can be subjected to any well-known model building and structure refinement techniques to provide a final, accurate structure of the unknown crystallized molecule or molecular complex [E. Lattman, "Use of the Rotation and Translation Functions", in *Meth. Enzymol.*, 115, pp. 55–77 (1985); M. G. Rossmann, ed., "The Molecular Replacement Method", *Int. Sci. Rev. Ser.*, No. 13, Gordon & Breach, New York (1972)].

The structure of any portion of any crystallized molecule or molecular complex that is sufficiently homologous to any portion of the NS3 helicase/oligonucleotide complex can be resolved by this method.

In a preferred embodiment, the method of molecular replacement is utilized to obtain structural information about another helicase. The structure coordinates of NS3 helicase as provided by this invention are particularly useful in solving the structure of other isoforms of NS3 helicase or other NS3 helicase-containing complexes.

Furthermore, the structure coordinates of NS3 helicase as provided by this invention are useful in solving the structure of NS3 helicase proteins that have amino acid substitutions, additions and/or deletions (referred to collectively as "NS3 helicase mutants", as compared to naturally occurring NS3 helicase isoforms. These NS3 helicase mutants may optionally be crystallized in co-complex with a chemical entity, such as a non-hydrolyzable NTP analogue or an oligonucleotide. The crystal structures of a series of such complexes may then be solved by molecular replacement and compared with that of wild-type NS3 helicase. Potential sites for modification within the various binding sites of the enzyme may thus be identified. This information provides an additional tool for determining the most efficient binding interactions, for example, increased hydrophobic interactions, between NS3 helicase and a chemical entity or compound.

The structure coordinates are also particularly useful to solve the structure of crystals of NS3 helicase or NS3 helicase homologues co-complexed with a variety of chemical entities. This approach enables the determination of the optimal sites for interaction between chemical entities, including between candidate NS3 helicase inhibitors and NS3 helicase. For example, high resolution X-ray diffraction data collected from crystals exposed to different types of solvent allows the determination of where each type of solvent molecule resides. Small molecules that bind tightly to those sites can then be designed and synthesized and tested for their NS3 helicase inhibition activity.

All of the complexes referred to above may be studied using well-known X-ray diffraction techniques and may be refined versus 1.5-3 Å resolution X-ray data to an R value of about 0.20 or less using computer software, such as X-PLOR [Yale University, ©1992, distributed by Molecular Simulations, Inc.; see, e.g., Blundell & Johnson, supra; *Meth. Enzymol.*, vol. 114 & 115, H. W. Wyckoff et al., eds., Academic Press (1985)]. This information may thus be used to optimize known NS3 helicase inhibitors, and more importantly, to design new NS3 helicase inhibitors.

In order that this invention be more fully understood, the following examples are set forth. These examples are for the purpose of illustration only and are not to be construed as limiting the scope of the invention in any way.

EXAMPLE 1

Cloning and Expression of NS3 Helicase

The HCV NS3 RNA helicase domain (encoded by nucleotides 502–1896 of SEQ ID NO:6) was subcloned from a cDNA of the HCV H strain [A. Grakoui et al., *J. Virol.*, 67, pp. 1385–95 (1993); C. Lin et al., *J. Virol.*, 68, pp. 8147–57 (1994), the disclosures of which are herein incorporated be reference] into a pET expression vector (Novagen, Madison, Wis.). The resulting plasmid, pET-BS(+)/HCV/NS3-C465-His (SEQ ID NO:4), also contained a methionine start codon, a linker encoded Gly-Ser-Gly-Ser sequence attached the C-terminal threonine of the NS3 helicase domain and a six-histidine tag fused to the C-terminus of the Gly-Ser-Gly-Ser sequence to facilitate protein purification. This plasmid was used as a template for single-stranded DNA-based site-directed mutagenesis essentially as described by (T. A. Kunkel, *Proc. Natl. Acad. Sci. USA*, 82, pp.488–492 (1985) and C. Lin et al., *Virology*, 192, pp.596–604 (1993), the disclosures of which are herein incorporated by reference) with the following modifications.

The single stranded phagemid DNA packaged in the presence of helper M13 phage corresponds to the HCV plus strand. A single colony of *E. coli* strain CJ 326, transformed with pET-BS(+)/HCV/NS3-C465-His, was grown in YT media containing 0.25 μg/ml of uridine and 50 μg/ml of carbenicillin. After three serial passages, M13 helper phage (Bio-Rad) was used to rescue uridylated phagemid single stranded DNA, which was then used as template for oligonucleotide-directed mutagenesis [T. A. Kunkel (1985), supra]. ABI automatic sequencing was used to identify mutations and ensure that there is no other unintended mutation within the HCV NS3 helicase domain sequences. Construct containing mutations were named according to the position of the substituted residue in the full-length HCV NS3 protein.

In this manner, we made NS3 helicase corresponding to the consensus sequence of the HCV genotype 1 (Pro at amino acid 332; Ser at amino acid 403; Ala at amino acid 410; and Thr at amino acid 505; hereinafter referred to as "wild type"); as well as NS3 helicase containing the following single amino acid mutations as compared to the consensus HCV genotype 1 NS3 helicase sequence: Ser231-to-Ala; Thr269-to-Ala; Ser370-to-Ala; Thr411-to-Ala; Trp501-to-Phe; Trp501-to-Leu; and Trp501-to-Ala.

*E. coli* BL21(DE3) cells, freshly transformed with the pET-BS(+)/HCV/NS3-C465-His plasmid or similar plasmids encoding the single amino acid mutant NS3 helicases described above, were grown at 30° C. in LB media supplemented with 50 μg/ml of carbenicillin. When the density reached an $OD_{600}$ of 1.0, the cells were induced for 3 hr at 30° C. by the addition of IPTG to a final concentration of 0.8 mM. After induction, the cells were harvested and stored frozen at −70° C. until purification.

All the protein purification procedures were performed at 4° C. Typically, 10 g of cell paste was resuspended in 50 ml of buffer A [50 mM HEPES (pH 8), 300 mM NaCl, 10% glycerol, and 2.5 mM β-mercaptoethanol] containing 0.2 mM phenylmethylsulfonyl fluoride (PMSF), and lysed using a microfluidizer. The lysate was clarified by centrifugation at 100,000×g for 35 min. We then added 5 mM imidazole (pH 8) to the supernatant and the resulting solution was incubated for 2 hours with 2 ml of Ni-NTA-agarose (Qiagen, Chatsworth, Calif.).

The resin was packed into a column and washed with 10 bed volumes of buffer A containing 5 mM and 15 mM imidazole, and eluted with buffer A containing 100 mM imidazole. The eluant was desalted to buffer B [50 mM HEPES (pH 8), 10% glycerol, and 2.5 mM β-mercaptoethanol] containing 50 mM NaCl on a PD-10 column (Pharmacia). The desalted solution was loaded onto a Heparin-Sepharose column (Pharmacia). The flow-through was then applied onto a Q-Sepharose column (Pharmacia) and washed with 10 bed volumes of buffer B containing 50 mM NaCl. The column was then eluted with a NaCl gradient from 50 mM to 2M in buffer B.

The peak fraction containing the HCV NS3 helicase domain protein was shown by gel-filtration chromatography to be monomeric. The purified protein was judged to be greater than 90% pure by sodium dodecyl sulfate (SDS) polyacrylamide gel electrophoresis (PAGE) and Coomassie R-250 staining.

For crystallization studies, the protein was concentrated to 10 mg/ml by ultrafiltration and slowly diluted with 5 volumes of 15 mM MES (pH 6.5), 2.5 mM βmercaptoethanol and again concentrated to 10 mg/ml. The dilution step was then repeated with 2 volumes of the MES buffer and concentrated to 13 mg/ml. We then added oligonucleotide ($dU_8$; Oligo Therapeutics, Inc., Wilsonville, Oreg.) to yield a 1:1 molar ration of protein to nucleic acid.

To produce recombinant full-length NS3 protein which was subsequently used for mutagenesis studies in the NTP binding pocket, we followed similar procedures as above. The full length NS3 coding sequence was also subcloned from the HCV H strain. It was placed in a pET expression vector to create the plasmid pET-BS(+)/HCV/FLNS3-His (SEQ ID NO:3). As with the helicase constructs previously described, the full-length NS3 coding sequence was preceded by a methionine start codon and had codons encoding Gly-Ser-Gly-Ser-$His_6$ in frame at the C-terminus of the NS3 coding region. That plasmid was used as a template for single-stranded DNA-based site-directed mutagenesis as described above.

In this manner, we made NS3 containing the following single amino acid mutations as compared to the consensus HCV genotype 1 NS3 helicase sequence: Gln460→Ala, Arg461→Ala, Arg462→Ala, Arg464→Ala and Arg467→Ala.

Both the wild-type full-length NS3 and the single amino acid mutants were purified as described above.

EXAMPLE 2

Crystallization and Data Collection

Crystals of the NS3 helicase:$dU_8$ complex were grown by hanging-drop vapor diffusion over wells containing 0.1 M Tris pH 8.0, 0.2 M Li$_2$SO$_4$, 18% Polyethylene glycol 6000, and 8 mM β-mercaptoethanol. Drops were macroseeded within 12 hours after being set up. Crystals grew over the course of 2–3 weeks to dimensions of 0.4×0.4×0.1 mm$^3$. The crystals belong to space group P2$_1$2$_1$2 with unit cell dimensions a=73.1 Åb=117.5 Å, c=63.4 Å, and contain one helicase:dU$_8$ complex per asymmetric unit.

Heavy atom soaks were carried out by transferring crystals to a solution containing 0.1 M Tris pH 8.0, 0.2 M Li$_2$SO$_4$, 17% Polyethylene glycol 6000, 8 mM β-mercaptoethanol, in addition to the heavy atom in question. Heavy atom soaks with K$_2$WO$_4$ were performed in the absence of Li$_2$SO$_4$.

Crystals were transferred to a solution containing 0.08 M Tris pH 8.0, 0.2 M Li$_2$SO$_4$, 16% Polyethylene glycol 6000, 8 mM β-mercaptoethanol, and 15% glycerol and immediately frozen in a dry nitrogen gas stream at 100 K (Molecular Structure Corp., Houston, Tex.) for data collection.

Data was acquired by oscillation photography on a Rigaku R-AXIS IIC phosphor imaging area detector mounted on a Rigaku RU200 rotating anode generator (MSC), operating at 50 kV and 100 mA. Measured intensities were integrated, scaled, and merged using the HKL software package [Z. Otwinowski et al., *Meth. Enzymol.*, 276, pp. 307–326 (1997)].

EXAMPLE 3

Phasing, Model Building and Refinement

Heavy atom positions were located from difference Patterson and anomalous difference Patterson maps and confirmed with difference Fourier syntheses. Heavy atom parameters were refined and phases computed to 2.3 Å using the program PHASES [W. Furey et al., *Meth. Enzymol.*, 277, pp. 590–620, (1997) need full cite]. MIR phases were improved by cycles of solvent flattening [B. C. Wang,. *Methods Enzymol.*, 115, pp. 90–112 (1985)] combined with histogram matching [K. Y. J. Zhang et al., *Acta Crystallogr.*, A46, pp.377–381 (1990)] using the CCP4 crystallographic package [CCP4; C. C. Project, *Acta Crystallogr.*, D50, pp. 760–763 (1994)].

Model building was carried out using QUANTA96 (Molecular Simulations), and all refinement done in XPLOR [A. T. Brunger, "X-PLOR: A System for X-Ray Crystallography and NMR," Yale University Press, New Haven, Conn. (1993)], using the free R-value [A. T. Brunger, *Nature*, 355, pp. 472–475 (1992)] to monitor the course of refinement. The current model, refined using data from 6.0–2.2 Å, consists of NS3 helicase residues 190–414 and 418–626, residues 3–8 of dU$_8$, 1 bound sulfate ion, and 159 well-ordered water molecules.

EXAMPLE 4

Structural Features of the NS3 Helicase-dU$_8$ Complex

The structure of the resolved portion of HCV NS3 helicase (NS3 residues 189–626 of SEQ ID NO:1, corresponding to HCV polyprotein residues 1215–1652) complexed with a deoxyuridine octamer (dU$_8$) was determined by multiple isomorphous replacement combined with anomalous scattering. The protein consists of three domains separated by a series of clefts (FIG. 5).

Domains 1 and 3 share a more extensive interface than either share with domain 2. This interface is largely accounted for by packing of helices α5 and α6 from domain 3 on helix α4 from domain 1. As a result, the clefts between domains 1 and 2 and domains 2 and 3 are the largest. A published crystal structure of HCV NS3 helicase domain demonstrated that domain 2 could undergo rigid body movements relative to domains 1 and 3 based on a comparison of two crystallographically independent molecules [N. Yao et al., *Nat. Struct. Biol.*, 4, pp. 463–467 (1997)]. Preliminary structural studies on HCV helicase in a different crystal form also show a rotation of domain 2 relative to the first and third, confirming that this domain is flexibly linked to the other two.

Domains 1 and 2 of the HCV helicase, which contain all of the conserved helicase sequence motifs, have similar topologies (FIG. 6) and are also similar to domains 1A and 2A of the four domain PcrA and Rep DNA helicases [H. S. Subramanya et al., *Nature*, 384, pp. 379–383 (1996); S. Korolev et al., *Cell*, 90, pp. 635–647 (1997)]. The structurally homologous domains of PcrA, Rep, and HCV helicases each contain a parallel six-stranded β-sheet flanked by α-helices. In addition, domain 1 of HCV helicase contains a seventh β-strand running antiparallel to the rest of the sheet.

Superposition of domains 1 and 2 yields an rms deviation of 2.0 Å for 76 C-alpha atoms that form the core of each domain. Domain 3 is predominantly α-helical and is associated with domain 2 by a pair of anti-parallel β-strands (FIG. 5). An interesting component of domain 3 is a 40 amino acid region preceding the C-terminal α-helix that lacks secondary structure elements. This may represent a flexible region of the protein that allows the C-terminus of NS3 to reach the active site of its own serine protease domain to facilitate cleavage at the NS3/NS4A junction during HCV polyprotein processing. This cleavage is believed to occur in cis [R. Bartenschlager et al., *J. Virol.*, 68, pp. 5045–5055 (1994)].

The N-terminal region of domain 1 contains a phosphate binding loop that is highly conserved among all helicases and commonly referred to as the Walker A box or motif I [J. E. Walker et al., *EMBO J.*, 1, pp. 945–951 (1982)]. In the structure presented here, this loop contains a bound sulfate ion (FIG. 7A). This phosphate binding loop is structurally similar to those found in a number of other ATPases [M. Saraste et al., *Trends Biochem. Sci.*, 15, 430–434 (1990)]. The sulfate ion is stabilized by hydrogen bonds from the amide nitrogens of Gly-207 and Gly-209, and the side chains of Ser-208, Lys-210, and Ser-211. Lys-210 makes an additional water-mediated contact to the conserved Asp-290 of the DECH motif (motif II or Walker motif B).

The side chains of Asp-290 and Glu-291, the most conserved residues in the DECH motif, point toward an open area beneath the phosphate binding loop that presumably is occupied by Mg$^2$+ and the y-phosphate of the bound Mg$^2$+-NTP substrate. Cys-292 is buried in the protein interior while the His-293 side chain points into the cleft between domains 1 and 2. The position of the sulfate in this structure appears to be very similar to that of the β-phosphate of ADP in the PcrA helicase:ADP complex [H. S. Subramanya et al., *Nature*, (1996), supra]. It is therefore likely that this sulfate ion occupies the position of the β-phosphate when NTP or NDP is bound to the HCV helicase.

Highly conserved residues Gln-460, Arg-464, and Arg-467 from domain 2 are solvent exposed in the interdomain cleft, while Arg-461 and Arg-462 are buried in domain 2 and stabilized by internal salt bridges and hydrogen bonds. The position of Arg-461 contrasts that described in the structure of the apo HCV NS3 helicase, which reported this side chain as being solvent exposed and interacting with the phosphate backbone of single stranded nucleic acid modeled into this cleft [N. Yao et al., *Nat. Struct. Biol.*, (1997), supra].

Protein-Single Stranded DNA Interactions

Studies of HCV NS3 helicase single stranded nucleic acid binding have demonstrated that poly(du) binds to the helicase with higher affinity than poly(rU) of the same length [F. Preugschat et al, *J. Biol. Chem.*, 271 (1996), supra]. Extrapolation of this data suggested that a deoxyoligonucleotide 8mer might be long enough to bind to the helicase with high affinity and not interfere with protein-protein contacts during crystallization. Therefore an oligo $dU_8$ was used for complex crystallization. In the structure presented here the first two residues of the oligonucleotide are disordered and have not been included in the model. The sugar-phosphate backbone of the third nucleotide is well represented in electron density maps (FIG. 7B) while density for the base is extremely weak. Electron density for residues 4–8 is very well defined for the sugar-phosphate backbone and slightly weaker for the bases. Preliminary studies with $du_{10}$ and $dU_{12}$ oligonucleotides show essentially the same electron density for the DNA.

The bound single stranded DNA ("ssDNA") lies in a channel approximately 16 angstroms in diameter that separates domain 3 from domains 1 and 2 (FIG. 10). The 5' end of the oligonucleotide resides at the interface of domains 2 and 3 and its 3' end at the interface of domains 1 and 3. This orientation of the DNA is roughly perpendicular to that of the ssRNA in a model derived from the apo HCV helicase structure, in which the ssRNA was placed in the cleft between domains 1 and 2 [N. Yao et al., *Nat. Struct. Biol.*, (1997), supra]. It is, however, consistent with the oligonucleotide binding site in the Rep helicase:DNA structure [S. Korolev et al., *Cell*, (1997), supra].

Interactions between the ssDNA and enzyme are mostly confined to the DNA backbone, as would be expected for a nonspecific protein-nucleic acid complex, and are concentrated at the two ends of the oligonucleotide. Protein contacts emanate mostly from loops between secondary structural elements in domains 1 and 2 (FIGS. 6A,B). Interestingly, these contacts arise from symmetrically equivalent residues in these two domains, so that protein contacts to the dU4 and dU5 backbone phosphates are nearly identical to those to the dU7 and dU8 phosphates.

At the 3' end of the DNA the dU8 phosphate is stabilized by a hydrogen bond with Thr-269 Oγ, which in turn accepts a hydrogen bond from the main chain NH of Lys-272, and by a hydrogen bond to the main chain NH of Gly-255. Equivalent contacts to the dUs phosphate are made by the Arg-393 main chain NH and Thr-411 Oγ, which accepts a hydrogen bond from the Ala-413 NH. The dU7 phosphate accepts a hydrogen bond from the Val-232 NH and interacts with the Ala-233 NH and Ser-231 Oγ via a bridging water molecule. The direct and water mediated main chain interactions are duplicated by Lys-371 and Lys-372 from domain 2 to the dU4 phosphate. Ser-370, the equivalent residue in domain 2 to Ser-231, makes a water mediated contact to the dU3 phosphate rather than dU4. Superposition of domains 1 and 2 of HCV helicase reveals that the residues involved in phosphate contacts are structurally equivalent (FIG. 6). This was an unanticipated finding based on the poor sequence homology between these two domains. Additionally, the four residues interacting with the phosphate backbone, Ser-231, Thr-269, Ser-370, and Thr-411, are absolutely conserved in all HCV NS3 sequences known to date. These findings suggest that these two domains may have arisen from a gene duplication event.

Residues dU4-dU8 are capped by interactions at each end with hydrophobic side chains. Trp-501 stacks with the base of dU8 while Val-432 interacts with the dU4 base (FIG. 10). These two side chains act as a pair of bookends, defining a central binding cavity occupied by five nucleotides. Both Val-432 and Trp-501 are highly conserved among HCV NS3 sequences but neither have been implicated in nucleic acid binding nor duplex unwinding. The Val-432:dU4 base interaction induces significant rotation about the phosphate backbone between dU3 and dU4 such that the bases are completely unstacked (FIG. 10). Stacking of Trp-501 with the dU8 base should similarly necessitate a large rotation about the phosphate of the following nucleotide. The resulting conformation of the DNA could be stabilized by phosphate interactions with Arg-253 and Lys-272 from domain 1 and Lys-372 and Lys-373 from domain 2, which lie outside the central binding cavity.

Domain 2 contains a pair of extended anti-parallel strands encompassing residues 430–452, which are involved in binding the 5' end of the oligonucleotide (FIG. 5). Two other single-strand polynucleotide binding proteins, SSB and tRNA synthetase, contain anti-parallel strands extending from their protein core that are thought to make up the nucleic acid binding site [S. Raghunathan et al.,*Proc. Natl. Acad. Sci. USA*, 94, pp. 6652–6657 (1997); M. Ruff et al., *Science*, 252, pp. 1682–1689 (1991)]. This region is termed the $L_{45}$ loop in this class of nucleic acid binding proteins. In the HCV helicase structure the oligonucleotide binds in a channel spanning two protein domains in a manner roughly similar to that seen for replication protein A (RPA) [A. Bochkarev et al., *Nature*, 385, pp. 176–181 (1997)]. In both structures, the oligonucleotide is most tightly bound at the 3' and 5' ends with few contacts with the central nucleotides. RPA also contains an $L_{45}$ loop, which binds to the 5' end of the oligonucleotide.

The five residues occupying the central binding cavity of HCV helicase adopt a conformation reminiscent of the central base pairs of DNA in the TBP-TATA box complex structures [Y. Kim et al., *Nature*, 365, pp. 512–520 (1993); J. L. Kim et al., *Nature*, 365, pp. 520–527 (1993)]. In both instances the DNA is underwound considerably and the backbone smoothly bent, compressing the edges of the bases. Comparison of the DNA structure here with the central pyrimidine stretch of the TATA box DNA reveals that this DNA is more underwound than that seen in the TBP-TATA box complex.

Our structure of the helicase:$dU_8$ complex does not offer a ready explanation as to why the enzyme binds to poly(dU) with higher affinity than to other homopolymer DNAs [F. Preugschat et al, *J. Biol. Chem.*, 271 (1996), supra]. Sequence specific interactions with the DNA bases are not observed within the central binding cavity of the helicase. Differences in DNA binding affinity between different sequences in this case may be a result of differences in energetics of DNA distortion and base stacking rather than base-specific hydrogen bonding patterns.

Location of Conserved Sequence Motifs

Figure 9B:
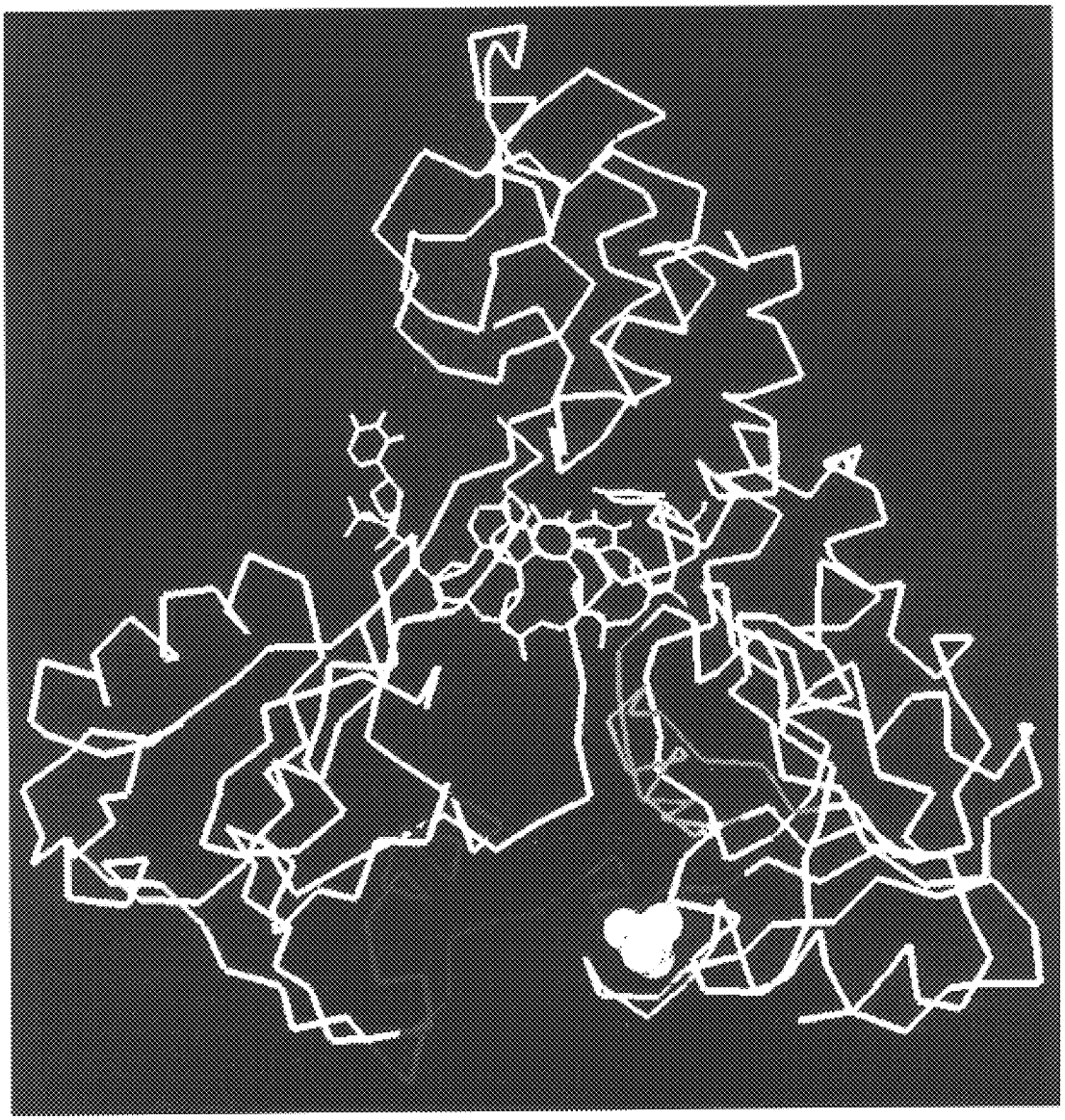

There is very high sequence conservation among various HCV strains in the NS3 RNA helicase domain with >80% sequence identity over the entire 456 amino acid polypeptide. The most highly conserved segments of these domains correspond to the canonical helicase sequence motifs (FIGS. 8, 9A) [A. Gorbalenya et al., *Curr. Opin. Struct. Biol.*, 3, pp. 419–429 (1993)]. In the three-dimensional structure residues from these motifs form the interface between the first two domains (FIG. 9B). Visual inspection of the structures of the PcrA DNA helicase from *Bacillus stearothermophilus* [H. S. Subramanya et al., *Nature*, (1996), supra] and *E. coli* Rep DNA helicase [S. Korolev et al., *Cell* (1997), suDra; coordinates not available] suggests overall structural similarity between domains 1A and 2A of these DNA helicases and domains 1 and 2 of the HCV helicase. The locations of the conserved DNA helicase sequence motifs overlap with those of the HCV helicase allowing an unambiguous alignment of these motifs. Mutagenesis of individual residues within these motifs in HCV helicase or in other RNA helicases have demonstrated that they are essential for enzyme activity. The individual phenotypes of these mutants can now be more fully explained using the enzyme structure.

Domain 1 of the HCV helicase has a fold similar to that found in a number of adenosine triphosphate transphosphorylases, such as adenylate and thymidine kinases. In particular, the phosphate binding loop formed by motif I (GSGKT) is virtually identical to the corresponding loop in the kinases. In these kinases this loop is involved in binding the β phosphate of ATP. HCV helicase has a sulfate bound in this exact location (FIG. 7A). Mutation of residues corresponding to HCV helicase Lys-210 in other helicases invariably leads to inactivation [J. W. George et al., *J. Mol. Biol.*, 235, 424–435 (1994); T. W. Seeley et al., *J. Biol. Chem.*, 265, pp. 7158–7165 (1990)].

Motif II (DExH) is proximal to the GSGKT phosphate binding loop and is expected to be involved in binding the $Mg^{2+}$-ATP substrate. In adenylate and thymidine kinases, a conserved aspartate binds $Mg^{2+}$, which helps orient the ATP for nucleophilic attack [M. E. Black et al., *J. Biol. Chem.*, 267, pp. 6801–6806 (1992); H. G. Yan et al., *Biochemistry*, 30, pp. 5539–5546 (1991)]. Mutation of the equivalent aspartate residue in these kinases or in other helicases inactivates ATP hydrolysis [M. E. Black et al., *J. Biol. Chem.*, (1992), suDra; C. H. Gross et al., *J. Virol.*, 69, pp. 4727–4736 (1995); R. M. Brosh Jr., et al.,*J. Bacteriol.*, 177, pp. 5612–562 (1995); A. Pause et al., *EMBO J.*, 11, pp. 2643–2654 (1992)]. His-293 is located at the bottom of the interdomain cleft and approximately 4 Å away from Val-456 and Gln-460. This histidine appears to be essential for coupling the ATPase activity to polynucleotide binding; mutations of this histidine in HCV NS3 and vaccinia NPH-II helicases result in a functional ATPase with no helicase activity [C. H. Gross et al., *J. Virol.*, (1995), supra; G. M. Heilek et al.*J. Virol.*, 71, 6264–6266 (1997)]. Unfortunately, the structure presented here does not provide an obvious explanation as to how this residue couples the NTPase and unwinding activities.

Studies in several helicases have looked at the effects of mutations in motif VI (QRxGRxGR), yet a role for this motif has not been clearly defined. In the HCV helicase residues in this motif are located in the 1:2 interdomain cleft. Gln-460 lies at the bottom of the cleft opposite from His-293. Mutation of the corresponding glutamine in vaccinia virus helicase and in eIF-4A leads to significant decreases in ATPase activity [A. Pause et al., *EMBO J.*, (1992), supra; C. H. Gross et al.,*J. Virol.*, 70, pp. 1706–1713 (1996)]. There are three conserved arginines in motif VI that were proposed by N. Yao et al., *Nat. Struct. Biol.* (1997), supra, to be involved in binding single-stranded RNA in the cleft between domains 1 and 2. Our structure of the helicase:$dU_8$ complex demonstrates that this interpretation is unlikely to be correct.

Here Arg-461 points away from the cleft and is hydrogen-bonded to Asp-412 and Asp-427. Mutation of this residue in a vaccinia virus helicase leads to decreases in RNA binding [C. H. Gross et al., *J. Virol.*, (1996), supra], possibly as a consequence of alterations in the conformation of Asp-412 which lines the polynucleotide binding channel. Arginines 464 and 467 extend into the interdomain cleft, directly across from the presumed locations of the γ and α phosphates of ATP. These residues appear to be poised to contact the ATP phosphates upon closure of this interdomain cleft. This would be similar to the function of conserved basic residues in the second domain of adenylate kinase.

Consistent with the possibility that Arg-464 and Arg-467 are directly involved in ATP binding, mutations of the corresponding residues to Ala or Gln in vaccinia NPH-II or eIF-4A reduce the ATPase activity to <20% of wild type levels [C. H. Gross et al., *J. Virol.*, (1996), supra; A. Pause et al., *Mol. Cell. Biol.*, 13, pp. 6789–6798 (1993)]. Arg-467 appears to be conserved among all three helicase superfamilies (FIG. 9A) [A. Gorbalenya et al., *Curr. Opin. Struct. Biol.* (1993), supra].

Motif III connects domains 1 and 2, and appears to be a flexible linker [N. Yao et al., *Nat. Struct. Biol.* (1997), supra]. Motif Ia forms part of the β sheet core of domain 1, but also extends to the oligonucleotide. Residues in motif V both contact the oligonucleotide and line the interface between the first two domains. In particular, Thr-411 makes a hydrogen bond to the phosphate of dU3 of the oligonucleotide.

The current structure lacks any region corresponding to motif IV in Rep and PcrA helicases [H. S. Subramanya et al., *Nature* (1996), supra; S. Korolev et al., *Cell*, (1997), supra], members of the superfamily I class of helicases. Previous sequence alignments that found similarities within motif IV between superfamily I and II helicases were done with rather weak criteria and may not have been significant. In the DNA helicases, motif IV is responsible for binding the adenine ring of ATP [H. S. Subramanya et al., *Nature* (1996), supra; S. Korolev et al., *Cell*, (1997), supra]. Mutation of a conserved arginine in this motif in UvrD increases the ATP Km by 37-fold [M. C. Hall et al., *J. Biol. Chem.*, 272, pp. 18614–18620 (1997)].

In HCV helicase either another protein segment which is not in the current structure substitutes for motif IV or the adenosine ring binds elsewhere. Residues from the putative motif IV in HCV helicase include Ser-370 and Lys-371, which contact the DNA via a water-mediated hydrogen bond and a backbone interaction, respectively. Therefore sequences corresponding to motif IV in superfamily I and superfamily II helicases occupy different regions and appear to have different functions. We suggest that a new motif, designated IVa, be used to describe residues corresponding to the putative HCV helicase motif IV. In *E. coli* UvrD, motif IVa may correspond to the sequence RSNAQSRVL (residues 355–363).

Proposed Domain Closure and Translocation

Conserved, basic residues from motif VI are positioned across the interdomain cleft from the expected location of the ATP γ phosphate in HCV helicase. A very similar situation is observed in the structures of the adenylate kinases, where basic residues lie across a cleft from the ATP binding site. Binding of ATP (or analogs) to these kinases leads to a conformational change in the enzyme, resulting in the burial of previously solvent-exposed phosphates [T. Bilderback et al., *Biochemistry*, 35, pp. 6100–6106 (1996)]. Mutation of these conserved basic residues in adenylate kinase results in an open structure with poor catalytic activity [G. E. Schulz, *Faraday Discuss.*, 93, pp. 85–93 (1992)].

We propose that an analogous closure occurs between domains 1 and 2 of HCV helicase upon ATP binding. This closure could be driven by interaction of basic residues in motif VI with the ATP phosphates. Sequence and structural conservation of these basic residues in motif VI among superfamily I and II helicases suggests that domain closure upon ATP binding is a general feature of these enzymes.

Gln-460 and His-293, from motifs VI and II respectively, lie on opposite sides of the interdomain cleft and possibly serve as gatekeepers, altering the equilibrium between the open and closed forms based on the binding of polynucleotide. Potential interaction of residues in these positions was predicted by the observation that helicases with the DExH motif II sequence usually contain a glutamine in motif VI, whereas those with a DEAD sequence contain a histidine [A. Gorbalenya et al., *Curr. Opin. Struct. Biol.* (1993), supra].

There is structural evidence that the linkage of the second domain in HCV helicase to the rest of the protein is flexible. In the HCV helicase structure reported by N. Yao et al., *Nat. Struct. Biol.* (1997), supra, the differences between the two molecules in the asymmetric unit can be attributed to a rotation of domain 2 by a few degrees. The relatively minor movement of domain 2 observed in their structures probably reflects changes in the local environment in the crystals. We propose a much more substantial conformational change would occur when the enzyme binds ATP or suitable analog. Our crystallographic results indicate that there are significant movements of this domain in different crystal forms. A conformational change could explain the observed two-stage kinetics of ATP binding to Rep where rapid initial binding is followed by a much slower step, leading to tighter binding [K. J. Moore et al., *Biochemistry*, 33, pp. 14550–14564 (1994)]. Evidence for conformational changes have been observed for Rep and helicase II based on alterations in protease sensitivity upon nucleotide binding [K. Chao et al., *J. Biol. Chem.*, 265, pp. 1067–1076 (1990)]. Binding of ATP to PcrA helicase has also been proposed to lead to a conformational change of the enzyme [H. S. Subramanya et al., *Nature* (1996), supra].

Large conformational changes in a DNA metabolizing enzyme are not unique, as they have been seen in the structures of mRNA capping enzyme in the presence of GTP [K. Hakansson et al., *Cell*, 89, pp. 545–553 (1997)]. In these structures the guanosine nucleotide is bound to the N-terminal domain with the phosphates located near the interface with the C-terminal domain. In the "open" conformation these domains are separated by a 10–13 Å cleft. Several residues which are highly conserved among mRNA capping enzymes are located in the C-terminal domain, including Arg-295 and Arg-298.

In the "closed" conformation, these residues are relocated by approximately 10 Å and are bound to the GTP β and γ phosphates. Closures of large interdomain clefts have also been proposed in the structurally homologous ATP-dependent DNA ligases, of which one structure has been solved in the open conformation [H. S. Subramanya et al., *Cell*, 85, pp. 607–615 (1996)].

The second domain of HCV helicase also interacts with the single-stranded polynucleotide. One could envision that movement of this domain results in concomitant movement of the nucleic acid substrate relative to the protein. Interactions between residues in domain 2 such as Val-432 and Thr-448 and the bases at the 5' end of the single stranded nucleic acid binding site would lead to translocation of the polynucleotide in the 5' to 3' direction as domain 2 closes.

Trp-501 in domain 3 stacks with a base near the 3' end of the single stranded oligonucleotide and disrupts stacking with neighboring bases. Closure of the interdomain cleft would force several bases to slip past Trp-501. Hydrolysis of ATP would then result in opening of the cleft and release of ADP. The orientation of Trp-501 favors movement of the polynucleotide in only the 5' to 3' direction such that opening of the cleft results in net movement of domain 2 in a 3' to 5' direction. By this mechanism the translocation reaction of the helicase resembles a ratchet. A general ratchet-like mechanism has been proposed for the RecB helicase based on conformational changes observed by protease mapping [R. J. Phillips et al., *Mol. Gen. Genet.*, 254, pp. 319–329 (1997)].

Such a model suggests that a single ATP hydrolysis event can result in protein translocation of several bases along a polynucleotide. Studies with the UvrD DNA helicase have demonstrated that the enzyme is capable of translocating more than one base per reaction cycle [J. A. Ali et al., *Science*, 275, pp. 377–380 (1997)], although the number of ATP hydrolysis events per observed reaction cycle was unknown in this experiment. Our model is consistent with predictions that helicases need not actively unwind the double-stranded substrate, but can function by capturing the single-stranded regions which arise due to thermal fluctuations at the fork [Y. Z. Chen et al., *J. Biomol. Struct. Dyn.*, 10, pp. 415–427 (1992)]. The translocation process proposed here would thus be considered an active process while the melting of double stranded structure at the fork would be passive.

The mechanism which we propose is substantially different from one described for the Rep helicase by Wong and Lohman [I. Wong et al., *Science*, 256, pp. 350–355 (1992)] and recently advanced in a paper describing the 3.0 and 3.2 Å structures of Rep bound to single-stranded DNA [S. Korolev et al., *Cell* (1997), supra]. As we previously noted there is overall structural similarity between domains 1 and 2 of HCV helicase and domains 1A and 2A of Rep. Important to our proposed mechanism, these two domains contain all the motifs conserved among DNA/RNA helicase sequences listed in FIG. 9A. In HCV helicase, there is no structural equivalent of Rep domain 2B which has been proposed to have a critical role in the active rolling mechanism [S. Korolev et al., *Cell* (1997), supra].

EXAMPLE 5

Assays

A. Helicase Assay

The standard 3'-tailed double-stranded RNA/DNA hybrid was prepared as described as follows. The long 98-nucleotide ("nt") RNA template was transcribed from a BsrBI-digested plasmid pSP65 (Promega, Madison, Wis.) in the presence of [α-$^{32}$P-GTP] (New England Nuclear, Boston, Mass.). The short 34-nt DNA release strand corresponds to a SP6 RNA transcript from a BamHI-digested pSP64 (Promega).

Standard helicase reactions (20 μl) were carried out as follows. HCV NS3 helicase (0.3 or 1 nM) was added to a mixture of 25 mM morpholinepropanesulfonic acid (MOPS)-NaOH (pH 6.5), 1 mM ATP, 0.5 mM $MnCl_2$, 2 mM dithiothreitol (DTT), 0.1 mg of bovine serum albumin (BSA) per ml, 4 units of RNasin (Promega), and 5 nM of 3'-tailed double-stranded RNA/DNA hybrid substrate. Mixtures were incubated for 20 min at 37° C. and stopped by the addition of 5 liters of 5× loading buffer [100 mM Tris-Cl (pH7.5), 20 mM EDTA, 50% glycerol, 0.5% SDS, 0.1% NP-40, 0.1% bromophenol blue, and 0.1% xylene cyanole). The reactions were then electrophoresed on 10% PAGE with 0.5× TBE and 0.1% SDS. Gels were dried and exposed using Fuji 1500 phosphorimager (Fuji, Stamford, Conn.). Helicase activity was determined by radioactivity of the double-stranded substrate and single-stranded template.

First, we characterized unwinding activity of the purified wild type NS3 helicase domain protein with regarding to the following parameters: protein concentration, incubation time course, incubation temperature, ATP concentration, pH, monovalent cation (Na$^+$), and divalent cation (Mn$^{2+}$ and Mg$^{2+}$) (FIG. 11).

The helicase unwinding activity increased as the protein concentration or incubation time increased (FIG. 11A). At 0.1 nM of the NS3 helicase, the reaction was almost linear with regard to the incubation time up to 30 min (FIG. 11A). Several NS3 helicase mutants purified by the same chromatograph method did not show any unwinding activity (see Table 1 and Example 6, below), indicating that the unwinding activity shown here is due to the purified HCV NS3 helicase, not containment proteins from E. coli.

Higher incubation temperature also led to more rapid unwinding of substrate (FIG. 11B), presumably due to lower energy required for break-down of hydrogen bonds between two strands at higher temperature. The unwinding activity of this NS3 helicase domain was optimal at pH 6.5, with a very narrow pH window of being active (FIG. 11C).

In addition, the unwinding reaction was very sensitive to the monovalent cation, such as Na$^+$ (FIG. 11D). Addition of 25 mM NaCl decreased the unwinding activity to about 15% of that in the absence of extra NaCl.

This helicase activity was absolutely dependent on the presence of ATP (FIG. 11E) or any other type of nucleotide triphosphate (NTP) (data not shown). The unwinding activity increased almost linearly as the concentration of ATP increased up to 1 mM (FIG. 11E). However, at 5 mM of ATP, the unwinding activity is lower than that at 1 mM of ATP, probably due to inhibition of extra Na$^+$ brought in with the ATP.

The helicase activity also absolutely require the presence of divalent cations, such as Mn$^{2+}$ or Mg$^{2+}$ (FIG. 11F). However, if the concentration of divalent cation was higher than that of ATP, inhibition of the helicase activity was observed. At equal concentration of ATP and divalent cation (1 mM or 5 mM), Mn$^{2+}$ showed higher unwinding activity than Mg$^{2+}$ (FIG. 11F).

B. Single Stranded RNA Binding Assay

The binding of single stranded RNA ("ssRNA") to the HCV NS3 helicase was measured by a nitrocellulose filter binding assay. A 34-nt RNA transcript was generated from BamHI-digested pSP64 plasmid using SP6 RNA polymerase in the presence of [α-$^{32}$P-GTP]. Standard ssRNA binding reactions (40 μl) were carried out as follows.

HCV NS3 helicase domain protein (6.25 nM) was added to a mixture of 25 mM morpholinepropanesulfonic acid (MOPS)-NaOH (pH 7.0), 2 mM dithiothreitol (DTT), 0.1 mg of bovine serum albumin (BSA) per ml, 4 units of RNasin (Promega), and 5 nM of [$^{32}$P]-ssRNA substrate. Mixtures were incubated for 15 min at 30° C. and filtered through a pre-wet nitrocellulose membrane. The filter were washed twice with washing buffer [50 mM MOPS-NaOH (pH 7.0) and 1 mM EDTA], dried and quantified in scintillation counter.

Next, we determine several parameters in the ssRNA binding to the purified NS3 helicase using a filter binding assay (FIG. 12). The association of $^{32}$P-labeled ssRNA to the NS3 helicase was very quick, usually close to completion within a couple minutes of incubation (data not shown). As shown in FIG. 12A, binding of ssRNA to the NS3 helicase is protein concentration-dependent. Under 8 nM of the NS3 helicase, the amount of ssRNA bound is a linear function of protein concentration (FIG. 12A, insert), and there is 0.445 molecule of ssRNA bound for every molecule of the NS3 helicase being present in the reaction. The maximal amount of ssRNA binding achieved in this reaction is about 94%.

The $K_d$ of the ssRNA-NS3 helicase complex is calculated to be 5.18 nM, at which the 50% of maximal binding of ssRNA to the NS3 helicase domain was observed.

We also measured the off rate constant of pre-formed ssRNA-NS3 helicase complex (FIG. 12B). In this case, $^{32}$P-labeled ssRNA was incubated with the NS3 helicase protein was incubated together for 15 minutes to allow the formation of $^{32}$P-ssRNA-NS3 helicase complex. Then 50-fold excess of $^3$H-labeled ssRNA with the same sequence was added to the reaction so that any $^{32}$P-labeled ssRNA dissociated from the complex with the NS3 helicase would have very little chance to re-associate with the NS3 protein again. The dissociation rate was determined to be 1.52×10$^{-2}$ min-1.

We also examined effect of pH, monovalent (Na$^+$) and divalent (Mn$^{2+}$) cations on the ssRNA binding to the NS3 helicase. In contrast to the unwinding activity, ssRNA binding of the NS3 helicase was less sensitive to the pH change (FIG. 12C). The optimal binding was observed at pH 7.0, although ssRNA binding did not change significantly between pH 6.5 to 8.0. NaCl (FIG. 12D) and MgCl$_2$ (FIG. 12E) has an inhibitory effect on the ssRNA binding, although this inhibition curve as a function of salt concentration is not as sharp as that on unwinding activity.

C. ATPase Assay

ATPase was measured by hydrolysis of ATP to ADP using a thin layer chromatography method [J.K. Tamura et. al., Virology, 193, pp.1–10 (1993)]. Standard ssRNA binding reactions (10 μl) were carried out as follows. HCV NS3 helicase domain protein (2 nM) was added to a mixture of 50 mM morpholinepropanesulfonic acid (MOPS)-NaOH (pH 7.0), 0.1 mM ATP, 2.5 μCi of [α-$^{32}$P-ATP] (NEN), 0.5 mM MgCl$_2$, 1 mM dithiothreitol (DTT), 0.1 mg of bovine serum albumin (BSA) per ml, and in the presence or absence of 5 μM poly U (Uridine concentration) (Pharmacia). Mixtures were incubated for 30 min at 37° C. and terminated by addition of EDTA to a final concentration of 20 mM. 0.5 μl of the reaction was spotted on a polyethyleneimine-cellulose plate, ATP and ADP were separated in 375 mM potassium phosphate (pH 3.5) and quantified by Fuji phosphorimager.

ATPase activity of the purified NS3 helicase was examined using this method. As shown in FIG. 13, this NS3 helicase domain has a basal ATPase activity in the absence of any polynucleotide, and the ATPase activity was stimulated up to 11-fold in the presence of poly(U). The order of ATPase stimulation by polynucleotides is poly(U)>poly(C)>poly(A)>poly(G) (data not shown).

EXAMPLE 6

Structure-Based Mutagenesis Study of RNA-Binding Residues of the NS3 Helicase

Mutagenesis experiments were performed to examine the roles of several residues predicted to be important in the NS3 helicase:oligonucleotide interaction based upon the crystal structure of that complex.

Ser231, Thr269, Ser370 and Thr411 formed direct water-mediated hydrogen bonds with the phosphate groups of the bound oligonucleotide. We replaced each one of these amino acids individually with alanine (see Example 1) and observed the effect of that mutation on various helicase activities. Alanine substitution at Ser231 or Ser370 had no observable effect on basal or polyU-stimulated ATPase activity, unwinding activity or ssRNA binding activity as compared to wild type helicase (see Table 1, below). Thus, it was concluded that those amino acids were not essential to define the oligonucleotide binding pocket in NS3 helicase.

In contrast, alanine substitution at Thr269 or Thr411 decreased the ssRNA binding to 20% of wild type level and completely abolished both polyu-stimulated ATPase activity and unwinding activity. Interestingly, basal ATPase activity was unaffected by either of these mutations.

The crystal structure also suggested that the side chain of Trp501 interacts with the bound oligonucleotide. Substitution of this Trp with either Ala or Leu resulted in decreased ssRNA binding and abolished polyu-stimulated ATPase activity and unwinding activity, although basal ATPase activity was unaffected. In contrast a Trp501-to-Phe mutation did not affect basal ATPase, unwinding and ssRNA binding activities. This mutant was, however, less sensitive to polyu-stimulation of ATPase activity as compared to the wild type helicase. Surprisingly, the ATPase activity of this mutant when stimulated by other polynucleotides, such as polyC, was similar to that of the wild type.

TABLE 1

Mutational Study of Amino Acids in the RNA Binding Site of HCV NS3 Helicase

| Amino Acid Mutation | Basal ATPase Activity (% of basal WT level) | Poly-U Stimulated ATPase Activity (% of basal WT level) | ssRNA Binding Activity (% of WT level) | ds RNA/ DNA Unwinding Activity (% of WT level) |
|---|---|---|---|---|
| None (WT) | 100 | 823 | 100 | 100 |
| S231 -> A | 260 | 709 | 121 | 99.8 |
| T269 -> A | 60 | 47 | 21 | 1 |
| S370 -> A | 104 | 694 | 124 | 109 |
| T411 -> A | 274 | 205 | 24 | 0.25 |
| W501 -> F | 99 | 197 | 100 | 112 |
| W501 -> L | 114 | 47 | 21 | 0.07 |
| W501 -> A | 101 | 49 | 40 | 0.36 |

Based upon these studies, it is apparent that Thr269, Thr411 and Trp501 are key residues for oligonucleotide binding. As indicated above, Thr269 and Trp501 make direct contacts with dU8. The minimal helicase amino acids which define the pocket in which dU8 lies are Val232, Thr254, Gly255, Thr269, Gly271, Lys272, Ala275, Trp501 and Tyr502. Thus, any compound which fits into a pocket comprising the structural coordinates ± a root mean square of 1.5 Å or less from the backbone atoms of these amino acids is a potential inhibitor of the NS3 helicase.

Additional amino acids that are located within 4 Å to 8 Å from the dU8 pocket are Pro230, Val256, Thr298, Ala497, Lys551, Gln552, Gly554, Glu555, Asn556 and Pro558. Thus, the combination of these amino acids with those above further define the dU8 pocket.

Based upon the crystal structure and these mutagenesis experiments, it is clear that Thr411 makes direct contact with dU4 and is a key residue in the U4 binding pocket. Other amino acids that are close enough to that U4 pocket to define its shape are His369, Ser370, Lys371, Tyr392, Arg393, Asp412, Ala413, Cys431, Val432, Gln434, Ile446, Thr448, Arg461, Glu493, Glu555, Asn556 and Phe557.

EXAMPLE 7

Structure-Based Mutagenesis Study of ATP-Binding Residues of the NS3 Helicase

Mutagenesis experiments were performed to examine the roles of several residues predicted to be important in the NS3 helicase:ATP interaction based upon the crystal structure of that complex.

The mutations were achieved by the methods described in Example 1.

TABLE 2

Mutational Study of Amino Acids in the ATP Binding Site of HCV NS3 Helicase

| Mutation | Basal ATPase (% of basal wt level) | Poly U-stimulated ATPase (% of basal wt level) | ssRNA binding (% of wt level) | dsRNA/ DNA unwinding (% of wt level) |
|---|---|---|---|---|
| wild-type | 100 | 581 | 100 | 100 |
| Q460 -> A | 23 | 32 | 97 | 3 |
| R461 -> A | 140 | 193 | 57 | 2 |
| R462 -> A | 247 | 337 | 99 | 81 |
| R464 -> A | 33 | 21 | 105 | <0.01 |
| R467 -> A | 7 | 14 | 116 | <0.05 |

In our model, R464 and R467 were predicted to bind to the γ- and α-phosphate groups of NTP, respectively. This is in contrast to what has previously been reported in the art, wherein these residues were predicted to be involved in RNA binding [T. Yao et al., *Nat. Struct. Biol.*, 4, pp. 463–467 (1997); C. Hyun-Soo et al., *J. Biol. Chem.*, 273, pp. 15045–15052 (1998)].

Two individual mutations, R464→A and R467→A, showed very low basal and polyu-stimulated ATPase activities. Although they had normal RNA binding ability, which suggested that the mutated protein has a proper fold, helicase unwinding activity was almost non-existent in these two mutant proteins, presumably due to the loss of NTPase activity. These results indicated that these two Arg residues are critical for NTPase activity.

The Q460→A mutation had a similar effect as two above-mentioned Arg-to-Ala mutations. This Gln was predicted to interact with and maintain the proper conformation of the imidazole ring of His-293 of the DECH motif.

The R461→A mutation led to lower RNA binding and less polyU stimulation of ATPase activity, which resulted in a very low helicase unwinding activity.

The R462→A mutation had no major effect on any of these four activities as predicted.

While we have hereinbefore presented a number of embodiments of this invention, it is apparent that my basic construction can be altered to provide other embodiments which utilize the methods of this invention. Therefore, it will be appreciated that the scope of this invention is to be defined by the claims appended hereto rather than the specific embodiments which have been presented hereinbefore by way of example.

We claim:

1. A computer for producing a three-dimensional representation of:

a. a molecule or molecular complex, wherein said molecule or molecular complex comprises a binding pocket defined by structure coordinates of NS3 amino acids Val232, Thr254, Gly255, Thr269, Gly271, Lys272, Ala275, Trp501 and Tyr502 according to FIG. 1; or b. a homologue of said molecule or molecular complex, wherein said homologue comprises a binding pocket that has a root mean square deviation from the backbone atoms of said amino acids of not more than 1.5 Å, wherein said computer comprises:
  (i) a computer-readable data storage medium comprising a data storage material encoded with computer-readable data, wherein said data comprises the structure coordinates of NS3 amino acids Val232, Thr254, Gly255, Thr269, Gly271, Lys272, Ala275, Trp501 and Tyr502 according to FIG. 1;
  (ii) a working memory for storing instructions for processing said computer-readable data;
  (iii) a central-processing unit coupled to said working memory and to said computer-readable data storage medium for processing said computer-machine readable data into said three-dimensional representation; and
  (iv) a display coupled to said central-processing unit for displaying said three-dimensional representation.

2. The computer according to claim 1, wherein said computer produces a three-dimensional representation of:
  a) a molecule or molecular complex comprising a binding pocket defined by the structure coordinates of NS3 helicase amino acids Val232, Thr254, Gly255, Thr269, Gly271, Lys272, Ala275, Trp501, Tyr502, Pro230, Val256, Thr298, Ala497, Lys551, Gln552, Gly554, Glu555, Asn556 and Pro558, according to FIG. 1; or
  b) a homologue of said molecule or molecular complex, wherein said homologue comprises a binding pocket that has a root mean square deviation from the backbone atoms of said amino acids of not more than 1.5 Å; and
  wherein said machine readable data comprises the structure coordinates of NS3 amino acids Val232, Thr254, Gly255, Thr269, Gly271, Lys272, Ala275, Trp501, Tyr502, Pro230, Val256, Thr298, Ala497, Lys551, Gln552, Gly554, Glu555, Asn556 and Pro558, according to FIG. 1.

3. A computer for producing a three-dimensional representation of:
  a) a molecule or molecular complex comprising a binding pocket defined by the structure coordinates of NS3 helicase amino acids His339, Ser370, Lys371, Tyr392, Arg393, Thr411, Asp412, Ala413, Cys431, Val432, Gln434, Ile446, Thr448, Arg461, Glu493, Glu555, Asn556 and Phe557, according to FIG. 1; or
  b) a homologue of said molecule or molecular complex, wherein said homologue comprises a binding pocket that has a root mean square deviation from the backbone atoms of said amino acids of not more than 1.5 Å, wherein said computer comprises:
    (i) a computer-readable data storage medium comprising a data storage material encoded with computer-readable data, wherein said data comprises the structure coordinates of NS3 amino acids His369, Ser370, Lys371, Tyr392, Arg393, Thr411, Asp412, Ala413, Cys431, Val432, Gln434, Ile446, Thr448, Arg461, Glu493, Glu555, Asn556 and Phe557, according to FIG. 1;
    (ii) a working memory for storing instructions for processing said computer-readable data;
    (iii) a central-processing unit coupled to said working memory and to said computer-readable data storage medium for processing said computer readable data into said three-dimensional representation; and
    (iv) a display coupled to said central-processing unit for displaying said three-dimensional representation.

4. A computer for producing a three-dimensional representation of:
  a) a molecule or molecular complex comprising a binding pocket defined by the structure coordinates of NS3 helicase amino acids Pro205, Thr206, Gly207, Ser208, Gly209, Lys210, Ser211, Thr212, Lys213, Asn229, Ala234, Gly237, Phe238, Tyr241, Asp290, Glu291, His293, Thr322, Ala323, Thr324, Gln460, Gly463, Arg464 and Arg467, according to FIG. 1; or
  b) a homologue of said molecule or molecular complex, wherein said homologue comprises a binding pocket that has a root mean square deviation from the backbone atoms of said amino acids of not more than 1.5 Å, wherein said computer comprises:
    (i) a computer-readable data storage medium comprising a data storage material encoded with computer-readable data, wherein said data comprises the structure coordinates of NS3 amino acids Pro205, Thr206, Gly207, Ser208, Gly209, Lys210, Ser211, Thr212, Lys213, Asn229, Ala234, Gly237, Phe238, Tyr241, Asp290, Glu291, His293, Thr322, Ala323, Thr324, Gln460, Gly463, Arg464 and Arg467, according to FIG. 1;
    (ii) a working memory for storing instructions for processing said computer-readable data;
    (iii) a central-processing unit coupled to said working memory and to said computer-readable data storage medium for processing said computer readable data into said three-dimensional representation; and
    (iv) a display coupled to said central-processing unit for displaying said three-dimensional representation.

5. The computer according to any one of claims 1 to 4, wherein said computer produces a three-dimensional representation of:
  a. a molecule or molecular complex defined by structure coordinates of all of the NS3 amino acids set forth in FIG. 1, or
  b. a homologue of said molecule or molecular complex, wherein said homologue comprises a binding pocket that has a root mean square deviation from the backbone atoms of said amino acids of not more than 1.5 Å; and
  wherein said computer readable data contains the coordinates of all of the NS3 helicase amino acids set forth in FIG. 1.

6. A computer for determining at least a portion of the structure coordinates corresponding to X-ray diffraction data obtained from a molecule or molecular complex, wherein said computer comprises:
  (a) a computer-readable data storage medium comprising a data storage material encoded with machine-readable data, wherein said data comprises at least a portion of the structural coordinates of NS3 helicase according to FIG. 1;
  (b) a computer-readable data storage medium comprising a data storage material encoded with computer-readable data, wherein said data comprises X-ray diffraction data obtained from said molecule or molecular complex;
  (c) a working memory for storing instructions for processing said computer-readable data of (a) and (b);
  (d) a central-processing unit coupled to said working memory and to said computer-readable data storage medium of (a) and (b) for performing a Fourier transform of the machine readable data of (a) and for processing said computer-readable data of (b) into structure coordinates; and (e) a display coupled to said central-processing unit for displaying said structure coordinates of said molecule or molecular complex.

7. The computer according to claim 6, wherein said molecule or molecular complex comprises a polypeptide having helicase activity.

8. A method for evaluating the potential of a chemical entity to associate with:
   a) a molecule or molecular complex comprising a binding pocket defined by structure coordinates of NS3 helicase amino acids Val232, Thr254, Gly255, Thr269, Gly271, Lys272, Ala275, Trp501 and Tyr502 according to FIG. 1, or
   b) a homologue of said molecule or molecular complex, wherein said homologue comprises a binding pocket that has a root mean square deviation from the backbone atoms of said amino acids of not more than 1.5 Å comprising the steps of:
      i) employing computational means to perform a fitting operation between the chemical entity and a binding pocket defined by structure coordinates of NS3 helicase amino acids Val232, Thr254, Gly255, Thr269, Gly271, Lys272, Ala275, Trp501 and Tyr502 according to FIG. 1 ± a root mean square deviation from the backbone atoms of said amino acids of not more than 1.5 Å; and
      ii) analyzing the results of said fitting operation to quantify the association between the chemical entity and the binding pocket.

9. The method according to claim 8, wherein said method evaluates the potential of a chemical entity to associate with:
   a) a molecule or molecular complex comprising a binding pocket defined by structure coordinates of NS3 helicase amino acids Val232, Thr254, Gly255, Thr269, Gly271, Lys272, Ala275, Trp501, Tyr502, Pro230, Val256, Thr298, Ala497, Lys551, Gln552, Gly554, Glu555, Asn556 and Pro558 according to FIG. 1, or
   b) a homologue of said molecule or molecular complex, wherein said homologue comprises a binding pocket that has a root mean square deviation from the backbone atoms of said amino acids of not more than 1.5 Å.

10. A method for evaluating the potential of a chemical entity to associate with:
   a) a molecule or molecular complex comprising a binding pocket defined by structure coordinates of NS3 helicase amino acids His369, Ser370, Lys371, Tyr392, Arg393, Thr411, Asp412, Ala413, Cys431, Val432, Gln434, Ile446, Thr448, Arg461, Glu493, Glu555, Asn556 and Phe557 according to FIG. 1, or
   b) a homologue of said molecule or molecular complex, wherein said homologue comprises a binding pocket that has a root mean square deviation from the backbone atoms of said amino acids of not more than 1.5 Å comprising the steps of:
      i) employing computational means to perform a fitting operation between the chemical entity and a binding pocket defined by structure coordinates of NS3 helicase amino acids His369, Ser370, Lys371, Tyr392, Arg393, Thr411, Asp412, Ala413, Cys431, Val432, Gln434, Ile446, Thr448, Arg461, Glu493, Glu555, Asn556 and Phe557 according to FIG. 1 ± a root mean square deviation from the backbone atoms of said amino acids of not more than 1.5 Å; and
      ii) analyzing the results of said fitting operation to quantify the association between the chemical entity and the binding pocket.

11. A method for evaluating the potential of a chemical entity to associate with:
   a) a molecule or molecular complex comprising a binding pocket defined by structure coordinates of NS3 helicase amino acids Pro205, Thr206, Gly207, Ser208, Gly209, Lys210, Ser211, Thr212, Lys213, Asn229, Ala234, Gly237, Phe238, Tyr241, Asp290, Glu291, His293, Thr322, Ala323, Thr324, Gln460, Gly463, Arg464 and Arg467 according to FIG. 1, or
   b) a homologue of said molecule or molecular complex, wherein said homologue comprises a binding pocket that has a root mean square deviation from the backbone atoms of said amino acids of not more than 1.5 Å comprising the steps of:
      i) employing computational means to perform a fitting operation between the chemical entity and a binding pocket defined by structure coordinates of NS3 helicase amino acids Pro205, Thr206, Gly207, Ser208, Gly209 Lys210, Ser211, Thr212, Lys213, Asn229, Ala234, Gly237, Phe238, Tyr241, Asp290, Glu291, His293, Thr322, Ala323, Thr324, Gln460, Gly463, Arg464 and Arg467 according to FIG. 1 ± a root mean square deviation from the backbone atoms of said amino acids of not more than 1.5 Å; and
      ii) analyzing the results of said fitting operation to quantify the association between the chemical entity and the binding pocket.

12. The method according to any one of claims 8 to 11, wherein said method evaluates the potential of a chemical entity to associate with a molecule or molecular complex:
   a. defined by structure coordinates of all of the NS3 helicase amino acids, as set forth in FIG. 1, or
   b. a homologue of said molecule or molecular complex having a root mean square deviation from the backbone atoms of said amino acids of not more than 1.5 Å.

13. A method for identifying a potential agonist or antagonist of a molecule comprising a NS3 helicase U8-like binding pocket comprising the steps of:
   a. using the atomic coordinates of Val232, Thr254, Gly255, Thr269, Gly271, Lys272, Ala275, Trp501 and Tyr502 according to FIG. 1 ± a root mean square deviation from the backbone atoms of said amino acids of not more than 1.5 Å, to generate a three-dimensional structure of molecule comprising a NS3 helicase U8-like binding pocket;
   b. employing said three-dimensional structure to design or select said potential agonist or antagonist;
   c. synthesizing said agonist or antagonist; and
   d. contacting said agonist or antagonist with said molecule to determine the ability of said potential agonist or antagonist to interact with said molecule.

14. The method according to claim 13, wherein the atomic coordinates used in step a. comprise Val232, Thr254, Gly255, Thr269, Gly271, Lys272, Ala275, Trp501, Tyr502, Pro230, Val256, Thr298, Ala497, Lys551, Gln552, Gly554, Glu555, Asn556 and Pro558 according to FIG. 1 ± a root mean square deviation from the backbone atoms of said amino acids of not more than 1.5 Å.

15. A method for identifying a potential agonist or antagonist of a molecule comprising a NS3 helicase U4-like binding pocket comprising the steps of:
   a. using the atomic coordinates of His369, Ser370, Lys371, Tyr392, Arg393, Thr411, Asp412, Ala413, Cys431, Val432, Gln434, Ile446, Thr448, Arg461, Glu493, Glu555, Asn556 and Phe557 according to FIG. 1 ± a root mean square deviation from the backbone atoms of said amino acids of not more than 1.5 Å, to generate a three-dimensional structure of molecule comprising a NS3 helicase U8-like binding pocket;

b. employing said three-dimensional structure to design or select said potential agonist or antagonist;

c. synthesizing said agonist or antagonist; and d. contacting said agonist or antagonist with said molecule to determine the ability of said potential agonist or antagonist to interact with said molecule.

16. A method for identifying a potential agonist or antagonist of a molecule comprising a NS3 helicase ATP-like binding pocket comprising the steps of:

a. using the atomic coordinates of Pro205, Thr206, Gly207, Ser208, Gly209, Lys210, Ser211, Thr212, Lys213, Asn229, Ala234, Gly237, Phe238, Tyr241, Asp290, Glu291, His293, Thr322, Ala323, Thr324, Gln460, Gly463, Arg464 and Arg467 according to FIG. 1 ± a root mean square deviation from the backbone atoms of said amino acids of not more than 1.5 Å, to generate a three-dimensional structure of molecule comprising a NS3 helicase U8-like binding pocket;

b. employing said three-dimensional structure to design or select said potential agonist or antagonist;

c. synthesizing said agonist or antagonist; and d. contacting said agonist or antagonist with said molecule to determine the ability of said potential agonist or antagonist to interact with said molecule.

17. The method according to any one of claims 13 to 16, wherein in step a., the atomic coordinates of all the amino acids of NS3 helicase according to FIG. 1 ± a root mean square deviation from the backbone atoms of said amino acids of not more than 1.5 Å are used.

* * * * *

SEQUENCE LISTING

<160> NUMBER OF SEQ ID NOS: 4

<210> SEQ ID NO 1
<211> LENGTH: 1932
<212> TYPE: DNA
<213> ORGANISM: Hepatitis C virus
<220> FEATURE:
<221> NAME/KEY: CDS
<222> LOCATION: (4)..(1896)
<223> OTHER INFORMATION: Full length HCV NS3 coding sequence
<220> FEATURE:
<221> NAME/KEY: misc_feature
<222> LOCATION: (504)..(1896)
<223> OTHER INFORMATION: Helicase domain

<400> SEQUENCE: 1

```
atg gcg ccc atc acg gcg tac gcc cag cag acg aga ggc aag ctt ggg         48
    Ala Pro Ile Thr Ala Tyr Ala Gln Gln Thr Arg Gly Lys Leu Gly
    1               5                  10                  15 tgt ata atc acc agc ctg act ggc cgg gac aaa aac caa gtg gag ggt         96
Cys Ile Ile Thr Ser Leu Thr Gly Arg Asp Lys Asn Gln Val Glu Gly
                20                  25                  30 gag gtc cag atc gtg tca act gct acc caa acc ttc ctg gca acg tgc        144
Glu Val Gln Ile Val Ser Thr Ala Thr Gln Thr Phe Leu Ala Thr Cys
            35                  40                  45 atc aat ggg gta tgc tgg act gtc tac cac ggg gcc gga acg agg acc        192
Ile Asn Gly Val Cys Trp Thr Val Tyr His Gly Ala Gly Thr Arg Thr
        50                  55                  60 atc gca tca ccc aag ggt cct gtc atc cag atg tat acc aat gtg gac        240
Ile Ala Ser Pro Lys Gly Pro Val Ile Gln Met Tyr Thr Asn Val Asp
    65                  70                  75 caa gac ctt gtg ggc tgg ccc gct cct caa ggt tcc cgc tca ttg aca        288
Gln Asp Leu Val Gly Trp Pro Ala Pro Gln Gly Ser Arg Ser Leu Thr
80                  85                  90                  95 ccc tgc acc tgc ggc tcc tcg gac ctt tac ctg gtt acg agg cac gcc        336
Pro Cys Thr Cys Gly Ser Ser Asp Leu Tyr Leu Val Thr Arg His Ala
                100                 105                 110 gac gtc atc ccg gtt cgc cgt cgc ggt gat agc cgt ggt agc ctg ctg        384
Asp Val Ile Pro Val Arg Arg Arg Gly Asp Ser Arg Gly Ser Leu Leu
            115                 120                 125 tct ccg cgt ccg att tcc tac ctg aaa ggc tcc tcg ggg ggt ccg ctg        432
Ser Pro Arg Pro Ile Ser Tyr Leu Lys Gly Ser Ser Gly Gly Pro Leu
        130                 135                 140 ttg tgc ccc gcg gga cac gcc gtg ggc cta ttc agg gcc gcg gtg tgc        480
Leu Cys Pro Ala Gly His Ala Val Gly Leu Phe Arg Ala Ala Val Cys
    145                 150                 155 acc cgt gga gtg gcc aag gcg gtg gac ttt atc cct gtg gag aac ctg        528
Thr Arg Gly Val Ala Lys Ala Val Asp Phe Ile Pro Val Glu Asn Leu
160                 165                 170                 175 gag acc acc atg cgt tcc ccg gtg ttc acg gac aac tcc tct cca cca        576
Glu Thr Thr Met Arg Ser Pro Val Phe Thr Asp Asn Ser Ser Pro Pro
                180                 185                 190 gct gtt ccc cag agc ttc cag gtg gcc cac ctg cat gct ccc acc ggc        624
Ala Val Pro Gln Ser Phe Gln Val Ala His Leu His Ala Pro Thr Gly
            195                 200                 205 agt ggt aag agc acc aag gtc ccg gct gcg tac gca gcc cag ggc tac        672
Ser Gly Lys Ser Thr Lys Val Pro Ala Ala Tyr Ala Ala Gln Gly Tyr
        210                 215                 220 aag gtg ttg gtg ctc aac ccc tct gtt gct gca acg ctg ggc ttt ggt        720
Lys Val Leu Val Leu Asn Pro Ser Val Ala Ala Thr Leu Gly Phe Gly
    225                 230                 235
```

-continued

```
gct tac atg tcc aag gcc cat ggg gtc gat cct aat atc cgc acc ggt    768
Ala Tyr Met Ser Lys Ala His Gly Val Asp Pro Asn Ile Arg Thr Gly
240             245                 250                 255 gtg cgt aca att acc act ggc agc ccc atc acg tac tcc acc tac ggc    816
Val Arg Thr Ile Thr Thr Gly Ser Pro Ile Thr Tyr Ser Thr Tyr Gly
                260                 265                 270 aag ttc ctt gcc gac ggc ggg tgc tca ggt ggc gct tat gat atc atc    864
Lys Phe Leu Ala Asp Gly Gly Cys Ser Gly Gly Ala Tyr Asp Ile Ile
            275                 280                 285 att tgt gac gag tgc cac tcc acg gat gcc aca tcc atc ttg ggc atc    912
Ile Cys Asp Glu Cys His Ser Thr Asp Ala Thr Ser Ile Leu Gly Ile
        290                 295                 300 ggc act gtc ctt gac caa gca gag act gcg ggg gcg aga ttg gtt gtg    960
Gly Thr Val Leu Asp Gln Ala Glu Thr Ala Gly Ala Arg Leu Val Val
    305                 310                 315 ctc gcc act gct acc cct ccg ggc tcc gtc acg gta ccg cat cct aac   1008
Leu Ala Thr Ala Thr Pro Pro Gly Ser Val Thr Val Pro His Pro Asn
320                 325                 330                 335 atc gag gag gtt gct ctg tcc acc acc gga gag atc cct ttc tac ggc   1056
Ile Glu Glu Val Ala Leu Ser Thr Thr Gly Glu Ile Pro Phe Tyr Gly
                340                 345                 350 aag gct atc ccc ctc gag gtg atc aag ggc ggc cgt cat ctc atc ttc   1104
Lys Ala Ile Pro Leu Glu Val Ile Lys Gly Gly Arg His Leu Ile Phe
            355                 360                 365 tgt cac tca aag aag aag tgc gac gag ctc gcc gcg aag ctg gtc gca   1152
Cys His Ser Lys Lys Lys Cys Asp Glu Leu Ala Ala Lys Leu Val Ala
        370                 375                 380 ttg ggc atc aat gcc gtg gcc tac tac cgc gga ctt gac gtg tct gtc   1200
Leu Gly Ile Asn Ala Val Ala Tyr Tyr Arg Gly Leu Asp Val Ser Val
    385                 390                 395 atc ccg acc agc ggc gat gtt gtc gtc gtg gcg acc gat gct ctc atg   1248
Ile Pro Thr Ser Gly Asp Val Val Val Val Ala Thr Asp Ala Leu Met
400                 405                 410                 415 act ggc ttt acc ggc gac ttc gac tct gtg ata gac tgc aac acg tgt   1296
Thr Gly Phe Thr Gly Asp Phe Asp Ser Val Ile Asp Cys Asn Thr Cys
                420                 425                 430 gtc act cag aca gtc gat ttc agc ctt gac cct acc ttt acc att gag   1344
Val Thr Gln Thr Val Asp Phe Ser Leu Asp Pro Thr Phe Thr Ile Glu
            435                 440                 445 aca acc acg ctc ccc cag gat gct gtc tcc agg act cag cgc cgt ggt   1392
Thr Thr Thr Leu Pro Gln Asp Ala Val Ser Arg Thr Gln Arg Arg Gly
        450                 455                 460 cgt acc ggc cgt ggg aag cca ggc atc tac aga ttt gtg gca ccg ggg   1440
Arg Thr Gly Arg Gly Lys Pro Gly Ile Tyr Arg Phe Val Ala Pro Gly
    465                 470                 475 gag cgc ccc tcc ggc atg ttc gac tcg tcc gtc ctc tgt gag tgc tat   1488
Glu Arg Pro Ser Gly Met Phe Asp Ser Ser Val Leu Cys Glu Cys Tyr
480                 485                 490                 495 gac gcg ggc tgt gct tgg tat gag ctc acg ccg gcg gag act aca gtt   1536
Asp Ala Gly Cys Ala Trp Tyr Glu Leu Thr Pro Ala Glu Thr Thr Val
                500                 505                 510 cgt ctg cgc gcg tac atg aac acc ccg ggg ctt ccc gtg tgc cag gac   1584
Arg Leu Arg Ala Tyr Met Asn Thr Pro Gly Leu Pro Val Cys Gln Asp
            515                 520                 525 cat ctt gaa ttt tgg gag ggc gtc ttt acg ggc ctc acc cat atc gat   1632
His Leu Glu Phe Trp Glu Gly Val Phe Thr Gly Leu Thr His Ile Asp
        530                 535                 540 gcc cac ttt ctg tcc cag aca aag cag agt ggg gag aac ttt cct tac   1680
Ala His Phe Leu Ser Gln Thr Lys Gln Ser Gly Glu Asn Phe Pro Tyr
```

-continued

```
            545                 550                 555
ctg gta gcg tac caa gcc acc gtg tgc gct cgt gcg caa gcc cct ccg    1728
Leu Val Ala Tyr Gln Ala Thr Val Cys Ala Arg Ala Gln Ala Pro Pro
560             565                 570                 575 cca tcg tgg gac cag atg tgg aag tgt ttg atc cgc ctt aaa ccc acc    1776
Pro Ser Trp Asp Gln Met Trp Lys Cys Leu Ile Arg Leu Lys Pro Thr
                580                 585                 590 ctc cat ggg cca aca ccg ctc ctg tac cgt ctg ggc gct gtt cag aat    1824
Leu His Gly Pro Thr Pro Leu Leu Tyr Arg Leu Gly Ala Val Gln Asn
            595                 600                 605 gaa gtc acc ctg acg cac cca atc acc aaa tac atc atg aca tgc atg    1872
Glu Val Thr Leu Thr His Pro Ile Thr Lys Tyr Ile Met Thr Cys Met
        610                 615                 620 tcg gcc gac ctg gag gtc gtc acg ggatctggct cgcatcatca tcatcatcac   1926
Ser Ala Asp Leu Glu Val Val Thr
625                 630 taatag                                                             1932
```

<210> SEQ ID NO 2
<211> LENGTH: 631
<212> TYPE: PRT
<213> ORGANISM: Hepatitis C virus

<400> SEQUENCE: 2

```
Ala Pro Ile Thr Ala Tyr Ala Gln Gln Thr Arg Gly Lys Leu Gly Cys
1               5                   10                  15

Ile Ile Thr Ser Leu Thr Gly Arg Asp Lys Asn Gln Val Glu Gly Glu
                20                  25                  30

Val Gln Ile Val Ser Thr Ala Thr Gln Thr Phe Leu Ala Thr Cys Ile
            35                  40                  45

Asn Gly Val Cys Trp Thr Val Tyr His Gly Ala Gly Thr Arg Thr Ile
        50                  55                  60

Ala Ser Pro Lys Gly Pro Val Ile Gln Met Tyr Thr Asn Val Asp Gln
65                  70                  75                  80

Asp Leu Val Gly Trp Pro Ala Pro Gln Gly Ser Arg Ser Leu Thr Pro
                85                  90                  95

Cys Thr Cys Gly Ser Ser Asp Leu Tyr Leu Val Thr Arg His Ala Asp
            100                 105                 110

Val Ile Pro Val Arg Arg Arg Gly Asp Ser Arg Gly Ser Leu Leu Ser
        115                 120                 125

Pro Arg Pro Ile Ser Tyr Leu Lys Gly Ser Ser Gly Gly Pro Leu Leu
130                 135                 140

Cys Pro Ala Gly His Ala Val Gly Leu Phe Arg Ala Ala Val Cys Thr
145                 150                 155                 160

Arg Gly Val Ala Lys Ala Val Asp Phe Ile Pro Val Glu Asn Leu Glu
                165                 170                 175

Thr Thr Met Arg Ser Pro Val Phe Thr Asp Asn Ser Ser Pro Pro Ala
            180                 185                 190

Val Pro Gln Ser Phe Gln Val Ala His Leu His Ala Pro Thr Gly Ser
        195                 200                 205

Gly Lys Ser Thr Lys Val Pro Ala Ala Tyr Ala Ala Gln Gly Tyr Lys
210                 215                 220

Val Leu Val Leu Asn Pro Ser Val Ala Ala Thr Leu Gly Phe Gly Ala
225                 230                 235                 240

Tyr Met Ser Lys Ala His Gly Val Asp Pro Asn Ile Arg Thr Gly Val
                245                 250                 255
```

-continued

```
Arg Thr Ile Thr Thr Gly Ser Pro Ile Thr Tyr Ser Thr Tyr Gly Lys
            260                 265                 270
Phe Leu Ala Asp Gly Gly Cys Ser Gly Gly Ala Tyr Asp Ile Ile Ile
            275                 280             285
Cys Asp Glu Cys His Ser Thr Asp Ala Thr Ser Ile Leu Gly Ile Gly
        290                 295                 300
Thr Val Leu Asp Gln Ala Glu Thr Ala Gly Ala Arg Leu Val Val Leu
305                 310                 315                 320
Ala Thr Ala Thr Pro Pro Gly Ser Val Thr Val Pro His Pro Asn Ile
                325                 330                 335
Glu Glu Val Ala Leu Ser Thr Thr Gly Glu Ile Pro Phe Tyr Gly Lys
            340                 345                 350
Ala Ile Pro Leu Glu Val Ile Lys Gly Gly Arg His Leu Ile Phe Cys
            355                 360                 365
His Ser Lys Lys Lys Cys Asp Glu Leu Ala Ala Lys Leu Val Ala Leu
        370                 375                 380
Gly Ile Asn Ala Val Ala Tyr Tyr Arg Gly Leu Asp Val Ser Val Ile
385                 390                 395                 400
Pro Thr Ser Gly Asp Val Val Val Ala Thr Asp Ala Leu Met Thr
                405                 410                 415
Gly Phe Thr Gly Asp Phe Asp Ser Val Ile Asp Cys Asn Thr Cys Val
                420                 425                 430
Thr Gln Thr Val Asp Phe Ser Leu Asp Pro Thr Phe Thr Ile Glu Thr
            435                 440                 445
Thr Thr Leu Pro Gln Asp Ala Val Ser Arg Thr Gln Arg Arg Gly Arg
        450                 455                 460
Thr Gly Arg Gly Lys Pro Gly Ile Tyr Arg Phe Val Ala Pro Gly Glu
465                 470                 475                 480
Arg Pro Ser Gly Met Phe Asp Ser Ser Val Leu Cys Glu Cys Tyr Asp
                485                 490                 495
Ala Gly Cys Ala Trp Tyr Glu Leu Thr Pro Ala Glu Thr Thr Val Arg
            500                 505                 510
Leu Arg Ala Tyr Met Asn Thr Pro Gly Leu Pro Val Cys Gln Asp His
            515                 520                 525
Leu Glu Phe Trp Glu Gly Val Phe Thr Gly Leu Thr His Ile Asp Ala
        530                 535                 540
His Phe Leu Ser Gln Thr Lys Gln Ser Gly Glu Asn Phe Pro Tyr Leu
545                 550                 555                 560
Val Ala Tyr Gln Ala Thr Val Cys Ala Arg Ala Gln Ala Pro Pro Pro
                565                 570                 575
Ser Trp Asp Gln Met Trp Lys Cys Leu Ile Arg Leu Lys Pro Thr Leu
            580                 585                 590
His Gly Pro Thr Pro Leu Leu Tyr Arg Leu Gly Ala Val Gln Asn Glu
            595                 600                 605
Val Thr Leu Thr His Pro Ile Thr Lys Tyr Ile Met Thr Cys Met Ser
        610                 615                 620
Ala Asp Leu Glu Val Val Thr
625                 630
```

<210> SEQ ID NO 3
<211> LENGTH: 8157
<212> TYPE: DNA
<213> ORGANISM: Artificial Sequence
<220> FEATURE:

<223> OTHER INFORMATION: Description of Artificial Sequence: Genetically
      engineered plasmid containing full-length HCV NS3
      coding sequence

<400> SEQUENCE: 3

| | | |
|---|---|---|
| ttaatacgac tcactatagg ggaattgtga gcggataaca attcccctct agaaataatt | 60 |
| ttgtttaact ttaagaagga gatataccat ggcgcccatc acggcgtacg cccagcagac | 120 |
| gagaggcaag cttgggtgta taatcaccag cctgactggc cgggacaaaa accaagtgga | 180 |
| gggtgaggtc cagatcgtgt caactgctac ccaaaccttc ctggcaacgt gcatcaatgg | 240 |
| ggtatgctgg actgtctacc acggggccgg aacgaggacc atcgcatcac ccaagggtcc | 300 |
| tgtcatccag atgtatacca atgtggacca agaccttgtg ggctggcccg ctcctcaagg | 360 |
| ttcccgctca ttgacaccct gcacctgcgg ctcctcggac ctttacctgg ttacgaggca | 420 |
| gccgacgtc atcccggttc gccgtcgcgg tgatagccgt ggtagcctgc tgtctccgcg | 480 |
| tccgatttcc tacctgaaag ctcctcgggg ggtccgctg ttgtgcccg cgggacacgc | 540 |
| cgtgggccta ttcagggccg cggtgtgcac ccgtggagtg gccaaggcgg tggactttat | 600 |
| ccctgtggag aacctggaga ccaccatgcg ttccccggtg ttcacggaca actcctctcc | 660 |
| accagctgtt ccccagagct tccaggtggc ccacctgcat gctcccaccg gcagtggtaa | 720 |
| gagcaccaag gtcccggctg cgtacgcagc ccagggctac aaggtgttgg tgctcaaccc | 780 |
| ctctgttgct gcaacgctgg gctttggtgc ttacatgtcc aaggcccatg gggtcgatcc | 840 |
| taatatccgc accggtgtgc gtacaattac cactggcagc cccatcacgt actccaccta | 900 |
| cggcaagttc cttgccgacg gcgggtgctc aggtggcgct tatgatatca tcatttgtga | 960 |
| cgagtgccac tccacggatg ccacatccat cttgggcatc ggcactgtcc ttgaccaagc | 1020 |
| agagactgcg ggggcgagat tggttgtgct cgccactgct acccctccgg gctccgtcac | 1080 |
| ggtaccgcat cctaacatcg aggaggttgc tctgtccacc accggagaga tccctttcta | 1140 |
| cggcaaggct atcccctcg aggtgatcaa gggcggccgt catctcatct ctgtcactc | 1200 |
| aaagaagaag tgcgacgagc tcgccgcgaa gctggtcgca ttgggcatca atgccgtggc | 1260 |
| ctactaccgc ggacttgacg tgtctgtcat cccgaccagc ggcgatgttg tcgtcgtggc | 1320 |
| gaccgatgct ctcatgactg gctttaccgg cgacttcgac tctgtgatag actgcaacac | 1380 |
| gtgtgtcact cagacagtcg atttcagcct tgaccctacc tttaccattg agacaaccac | 1440 |
| gctcccccag gatgctgtct ccaggactca gcgccgtggt cgtaccggcc gtgggaagcc | 1500 |
| aggcatctac agatttgtgg caccggggga cgcccctcc ggcatgttcg actcgtccgt | 1560 |
| cctctgtgag tgctatgacg cgggctgtgc ttggtatgag ctcacgccgg cggagactac | 1620 |
| agttcgtctg cgcgcgtaca tgaacacccc ggggcttccc gtgtgccagg accatcttga | 1680 |
| attttgggag ggcgtcttta cgggcctcac ccatatcgat gcccactttc tgtcccagac | 1740 |
| aaagcagagt ggggagaact tccttacct ggtagcgtac caagccaccg tgtgcgctcg | 1800 |
| tgcgcaagcc cctccgccat cgtgggacca gatgtggaag tgtttgatcc gccttaaacc | 1860 |
| caccctccat gggccaacac cgctcctgta ccgtctgggc gctgttcaga atgaagtcac | 1920 |
| cctgacgcac ccaatcacca atacatcat gacatgcatg tcggccgacc tggaggtcgt | 1980 |
| cacgggatct ggctcgcatc atcatcatca tcactaatag aattcggatc cggctgctaa | 2040 |
| caaagcccga aaggaagctg agttggctgc tgccaccgct gagcaataac tagcataacc | 2100 |
| ccttggggcc tctaaacggg tcttgagggg ttttttgctg aaaggaggaa ctatatccgg | 2160 |
| atatcccgca agaggcccgg cagtaccggc ataaccaagc ctatgcctac agcatccagg | 2220 |

-continued

```
gtgacggtgc cgaggatgac gatgagcgca ttgttagatt tcatacacgg tgcctgactg    2280
cgttagcaat ttaactgtga taaactaccg cattaaagct tatcgatacc gtcgacctcg    2340
agggggggcc cggtacccaa ttcgccctat agtgagtcgt attacgcgcg ctcactggcc    2400
gtcgttttac aacgtcgtga ctgggaaaac cctggcgtta cccaacttaa tcgccttgca    2460
gcacatcccc ctttcgccag ctggcgtaat agcgaagagg cccgcaccga tcgcccttcc    2520
caacagttgc gcagcctgaa tggcgaatgg gacgcgccct gtagcggcgc attaagcgcg    2580
gcgggtgtgg tggttacgcg cagcgtgacc gctacacttg ccagcgccct agcgcccgct    2640
cctttcgctt tcttcccttc ctttctcgcc acgttcgccg gctttccccg tcaagctcta    2700
aatcgggggc tccctttagg gttccgattt agtgctttac ggcacctcga cccaaaaaa    2760 cttgattagg gtgatggttc acgtagtggg ccatcgccct gatagacggt ttttcgccct    2820
ttgacgttgg agtccacgtt ctttaatagt ggactcttgt tccaaactgg aacaacactc    2880
aaccctatct cggtctattc ttttgattta agggatttt gccgatttc ggcctattgg    2940 ttaaaaaatg agctgattta acaaaaattt aacgcgaatt ttaacaaaat attaacgctt    3000
acaatttagg tggcactttt cggggaaatg tgcgcggaac ccctatttgt ttattttct    3060 aaatacattc aaatatgtat ccgctcatga gacaataacc ctgataaatg cttcaataat    3120
attgaaaaag gaagagtatg agtattcaac atttccgtgt cgcccttatt cccttttttg    3180
cggcattttg ccttcctgtt tttgctcacc cagaaacgct ggtgaaagta aaagatgctg    3240
aagatcagtt gggtgcacga gtgggttaca tcgaactgga tctcaacagc ggtaagatcc    3300
ttgagagttt tcgccccgaa gaacgtttc caatgatgag cacttttaaa gttctgctat    3360
gtggcgcggt attatcccgt attgacgccg ggcaagagca actcggtcgc cgcatacact    3420
attctcagaa tgacttggtt gagtactcac cagtcacaga aaagcatctt acggatggca    3480
tgacagtaag agaattatgc agtgctgcca taaccatgag tgataacact gcggccaact    3540
tacttctgac aacgatcgga ggaccgaagg agctaaccgc ttttttgcac aacatggggg    3600
atcatgtaac tcgccttgat cgttgggaac cggagctgaa tgaagccata ccaaacgacg    3660
agcgtgacac cacgatgcct gcagcaatgg caacaacgtt gcgcaaacta ttaactggcg    3720
aactacttac tctagcttcc cggcaacaat taatagactg gatggaggcg gataaagttg    3780
caggaccact tctgcgctcg gcccttccgg ctggctggtt tattgctgat aaatctggag    3840
ccggtgagcg tgggtctcgc ggtatcattg cagcactggg gccagatggt aagccctccc    3900
gtatcgtagt tatctacacg acggggagtc aggcaactat ggatgaacga atagacaga    3960 tcgctgagat aggtgcctca ctgattaagc attggtaact gtcagaccaa gtttactcat    4020
atatacttta gattgattta aaacttcatt tttaatttaa aaggatctag gtgaagatcc    4080
tttttgataa tctcatgacc aaaatccctt aacgtgagtt ttcgttccac tgagcgtcag    4140
accccgtaga aaagatcaaa ggatcttctt gagatccttt ttttctgcgc gtaatctgct    4200
gcttgcaaac aaaaaaacca ccgctaccag cggtggtttg tttgccggat caagagctac    4260
caactctttt tccgaaggta actggcttca gcagagcgca gataccaaat actgtccttc    4320
tagtgtagcc gtagttaggc caccacttca agaactctgt agcaccgcct acatacctcg    4380
ctctgctaat cctgttacca gtggctgctg ccagtggcga taagtcgtgt cttaccgggt    4440
tggactcaag acgatagtta ccggataagg cgcagcggtc gggctgaacg ggggggttcgt    4500 gcacacagcc cagcttggag cgaacgacct acaccgaact gagatacca cagcgtgagc    4560
```

-continued

```
tatgagaaag cgccacgctt cccgaaggga gaaaggcgga caggtatccg gtaagcggca    4620
gggtcggaac aggagagcgc acgagggagc ttccaggggg aaacgcctgg tatctttata    4680
gtcctgtcgg gtttcgccac ctctgacttg agcgtcgatt tttgtgatgc tcgtcagggg    4740
ggcggagcct atggaaaaac gccagcaacg cggccttttt acggttcctg gccttttgct    4800
ggccttttgc tcacatgttc tttcctgcgt tatcccctga ttctgtggat aaccgtatta    4860
ccgcctttga gtgagctgat accgctcgcc gcagccgaac gaccgagcgc agcgagtcag    4920
tgagcgagga gcggaagag cgcctgatgc ggtattttct ccttacgcat ctgtgcggta    4980
tttcacaccg catatatggt gcactctcag tacaatctgc tctgatgccg catagttaag    5040
ccagtataca ctccgctatc gctacgtgac tgggtcatgg ctgcgccccg acacccgcca    5100
acacccgctg acgcgccctg acgggcttgt ctgctcccgg catccgctta cagacaagct    5160
gtgaccgtct ccgggagctg catgtgtcag aggttttcac cgtcatcacc gaaacgcgcg    5220
aggcagctgc ggtaaagctc atcagcgtgg tcgtgaagcg attcacagat gtctgcctgt    5280
tcatccgcgt ccagctcgtt gagtttctcc agaagcgtta atgtctggct tctgataaag    5340
cgggccatgt taagggcggt tttttcctgt ttggtcactg atgcctccgt gtaaggggga    5400
tttctgttca tggggtaat gataccgatg aaacgagaga ggatgctcac gatacgggtt    5460
actgatgatg aacatgcccg gttactggaa cgttgtgagg gtaaacaact ggcggtatgg    5520
atgcggcggg accagagaaa aatcactcag ggtcaatgcc agcgcttcgt taatacagat    5580
gtaggtgttc cacagggtag ccagcagcat cctgcgatgc agatccggaa cataatggtg    5640
cagggcgctg acttccgcgt ttccagactt tacgaaacac ggaaaccgaa gaccattcat    5700
gttgttgctc aggtcgcaga cgttttgcag cagcagtcgc ttcacgttcg ctcgcgtatc    5760
ggtgattcat tctgctaacc agtaaggcaa ccccgccagc ctagccgggt cctcaacgac    5820
aggagcacga tcatgcgcac ccgtggccag gacccaacgc tgcccgagat cgccgcgtg    5880
cggctgctgg agatggcgga cgcgatggat atgttctgcc aagggttggt ttgcgcattc    5940
acagttctcc gcaagaattg attggctcca attcttggag tggtgaatcc gttagcgagg    6000
tgccgccggc ttccattcag gtcgaggtgg cccggctcca tgcaccgcga cgcaacgcgg    6060
ggaggcagac aaggtatagg gcggcgccta caatccatgc caacccgttc catgtgctcg    6120
ccgaggcggc ataaatcgcc gtgacgatca gcggtccagt gatcgaagtt aggctggtaa    6180
gagccgcgag cgatccttga agctgtccct gatggtcgtc atctacctgc ctggacagca    6240
tggcctgcaa cgcgggcatc ccgatgccgc cggaagcgag aagaatcata tgggaagg    6300
ccatccagcc tcgcgtcgcg aacgccagca agacgtagcc cagcgcgtcg gccgccatgc    6360
cggcgataat ggcctgcttc tcgccgaaac gtttggtggc gggaccagtg acgaaggctt    6420
gagcgagggc gtgcaagatt ccgaataccg caagcgacag gccgatcatc gtcgcgctcc    6480
agcgaaagcg gtcctcgccg aaaatgaccc agagcgctgc cggcacctgt cctacgagtt    6540
gcatgataaa gaagacagtc ataagtgcgg cgacgatagt catgccccgc gcccaccgga    6600
aggagctgac tgggttgaag gctctcaagg gcatcggtcg agatcccggt gcctaatgag    6660
tgagctaact tacattaatt gcgttgcgct cactgcccgc tttccagtcg ggaaacctgt    6720
cgtgccagct gcattaatga atcggccaac gcgcgggag aggcggtttg cgtattgggc    6780
gccagggtgg ttttctttt caccagtgag acgggcaaca gctgattgcc cttcaccgcc    6840
tggccctgag agagttgcag caagcggtcc acgctggttt gccccagcag gcgaaaatcc    6900
tgtttgatgg tggttaacgg cgggatataa catgagctgt cttcggtatc gtcgtatccc    6960
```

| | |
|---|---|
| actaccgaga tatccgcacc aacgcgcagc ccggactcgg taatggcgcg cattgcgccc | 7020 |
| agcgccatct gatcgttggc aaccagcatc gcagtgggaa cgatgccctc attcagcatt | 7080 |
| tgcatggttt gttgaaaacc ggacatggca ctccagtcgc cttcccgttc cgctatcggc | 7140 |
| tgaatttgat tgcgagtgag atatttatgc cagccagcca gacgcagacg cgccgagaca | 7200 |
| gaacttaatg ggcccgctaa cagcgcgatt tgctggtgac ccaatgcgac cagatgctcc | 7260 |
| acgcccagtc gcgtaccgtc ttcatgggag aaaataatac tgttgatggg tgtctggtca | 7320 |
| gagacatcaa gaaataacgc cggaacatta gtgcaggcag cttccacagc aatggcatcc | 7380 |
| tggtcatcca gcggatagtt aatgatcagc ccactgacgc gttgcgcgag aagattgtgc | 7440 |
| accgccgctt tacaggcttc gacgccgctt cgttctacca tcgacaccac cacgctggca | 7500 |
| cccagttgat cggcgcgaga tttaatcgcc gcgacaattt gcgacggcgc gtgcagggcc | 7560 |
| agactggagg tggcaacgcc aatcagcaac gactgtttgc ccgccagttg ttgtgccacg | 7620 |
| cggttgggaa tgtaattcag ctccgccatc gccgcttcca cttttttccg cgttttcgca | 7680 |
| gaaacgtggc tggcctggtt caccacgcgg gaaacggtct gataagagac accggcatac | 7740 |
| tctgcgacat cgtataacgt tactggtttc acattcacca ccctgaattg actctcttcc | 7800 |
| gggcgctatc atgccatacc gcgaaaggtt ttgcgccatt cgatggtgtc cgggatctcg | 7860 |
| acgctctccc ttatgcgact cctgcattag gaagcagccc agtagtaggt tgaggccgtt | 7920 |
| gagcaccgcc gccgcaagga atggtgcatg caaggagatg gcgcccaaca gtcccccggc | 7980 |
| cacggggcct gccaccatac ccacgccgaa acaagcgctc atgagcccga agtggcgagc | 8040 |
| ccgatcttcc ccatcggtga tgtcggcgat ataggcgcca gcaaccgcac ctgtggcgcc | 8100 |
| ggtgatgccg gccacgatgc gtccggcgta gaggatcgag atctcgatcc cgcgaaa | 8157 |

<210> SEQ ID NO 4
<211> LENGTH: 7659
<212> TYPE: DNA
<213> ORGANISM: Artificial Sequence
<220> FEATURE:
<223> OTHER INFORMATION: Description of Artificial Sequence: Genetically engineered plasmid containing helicase domain of HCV NS3

<400> SEQUENCE: 4

| | |
|---|---|
| ttaatacgac tcactatagg ggaattgtga gcggataaca attcccctct agaaataatt | 60 |
| ttgtttaact ttaagaagga gatataccat ggtggacttt atccctgtgg agaacctgga | 120 |
| gaccaccatg cgttcccgg tgttcacgga caactcctct ccaccagctg ttccccagag | 180 |
| cttccaggtg gcccacctgc atgctcccac cggcagtggt aagagcacca aggtcccggc | 240 |
| tgcgtacgca gcccagggct acaaggtgtt ggtgctcaac ccctctgttg ctgcaacgct | 300 |
| gggctttggt gcttacatgt ccaaggccca tgggggtcgat cctaatatcc gcaccggtgt | 360 |
| gcgtacaatt accactggca gccccatcac gtactccacc tacggcaagt tccttgccga | 420 |
| cggcgggtgc tcaggtggcg cttatgatat catcatttgt gacgagtgcc actcccacgga | 480 |
| tgccacatcc atcttgggca tcggcactgt ccttgaccaa gcagagactg cggggggcgag | 540 |
| attggttgtg ctcgccactg ctaccccctc gggctccgtc acgtaccgc atcctaacat | 600 |
| cgaggaggtt gctctgtcca ccaccggaga gatccctttc tacggcaagg ctatccccct | 660 |
| cgaggtgatc aagggcggcc gtcatctcat cttctgtcac tcaaagaaga agtgcgacga | 720 |
| gctcgccgcg aagctggtcg cattgggcat caatgccgtg gcctactacc gcggacttga | 780 |

```
cgtgtctgtc atcccgacca gcggcgatgt tgtcgtcgtg gcgaccgatg ctctcatgac    840
tggctttacc ggcgacttcg actctgtgat agactgcaac acgtgtgtca ctcagacagt    900
cgatttcagc cttgacccta cctttaccat tgagacaacc acgctccccc aggatgctgt    960
ctccaggact cagcgccgtg gtcgtaccgg ccgtgggaag ccaggcatct acagatttgt   1020
ggcaccgggg gagcgcccct ccggcatgtt cgactcgtcc gtcctctgtg agtgctatga   1080
cgcgggctgt gcttggtatg agctcacgcc ggcggagact acagttcgtc tgcgcgcgta   1140
catgaacacc ccggggcttc ccgtgtgcca ggaccatctt gaattttggg agggcgtctt   1200
tacgggcctc acccatatcg atgcccactt tctgtcccag acaaagcaga gtggggagaa   1260
ctttccttac ctggtagcgt accaagccac cgtgtgcgct cgtgcgcaag ccctccgcc    1320 atcgtgggac cagatgtgga agtgtttgat ccgccttaaa cccacccctcc atgggccaac   1380 accgctcctg taccgtctgg gcgctgttca gaatgaagtc accctgacgc acccaatcac   1440
caaatacatc atgacatgca tgtcggccga cctggaggtc gtcacgggat ctggctcgca   1500
tcatcatcat catcactaat agaattcgga tccggctgct aacaaagccc gaaaggaagc   1560
tgagttggct gctgccaccg ctgagcaata actagcataa ccccttgggg cctctaaacg   1620
ggtcttgagg ggttttttgc tgaaaggagg aactatatcc ggatatcccg caagaggccc   1680
ggcagtaccg gcataaccaa gcctatgcct acagcatcca gggtgacggt gccgaggatg   1740
acgatgagcg cattgttaga tttcatacac ggtgcctgac tgcgttagca atttaactgt   1800
gataaactac cgcattaaag cttatcgata ccgtcgacct cgagggggggg cccggtaccc   1860 aattcgccct atagtgagtc gtattacgcg cgctcactgg ccgtcgtttt acaacgtcgt   1920
gactgggaaa accctggcgt tacccaactt aatcgccttg cagcacatcc ccctttcgcc   1980
agctggcgta atagcgaaga ggcccgcacc gatcgccctt cccaacagtt gcgcagcctg   2040
aatggcgaat gggacgcgcc ctgtagcggc gcattaagcg cggcgggtgt ggtggttacg   2100
cgcagcgtga ccgctacact tgccagcgcc ctagcgcccg ctcctttcgc tttcttccct   2160
tcctttctcg ccacgttcgc cggctttccc cgtcaagctc taaatcgggg gctccctttta  2220 gggttccgat ttagtgcttt acggcacctc gaccccaaaa aacttgatta gggtgatggt   2280
tcacgtagtg ggccatcgcc ctgatagacg gttttcgcc ctttgacgtt ggagtccacg    2340
ttctttaata gtggactctt gttccaaact ggaacaacac tcaaccctat ctcggtctat   2400
tcttttgatt tataagggat tttgccgatt tcggcctatt ggttaaaaaa tgagctgatt   2460
taacaaaaat ttaacgcgaa ttttaacaaa atattaacgc ttacaattta ggtggcactt   2520
ttcggggaaa tgtgcgcgga acccctattt gtttattttt ctaaatacat tcaaatatgt   2580
atccgctcat gagacaataa ccctgataaa tgcttcaata atattgaaaa aggaagagta   2640
tgagtattca acatttccgt gtcgccctta ttcccttttt tgcggcattt tgccttcctg   2700
tttttgctca cccagaaacg ctggtgaaag taaaagatgc tgaagatcag ttgggtgcac   2760
gagtgggtta catcgaactg gatctcaaca gcggtaagat ccttgagagt tttcgccccg   2820
aagaacgttt tccaatgatg agcactttta aagttctgct atgtggcgcg gtattatccc   2880
gtattgacgc cgggcaagag caactcggtc gccgcataca ctattctcag aatgacttgg   2940
ttgagtactc accagtcaca gaaaagcatc ttacggatgg catgacagta agagaattat   3000
gcagtgctgc cataaccatg agtgataaca ctgcggccaa cttacttctg acaacgatcg   3060
gaggaccgaa ggagctaacc gcttttttgc acaacatggg ggatcatgta actcgccttg   3120
atcgttggga accggagctg aatgaagcca taccaaacga cgagcgtgac accacgatgc   3180
```

```
ctgcagcaat ggcaacaacg ttgcgcaaac tattaactgg cgaactactt actctagctt    3240
cccggcaaca attaatagac tggatggagg cggataaagt tgcaggacca cttctgcgct    3300
cggcccttcc ggctggctgg tttattgctg ataaatctgg agccggtgag cgtgggtctc    3360
gcggtatcat tgcagcactg gggccagatg gtaagccctc ccgtatcgta gttatctaca    3420
cgacggggag tcaggcaact atggatgaac gaaatagaca gatcgctgag ataggtgcct    3480
cactgattaa gcattggtaa ctgtcagacc aagtttactc atatatactt tagattgatt    3540
taaaacttca tttttaattt aaaaggatct aggtgaagat cctttttgat aatctcatga    3600
ccaaaatccc ttaacgtgag ttttcgttcc actgagcgtc agaccccgta gaaaagatca    3660
aaggatcttc ttgagatcct ttttttctgc gcgtaatctg ctgcttgcaa acaaaaaaac    3720
caccgctacc agcggtggtt tgtttgccgg atcaagagct accaactctt tttccgaagg    3780
taactggctt cagcagagcg cagataccaa atactgtcct tctagtgtag ccgtagttag    3840
gccaccactt caagaactct gtagcaccgc ctacatacct cgctctgcta atcctgttac    3900
cagtggctgc tgccagtggc gataagtcgt gtcttaccgg gttggactca agacgatagt    3960
taccggataa ggcgcagcgg tcgggctgaa cggggggttc gtgcacacag cccagcttgg    4020
agcgaacgac ctacaccgaa ctgagatacc tacagcgtga gctatgagaa agcgccacgc    4080
ttcccgaagg agaaaggcg gacaggtatc cggtaagcgg cagggtcgga acaggagagc    4140
gcacgaggga gcttccaggg ggaaacgcct ggtatcttta tagtcctgtc gggtttcgcc    4200
acctctgact tgagcgtcga ttttttgtgat gctcgtcagg ggggcggagc ctatggaaaa    4260
acgccagcaa cgcggccttt ttacggttcc tggcctttg ctggccttt gctcacatgt    4320 tctttcctgc gttatcccct gattctgtgg ataaccgtat taccgccttt gagtgagctg    4380
ataccgctcg ccgcagccga acgaccgagc gcagcgagtc agtgagcgag gaagcggaag    4440
agcgcctgat gcggtatttt ctccttacgc atctgtgcgg tatttcacac cgcatatatg    4500
gtgcactctc agtacaatct gctctgatgc cgcatagtta agccagtata cactccgcta    4560
tcgctacgtg actgggtcat ggctgcgccc cgacacccgc caacacccgc tgacgcgccc    4620
tgacgggctt gtctgctccc ggcatccgct tacagacaag ctgtgaccgt ctccgggagc    4680
tgcatgtgtc agaggttttc accgtcatca ccgaaacgcg cgaggcagct gcggtaaagc    4740
tcatcagcgt ggtcgtgaag cgattcacag atgtctgcct gttcatccgc gtccagctcg    4800
ttgagtttct ccagaagcgt taatgtctgg cttctgataa agcgggccat gttaagggcg    4860
gttttttcct gtttggtcac tgatgcctcc gtgtaagggg gatttctgtt catgggggta    4920
atgataccga tgaaacgaga gaggatgctc acgatacggg ttactgatga tgaacatgcc    4980
cggttactgg aacgttgtga gggtaaacaa ctggcggtat ggatgcggcg ggaccagaga    5040
aaaatcactc agggtcaatg ccagcgcttc gttaatacag atgtaggtgt tccacagggt    5100
agccagcagc atcctgcgat gcagatccgg aacataatgg tgcagggcgc tgacttccgc    5160
gtttccagac tttacgaaac acggaaaccg aagaccattc atgttgttgc tcaggtcgca    5220
gacgttttgc agcagcagtc gcttcacgtt cgctcgcgta tcggtgattc attctgctaa    5280
ccagtaaggc aaccccgcca gcctagccgg gtcctcaacg acaggagcac gatcatgcgc    5340
acccgtggcc aggacccaac gctgcccgag atgcgccgcg tgcggctgct ggagatggcg    5400
gacgcgatga tatgttctg ccaagggttg gtttgcgcat tcacagttct ccgcaagaat    5460
tgattggctc caattcttgg agtggtgaat ccgttagcga ggtgccgccg gcttccattc    5520
```

```
aggtcgaggt ggcccggctc catgcaccgc gacgcaacgc ggggaggcag acaaggtata    5580
gggcggcgcc tacaatccat gccaacccgt tccatgtgct cgccgaggcg cataaatcg    5640 ccgtgacgat cagcggtcca gtgatcgaag ttaggctggt aagagccgcg agcgatcctt    5700
gaagctgtcc ctgatggtcg tcatctacct gcctggacag catggcctgc aacgcgggca    5760
tcccgatgcc gccggaagcg agaagaatca taatggggaa ggccatccag cctcgcgtcg    5820
cgaacgccag caagacgtag cccagcgcgt cggccgccat gccggcgata atggcctgct    5880
tctcgccgaa acgtttggtg gcgggaccag tgacgaaggc ttgagcgagg gcgtgcaaga    5940
ttccgaatac cgcaagcgac aggccgatca tcgtcgcgct ccagcgaaag cggtcctcgc    6000
cgaaaatgac ccagagcgct gccggcacct gtcctacgag ttgcatgata agaagacag    6060 tcataagtgc ggcgacgata gtcatgcccc gcgcccaccg gaaggagctg actgggttga    6120
aggctctcaa gggcatcggt cgagatcccg gtgcctaatg agtgagctaa cttacattaa    6180
ttgcgttgcg ctcactgccc gctttccagt cgggaaacct gtcgtgccag ctgcattaat    6240
gaatcggcca acgcgcgggg agaggcggtt tgcgtattgg gcgccagggt ggttttctt    6300 ttcaccagtg agacgggcaa cagctgattg cccttcaccg cctggccctg agagagttgc    6360
agcaagcggt ccacgctggt ttgccccagc aggcgaaaat cctgtttgat ggtggttaac    6420
ggcgggatat aacatgagct gtcttcggta tcgtcgtatc ccactaccga gatatccgca    6480
ccaacgcgca gcccggactc ggtaatggcg cgcattgcgc ccagcgccat ctgatcgttg    6540
gcaaccagca tcgcagtggg aacgatgccc tcattcagca tttgcatggt ttgttgaaaa    6600
ccggacatgg cactccagtc gccttcccgt tccgctatcg gctgaatttg attgcgagtg    6660
agatatttat gccagccagc cagacgcaga cgcgccgaga cagaacttaa tgggcccgct    6720
aacagcgcga tttgctggtg acccaatgcg accagatgct ccacgcccag tcgcgtaccg    6780
tcttcatggg agaaaataat actgttgatg ggtgtctggt cagagacatc aagaaataac    6840
gccggaacat tagtgcaggc agcttccaca gcaatggcat cctggtcatc cagcggatag    6900
ttaatgatca gcccactgac gcgttgcgcg agaagattgt gcaccgccgc tttacaggct    6960
tcgacgccgc ttcgttctac catcgacacc accacgctgg cacccagttg atcggcgcga    7020
gatttaatcg ccgcgacaat ttgcgacggc gcgtgcaggg ccagactgga ggtggcaacg    7080
ccaatcagca acgactgttt gcccgccagt tgttgtgcca cgcggttggg aatgtaattc    7140
agctccgcca tcgccgcttc cacttttttcc cgcgttttcg cagaaacgtg gctggcctgg    7200
ttcaccacgc gggaaacggt ctgataagag acaccggcat actctgcgac atcgtataac    7260
gttactggtt tcacattcac caccctgaat tgactctctt ccgggcgcta tcatgccata    7320
ccgcgaaagg ttttgcgcca ttcgatggtg tccgggatct cgacgctctc ccttatgcga    7380
ctcctgcatt aggaagcagc ccagtagtag gttgaggccg ttgagcaccg ccgccgcaag    7440
gaatggtgca tgcaaggaga tggcgcccaa cagtcccccg gccacggggc ctgccaccat    7500
acccacgccg aaacaagcgc tcatgagccc gaagtggcga gcccgatctt ccccatcggt    7560
gatgtcggcg atataggcgc cagcaaccgc acctgtggcg ccggtgatgc cggccacgat    7620
gcgtccggcg tagaggatcg agatctcgat cccgcgaaa                          7659
```